(12) United States Patent
Anderson et al.

(10) Patent No.: US 8,889,145 B2
(45) Date of Patent: *Nov. 18, 2014

(54) IMMUNOGENIC COMPOSITIONS OF STAPHYLOCOCCUS AUREUS ANTIGENS

(71) Applicant: Wyeth LLC, Madison, NJ (US)

(72) Inventors: Annaliesa Anderson, Upper Saddle River, NJ (US); Viliam Pavliak, Montebello, NY (US); Kathrin Ute Jansen, New York, NY (US); Ingrid Lea Scully, Cornwall, NY (US); Steven Morris Baker, Springwater, NY (US); Jasdeep Singh Nanra, Suffern, NY (US); Ellen Murphy, City Island, NY (US); Bruce Arthur Green, New City, NY (US); Mark Edward Ruppen, Garnerville, NY (US); Yekaterina Timofeyeva, Pomona, NY (US)

(73) Assignee: Wyeth LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/032,534

(22) Filed: Sep. 20, 2013

(65) Prior Publication Data

US 2014/0017271 A1 Jan. 16, 2014

Related U.S. Application Data

(62) Division of application No. 13/379,216, filed as application No. PCT/US2010/039510 on Jun. 22, 2010, now Pat. No. 8,568,735.

(60) Provisional application No. 61/219,134, filed on Jun. 22, 2009.

(51) Int. Cl.
*A61K 39/085* (2006.01)
*A61K 39/40* (2006.01)
*C07K 16/12* (2006.01)
*A61K 39/00* (2006.01)

(52) U.S. Cl.
CPC .......... *A61K 39/085* (2013.01); *C07K 16/1271* (2013.01); *C07K 2317/21* (2013.01); *A61K 2039/505* (2013.01); *A61K 2039/55505* (2013.01); *A61K 2039/6037* (2013.01); *C07K 2316/96* (2013.01)
USPC ................. 424/197.11; 424/165.1; 424/243.1

(58) Field of Classification Search
None
See application file for complete search history.

(56) References Cited

U.S. PATENT DOCUMENTS

| 4,134,214 A | 1/1979 | Graham et al. |
|---|---|---|
| 4,673,574 A | 6/1987 | Anderson |
| 4,708,871 A | 11/1987 | Geysen |
| 4,902,506 A | 2/1990 | Anderson et al. |
| 4,912,094 A | 3/1990 | Myers et al. |
| 5,057,540 A | 10/1991 | Kensil et al. |
| 5,078,996 A | 1/1992 | Conlon, III et al. |
| 5,189,015 A | 2/1993 | Hook et al. |
| 5,254,339 A | 10/1993 | Morein |
| 5,614,382 A | 3/1997 | Metcalf |
| 5,635,348 A | 6/1997 | Leong |
| 5,700,928 A | 12/1997 | Hodgson et al. |
| 5,723,127 A | 3/1998 | Scott et al. |
| 5,730,978 A | 3/1998 | Wayner |
| 5,801,234 A | 9/1998 | Hodgson et al. |
| 5,980,908 A | 11/1999 | Hook et al. |
| 6,027,925 A | 2/2000 | Pollock et al. |
| 6,113,918 A | 9/2000 | Johnson et al. |
| 6,146,902 A | 11/2000 | McMaster |
| 6,149,919 A | 11/2000 | Domenighini et al. |
| 6,165,995 A | 12/2000 | Hilgers |
| 6,177,084 B1 | 1/2001 | Foster et al. |
| 6,207,646 B1 | 3/2001 | Krieg et al. |
| 6,299,884 B1 | 10/2001 | Van Nest et al. |
| 6,380,370 B1 | 4/2002 | Doucette-Stamm et al. |
| 6,593,114 B1 | 7/2003 | Kunsch et al. |
| 6,596,861 B1 | 7/2003 | Moreau |
| 6,610,310 B2 | 8/2003 | Hilgers |
| 6,703,025 B1 | 3/2004 | Patti et al. |
| 6,737,248 B2 | 5/2004 | Kunsch et al. |
| 6,994,855 B1 | 2/2006 | Foster et al. |
| 7,060,458 B1 | 6/2006 | Doucette-Stamm et al. |
| 7,115,730 B1 | 10/2006 | Pizza et al. |
| 7,183,083 B2 | 2/2007 | Doucette-Stamm et al. |
| 7,252,828 B2 | 8/2007 | Pier et al. |
| 7,285,281 B2 | 10/2007 | Green et al. |
| 7,291,588 B2 | 11/2007 | Pizza et al. |
| 7,332,174 B2 | 2/2008 | Green et al. |
| 7,361,355 B2 | 4/2008 | Green et al. |

(Continued)

FOREIGN PATENT DOCUMENTS

| CA | 2351018 A1 | 9/2003 |
|---|---|---|
| EP | 0468714 A2 | 1/1992 |

(Continued)

OTHER PUBLICATIONS

Fattom, A.I., et al., "Staphylococcal Vaccines: a Realistic Dream", Annals of Medicine, 28(1):43-46 (1996).

(Continued)

*Primary Examiner* — Padma V Baskar
(74) *Attorney, Agent, or Firm* — Victoria S. Molenda

(57) ABSTRACT

The present invention relates to immunogenic compositions, comprising polypeptides and polysaccharides from *Staphylococcus aureus*. The present invention also relates to immunogenic compositions, comprising *Staphylococcus aureus* capsule polysaccharides conjugated to a carrier protein. In addition, the invention relates to methods of inducing an immune response in subjects against *Staphylococcus aureus* using immunogenic compositions of the *Staphylococcus aureus* polypeptides and capsule polysaccharides.

18 Claims, 29 Drawing Sheets

(56) References Cited

U.S. PATENT DOCUMENTS

| | | |
|---|---|---|
| 7,364,738 B2 | 4/2008 | Patti et al. |
| 7,368,112 B2 | 5/2008 | Foster et al. |
| 7,384,640 B1 | 6/2008 | Holmes et al. |
| 7,416,862 B2 | 8/2008 | Doucette-Stamm et al. |
| 7,537,766 B2 | 5/2009 | Pavliak et al. |
| 7,566,776 B2 | 7/2009 | Doucette-Stamm et al. |
| 7,588,920 B2 | 9/2009 | Doucette-Stamm et al. |
| 7,608,450 B2 | 10/2009 | Doucette-Stamm et al. |
| 7,666,438 B1 | 2/2010 | Patti et al. |
| 7,709,008 B2 | 5/2010 | Foster et al. |
| 7,838,012 B2 | 11/2010 | Foster et al. |
| 8,017,133 B2 | 9/2011 | Patti et al. |
| 8,110,198 B2 | 2/2012 | Doucette-Stamm et al. |
| 2004/0185058 A1 | 9/2004 | Zagury et al. |
| 2007/0053936 A1 | 3/2007 | Doucette-Stamm et al. |
| 2007/0087014 A1 | 4/2007 | Pavliak et al. |
| 2007/0141077 A1 | 6/2007 | Pavliak et al. |
| 2007/0265218 A1 | 11/2007 | Doucette-Stamm et al. |
| 2007/0292450 A1 | 12/2007 | Sellman et al. |
| 2008/0286838 A1 | 11/2008 | Yuan et al. |
| 2011/0070626 A1 | 3/2011 | Doucette-Stamm et al. |

FOREIGN PATENT DOCUMENTS

| | | |
|---|---|---|
| EP | 1296713 B1 | 9/2003 |
| EP | 1326634 B1 | 4/2006 |
| JP | 4078417 B | 2/2008 |
| WO | 8505553 A1 | 12/1985 |
| WO | 8606635 A1 | 11/1986 |
| WO | 9204915 A1 | 4/1992 |
| WO | 9309811 A1 | 5/1993 |
| WO | 9319373 A1 | 9/1993 |
| WO | 9508348 A1 | 3/1995 |
| WO | 9609321 A1 | 3/1996 |
| WO | 9748727 A1 | 12/1997 |
| WO | 9903871 A1 | 1/1999 |
| WO | 9927109 A2 | 6/1999 |
| WO | 0012131 A1 | 3/2000 |
| WO | 0056357 A2 | 9/2000 |
| WO | 0056359 A2 | 9/2000 |
| WO | 0071585 A1 | 11/2000 |
| WO | 0134809 A2 | 5/2001 |
| WO | 0170685 A2 | 9/2001 |
| WO | 0172337 A1 | 10/2001 |
| WO | 0198499 A1 | 12/2001 |
| WO | 02059148 A2 | 8/2002 |
| WO | 03/080678 A1 | 1/2003 |
| WO | 03011899 A2 | 2/2003 |
| WO | 03061558 A2 | 7/2003 |
| WO | 03076470 A1 | 9/2003 |
| WO | 03086471 A2 | 10/2003 |
| WO | 2004/019992 A1 | 3/2004 |
| WO | 2004043405 A2 | 5/2004 |
| WO | 2004080490 A2 | 9/2004 |
| WO | 2004083251 A2 | 9/2004 |
| WO | 2004087746 A2 | 10/2004 |
| WO | 2005033148 A1 | 4/2005 |
| WO | 2005/058940 A2 | 6/2005 |
| WO | 2006032472 A2 | 3/2006 |
| WO | 2006032475 A2 | 3/2006 |
| WO | 2006032500 A2 | 3/2006 |
| WO | 2006065553 A2 | 6/2006 |
| WO | 2007000322 A1 | 1/2007 |
| WO | 2007113222 A2 | 10/2007 |
| WO | 2007113223 A2 | 10/2007 |
| WO | 2007127668 A2 | 11/2007 |
| WO | 2008019162 A2 | 2/2008 |
| WO | 2009095453 A1 | 8/2009 |
| WO | 2009109550 A1 | 9/2009 |
| WO | 2010151544 A1 | 12/2010 |
| WO | 2011007004 A1 | 1/2011 |
| WO | 2011015590 A1 | 2/2011 |
| WO | 2011015591 A1 | 2/2011 |
| WO | 2011041003 A2 | 4/2011 |
| WO | 2011051917 A1 | 5/2011 |
| WO | 2012085872 A2 | 6/2012 |

OTHER PUBLICATIONS

Fattom, A.I., et al., "*Staphylococcus aureus* vaccination for dialysis patients—an update", Advances in Renal Replacement Therapy, 3(4):302-308, (1996).

Feil, E.J., "Small change: keeping pace with microevolution", Nature Reviews: Microbiology, 2(6):483-495 (2004).

Fey, P.D., et al., "Characterization of the relationship between polysaccharide intercellular adhesin and hemagglutination in *Staphylococcus epidermidis*", Journal of Infectious Diseases, 179(6):1561-1564 (1999).

Fitzgerald, J.R., et al., "Evolutionary genomics of pathogenic bacteria", Trends in Microbiology, 9(11):547-553 (2001).

Fitzgerald, J.R., et al., "Evolutionary genomics of *Staphylococcus aureus*: Insights into the origin of methicillin-resistant strains and the toxic shock syndrome epidemic", PNAS, 98(15):8821-8826 (2001).

Foster, T.J., "Immune evasion by staphylococci", Nature Reviews: Microbiology, 3:948-958 (2005).

Foster, T.J., et al., "Surface protein adhesins of *Staphylococcus aureus*", Trends in Microbiology, 6(12):484-488 (1998).

Foster, T.J., et al., "Surface-associated proteins of *Staphylococcus aureus*: Their possible roles in virulence", FEMS Microbiology Letters, 118:199-206 (1994).

Fournier, B., et al., "Recognition of *Staphylococcus aureus* by the innate immune system", Clinical Microbiology Reviews, 18(3):521-540 (2005).

Fournier, J.M., et al., "Isolation of Type 5 Capsular Polysaccharide from *Staphylococcus aureus*", Ann. Inst. Pasteur/Microbiol., 138:561-567 (1987).

Fournier, J.M., et al., "Purification and characterization of *Staphylococcus aureus* type 8 capsular polysaccharide", Infection and Immunity, 45(1):87-93 (1984).

Garcia-Lara, J., et al., "Anti-*Staphylococcus aureus* immunotherapy: current status and prospects", Current Opinion in Pharmacology, 9:552-557 (2009).

Miller, M.D., et al., "Poster Session 41214:HIV-1 expressing the 3TC-associated M184V mutation in Reverse Transcriptase (RT) shows increased sensitivity to Adefovir and PMPA as well as decreased replication capacity in vitro", 12th World AIDS Conference, Geneva, Switzerland (Jun. 28 to Jul. 3, 1998).

Garrison, P.K., et al., "Experimental Endocarditis I. Staphylococcal endocarditis in rabbits resulting from placement of a polyethylene catheter in the right side of the heart", Yale J. Biol. Med., 42:394-410 (1970).

Gerhold, D., et al., "It's the genes! EST access to human genome content", BioEssays, 18(12):973-981 (1996).

Geysen, H.M., et al., "A priori delineation of a peptide which mimics a discontinuous antigenic determinant", Molec. Immunol., 23(7):709-715 (1986).

Geysen, H.M., et al., "Use of peptide synthesis to probe viral antigens for epitopes to a resolution of a single amino acid", Proc. Natl. Acad. Sci. USA, 81(13):3998-4002 (1984).

Gilbert, F.B., et al., "Immunogenicity in cows of *Staphylococcus aureus* type 5 capsular polysaccharide-ovalbumin conjugate", Vaccine, 12(4):369-374 (1994).

Gill, S.R., et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidermidis* Strain", Journal of Bacteriology, 187(7):2426-2438 (2005).

Goncalves, V.M., et al., "Simple and efficient method of bacterial polysaccharides purification for vaccines production using hydrolytic enzymes and tangential flow ultrafiltration", Communicating Current Research and Educational Topics and Trends in Applied Microbiology, A. Mendez-Vilas, ed., (Formatex), vol. 1, pp. 450-457 (2007).

Haley, R.W., et al., "The nationwide nosocomial infection rate: A new need for vital statistics", Am. J. Epidemiol, 121 (2):159-167 (1985).

(56) References Cited

OTHER PUBLICATIONS

Hartford, O., et al., "Matrix-binding proteins of *Staphylococcus aureus*: functional analysis of mutant and hybrid molecules", Microbiology, 145:2497-2505 (1999).

Havaei, S.A., et al., "The capsular turnover product of *Staphylococcus aureus* strain Smith", FEMS Microbiology Letters, 118(1-2):37-44 (1994).

Hawiger, J., et al., "Identification of a Region of Human Fibrinogen Interacting with Staphylococcal Clumping Factor", Biochemistry, 21(6):1407-1413 (1982).

Hawiger, J., et al., "Interaction of human fibrinogen with staphylococci: Presence of a binding region on normal and abnormal fibrinogen variants and fibrinogen derivatives", Blood, 51(5):799-812 (1978).

Herrmann, M., et al., "Adhesion of *Staphylococcus aureus* to Surface-Bound Platelets: Role of Fibrinogen/Fibrin and Platelet Integrins", J. Infect. Dis., 167(2):312-322 (1993).

Hestrin, S. "The Reaction of Acetylcholine and Other Carboxylic Acid Derivatives with Hydroxylamine, and its Analytical Application", J. Biol. Chem., 180:249-261 (1949).

Hunt, J.D., et al., "Manipulation of the helper T cell response to influence antigenic competition occurring with a multivalent vaccine", Immunology and Cell Biology, 74:81-89 (1996).

Ip, D., et al., "Implications of the changing pattern of bacterial infections following total joint replacements", J.Orthop. Surg., 13(2):125-130 (2005).

Jones, C., "Revised structures for the capsular polysaccharides from *Staphylococcus aureus* Types 5 and 8, components of novel glycoconjugate vaccines", Carbohydrate Research, 340(6):1097-1106 (2005).

Jones, C., et al., "Use and validation of NMR assays for the identity and O-Acetyl content of capsular polysaccharides from *Neisseria meningitidis* used in vaccine manufacture", Journal of Pharmaceutical and Biomedical Analysis, 30:1233-1247 (2002).

Jones, T., "Staff VAX Nabi", Current Opinion in Investigational Drugs, 3(1):48-50 (2002).

Josefsson, E., et al., "Fibrinogen binding sites P336 and Y338 of clumping factor A are crucial for *Staphylococcus aureus* virulence", PLoS One, 3(5):e2206 (2008) (7 pages).

Josefsson, E., et al., "Protection against Experimental *Staphylococcus aureus* Arthritis by Vaccination with Clumping Factor A, a Novel Virulence Determinant", Journal of Infectious Diseases, 184(12):1572-1580 (2001).

Josefsson, E., et al., "Protection against *Staphylococcus aureus* arthritis by vaccination with Clumping Factor A, a novel virulence determinant", Immunology Letters, 73(2):153-154 (2000) (Abstract 324).

Josefsson, E., et al., "Three new members of the serine-aspartate repeat protein multigene family of *Staphylococcus aureus*", Microbiology, 144(12):3387-3395 (1998).

Karakawa, W.W., "The Role of Capsular Antigens in *Staphylococcus aureus* Immunity", Zentralblatt fur Bakteriologie, 277(4):415-418 (1992).

Karakawa, W.W., et al., "Capsular Antibodies Induce Type-Specific Phagocytosis of Capsulated *Staphylococcus aureus* by Human Polymorphonuclear Leukocytes", Infection and Immunity, 56(5):1090-1095 (1988).

Karakawa, W.W., et al., "Chapter 40: Capsular Polysaccharides of *Staphylococcus aureus*", Seminars in infectious disease, vol. IV: Bacterial Vaccines, L. Weinstein and B.N. Fields, eds., (Thieme-Stratton, New York), pp. 285-293 (1982).

Karakawa, W.W., et al., "Method for the Serological Typing of the Capsular Polysaccharides of *Staphylococcus aureus*", J. Clin. Microbiol. 22(3):445-447 (1985).

Klevens, R.M., et al., "Invasive Methicillin-Resistant *Staphylococcus aureus* Infections in the United States", JAMA, 298(15):1763-1771 (2007).

Kochwa, S., et al., "Blood elements at foreign surfaces: A biochemical approach to the study of the adsorption of plasma proteins", Annals New York Academy of Sciences, 283:37-49 (1977).

Kristinsson, K.G., "Adherence of staphylococci to intravascular catheters", J. Med. Microbiol. 28:249-257 (1989).

Kuehnert, M.J., et al., "Prevalence of *Staphylococcus aureus* nasal colonization in the United States, 2001-2002", JID, 193(2):172-179 (2006).

Kuhn, G., et al., "Evidence for Clonal Evolution among Highly Polymorphic Genes in Methicillin-Resistant *Staphylococcus aureus*", J. Bacteriol., 188(1):169-178 (2006).

Kuklin, N.A., et al., "A Novel *Staphylococcus aureus* Vaccine: Iron Surface Determinant B Induces Rapid Antibody Responses in Rhesus Macaques and Specific Increased Survival in a Murine *S. aureus* Sepsis Model", Infection and Immunity, 74(4):2215-2223 (2006).

Lantz, M.S., et al., "Bacteroides gingivalis and Bacteroides intermedius Recognize Different Sites on Human Fibrinogen", J. Bacteriol. 172(2):716-726 (1990).

Lazar, E., et al., "Transforming Growth Factor α: Mutation of Aspartic Acid 47 and Leucine 48 Results in Different Biological Activities", Mol. Cell. Biol., 8(3):1247-1252 (1988).

Lederman, S., et al., "A Single Amino Acid Substitution in a Common African Allele of the CD4 Molecule Ablates Binding of the monoclonal Antibody, OKT4," Molecular Immunology, 28(11):1171-1181 (1991).

Amann, E., et al., "'ATG vectors' for regulated high-level expression of cloned genes in *Escherichia coli*", Gene, 40:183-190 (1985).

Arbeit, R.D., et al., "Predominance of two newly described capsular polysaccharide types among clinical isolates of *Staphylococcus aureus*", Diagn. Microbiol. Infect. Dis., 2(2):85-91 (1984).

Attwood, T.K., "The Babel of Bioinformatics", Science, 290:471-473 (2000).

Baier, R.E.,"The organization of blood components near interfaces", Annals New York Academy of Sciences, 283:17-36 (1977).

Bergmann, C., et al., "An endogenously synthesized decamer peptide efficiently primes cytotoxic T cells specific for the HIV-1 envelope glycoprotein", Eur. J. Immunol., 23(11):2777-2781 (1993).

Bergmann, C.C., et al., "Flanking residues alter antigenicity and immunogenicity of multi-unit CTL epitopes", J. Immunol., 157(8):3242-3249 (1996).

Berti, F., et al., "Water Accessibility, Aggregation, and Motional Features of Polysaccharide-Protein Conjugate Vaccines", Biophysical Journal, 86:3-9 (2004).

Bhasin, N., et al.,"Identification of a gene essential for O-acetylation of the *Staphylococcus aureus* type 5 capsular polysaccharide", Molecular Microbiology, 27(1):9-21 (1998).

Blair, J.E., et al., "Phage Typing of Staphylococci", Bull. Wld. Hlth. Org., 24:771-784 (1961).

Boden, M.K., et al., "Cloning and characterization of a gene for a 19 kDa fibrinogen-binding protein from *Staphylococcus aureus*", Molecular Microbiology, 12(4):599-606 (1994).

Boden, M.K., et al., "Evidence for three different fibrinogen-binding proteins with unique properties from *Staphylococcus aureus* strain Newman", Microbial Pathogenesis, 12(4):289-298 (1992).

Boden, M.K., et al., "Fibrinogen-binding protein/clumping factor from *Staphylococcus aureus*", Infection and Immunity, 57(8):2358-2363 (1989).

Bowie, J.U., et al., "Deciphering the Message in Protein Sequences: Tolerance to Amino Acid Substitutions", Science, 247:1306-1310 (1990).

Brouillette, E., et al., "DNA immunization against the clumping factor A (ClfA) of *Staphylococcus aureus*", Vaccine, 20:2348-2357 (2002).

Chen, H.L., "Research development on the immunomodulatory effect of polysaccharide and its mechanism", Chinese Pharmacological Bulletin, 18(3): 249-252 (2002) (English Abstract).

Chen, Z., et al., "Rapid screening of highly efficient vaccine candidates by immunoproteomics", Proteomics 4:3203-3213 (2004).

Chenna, R., et al., "Multiple sequence alignment with the clustal series of programs", Nucleic Acids Research, 31 (13):3497-3500 (2003).

Cheung, A.L., et al., "Fibrinogen Acts as a Bridging Molecule in the Adherence of *Staphylococcus aureus* to Cultured Human Endothelial Cells", J. Clin. Invest. 87(6):2236-2245 (1991).

(56) References Cited

OTHER PUBLICATIONS

Cheung, A.L., et al., "Role of the sar Locus of *Staphylococcus aureus* in Induction of Endocarditis in Rabbits", Infection and Immunity, 62(5):1719-1725 (1994).
Cheung, A.L., et al., "The role of Fibrinogen in Staphylococcal Adherence to Catheters In Vitro", J. Infect. Dis., 161:1177-1186 (1990).
Chhatwal, G.S., et al., "Interaction between fibronectin and purified staphylococcal clumping factor", FEMS Microbiology Letters, 44:147-151 (1987).
Clarke, S.R., et al., "Identification of in vivo-expressed antigens of *Staphylococcus aureus* and their use in vaccinations for protection against nasal carriage", Journal of Infectious Diseases, 193:1098-1108 (2006).
Cocchiaro, J.L., et al., "Molecular characterization of the capsule locus from non-typeable *Staphylococcus aureus*", Mol. Microbiol., 59(3):948-960 (2006).
Cockayne, A., et al., "Molecular Cloning of a 32-Kilodalton Lipoprotein Component of a Novel Iron-Regulated *Staphylococcus epidermidis* ABC Transporter", Infection and Immunity, 66(8):3767-3774 (1998).
Collier, R.J., "Diphtheria Toxin: Mode of Action and Structure", Bacteriological Reviews, 39(1):54-85 (1975).
Colman, P.M., "Effects of amino acid sequence changes on antibody-antigen interactions", Research in Immunology, 145(1):33-36 (1994).
Cooper, J.E., et al., "The phylogeny of *Staphylococcus aureus*—which genes make the best intra-species markers?", Microbiology, 152:1297-1305 (2006).
Cottonaro, C.N., et al., "Quantitation and Characterization of Competitive Protein Binding to Polymers", Trans. Am. Soc. Artif. Intern. Organs, 27:391-395 (1981).
Creech II, C.B., et al., "Community-associated methicillin-resistant *Staphylococcus aureus*: The way to the wound is through the nose", JID, 193(2):169-171 (2006).
Deivanayagam, C.C.S., et al., "A novel variant of the immunoglobulin fold in surface adhesins of *Staphylococcus aureus*: crystal structure of the fibrinogen-binding MSCRAMM, clumping factor A", The EMBO Journal, 21 (24):6660-6672 (2002).
Doe, B., et al., "Induction of HIV-1 envelope (gp120)-specific cytotoxic T lymphocyte responses in mice by recombinant CHO cell-derived gp120 is enhanced by enzymatic removal of N-linked glycans", Eur. J. Immunol., 24 (10):2369-2376 (1994).
Dominiecki, M.E., et al., "Antibacterial Action of Extracellular Mammalian Group IIA Phospholipase A2 against Grossly Clumped *Staphylococcus aureus*", Infection and Immunity, 67(5):2299-2305 (1999).
Dunne, W.M., "Bacterial Adhesion: Seen Any Good Biofilms Lately?", Clin. Microbiol. Rev., 15(2);155-166 (2002).
Edgar, R.C., "MUSCLE: multiple sequence alignment with high accuracy and high throughput", Nucleic Acids Research, 32(5):1792-1797 (2004).
Eidhin, D.N., et al., "Clumping factor B (ClfB), a new surface-located fibrinogen-binding adhesin of *Staphylococcus aureus*", Molecular Microbiology, 30(2):245-257 (1998).
Erickson, A.L., et al., "Hepatitis C virus-specific CTL responses in the liver of chimpanzees with acute and chronic hepatitis C", J. Immunol., 151(8):4189-4199 (1993).
Espersen, F., et al., "Immunization of mice with the fibronectin-binding protein and clumping factor from *Staphylococcus aureus*: antibody response and resistance against intraperitoneal infection", ACTA Pathologica Microbiologica Et Immunologica Scandinavica Section C, 93(2):53-58 (1985).
Espersen, F., et al., Isolation of *Staphylococcus aureus* clumping factor, Infection and Immunity, 49(3):700-708 (1985).
Essawi, T., et al., "Molecular, antibiogram and serological typing of *Staphylococcus aureus* isolates recovered from Al-Makased Hospital in East Jerusalem", Tropical Medicine & International Health, 3(7):576-583 (1998).

Etz, H., et al., "Identification of in vivo expressed vaccine candidate antigens from *Staphylococcus aureus*", PNAS, 99 (10):6573-6578 (2002).
Farres, J., et al., "A simple and efficient method for the purification of an exopolysaccharide from *Klebsiella* sp. I-714", Biotechnology Techniques, 10(5):375-380 (1996).
Fattom, A. et al., "Effect of conjugation methodology, carrier protein, and adjuvants on the immune response to *Staphylococcus aureus* capsular polysaccharides", Vaccine, 13(14):1288-1293 (1995).
Fattom, A., et al., "Synthesis and immunologic properties in mice of vaccines composed of *Staphylococcus aureus* type 5 and type 8 capsular polysaccharides conjugated to *Pseudomonas aeruginosa* Exotoxin A", Infection and Immunity, 58(7):2367-2374 (1990).
Fattom, A., et al., "Comparative immunogenicity of conjugates composed of the *Staphylococcus aureus* type 8 capsular polysaccharide bound to carrier proteins by adipic acid dihydrazide or N-succinimidyl-3-(2-pyridyldithio) propionate", Infection and Immunity, 60(2):584-589 (1992).
Fattom, A., et al., "Epitopic overload at the site of injection may result in suppression of the immune response to combined capsular polysaccharide conjugate vaccines", Vaccine, 17(2):126-133 (1999).
Fattom, A., et al., "Safety and immunogenicity of a booster dose of *Staphylococcus aureus* types 5 and 8 capsular polysaccharide conjugate vaccine (StaphVAX®) in hemodialysis patients", Vaccine 23:656-663 (2004).
Fattom, A., et al.,"Laboratory and clinical evaluation of conjugate vaccines composed of *Staphylococcus aureus* type 5 and type 8 capsular polysaccharides bound to *Pseudomonas aeruginosa* recombinant exoprotein A", Infection and Immunity, 61(3):1023-1032 (1993).
Fattom, A.I., et al., "A *Staphylococcus aureus* capsular polysaccharide (CP) vaccine and CP-specific antibodies protect mice against bacterial challenge", Infection and Immunity, 64(5):1659-1665 (1996).
Fattom, A.I., et al., "Antigenic Determinants of *Staphylococcus aureus* Type 5 and Type 8 Capsular Polysaccharide Vaccines", Infection and Immunity, 66(10):4588-4592 (1998).
Fattom, A.I., et al., "Development of StaphVAX™, a polysaccharide conjugate vaccine against *S. aureus* infection: from the lab bench to phase III clinical trials", Vaccine, 22(7):800-887 (2004).
Lee, C.J., et al., "Chapter 28: Vaccine-Based Strategies for Prevention of Staphylococcal Diseases", The Staphylococci in Human Disease, K.B. Crossley and G.L. Archer, eds., (Churchill Livingston, New York), pp. 631-654 (1997).
Lee, C.J., et al., "Protective Immunity of Pneumococcal Glycoconjugates", Crit. Rev. Microbiol., 29(4):333-349 (2003).
Lee, C.Y., et al., "Construction of single-copy integration vectors for *Staphylococcus aureus*", Gene, 103:101-105 (1991).
Lee, J.C., "The prospects for developing a vaccine against *Staphylococcus aureus*", Trends in Microbiology, 4(4):162-166 (1996).
Lee, J.C., et al., "Protective efficacy of antibodies to the *Staphylococcus aureus* type 5 capsular polysaccharide in a modified model of endocarditis in rats", Infection and Immunity, 65(10):4146-4151 (1997).
Lee, J.C., et al., "Purified capsular polysaccharide-induced immunity to *Staphylococcus aureus* infection", J. Infect. Dis., 157(4):723-730 (1988).
Lemercinier, X., et al., "Full 1H NMR assignment and detailed O-acetylation patterns of capsular polysaccharides from *Neisseria meningitidis* used in vaccine producction", Carbohydrate Research, 296:83-96 (1996).
Li, C.H., et al., "β-Endorphin omission analogs: Dissociation of immunoreactivity from other biological activities," Proc. Natl. Acad. Sci. USA, 77(6):3211-3214 (1980).
Liu, C.Z., et al., "A segment of *Staphylococcus aureus* clumping factor A with fibrinogen-binding activity (ClfA221-550) inhibits platelet-plug formation in mice", Thrombosis Research, 121:183-191 (2007).
Liu, C.Z., et al., "ClfA221-550, a fibrinogen-binding segment of *Staphylocococus aureus* clumping factor A, disrupts fibrinogen function", Thromb. Haemost., 94:286-294 (2005).

(56) References Cited

OTHER PUBLICATIONS

Loughman, A., et al., "Roles for fibrinogen, immunoglobulin and complement in platelet activation promoted by *Staphylococcus aureus* clumping factor A", Molecular Microbiology, 57(3):804-818 (2005).

Lowy, F.D., "*Staphylococcus aureus* Infections", N. Eng. J. Med., 339(8):520-532 (1998).

Lukac, M., et al., "Toxoid of *Pseudomonas aeruginosa* Exotoxin A Generated by Deletion of an Active-Site Residue", Infection and Immunity, 56(12):3095-3098 (1988).

Mack, D., et al., "The Intercellular Adhesin Involved in Biofilm Accumulation of *Staphylococcus epidermidis* is a Linear β-1,6-Linked Glucosaminoglycan: Purification and Structural Analysis", Journal of Bacteriology, 178(1):175-183 (1996).

Maira-Litran, T., et al., "Comparative Opsonic and Protective Activities of *Staphylococcus aureus* Conjugate Vaccines Containing Native or Deacetylated Staphylococcal Poly-N-Acetyl-β-(1-6)-Glucosamine", Infection and Immunity, 73(10):6752-6762 (2005).

Maira-Litran, T., et al., "Immunochemical Properties of the Staphylococcal Poly-N-Acetylglucosamine Surface Polysaccharide", Infection and Immunity, 70(8):4433-4440 (2002).

Maki, D.G., "Infections associated with intravascular lines", Current Clinical Topics in Infectious Diseases, J.S. Remington and M.N. Swartz, eds., (McGraw Hill, New York), vol. 3, pp. 309-363 (1982).

Mamo, W., et al., "Vaccination with *Staphylococcus aureus* fibrinogen binding proteins (FgBPs) reduces colonisation of *S. aureus* in a mouse mastitis model", FEMS Immunol. Med. Microbiol., 10(1):47-53 (1994).

Mazmanian, S.K., et al., "An iron-regulated sortase anchors a class of surface protein during *Staphylococcus aureus* pathogenesis", Proc. Natl. Acad. Sci. USA, 99(4):2293-2298 (2002).

McAleese, F.M., et al., "Loss of Clumping Factor B Fibrinogen Binding Activity by *Staphylococcus aureus* Involves Cessation of Transcription, Shedding and Cleavage by Metalloprotease", The Journal of Biological Chemistry, 276 (32):29969-29978 (2001).

McCrea, K.W., et al., "B-47. A family of putative adherence proteins related to the clumping factor of *Staphylococcus aureus*", Abstracts of the 98th General Meeting of the American Society for Microbiology, Atlanta, GA, p. 63 (May 17-21, 1998).

McDevitt, D., et al., "Genetic Evidence that Bound Coagulase of *Staphylococcus aureus* is not Clumping Factor", Infection and Immunity, 60(4):1514-1523 (1992).

McDevitt, D., et al., "Characterization of the interaction between the *Staphylococcus aureus* clumping factor (ClfA) and fibrinogen", Eur. J. Biochem., 247:416-424 (1997).

McDevitt, D., et al., "Identification of the ligand-binding domain of the surface-located fibrinogen receptor (clumping factor) of *Staphylococcus aureus*", Molecular Microbiology, 16(5):895-907 (1995).

McDevitt, D., et al., "Molecular characterization of the clumping factor (fibrinogen receptor) of *Staphylococcus aureus*", Molecular Microbiology, 11(2):237-248 (1994).

McGavin, M.H., et al., "Identification of a *Staphylococcus aureus* Extracellular Matrix-Binding Protein with Broad Specificity", Infection and Immunity, 61(6):2479-2485 (1993).

McKenney, D., et al., "Broadly Protective Vaccine for *Staphylococcus aureus* Based on an in Vivo-Expressed Antigen", Science, 284(5419):1523-1527 (1999).

McKenney, D., et al., "The ica Locus of *Staphylococcus epidermidis* Encodes Production of the Capsular Polysaccharide/Adhesin", Infection and Immunity, 66(10):4711-4720 (1998).

Menzies, B.E., et al., "Site-Directed Mutagenesis of the Alpha-Toxin Gene of *Staphylococcus aureus*: Role of Histidines in Toxin Activity In Vitro and in a Murine Model", Infection and Immunity, 62(5):1843-1847 (1994).

Moreau, M., et al., "Structure of the type 5 capsular polysaccharide of *Staphylococcus aureus*", Carbohydrate Research, 201:285-297 (1990).

Moreillon, P., et al., "Role of *Staphylococcus aureus* Coagulase and Clumping Factor in Pathogenesis of Experimental Endocarditis", Infection and Immunity, 63(12):4738-4743 (1995).

Nabi Biopharmaceuticals, "Nabi Biopharmaceuticals Announces Completion of Outside Advisory Panel Assessment of Gram-Positive Program", News Release from www.nabi.com last visited Aug. 12, 2008, 7 pages (Mar. 21, 2006).

Nabi Biopharmaceuticals, "Nabi Biopharmaceuticals Announces Results of StaphVAX® Confirmatory Phase III Clinical Trial", News Release from www.nabi.com last visited Aug. 12, 2008, 3 pages (Nov. 1, 2005).

Nada, T., et al., "Types of Methicillin-Resistant *Staphylococcus aureus* Associated with High Mortality in Patients with Bacteremia", European Journal of Clinical Microbiology & Infectious Diseases, 15(4):340-343 (1996).

Nanra, J.S., et al., "Heterogeneous in vivo expression of clumping factor A and capsular polysaccharide by *Staphylococcus aureus*: Implications for vaccine design", Vaccine, 27:3276-3280 (2009).

Na'Was, T, et al., "Phenotypic and Genotypic Characterization of Nosocomial *Staphylococcus aureus* isolates from trauma patients", Journal of Clinical Microbiology, 36(2):414-420 (1998).

Rukhman, V., et al., "The MntC Crystal Structure Suggests that Import of Mn2+ in Cyanobacteria is Redox Controlled", J. Mol. Biol., 348:961-969 (2005).

Nilsson, I.M., et al., "Protection against *Staphylococcus aureus* Sepsis by Vaccination with Recombinant Staphylococcal Enterotoxin A Devoid of Superantigenicity", The Journal of Infectious Diseases, 180:1370-1373 (1999).

Nilsson, I.M., et al., "The Role of Staphylococcal Polysaccharide Microcapsule Expression in Septicemia and Septic Arthritis", Infection & Immunity 65(10):4216-4221 (1997).

Nilsson, I.M., et al., "Vaccination with a Recombinant Fragment of Collagen Adhesion Provides Protection against *Staphylococcus aureus*—mediated Septic Death", J. Clin, Invest., 101(12):2640-2649 (1998).

Nilsson, M., et al., "A Fibrinogen-Binding Protein of *Staphylococcus epidermidis*", Infection and Immunity, 66(6):2666-2673 (1998).

NNIS Personnel, "National Nosocomial Infections Surveillance (NNIS) Report, Data Summary from Oct. 1986-Apr. 1997, Issued May 1997", Am. J. Infect. Control, 25(6):477-487 (1997).

Noskin, G.A., "National Trends in *Staphylococcus aureus* Infection Rates: Impact on Economic Burden and Mortality over a 6-Year Period (1998-2003)", CID, 45:1132-1140 (2007).

O'Connell, D.P., et al., "The fibrinogen-binding MSCRAMM (clumping factor) of *Staphylococcus aureus* has a Ca2+—dependent inhibitory site", J. Biol. Chem., 273(12):6821-6829 (1998).

Opdebeeck, J.P., et al., "The expression of capsule in serum-soft agar by *Staphylococcus arueus* isolated from human clinical sources", J. Med. Microbiol., 20(2):275-278 (1985).

O'Riordan, K., et al., "*Staphylococcus aureus* Capsular Polysaccharides", Clinical Microbiology Reviews, 17(1):218-234 (2004).

Palma, M., et al., "Lack of the Extracellular 19-Kilodalton Fibrinogen-Binding Protein from *Staphylococcus aureus* Decreases Virulence in Experimental Wound Infection", Infection and Immunity, 64(12):5284-5289 (1996).

Paoletti, L.C., "Potency of clinical group B streptococcal conjugate vaccines", Vaccine, 19:2118-2126 (2001).

Park, H.M., et al., "Immunogenicity of Alpha-Toxin, Capsular Polysaccharide (CPS) and Recombinant Fibronectin-Binding Protein (r-FnBP) of *Staphylococcus aureus* in Rabbit", J. of Vet. Med. Sci., 61(9):995-1000 (1999).

Patti, J.M., et al., "Critical Residues in the Ligand-binding Site of the *Staphylococcus aureus* Collagen-binding Adhesin (MSCRAMM)", J. Biol. Chem., 270(20):12005-12011 (1995).

Gilbert, F.B., et al., "Purification of type 5 capsular polysaccharide from *Staphylococcus aureus* by a simple efficient method", Journal of Microbiological Methods, 20:39-46 (1994).

Ho, M.M., et al., "Preclinical Laboratory Evaluation of a Bivalent *Staphylococcus aureus* Saccharide-Exotoxin A Protein Conjugate Vaccine", Human Vaccines, 2(3):89-98 (2006).

Imabori, K., et al., "Seikagaku Jiten (Biochemistry Encyclopedia)", 3rd edition (Tokyo-kagakudoujin K.K., Tokyo, Japan), pp. 490 & 1419 (1998).

(56) References Cited

OTHER PUBLICATIONS

Nishioka, K., et al., "Yakunitatsu Meneki Jikkenhou (Useful Immunological Experimental Protocols)", (Kodansha K.K., Tokyo, Japan), pp. 7-17 (1985).
Molecularinfo.com, "Protein Purification by Gel Filtration Chromatography", Available at http://www.molecularinfo.com/MTM/G/G3/G3-1/G3-1-1.html, Last accessed on Jan. 27, 2014.
Patti, J.M., et al., "Microbial adhesins recognizing extracellular matrix macromolecules", Current Opinion in Cell Biology, 6:752-758 (1994).
Patti, J.M., et al., "MSCRAMM-Mediated Adherence of Microorganisms to Host Tissues", Annu. Rev. Microbiol., 48:585-617 (1994).
Reeves, P.R., et al., "Bacterial polysaccharide synthesis and gene nomenclature", Trends in Microbiology, 4(12):495-503 (1996).
Reynaud-Rondier, L., et al., "Conjugation of capsular polysaccharide to α-haemolysin from Staphylococcus aureus as a glycoprotein antigen", FEMS Microbiol. Immunol., 76:193-199 (1991).
Rice, P., et al., "EMBOSS: The European Molecular Biology Open Software Suite", Trends in Genetics, 16(6):276-277 (2000).
Risley, A.L., "Capsular Polysaccharide Masks Clumping Factor A-Mediated Adherence of Staphylococus aureus to Fribrinogen and Platelets", The Journal of Infectious Diseases, 196:919-927 (2007).
Roche, F.M., "Characterization of novel LPXTG-containing proteins of Staphylococcus aureus identified from genome sequences", Microbiology 149:643-654 (2003).
Romero-Steiner, S., et al., "Standardization of an opsonophagocytic assay for the measurement of functional antibody activity against Streptococcus pneumoniae using differentiated HL-60 cells", Clin. Diagn. Lab. Immunol., 4(4):415-422 (1997).
Rudinger, J., "Characteristics of the amino acids as components of a peptide hormone sequence", Peptide Hormones, Parsons, J.A., ed., (The Macmillan Press Ltd.), pp. 1-7 (1976).
Sau, S., et al., "The Staphylococcus aureus allelic genetic loci for serotype 5 and 8 capsule expression contain the type-specific genes flanked by common genes", Microbiology, 143:2395-2405 (1997).
Schaffer, A.C., et al., "Immunization with Staphylococcus aureus Clumping Factor B, a Major Determinant in Nasal Carriage, Reduces Nasal Colonization in a Murine Model", Infection and Immunity, 74(4):2145-2153 (2006).
Schaffer, A.C., et al., "Vaccination and passive immunisation against Staphylococcus aureus", International Journal of Antimicrobial Agents, 32(1):S71-S78 (2008).
Schneerson, R., et al., "Evaluation of Monophosphoryl Lipid A (MPL) as an Adjuvant. Enhancement of the Serum Antibody Response in Mice to Polysaccharide-Protein Conjugates by Concurrent Injection with MPL", The Journal of Immunology, 147(7):2136-2140 (1991).
Schneewind, O., et al., "Cell wall sorting signals in surface proteins of Gram-positive bacteria", The EMBO Journal, 12(12):4803-4811 (1993).
Sellman, B.R., et al., "Identification of Immunogenic and Serum Binding Proteins of Staphylococcus epidermidis", Infection and Immunity, 73(10):6591-6600 (2005).
Shinefield, H., et al., "Use of a Staphylococcus aureus conjugate vaccine in patients receiving Hemodialysis", New England Journal of Medicine, 346(7):491-496 (2002).
Smeltzer, M.S., et al., "Prevalence and chromosomal map location of Staphylococcus aureus adhesin genes", Gene, 196(1-2):249-259 (1997).
Sompolinsky, D., et al., "Encapsulation and Capsular Types in Isolates of Staphylococcus aureus from Different Sources and Relationship to Phage Types", Journal of Clinical Microbiology, 22(5):828-834 (1985).
Storch, G.A., et al., "Methicillin-resistant Staphylococcus aureus bacteremia in children", Pediatric Infectious Disease, 5(1):59-67 (1986).

Switalski, L.M., "Isolation and purification of staphylococcal clumping factor", Staphylococci and Staphylococcal Diseases: Proceedings of 3. International Symposium on Staphylococci and Staphylococcal Infections, 1975, J. Jeljaszewicz, (ed) (Gustav Fischer Verlag, Stuttgart), pp. 414-425 (1976).
Tamura, K., et al., "MEGA4: Molecular Evolutionary Genetics Analysis (MEGA) Software Version 4.0", Molecular Biology & Evolution, 24(8):1596-1599 (2007).
Tanizaki, M.M., et al., "Purification of meningococcal group C polysaccharide by a procedure suitable for scale-up", J. Microbiol. Methods, 27(1):19-23 (1996).
Thakker, M., et al., "Staphylococcus aureus Serotype 5 Capsular Polysaccharide is Antiphagocytic and Enhances Bacterial Virulence in a Murine Bacteremia Model", Infection and Immunity, 66(11):5183-5189 (1998).
Tollersrud, T., "Staphylococcus aureus capsular polysaccharide type 5 conjugate and whole cell vaccines stimulate antibody responses in cattle", Vaccine, 19(28-29):3896-3903 (2001).
Tzianabos, A.O., et al., "Structural rationale for the modulation of abscess formation by Staphylococcus aureus capsular polysaccharides", Proceedings from the National Academy of Sciences, 98(16):9365-9370 (2001).
Usui, Y., "Biochemical properties of fibrinogen binding protein (clumping factor) of the staphylococcal cell surface", Zbl. Bakt. Hyg. A 262:287-297 (1986).
Vandamme, P., et al., "Polyphasic Taxonomy, a Consensus Approach to Bacterial Systematics", Microbiol. Rev., 60(2):407-438 (1996).
Vandenbergh, M.F.Q., et al., "Follow-up of Staphylococcus aureus nasal carriage after 8 years: Redefining the persistent carrier state", J. Clin. Micro., 37(10):3133-3140 (1999).
Vann, W.F., et al., "Structure and immunochemistry of Staphylococcus aureus capsular polysaccharide", UCLA Symp. Mol. Cell. Biol. New. Ser., 64:187-198, (1987).
Vaudaux, P., et al. "Fibronectin is More Active than Fibrin or Fibrinogen in Promoting Staphylococcus aureus Adherence to Inserted Intravascular Catheters", J. Infect. Dis., 167(3):633-641 (1993).
Vaudaux, P., et al., "Host Factors Selectively Increase Staphylococcal Adherence on Inserted Catheters: A Role for Fibronectin and Fibrinogen or Fibrin", J. Infect. Dis., 160(5):865-875 (1989).
Vaudaux, P.E., et al., "Use of Adhesion-Defective Mutants of Staphylococcus aureus to Define the Role of Specific Plasma Proteins in Promoting Bacterial Adhesion to Canine Arteriovenous Shunts", Infection and Immunity, 63(2):585-590 (1995).
Verheul, A.F.M., et al., "Preparation, Characterization, and Immunogenicity of Meningococcal Immunotype L2 and L3,7,9 Phosphoethanolamine Group-Containing Oligosaccharide-Protein Conjugates", Infection and Immunity, 59(3):843-851 (1991).
Vernachio, J.H., et al., "Human Immunoglobulin G Recognizing Fibrinogen-Binding Surface Proteins is Protective against both Staphylococcus aureus and Staphylococcus epidermidis Infections In Vivo", Antimicrobial Agents and Chemotherapy, 50(2):511-518 (2006).
Von Eiff, C., et al., "Nasal carriage as a source of Staphylococcus aureus bacteremia", N. Engl. J. Med. 344(1):11-16 (2001).
Vytvytska, O., et al., "Identification of vaccine candidate antigens of Staphylococcus aureus by serological proteome analysis", Proteomics, 2:580-590 (2002).
Walsh, E.J., et al., "Identification of the Staphylococcus aureus MSCRAMM clumping factor B (ClfB) binding site in the αC-domain of human fibrinogen", Microbiology, 154:550-558 (2008).
Wang, R., "Identification of novel cytolytic peptides as key virulence determinants for community-associated MRSA", Nature Medicine, published online at http://www.nature.com/naturemedicine, 5 pages (2007).
Wang, X, et al., "The pgaABCD Locus of Escherichia coli Promotes the Synthesis of a Polysaccharide Adhesin Required for Biofilm Formation", Journal of Bacteriology, 186(9):2724-2734 (2004).
Watts, A., et al., "Staphylococcus aureus strains that express serotype 5 or serotype 8 capsular polysaccharides differ in virulence", Infection and Immunity 73(6):3502-3511 (2005).
Welch, P.G., et al., "Safety and Immunogenicity of Staphylococcus aureus Type 5 Capsular Polysaccharide—Pseudomonas aeruginosa

(56) References Cited

OTHER PUBLICATIONS

Recombinant Exoprotein A Conjugate Vaccine in Patients on Hemodialysis", Journal of the American Society of Nephrology, 7(2):247-253 (1996).

Wertheim, H.F.L., et al., "Risk and outcome of nosocomial *Staphylococcus aureus* bacteraemia in nasal carriers versus non-carriers", Lancet, 364:703-705 (2004).

Wiltshire, M.D., et al., "Identification and Analysis of *Staphylococcus aureus* Components Expressed by a Model System of Growth in Serum", Infection and Immunity, 69(8):5198-5202 (2001).

Yanisch-Perron, C., et al., "Improved M13 phage cloning vectors and host strains: nucleotide sequences of the M13mp18 and pUC19 vectors", Gene, 33:103-119 (1985).

Youngman, P., "Chapter 4: Plasmid vectors for recovering and exploiting Tn917 transpositions in *Bacillus* and other Gram-positives", Plasmids: A Practical Approach, K. Hardy, ed, (IRL Press, Oxford), pp. 79-103 (1985).

Zagursky, R.J., et al., Application of genomics in bacterial vaccine discovery: a decade in review:, Current Opinion in Pharmacology, 8(5):632-638 (2008).

Projan, S.J., et al., "Staphylococcal vaccines and immunotherapy: to dream the impossible dream?", Current Opinion in Pharmacology, 6(5):473-479 (2006).

Suhrbier, A., "Multi-epitope DNA vaccines", Immunol. Cell Biol., 75(4):402-408 (1997).

Pavliak, V., "*Staphylococcus aureus* capsular polysaccaride—MSCRAMM protein conjugate vaccines", 232nd ACS National Meeting, San Francisco, CA (Sep. 10-14, 2006) (Abstract).

FIGURE 4
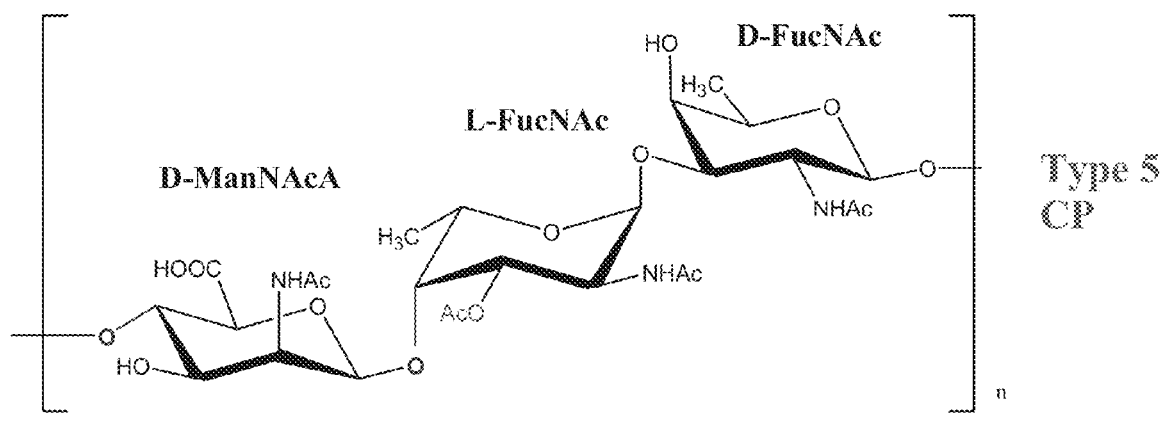
[-4)-β-D-ManNAcA-(1-4)-α-L-FucNAc(3-O-Ac)-(1-3)-β-D-FucNAc-(1-]ₙ
Type 5 CP
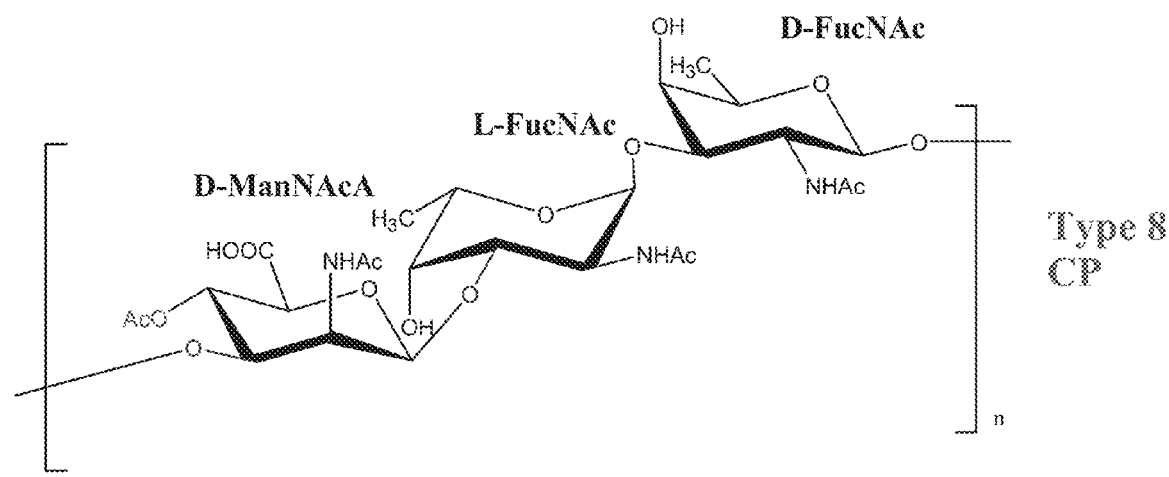
[-3)-β-D-ManNAcA(4-O-Ac)-(1-3)-α-L-FucNAc-(1-3)-α-D-FucNAc-(1-]ₙ
Type 8 CP FIGURE 5
A.
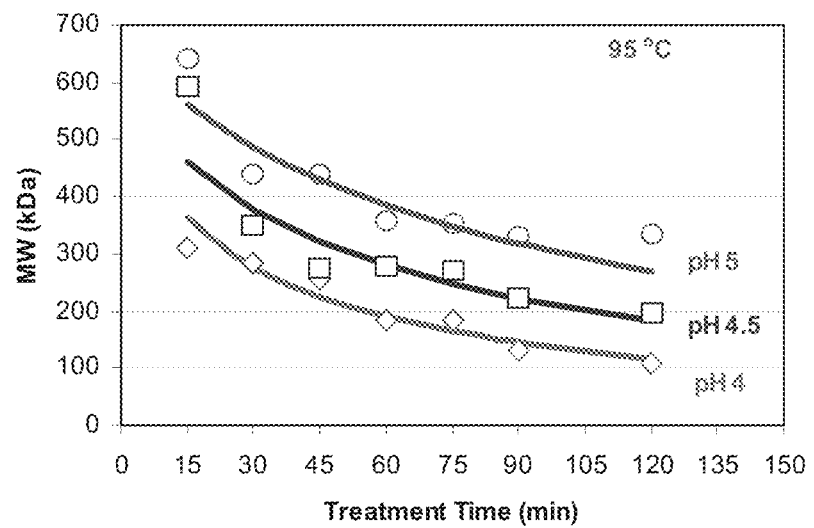
B.
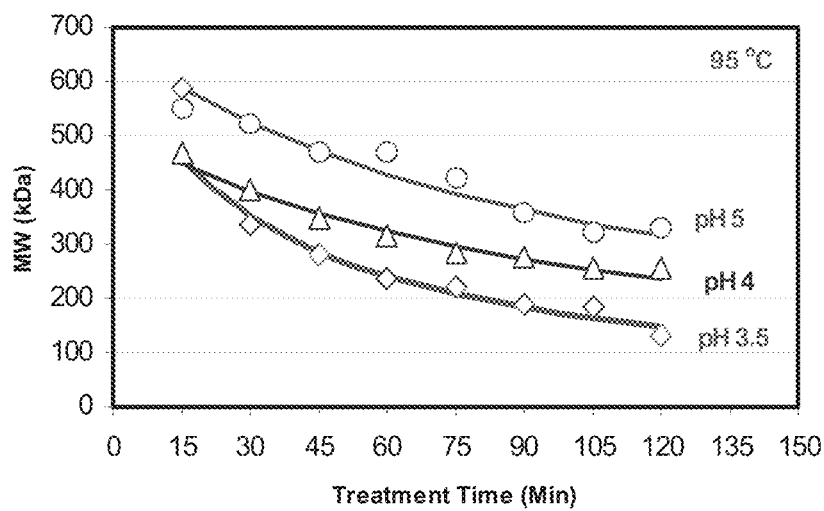

FIGURE 6
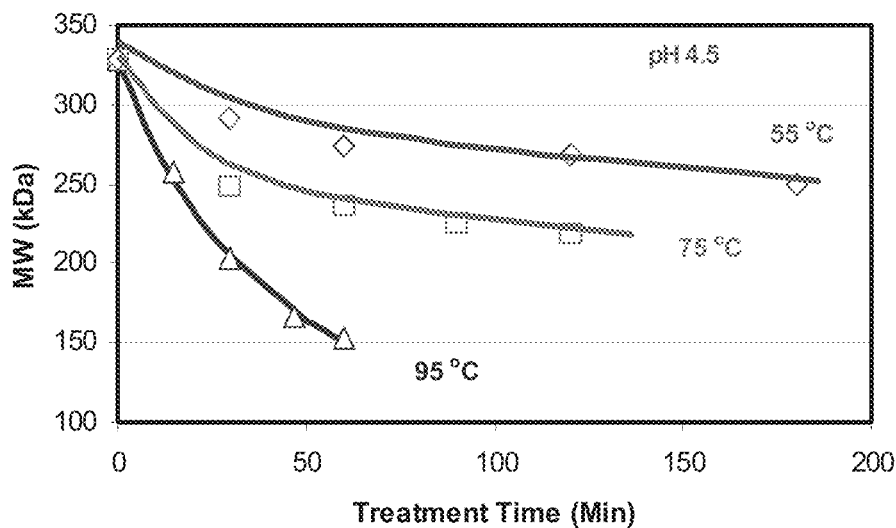
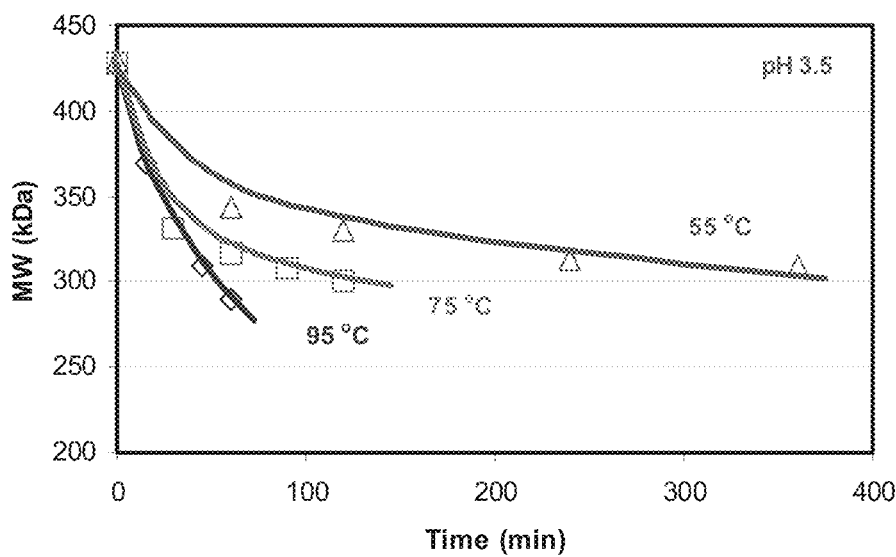

FIGURE 8A  ClfA align

```
                  10        20        30        40        50        60
         ----:----|----:----|----:----|----:----|----:----|----:----|
clfA_001[22] MNMKKKEKHAIRKKSIGVASVLVGTLIGFGLLSSKEADASENSVTQSDSASNESKSNDSS
clfA_002[19] ............................................................
clfA_004[15] .....Q..............................M..TENT...............P.
clfA_012[10] ............................................................
clfA_005[5]  ............................................................
clfA_022[5]  ............................................................
clfA_003[4]  ............................................................
clfA_009[4]  .....Q..................................TENT...............
clfA_013[3]  ............................................................
clfA_014[3]  ............................................................
clfA_015[3]  ............................................................
clfA_006[2]  ............................................................
clfA_007[2]  ............................................................
clfA_008[2]  ............................................................
clfA_010[2]  ............................................................
clfA_017[2]  ...........................................................P.
clfA_011[1]  ............................................................
clfA_016[1]  ............................................................
clfA_018[1]  ............................................................
clfA_019[1]  ............................................................
clfA_020[1]  ............................................................
clfA_021[1]  ............................................................
clfA_023[1]  ..........................................................NP.
clfA_024[1]  .....Q..............................M..TENT...............P.

70        80        90       100       110       120
         ----:----|----:----|----:----|----:----|----:----|----:----|
clfA_001[22] SVSAAPKTDDTNVSDTKTSSNTNNGETSVAQNPAQQETTQSSSTNATTEETPVTGEATTT
clfA_002[19] ............................................................
clfA_004[15] ..N......N.....SN.TT...SD..N............A..................V...
clfA_012[10] ......................................AL..................-
clfA_005[5]  .IN......N.......PT.....................A..................
clfA_022[5]  .......V.......T....S...................A............A........
clfA_003[4]  ............................................................
clfA_009[4]  ..N......N.....SN.TT...SD..N............A..................V...
clfA_013[3]  ......................................AL..............L......A
clfA_014[3]  ..N......N.....T.......YL......V............................-
clfA_015[3]  ......................................AL......................A
clfA_006[2]  ............................................................
clfA_007[2]  .IN......N.....T........................A..................T...
clfA_008[2]  ..N......N.....T........................I..A...............
clfA_010[2]  ............................................................
clfA_017[2]  ..N......N..............................L..................-
clfA_011[1]  ............................................................
clfA_016[1]  ........................................L..................-
clfA_018[1]  ...........................L..........................
clfA_019[1]  ......................................AL..............L......A
clfA_020[1]  ......................................AL......................A
clfA_021[1]  ............................................................
clfA_023[1]  ..N......N.....T....S...................A..................G...
clfA_024[1]  ..N......N.....SN.TT...SD..N............A..................V...
```

FIGURE 8B ClfA align

```
                   130       140       150       160       170       180
             ----:----|----:----|----:----|----:----|----:----|----:----|
clfA_001[22] TTNQANTPATTQSSNTNAEELVNQTSNETTSNDTNTVSSVNSPQNSTNAENVSTTQDTST
clfA_002[19] ............................................................
clfA_004[15] A...............S..........................................I..
clfA_012[10] A...........................................................
clfA_005[5]  ............................................................
clfA_022[5]  A......................N....................................
clfA_003[4]  ............................................................
clfA_009[4]  A...................KS......................................
clfA_013[3]  .-..........................................................
clfA_014[3]  A...........................................................
clfA_015[3]  .-..........................................................
clfA_006[2]  ............................................................
clfA_007[2]  A...........................................................
clfA_008[2]  A.K.........................................................
clfA_010[2]  ............................................................
clfA_017[2]  A...........................................................
clfA_011[1]  ...........................F................................
clfA_016[1]  A...........................................................
clfA_018[1]  ............................................................
clfA_019[1]  .-..........................................................
clfA_020[1]  .-..........................................................
clfA_021[1]  ............................................................
clfA_023[1]  A........A...N..............................................
clfA_024[1]  A...............S..........................................I..

190       200       210       220       230       240
             ----:----|----:----|----:----|----:----|----:----|----:----|
clfA_001[22] EATPSNNESAPQSTDASNKDVVNQAVNTSAPRMRAFSLAAVAADAPAAGTDITNQLTNVT
clfA_002[19] ...........N........S....P.T.............................D.K
clfA_004[15] .........................................K.................
clfA_012[10] ...............................S.........K.................
clfA_005[5]  .........................K...............................D.K
clfA_022[5]  ..........................................................D.K
clfA_003[4]  ............................................................
clfA_009[4]  ..K.........................................................
clfA_013[3]  ..........................................................D.K
clfA_014[3]  ............................................................
clfA_015[3]  ...........N.............K................................D.K
clfA_006[2]  ...........N........S....P.T.............................D.K
clfA_007[2]  ..........................................................D.K
clfA_008[2]  ..........................................................D.K
clfA_010[2]  .................................................V.........
clfA_017[2]  ............L.............................................D.K
clfA_011[1]  ............................................................
clfA_016[1]  ............L.............................................D.K
clfA_018[1]  ............................................................
clfA_019[1]  ..........................................................D.K
clfA_020[1]  ...........N.............K................................D.K
clfA_021[1]  ............................................................
clfA_023[1]  ....................S....P...............................D..
clfA_024[1]  .........................K.................................
```

FIGURE 8C  ClfA align

```
                    250        260        270        280        290        300
                ----:----|----:----|----:----|----:----|----:----|----:----|
clfA_001[22]    VGIDSGTTVYPHQAGYVKLNYGFSVPNSAVKGDTFKITVPKELNLNGVTSTAKVPPIMAG
clfA_002[19]    .T..........................................................
clfA_004[15]    .....D...................E..Q..............................
clfA_012[10]    .....D......................................................
clfA_005[5]     .T..........................................................
clfA_022[5]     .T..........................................................
clfA_003[4]     ............................................................
clfA_009[4]     ......D..................Q..................................
clfA_013[3]     .T..........................................................
clfA_014[3]     ............................................................
clfA_015[3]     .T..........................................................
clfA_006[2]     .T.......................P..................................
clfA_007[2]     .T..........................................................
clfA_008[2]     .T..........................................................
clfA_010[2]     ............................................................
clfA_017[2]     .T..........................................................
clfA_011[1]     ............................................................
clfA_016[1]     .T..........................................................
clfA_018[1]     ............................................................
clfA_019[1]     ............................................................
clfA_020[1]     .T..................................................A.......
clfA_021[1]     .....D......................................................
clfA_023[1]     ...E..D......................................................
clfA_024[1]     ......D..................E..Q................................

310        320        330        340        350        360
                ----:----|----:----|----:----|----:----|----:----|----:----|
clfA_001[22]    DQVLANGVIDSDGNVIYTFTDYVNTKDDVKATLTMPAYIDPENVKKTGNVTLATGIGSTT
clfA_002[19]    .....................DN.EN.T.NI..........T.........T....TN.
clfA_004[15]    ..........................................T.................
clfA_012[10]    ......................D..EN.T.NI..........T.........T.......
clfA_005[5]     .....................DN.EN.T.NI..........T.........T....TN.
clfA_022[5]     .....................DN.EN.T.NI..........T.........T....TN.
clfA_003[4]     ..........................................N.................
clfA_009[4]     ...................................V......Y.TH............N..
clfA_013[3]     .....................D..N........V......T.........K....TN.
clfA_014[3]     ...........N.................................T...............
clfA_015[3]     .....................DN.EN.T.NI..........T.........T....TN.
clfA_006[2]     .....................DN.EN.T.NI..........T.........T....TN.
clfA_007[2]     .....................DN.EN.T.NI..........T.........T....TN.
clfA_008[2]     ..........................................T..................
clfA_010[2]     ..............................................................
clfA_017[2]     .....................D..EN.T.NI..........T.........T.........
clfA_011[1]     ..............................................................
clfA_016[1]     .....................DN.N................T.........T.........
clfA_018[1]     ..........................................T.................N..
clfA_019[1]     .....................DN.N........V........T.........T....TN.
clfA_020[1]     .....................DN.EN.T.NI..........T.........T....TN.
clfA_021[1]     ..........................................T.................N..
clfA_023[1]     ...................................V......Y.TH............N..
clfA_024[1]     ..........................................T..................
```

FIGURE 8D  ClfA align

```
                        370        380        390        400        410        420
                 ----:----|----:----|----:----|----:----|----:----|----:----|
clfA_001[22]     ANKTVLVDYEKYGKFYNLSIKGTIDQIDKTNNTYRQTIYVNPSGDNVIAPVLTGNLKPNT
clfA_002[19]     .S....I......Q.H......................VL.A.....I...
clfA_004[15]     ............................................................
clfA_012[10]     ............................................................
clfA_005[5]      .S....I......Q.H......................VL.A.....I...
clfA_022[5]      .S....I......Q.H......................VL.A.....I...
clfA_003[4]      ............................................................
clfA_009[4]      ............................................................
clfA_013[3]      DS....I......Q.H......................VL.A.....I...
clfA_014[3]      ............................................................
clfA_015[3]      .S....I......Q.H......................VL.A.....I...
clfA_006[2]      .S....I......Q.H......................VL.A.....I...
clfA_007[2]      .S....I......Q.H......................VL.A.....I...
clfA_008[2]      ............................................................
clfA_010[2]      ............................................................
clfA_017[2]      ............................................................
clfA_011[1]      ............................................................
clfA_016[1]      ............................................................
clfA_018[1]      ............................................................
clfA_019[1]      .S....I......Q.H......................VL.......I.KS
clfA_020[1]      .S....I......Q.H......................VL.A.....I...
clfA_021[1]      ............................................................
clfA_023[1]      ....................V.......................................
clfA_024[1]      ............................................................

430        440        450        460        470        480
                 ----:----|----:----|----:----|----:----|----:----|----:----|
clfA_001[22]     DSNALIDQQNTSIKVYKVDNAADLSESYFVNPENFEDVTNSVNITFPNPNQYKVEFNTPD
clfA_002[19]     K.....AK..D....R....N......Y...SD......Q.R.S...A.......P.D.
clfA_004[15]     .......A............S......Y...D......D....................
clfA_012[10]     ............................................................
clfA_005[5]      K.....AK..D....R....N......Y...SD......Q.R.S...A.......P.D.
clfA_022[5]      K.....AK..D....R....N......Y...SD......Q.R.S...A.......P.D.
clfA_003[4]      ............................................................
clfA_009[4]      E...........................................................
clfA_013[3]      K.....AK..D....R....N......Y...SD......Q.R.S...A.......P.D.
clfA_014[3]      ......................................................P.D.
clfA_015[3]      K.....AK..D....R....N......Y...SD......Q.R.S...A.......P.D.
clfA_006[2]      K.....AK..D....R....N......Y...SD......Q.R.S...A.......P.D.
clfA_007[2]      K.....AK..D....R....N......Y...SD......Q.R.S...A.......P.D.
clfA_008[2]      ............................................................
clfA_010[2]      ............................................................
clfA_017[2]      ............................................................
clfA_011[1]      ............................................................
clfA_016[1]      ............................................................
clfA_018[1]      ............................................................
clfA_019[1]     N.....AN..N.........N......Y...SD......Q.R.S...A.......P.D.
clfA_020[1]      K.....AK..D....R....N......Y...SD......Q.R.S...A.......P.D.
clfA_021[1]      ............................................................
clfA_023[1]      ............................................................
clfA_024[1]      .......A............S......Y...D......D....................
```

FIGURE 8E ClfA align

```
                    490       500       510       520       530       540
               ----:----|----:----|----:----|----:----|----:----|----:----|
clfA_001[22]   DQITTPYIVVVNGHIDPNSKGDLALRSTLYGYNSNIIWRSMSWDNEVAFNNGSGSGDGID
clfA_002[19]   .....................A.T........F...D..F...................
clfA_004[15]   ............................................................
clfA_012[10]   ..............................D.RFV........................
clfA_005[5]    .....................A.T........F...D..F...................
clfA_022[5]    .....................A.T........F...D..F...................
clfA_003[4]    ............................................................
clfA_009[4]    ............................................................
clfA_013[3]    .....................A.T........F...D..F...................
clfA_014[3]    ............................................................
clfA_015[3]    .....................A.T........F...D..F...................
clfA_006[2]    .....................A.T........F...D..F...................
clfA_007[2]    .....................A.T........F...D..F...................
clfA_008[2]    ..............................D.RFV........................
clfA_010[2]    ............................................................
clfA_017[2]    ............................................................
clfA_011[1]    ............................................................
clfA_016[1]    ............................................................
clfA_018[1]    ............................................................
clfA_019[1]    .....................A.T........F...D..F...................
clfA_020[1]    .....................A.T........F...D..F...................
clfA_021[1]    ..............................D.RFV........................
clfA_023[1]    ............................................................
clfA_024[1]    ....................................................F.......

550       560       570       580       590       600
               ----:----|----:----|----:----|----:----|----:----|----:----|
clfA_001[22]   KPVVPEQPDEPGEIEPIPE
clfA_002[19]   ...................
clfA_004[15]   ...................
clfA_012[10]   ...................
clfA_005[5]    ...................
clfA_022[5]    ...................
clfA_003[4]    ...................
clfA_009[4]    ...................
clfA_013[3]    ...................
clfA_014[3]    ...................
clfA_015[3]    ...................
clfA_006[2]    ...................
clfA_007[2]    ...................
clfA_008[2]    ...................
clfA_010[2]    ...................
clfA_017[2]    ...................
clfA_011[1]    ...................
clfA_016[1]    ...................
clfA_018[1]    ...................
clfA_019[1]    ...................
clfA_020[1]    ...................
clfA_021[1]    ...................
clfA_023[1]    ...................
clfA_024[1]    ...................
```

ClfA Phylogenetic Tree

FIGURE 10A ClfB Align

```
                    10        20        30        40        50        60
              ----:----|----:----|----:----|----:----|----:----|----:----|
clfB_006[29]  LKKRIDYLSNKQNKYSIRRFTVGTTSVIVGATILFGIGNHQAQASEQSNDTTQSSKNNAS
clfB_007[12]  ............................................................
clfB_009[12]  ............................................................
clfB_002[11]  ............................................................
clfB_021[4]   ............................................................
clfB_010[3]   ............................................................
clfB_011[3]   ............................................................
clfB_008[2]   ............................................................
clfB_001[1]   ............................................................
clfB_003[1]   ............................................................
clfB_004[1]   ............................................................
clfB_005[1]   ............................................................
clfB_013[1]   ............................................................
clfB_014[1]   ............................................................
clfB_015[1]   ..........R.................................................
clfB_016[1]   ............................................................
clfB_017[1]   ............................................................
clfB_018[1]   ............................................................
clfB_019[1]   ............................................................
clfB_020[1]   ............................................................
clfB_022[1]   ............................................................
clfB_023[1]   ............................................................
clfB_024[1]   ............................................................

70        80        90       100       110       120
              ----:----|----:----|----:----|----:----|----:----|----:----|
clfB_006[29]  ADSEKNNMIETPQLNTTANDTSDISANTNSANVDSTTKPMSTQTSNTTTTEPASTNETPQ
clfB_007[12]  ............................................................
clfB_009[12]  .....................................A......................
clfB_002[11]  .......T.............................A.T....................
clfB_021[4]   .....................................A......................
clfB_010[3]   .....................................A......................
clfB_011[3]   .....................................A......................
clfB_008[2]   .....................................A......................
clfB_001[1]   .......T.............................A....................H
clfB_003[1]   .......T.............................A......................
clfB_004[1]   .......T.............................A......................
clfB_005[1]   .......T.--..........................A......................
clfB_013[1]   ............................................................
clfB_014[1]   .....................................A......................
clfB_015[1]   ............................................................
clfB_016[1]   ............................................................
clfB_017[1]   .....................................A......................
clfB_018[1]   .......T.............................A......................
clfB_019[1]   .....................................A......................
clfB_020[1]   .....................................A......................
clfB_022[1]   .....................................A......................
clfB_023[1]   .......T.............................A.T....................
clfB_024[1]   ............................................................
```

FIGURE 10B ClfB Align

```
                130       140       150       160       170       180
           ----:----|----:----|----:----|----:----|----:----|----:----|
clfB_006[29] PTAIKNQATAAKMQDQTVPQEANSQVDNKTTNDANSIATNSELKNSQTLDLPQSSPQTIS
clfB_007[12] ............................................................
clfB_009[12] L....D......................................P...............
clfB_002[11] .....D..............................N.......P...............
clfB_021[4]  .....D..............................N.......P...............
clfB_010[3]  L....D......................................P...............
clfB_011[3]  .....D......................................P...............
clfB_008[2]  .....D......................................P...............
clfB_001[1]  .....D......................................P...............
clfB_003[1]  .....D......................................P.S.............
clfB_004[1]  .....D..........R...................T.......P...............
clfB_005[1]  .....D..........R...................T.......P...............
clfB_013[1]  .....D......................................P...............
clfB_014[1]  .....D......................................P...............
clfB_015[1]  ............................................................
clfB_016[1]  ....................................T.......................
clfB_017[1]  .....D.................................C....P...............
clfB_018[1]  .....D......................................P...............
clfB_019[1]  .....D......................................P...............
clfB_020[1]  .....D..............................N.....G..P..............
clfB_022[1]  .....D......................................P...............
clfB_023[1]  .....D..............................N.......P...............
clfB_024[1]  ............................................................

190       200       210       220       230       240
           ----:----|----:----|----:----|----:----|----:----|----:----|
clfB_006[29] NAQGTSKPSVRTRAVRSLAVAEPVVNAADAKGTNVNDKVTASNFKLEKTTFDPNQSGNTF
clfB_007[12] ............................................................
clfB_009[12] .........................................KD.Q...............
clfB_002[11] .......................................D......A.............
clfB_021[4]  .......................................D....................
clfB_010[3]  .........................................KD.Q...............
clfB_011[3]  .........................................LQ.Q...............
clfB_008[2]  ...R................................GQ....D.................
clfB_001[1]  ........T...........................GQ....D.................
clfB_003[1]  .........................................KD.Q...............
clfB_004[1]  .........................................KD.Q...............
clfB_005[1]  .........................................KD.Q...............
clfB_013[1]  .........................................KD.Q...............
clfB_014[1]  ....................................GQ....D.................
clfB_015[1]  ............................................................
clfB_016[1]  ............................................................
clfB_017[1]  .........................................KD.Q...............
clfB_018[1]  ....E...................................D...................
clfB_019[1]  ...R.....................................LQ.Q...............
clfB_020[1]  .......................................D....................
clfB_022[1]  .........................................KD.Q...............
clfB_023[1]  .........................................DL....A.............
clfB_024[1]  .......................................D....................
```

FIGURE 10C ClfB Align

```
              250       260       270       280       290       300
         ----:----|----:----|----:----|----:----|----:----|----:----|
clfB_006[29] MAANFTVTDKVKSGDYFTAKLPDSLTGNGDVDYSNSNNTMPIADIKSTNGDVVAKATYDI
clfB_007[12] ............................................................
clfB_009[12] .......GQ..........V.......................VNDKNE...........
clfB_002[11] .....K..GQ.........V........................................
clfB_021[4]  .........................................................T...N.
clfB_010[3]  .......GQ..........V........................................
clfB_011[3]  ............................................................
clfB_008[2]  ..V..K.AG........Y..........................................
clfB_001[1]  .....K.AG..........V........................................
clfB_003[1]  .......GQ..........V.......................VNDKNE...........
clfB_004[1]  .......GQ..........E........................N...............
clfB_005[1]  .......GQ..........E........................N...............
clfB_013[1]  .......GQ..........V........................................
clfB_014[1]  ...K....GQ..A......VN........................................
clfB_015[1]  ............................................................
clfB_016[1]  ............................................................
clfB_017[1]  .......GQ..........V........................................
clfB_018[1]  .....K.AG..........V.......................VNDKKE...........
clfB_019[1]  ............................................................
clfB_020[1]  .........................................................T...N.
clfB_022[1]  .......GQ..........V........................................
clfB_023[1]  .....K..GQ.........V........................................
clfB_024[1]  ............................................................

310       320       330       340       350       360
         ----:----|----:----|----:----|----:----|----:----|----:----|
clfB_006[29] LTKTYTFVFTDYVNNKENINGQFSLPLFTDRAKAPKSGTYDANINIADEMFNNKITYNYS
clfB_007[12] ............................................................
clfB_009[12] ............D.Q....K........................................
clfB_002[11] ............D...............................D................
clfB_021[4]  ............D................................................
clfB_010[3]  ............E...............................D................
clfB_011[3]  ............D................................................
clfB_008[2]  ............D................................................
clfB_001[1]  ............D................................................
clfB_003[1]  ............D.Q....K........I................................
clfB_004[1]  ............D................................................
clfB_005[1]  ............D................................................
clfB_013[1]  ............E...............................D................
clfB_014[1]  ............................................................
clfB_015[1]  ............................................................
clfB_016[1]  ............................................................
clfB_017[1]  ............................................................
clfB_018[1]  ............D...............................Q................
clfB_019[1]  ............D................................................
clfB_020[1]  ............D................................................
clfB_022[1]  ............................................................
clfB_023[1]  ............D...............................D................
clfB_024[1]  ............................................................
```

FIGURE 10D ClfB Align

```
                    370        380        390        400        410        420
              ----:----|----:----|----:----|----:----|----:----|----:----|
clfB_006[29]  SPIAGIDKPNGANISSQIIGVDTASGQNTYKQTVFVNPKQRVLGNTWVYIKGYQDKIEES
clfB_007[12]  ............................................................
clfB_009[12]  ............................................................
clfB_002[11]  ............................................................
clfB_021[4]   ............................................................
clfB_010[3]   ............................................................
clfB_011[3]   ............................................................
clfB_008[2]   ............................................................
clfB_001[1]   ............................................................
clfB_003[1]   ............................................................
clfB_004[1]   ............................................................
clfB_005[1]   ............................................................
clfB_013[1]   ............................................................
clfB_014[1]   .........................Y..................................
clfB_015[1]   ............................................................
clfB_016[1]   ............................................................
clfB_017[1]   ............................................................
clfB_018[1]   ............................................................
clfB_019[1]   ............................................................
clfB_020[1]   ............................................................
clfB_022[1]   ............................................................
clfB_023[1]   ............................................................
clfB_024[1]   ............................................................

430        440        450        460        470        480
              ----:----|----:----|----:----|----:----|----:----|----:----|
clfB_006[29]  SGKVSATDTKLRIFEVNDTSKLSDSYYADPNDSNLKEVTDQFKNRIYYEHPNVASIKFGD
clfB_007[12]  ..............I.............................................
clfB_009[12]  ..........................................DK.T.KYQ.....N...
clfB_002[11]  .......................................GE..DK.S.KYD.....N...
clfB_021[4]   ..........................................NE..DK.T.KYQ.....N...
clfB_010[3]   ..........................................NE..DK.T.KYQ.....N...
clfB_011[3]   ..........................................DK.T.KYQ.....N...
clfB_008[2]   ..........................................NE..DK.T.KYQ.....N...
clfB_001[1]   ..........................................DK.S.KYD.....N...
clfB_003[1]   .......................................GE.N...F.........N...
clfB_004[1]   ..........................................DK.T.KYQ.....N...
clfB_005[1]   ..........................................DK.T.KYQ.....N...
clfB_013[1]   ..........................................NE..DK.T.KYQ.....N...
clfB_014[1]   ..........................................NE..DK.T.KYQ.....N...
clfB_015[1]   ............................................................
clfB_016[1]   ............................................................
clfB_017[1]   ..........................................NE..DK.T.KYQ.....N...
clfB_018[1]   ..........................................NE..DK.T.KYQ.....N...
clfB_019[1]   ......K...................................................N...
clfB_020[1]   ..........................................NE..DK.T.KYQ.....N...
clfB_022[1]   ..........................................NE..DK.T.KYQ.....N...
clfB_023[1]   .......................................GE..DK.S.KYD.....N...
clfB_024[1]   ............................................................
```

FIGURE 10E ClfB Align

```
                      490        500        510        520        530        540
                 ----:----|----:----|----:----|----:----|----:----|----:----|
clfB_006[29]     ITKTYVVLVEGHYDNTGKNLKTQVIQENVDPVTNRDYSIFGWNNENVVRYGGGSADGDSAVN
clfB_007[12]     ............................................................
clfB_009[12]     .N............K.....................A.GK...................
clfB_002[11]     .N..................................I..A.GK...................
clfB_021[4]      ....................................I..A.GK...................
clfB_010[3]      ....................................I..A.GK...................
clfB_011[3]      .N..................................I..A.GK...................
clfB_008[2]      ....................................I..A.GK...................
clfB_001[1]      .N..................................I..A.GK...................
clfB_003[1]      .N..................................I..A.GK...................
clfB_004[1]      ....................................I..A.GK...................
clfB_005[1]      ....................................I..A.GK...................
clfB_013[1]      ....................................I..A.GK...................
clfB_014[1]      ....................................I..A.GK...................
clfB_015[1]      ............................................................
clfB_016[1]      ............................................................
clfB_017[1]      ....................................I..A.GK...................
clfB_018[1]      .N..................................I..A.GK...................
clfB_019[1]      ....................................I..A.GK...................
clfB_020[1]      ....................................I..A.GK...................
clfB_022[1]      ....................................I..A.GK...................
clfB_023[1]      .N..................................I.SA.GK...................
clfB_024[1]      ............................................................
```

ClfB PhylogeneticTree

FIGURE 12   MntC Alignment

```
                      10        20        30        40        50        60
                ----:----|----:----|----:----|----:----|----:----|----:----|
305_001[94]     MKKLVPLLLALLLLVAACGTGGKQSSDKSNGKLKVVTTNSILYDMAKNVGGDNVDIHSIV
305_006[3]      ............................................................
305_007[3]      .......................D....................................
305_002[2]      ............................................................
305_003[2]      ............................................................
305_009[1]      ............................................................
305_008[1]      ............................................................

70        80        90       100       110       120
                ----:----|----:----|----:----|----:----|----:----|----:----|
305_001[94]     PVGQDPHEYEVKPKDIKKLTDADVILYNGLNLETGNWFEKALEQAGKSLKDKKVIAVSK
305_006[3]      ............................................................
305_007[3]      ............................................................
305_002[2]      .....................I......................................
305_003[2]      ............................................................
305_009[1]      ............................................................
305_008[1]      ............................................................

130       140       150       160       170       180
                ----:----|----:----|----:----|----:----|----:----|----:----|
305_001[94]     DVKPIYLNGEEGNKDKQDPHAWLSLDNGIKYVKTIQQTFIDNDKKHKADYEKQGNKYIAQ
305_006[3]      ............................................................
305_007[3]      ............................................................
305_002[2]      ............................................................
305_003[2]      ............................................................
305_009[1]      ............................................................
305_008[1]      ...........................................Y................

190       200       210       220       230       240
                ----:----|----:----|----:----|----:----|----:----|----:----|
305_001[94]     LEKLNNDSKD---KFNDIPKEQRAMITSEGAFKYFSKQYGITPGYIWEINTEKQGTPEQM
305_006[3]      ..........---...............................................
305_007[3]      ..........---...............................................
305_002[2]      ..........---...............................................
305_003[2]      .........SKD................................................
305_009[1]      ..........---...X...........................................
305_008[1]      ..........---...............................................

250       260       270       280       290       300
                ----:----|----:----|----:----|----:----|----:----|----:----|
305_001[94]     RQAIEFVKKHKLKHLLVETSVDKKAMESLSEETKKDIFGEVYTDSIGKEGTKGDSYYKMM
305_006[3]      ............................................................
305_007[3]      ............................................................
305_002[2]      ............................................................
305_003[2]      ............................................................
305_009[1]      ............................................................
305_008[1]      ............................................................

310       320       330       340       350       360
                ----:----|----:----|----:----|----:----|----:----|----:----|
305_001[94]     KSNIETVHGSMK
305_006[3]      ....D.......
305_007[3]      ............
305_002[2]      ............
305_003[2]      ............
305_009[1]      ....D.......
305_008[1]      ....D.......
```

Meta analysis p= < 0.0001
Shaded area is serotype 5 polysaccharide conjugate-immunized group

SEQUENCE LISTING

<160> NUMBER OF SEQ ID NOS: 131

<210> SEQ ID NO 1
<211> LENGTH: 927
<212> TYPE: DNA
<213> ORGANISM: Staphylococcus aureus

<400> SEQUENCE: 1

```
atgaaaaaat tagtaccttt attattagcc ttattacttc tagttgctgc atgtggtact      60
ggtggtaaac aaagcagtga taagtcaaat ggcaaattaa aagtagtaac gacgaattca     120
attttatatg atatggctaa aaatgttggt ggagacaacg tcgatattca tagtattgta     180
cctgttggtc aagatcctca tgaatatgaa gttaaaccta aagatattaa aaagttaact     240
gacgctgacg ttattttata caacggatta aatttagaga ctggtaacgg ttggtttgaa     300
aaagccttag aacaggctgg taaatcatta aaagataaaa aagttatcgc agtatcaaaa     360
gatgttaaac ctatctattt aaacggtgaa gaaggcaaca aagataaaca agatccacac     420
gcatggttaa gtttagataa cggtattaaa tacgtaaaaa caattcaaca aacatttatc     480
gataacgaca aaaaacataa agcagattat gaaaagcaag gtaacaaata cattgctcaa     540
ttggaaaaat taaataatga cagtaaagac aaatttaatg acattccaaa agaacaacgt     600
gccatgatta caagtgaagg tgccttcaag tacttctcaa aacaatacgg tattacacca     660
ggttatattt gggaaattaa cactgaaaaa caaggtacac cagaacaaat gagacaagct     720
attgagtttg ttaaaaagca caaattaaaa cacttattag tagaaacaag tgttgataag     780
aaagcaatgg aaagtttatc tgaagaaacg aagaaagata tctttggtga agtgtacaca     840
gattcaatcg gtaaagaagg cactaaaggt gactcttact acaaaatgat gaaatcaaat     900
attgaaactg tacacggaag catgaaa                                        927
```

<210> SEQ ID NO 2
<211> LENGTH: 309
<212> TYPE: PRT
<213> ORGANISM: Staphylococcus aureus

<400> SEQUENCE: 2

```
Met Lys Lys Leu Val Pro Leu Leu Leu Ala Leu Leu Leu Val Ala
 1               5                  10                  15
```

```
Ala Cys Gly Thr Gly Gly Lys Gln Ser Ser Asp Lys Ser Asn Gly Lys
            20                  25                  30

Leu Lys Val Val Thr Thr Asn Ser Ile Leu Tyr Asp Met Ala Lys Asn
        35                  40                  45

Val Gly Gly Asp Asn Val Asp Ile His Ser Ile Val Pro Val Gly Gln
    50                  55                  60

Asp Pro His Glu Tyr Glu Val Lys Pro Lys Asp Ile Lys Lys Leu Thr
65                  70                  75                  80

Asp Ala Asp Val Ile Leu Tyr Asn Gly Leu Asn Leu Glu Thr Gly Asn
                85                  90                  95

Gly Trp Phe Glu Lys Ala Leu Glu Gln Ala Gly Lys Ser Leu Lys Asp
            100                 105                 110

Lys Lys Val Ile Ala Val Ser Lys Asp Val Lys Pro Ile Tyr Leu Asn
        115                 120                 125

Gly Glu Glu Gly Asn Lys Asp Lys Gln Asp Pro His Ala Trp Leu Ser
    130                 135                 140

Leu Asp Asn Gly Ile Lys Tyr Val Lys Thr Ile Gln Gln Thr Phe Ile
145                 150                 155                 160

Asp Asn Asp Lys Lys His Lys Ala Asp Tyr Glu Lys Gln Gly Asn Lys
                165                 170                 175

Tyr Ile Ala Gln Leu Glu Lys Leu Asn Asn Asp Ser Lys Asp Lys Phe
            180                 185                 190

Asn Asp Ile Pro Lys Glu Gln Arg Ala Met Ile Thr Ser Glu Gly Ala
        195                 200                 205

Phe Lys Tyr Phe Ser Lys Gln Tyr Gly Ile Thr Pro Gly Tyr Ile Trp
    210                 215                 220

Glu Ile Asn Thr Glu Lys Gln Gly Thr Pro Glu Gln Met Arg Gln Ala
225                 230                 235                 240

Ile Glu Phe Val Lys Lys His Lys Leu Lys His Leu Leu Val Glu Thr
                245                 250                 255

Ser Val Asp Lys Lys Ala Met Glu Ser Leu Ser Glu Glu Thr Lys Lys
            260                 265                 270

Asp Ile Phe Gly Glu Val Tyr Thr Asp Ser Ile Gly Lys Glu Gly Thr
        275                 280                 285

Lys Gly Asp Ser Tyr Tyr Lys Met Met Lys Ser Asn Ile Glu Thr Val
    290                 295                 300

His Gly Ser Met Lys
305

<210> SEQ ID NO 3
<211> LENGTH: 927
<212> TYPE: DNA
<213> ORGANISM: Staphylococcus aureus

<400> SEQUENCE: 3
atgaaaaaat tagtaccttt attattagcc ttattacttc tagttgctgc atgtggtact     60
ggtggtaaac aaagcagtga taagtcaaat ggcaaattaa agtagtaac gacgaattca    120 attttatatg atatggctaa aaatgttggt ggagacaacg tcgatattca tagtattgta    180
cctgttggtc aagatcctca tgaatatgaa gttaaaccta agatattaa aaagttaact    240 gacgctgaca ttatttttata caacggatta aatttagaga ctggtaacgg ttggtttgaa    300
aaagccttag aacaggctgg taatcatta aagataaaa agttatcgc agtatcaaaa    360 gatgttaaac ctatctattt aaacggtgaa gaaggcaaca agataaaca agatccacac    420
```

-continued

```
gcatggttaa gtttagataa tggtattaaa tacgtaaaaa caattcaaca aacatttatc    480
gataacgaca aaaacataa agcagattat gaaaagcaag gtaacaaata cattgctcaa     540
ttggaaaaat taaataatga cagtaaagac aaatttaatg acattccaaa agaacaacgt    600
gccatgatta caagtgaagg tgccttcaag tacttctcaa acaatacgg tattacacca    660 ggttatattt gggaaattaa cactgaaaaa caaggtacac ctgaacaaat gagacaagct    720
attgagtttg ttaaaaagca caattaaaa cacttattag tagaaacaag tgttgataag    780
aaagcaatgg aaagtttatc tgaagaaacg aagaaagata tctttggtga agtgtacaca    840
gattcaatcg gtaaagaagg cactaaaggt gactcttatt acaaaatgat gaaatcaaat    900
attgaaactg tacacggaag catgaaa                                         927
```

<210> SEQ ID NO 4
<211> LENGTH: 309
<212> TYPE: PRT
<213> ORGANISM: Staphylococcus aureus

<400> SEQUENCE: 4

```
Met Lys Lys Leu Val Pro Leu Leu Ala Leu Leu Leu Val Ala
1               5                   10                  15

Ala Cys Gly Thr Gly Lys Gln Ser Ser Asp Lys Ser Asn Gly Lys
            20                  25                  30

Leu Lys Val Val Thr Thr Asn Ser Ile Leu Tyr Asp Met Ala Lys Asn
            35                  40                  45

Val Gly Gly Asp Asn Val Asp Ile His Ser Ile Val Pro Val Gly Gln
    50                  55                  60

Asp Pro His Glu Tyr Glu Val Lys Pro Lys Asp Ile Lys Lys Leu Thr
65                  70                  75                  80

Asp Ala Asp Ile Ile Leu Tyr Asn Gly Leu Asn Leu Glu Thr Gly Asn
                85                  90                  95

Gly Trp Phe Glu Lys Ala Leu Glu Gln Ala Gly Lys Ser Leu Lys Asp
                100                 105                 110

Lys Lys Val Ile Ala Val Ser Lys Asp Val Lys Pro Ile Tyr Leu Asn
            115                 120                 125

Gly Glu Glu Gly Asn Lys Asp Lys Gln Asp Pro His Ala Trp Leu Ser
    130                 135                 140

Leu Asp Asn Gly Ile Lys Tyr Val Lys Thr Ile Gln Gln Thr Phe Ile
145                 150                 155                 160

Asp Asn Asp Lys Lys His Lys Ala Asp Tyr Glu Lys Gln Gly Asn Lys
                165                 170                 175

Tyr Ile Ala Gln Leu Glu Lys Leu Asn Asn Asp Ser Lys Asp Lys Phe
            180                 185                 190

Asn Asp Ile Pro Lys Glu Gln Arg Ala Met Ile Thr Ser Glu Gly Ala
            195                 200                 205

Phe Lys Tyr Phe Ser Lys Gln Tyr Gly Ile Thr Pro Gly Tyr Ile Trp
    210                 215                 220

Glu Ile Asn Thr Glu Lys Gln Gly Thr Pro Glu Gln Met Arg Gln Ala
225                 230                 235                 240

Ile Glu Phe Val Lys Lys His Lys Leu Lys His Leu Leu Val Glu Thr
                245                 250                 255

Ser Val Asp Lys Lys Ala Met Glu Ser Leu Ser Glu Glu Thr Lys Lys
            260                 265                 270

Asp Ile Phe Gly Glu Val Tyr Thr Asp Ser Ile Gly Lys Glu Gly Thr
        275                 280                 285
```

Lys Gly Asp Ser Tyr Tyr Lys Met Met Lys Ser Asn Ile Glu Thr Val
    290                 295                 300

His Gly Ser Met Lys
305

<210> SEQ ID NO 5
<211> LENGTH: 936
<212> TYPE: DNA
<213> ORGANISM: Staphylococcus aureus

<400> SEQUENCE: 5

```
atgaaaaaat tagtaccttt attattagcc ttattacttc tagttgctgc atgtggtact      60
ggtggtaaac aaagcagtga taagtcaaat ggcaaattaa agtagtaac gacgaattca     120
attttatatg atatggctaa aaatgttggt ggagacaacg tcgatattca tagtattgta    180
cctgttggtc aagatcctca tgaatatgaa gttaaaccta agatattaa aagttaact     240
gacgctgacg ttattttata caacggatta aatttagaga ctggtaacgg ttggtttgaa    300
aaagccttag aacaggctgg taaatcatta aaagataaaa agttatcgc agtatcaaaa    360
gatgttaaac ctatctattt aaacggtgaa gaaggcaaca agataaaca agatccacac    420
gcatggttaa gtttagataa cggtattaaa tacgtaaaaa caattcaaca aacatttatc    480
gataacgaca aaaacataa agcagattat gaaaagcaag gtaacaaata cattgctcaa    540
ttggaaaaat taataatga cagtaaagac agtaaagaca aatttaatga cattccaaaa    600
gaacaacgtg ccatgattac aagtgaaggt gccttcaagt acttctcaaa acaatacggt    660
attacaccag ttatatttg ggaaattaac actgaaaaac aaggtacacc tgaacaaatg    720
agacaagcta ttgagtttgt taaaaagcac aaattaaaac acttattagt agaaacaagt    780
gttgataaga agcaatgga agtttatct gaagaaacga agaaagatat ctttggtgaa    840
gtgtacacag attcaatcgg taagaaggc actaaaggtg actcttacta caaaatgatg    900
aaatcaaata ttgaaactgt acacggaagc atgaaa                            936
```

<210> SEQ ID NO 6
<211> LENGTH: 312
<212> TYPE: PRT
<213> ORGANISM: Staphylococcus aureus

<400> SEQUENCE: 6

Met Lys Lys Leu Val Pro Leu Leu Ala Leu Leu Leu Val Ala
1               5                   10                  15

Ala Cys Gly Thr Gly Gly Lys Gln Ser Ser Asp Lys Ser Asn Gly Lys
                20                  25                  30

Leu Lys Val Val Thr Thr Asn Ser Ile Leu Tyr Asp Met Ala Lys Asn
            35                  40                  45

Val Gly Gly Asp Asn Val Asp Ile His Ser Ile Val Pro Val Gly Gln
        50                  55                  60

Asp Pro His Glu Tyr Glu Val Lys Pro Lys Ile Lys Lys Leu Thr
65                  70                  75                  80

Asp Ala Asp Val Ile Leu Tyr Asn Gly Leu Asn Leu Glu Thr Gly Asn
                85                  90                  95

Gly Trp Phe Glu Lys Ala Leu Glu Gln Ala Gly Lys Ser Leu Lys Asp
                100                 105                 110

Lys Lys Val Ile Ala Val Ser Lys Asp Val Lys Pro Ile Tyr Leu Asn
            115                 120                 125

```
Gly Glu Glu Gly Asn Lys Asp Lys Gln Asp Pro His Ala Trp Leu Ser
        130                 135                 140

Leu Asp Asn Gly Ile Lys Tyr Val Lys Thr Ile Gln Gln Thr Phe Ile
145                 150                 155                 160

Asp Asn Asp Lys Lys His Lys Ala Asp Tyr Glu Lys Gln Gly Asn Lys
                165                 170                 175

Tyr Ile Ala Gln Leu Glu Lys Leu Asn Asn Asp Ser Lys Asp Ser Lys
            180                 185                 190

Asp Lys Phe Asn Asp Ile Pro Lys Glu Gln Arg Ala Met Ile Thr Ser
        195                 200                 205

Glu Gly Ala Phe Lys Tyr Phe Ser Lys Gln Tyr Gly Ile Thr Pro Gly
    210                 215                 220

Tyr Ile Trp Glu Ile Asn Thr Glu Lys Gln Gly Thr Pro Glu Gln Met
225                 230                 235                 240

Arg Gln Ala Ile Glu Phe Val Lys Lys His Lys Leu Lys His Leu Leu
                245                 250                 255

Val Glu Thr Ser Val Asp Lys Lys Ala Met Glu Ser Leu Ser Glu Glu
            260                 265                 270

Thr Lys Lys Asp Ile Phe Gly Glu Val Tyr Thr Asp Ser Ile Gly Lys
        275                 280                 285

Glu Gly Thr Lys Gly Asp Ser Tyr Tyr Lys Met Met Lys Ser Asn Ile
    290                 295                 300

Glu Thr Val His Gly Ser Met Lys
305                 310

<210> SEQ ID NO 7
<211> LENGTH: 927
<212> TYPE: DNA
<213> ORGANISM: Staphylococcus aureus

<400> SEQUENCE: 7
atgaaaaaat tagtaccttt attattagcc ttattacttt tagttgctgc atgtggtact      60
ggtggtaaac aaagcagtga taagtcaaat ggcaaactaa agtagtaac gacgaattca     120 attttatatg atatggctaa aaatgttggt ggagacaacg tcgatattca tagtattgta     180
cctgttggtc aagatcctca tgaatatgaa gttaaaccta agatattaa aaagttaact     240 gacgctgacg ttattttata caacggatta aatttagaga ctggtaacgg ttggtttgaa     300
aaagccttag aacaggctgg taaatcatta aaagataaaa agttatcgc agtatcaaaa     360 gatgttaaac ctatctattt aaacggtgaa gaaggcaaca agataaaca agatccacac     420 gcatggttaa gtttagataa cggtattaaa tacgtaaaaa caattcaaca acatttatc     480 gataacgaca aaaacataa agcagattat gaaaagcaag gtaacaaata cattgctcaa     540
ttggaaaaat taaataatga cagtaaagac aaatttaatg acattccaaa agaacaacgt     600
gccatgatta agtgaagg tgccttcaaa tacttctcaa acaatacgg tattaccaca     660 ggttatattt gggaaattaa cactgaaaaa caaggtacac agaacaaat gagacaagct     720 attgagtttg ttaaaaaaca caattaaaa cacttattag tagaaacaag tgttgataag     780
aaagcaatgg aaagtttatc tgaagaaacg aagaaagata tctttggtga agtgtacaca     840
gattcaatcg gtaaagaagg cactaaaggt gactcttact acaaaatgat gaaatcaaat     900
attgatactg tacacggaag catgaaa                                        927

<210> SEQ ID NO 8
<211> LENGTH: 309
```

<212> TYPE: PRT
<213> ORGANISM: Staphylococcus aureus

<400> SEQUENCE: 8

```
Met Lys Lys Leu Val Pro Leu Leu Leu Ala Leu Leu Leu Val Ala
1               5                   10                  15

Ala Cys Gly Thr Gly Gly Lys Gln Ser Ser Asp Lys Ser Asn Gly Lys
            20                  25                  30

Leu Lys Val Val Thr Thr Asn Ser Ile Leu Tyr Asp Met Ala Lys Asn
        35                  40                  45

Val Gly Gly Asp Asn Val Asp Ile His Ser Ile Val Pro Val Gly Gln
    50                  55                  60

Asp Pro His Glu Tyr Glu Val Lys Pro Lys Asp Ile Lys Lys Leu Thr
65                  70                  75                  80

Asp Ala Asp Val Ile Leu Tyr Asn Gly Leu Asn Leu Glu Thr Gly Asn
                85                  90                  95

Gly Trp Phe Glu Lys Ala Leu Glu Gln Ala Gly Lys Ser Leu Lys Asp
            100                 105                 110

Lys Lys Val Ile Ala Val Ser Lys Asp Val Lys Pro Ile Tyr Leu Asn
        115                 120                 125

Gly Glu Glu Gly Asn Lys Asp Lys Gln Asp Pro His Ala Trp Leu Ser
    130                 135                 140

Leu Asp Asn Gly Ile Lys Tyr Val Lys Thr Ile Gln Gln Thr Phe Ile
145                 150                 155                 160

Asp Asn Asp Lys Lys His Lys Ala Asp Tyr Glu Lys Gln Gly Asn Lys
                165                 170                 175

Tyr Ile Ala Gln Leu Glu Lys Leu Asn Asn Asp Ser Lys Asp Lys Phe
            180                 185                 190

Asn Asp Ile Pro Lys Glu Gln Arg Ala Met Ile Thr Ser Glu Gly Ala
        195                 200                 205

Phe Lys Tyr Phe Ser Lys Gln Tyr Gly Ile Thr Pro Gly Tyr Ile Trp
    210                 215                 220

Glu Ile Asn Thr Glu Lys Gln Gly Thr Pro Glu Gln Met Arg Gln Ala
225                 230                 235                 240

Ile Glu Phe Val Lys Lys His Lys Leu Lys His Leu Leu Val Glu Thr
                245                 250                 255

Ser Val Asp Lys Lys Ala Met Glu Ser Leu Ser Glu Glu Thr Lys Lys
            260                 265                 270

Asp Ile Phe Gly Glu Val Tyr Thr Asp Ser Ile Gly Lys Glu Gly Thr
        275                 280                 285

Lys Gly Asp Ser Tyr Tyr Lys Met Met Lys Ser Asn Ile Asp Thr Val
    290                 295                 300

His Gly Ser Met Lys
305
```

<210> SEQ ID NO 9
<211> LENGTH: 927
<212> TYPE: DNA
<213> ORGANISM: Staphylococcus aureus

<400> SEQUENCE: 9

```
atgaaaaaat tagtaccttt attattagcc ttattacttc tagttgctgc atgtggtact      60
gatggtaaac aaagcagtga taagtcaaat ggcaaattaa agtagtaac gacgaattca     120 attttatatg atatggctaa aaatgttggt ggagacaacg tcgatattca gtattgta      180
```

```
cctgttggtc aagatcctca tgaatatgaa gttaaaccta agatattaa aaagttaact      240
gacgctgacg ttatttata caacggatta aatttagaga ctggtaacgg ttggtttgaa      300
aaagccttag aacaggctgg taaatcatta aaagataaaa aagttatcgc agtatcaaaa      360
gatgttaaac ctatctattt aaacggtgaa gaaggcaaca agataaaca agatccacac      420
gcatggttaa gtttagataa cggtattaaa tacgtaaaaa caattcaaca acatttatc      480
gataacgaca aaaacataa agcagattat gaaaagcaag gtaacaaata cattgctcaa      540
ttggaaaaat taaataatga cagtaaagac aaatttaatg acattccaaa agaacaacgt      600
gccatgatta caagtgaagg tgccttcaag tacttctcaa acaatacgg tattacacca      660
ggttatattt gggaaattaa cactgaaaaa caaggtacac ctgaacaaat gagacaagct      720
attgagtttg ttaaaaagca caattaaaa cacttattag tagaaacaag tgttgataag      780
aaagcaatgg aaagtttatc tgaagaaacg aagaaagata tctttggtga agtgtacaca      840
gattcaatcg gtaaagaagg cactaaaggt gactcttact acaaaatgat gaaatcaaat      900
attgaaactg tacacggaag catgaaa                                          927

<210> SEQ ID NO 10
<211> LENGTH: 309
<212> TYPE: PRT
<213> ORGANISM: Staphylococcus aureus

<400> SEQUENCE: 10

Met Lys Lys Leu Val Pro Leu Leu Ala Leu Leu Leu Val Ala
1               5                   10                  15

Ala Cys Gly Thr Asp Gly Lys Gln Ser Ser Asp Lys Ser Asn Gly Lys
                20                  25                  30

Leu Lys Val Val Thr Thr Asn Ser Ile Leu Tyr Asp Met Ala Lys Asn
            35                  40                  45

Val Gly Gly Asp Asn Val Asp Ile His Ser Ile Val Pro Val Gly Gln
        50                  55                  60

Asp Pro His Glu Tyr Glu Val Lys Pro Lys Asp Ile Lys Lys Leu Thr
65                  70                  75                  80

Asp Ala Asp Val Ile Leu Tyr Asn Gly Leu Asn Leu Glu Thr Gly Asn
                85                  90                  95

Gly Trp Phe Glu Lys Ala Leu Glu Gln Ala Gly Lys Ser Leu Lys Asp
            100                 105                 110

Lys Lys Val Ile Ala Val Ser Lys Asp Val Lys Pro Ile Tyr Leu Asn
        115                 120                 125

Gly Glu Glu Gly Asn Lys Asp Lys Gln Asp Pro His Ala Trp Leu Ser
    130                 135                 140

Leu Asp Asn Gly Ile Lys Tyr Val Lys Thr Ile Gln Gln Thr Phe Ile
145                 150                 155                 160

Asp Asn Asp Lys Lys His Lys Ala Asp Tyr Glu Lys Gln Gly Asn Lys
                165                 170                 175

Tyr Ile Ala Gln Leu Glu Lys Leu Asn Asn Asp Ser Lys Asp Lys Phe
            180                 185                 190

Asn Asp Ile Pro Lys Glu Gln Arg Ala Met Ile Thr Ser Glu Gly Ala
        195                 200                 205

Phe Lys Tyr Phe Ser Lys Gln Tyr Gly Ile Thr Pro Gly Tyr Ile Trp
    210                 215                 220

Glu Ile Asn Thr Glu Lys Gln Gly Thr Pro Glu Gln Met Arg Gln Ala
225                 230                 235                 240
```

```
Ile Glu Phe Val Lys Lys His Lys Leu Lys His Leu Leu Val Glu Thr
                245                 250                 255

Ser Val Asp Lys Lys Ala Met Glu Ser Leu Ser Glu Glu Thr Lys Lys
            260                 265                 270

Asp Ile Phe Gly Glu Val Tyr Thr Asp Ser Ile Gly Lys Glu Gly Thr
        275                 280                 285

Lys Gly Asp Ser Tyr Tyr Lys Met Met Lys Ser Asn Ile Glu Thr Val
    290                 295                 300

His Gly Ser Met Lys
305

<210> SEQ ID NO 11
<211> LENGTH: 927
<212> TYPE: DNA
<213> ORGANISM: Staphylococcus aureus

<400> SEQUENCE: 11
atgaaaaaat tagtaccttt attattagcc ttattacttc tagttgctgc atgtggtact    60
ggtggtaaac aaagcagtga taagtcaaat ggcaaattaa agtagtaac gacgaattca   120 attttatatg atatggctaa aaatgttggt ggagacaacg tcgatattca gtagtattgta  180 cctgttggtc aagatcctca tgaatatgaa gttaaaccta agatattaa aaagttaact   240 gacgctgacg ttatttttata caacggatta aatttagaga ctggtaacgg ttggtttgaa  300
aaagccttag aacaggctgg taatcatta aaagataaaa agttatcgc agtatcaaaa   360 gatgttaaac ctatctattt aaacggtgaa gaaggcaaca agataaaca agatccacac   420 gcatggttaa gtttagataa cggtattaaa tacgtaaaaa caattcaaca acatttatc   480 gataacgcaa aaaacataa agcatattat gaaaagcaag gtaacaaata cattgctcaa   540
ttggaaaaat taaataatga cagtaaagac aaatttaatg acattccaaa agaacaacgt   600
gccatgatta caagtgaagg tgccttcaag tacttctcaa aacaatacgg tattacacca   660
ggttatattt gggaaattaa cactgaaaaa caaggtacac ctgaacaaat gagacaagct   720
attgagtttg ttaaaaagca caaattaaaa cacttattag tagaaacaag tgttgataag   780
aaagcaatgg aaagtttatc tgaagaaacg aagaaagata tctttggtga agtgtacaca   840
gattcaatcg gtaaagaagg cactaaaggt gactcttact acaaaatgat gaaatcaaat   900
attgatactg tacacggaag catgaaa                                       927

<210> SEQ ID NO 12
<211> LENGTH: 309
<212> TYPE: PRT
<213> ORGANISM: Staphylococcus aureus

<400> SEQUENCE: 12

Met Lys Lys Leu Val Pro Leu Leu Ala Leu Leu Leu Val Ala
1               5                   10                  15

Ala Cys Gly Thr Gly Gly Lys Gln Ser Ser Asp Lys Ser Asn Gly Lys
            20                  25                  30

Leu Lys Val Val Thr Thr Asn Ser Ile Leu Tyr Asp Met Ala Lys Asn
        35                  40                  45

Val Gly Gly Asp Asn Val Asp Ile His Ser Ile Val Pro Val Gly Gln
    50                  55                  60

Asp Pro His Glu Tyr Glu Val Lys Pro Lys Asp Ile Lys Lys Leu Thr
65                  70                  75                  80

Asp Ala Asp Val Ile Leu Tyr Asn Gly Leu Asn Leu Glu Thr Gly Asn
```

```
              85                  90                  95
Gly Trp Phe Glu Lys Ala Leu Glu Gln Ala Gly Lys Ser Leu Lys Asp
            100                 105                 110

Lys Lys Val Ile Ala Val Ser Lys Asp Val Lys Pro Ile Tyr Leu Asn
        115                 120                 125

Gly Glu Gly Asn Lys Lys Gln Asp Pro His Ala Trp Leu Ser
    130                 135                 140

Leu Asp Asn Gly Ile Lys Tyr Val Lys Thr Ile Gln Gln Thr Phe Ile
145                 150                 155                 160

Asp Asn Asp Lys Lys His Lys Ala Tyr Tyr Glu Lys Gln Gly Asn Lys
                165                 170                 175

Tyr Ile Ala Gln Leu Glu Lys Leu Asn Asn Asp Ser Lys Asp Lys Phe
            180                 185                 190

Asn Asp Ile Pro Lys Glu Gln Arg Ala Met Ile Thr Ser Glu Gly Ala
        195                 200                 205

Phe Lys Tyr Phe Ser Lys Gln Tyr Gly Ile Thr Pro Gly Tyr Ile Trp
    210                 215                 220

Glu Ile Asn Thr Glu Lys Gln Gly Thr Pro Glu Gln Met Arg Gln Ala
225                 230                 235                 240

Ile Glu Phe Val Lys Lys His Lys Leu Lys His Leu Leu Val Glu Thr
                245                 250                 255

Ser Val Asp Lys Lys Ala Met Glu Ser Leu Ser Glu Glu Thr Lys Lys
            260                 265                 270

Asp Ile Phe Gly Glu Val Tyr Thr Asp Ser Ile Gly Lys Glu Gly Thr
        275                 280                 285

Lys Gly Asp Ser Tyr Tyr Lys Met Met Lys Ser Asn Ile Asp Thr Val
    290                 295                 300

His Gly Ser Met Lys
305

<210> SEQ ID NO 13
<211> LENGTH: 927
<212> TYPE: DNA
<213> ORGANISM: Staphylococcus aureus

<400> SEQUENCE: 13
atgaaaaaat tagtaccttt attattagcc ttattacttc tagttgctgc atgtggtact      60
ggtggtaaac aaagcagtga taagtcaaat ggcaaattaa agtagtaac  gacgaattca     120 attttatatg atatggctaa aaatgttggt ggagacaacg tcgatattca tagtattgta     180
cctgttggtc aagatcctca tgaatatgaa gttaaaccta agatattaa  aaagttaact     240 gacgctgacg ttattttata caacggatta aatttagaga ctggtaacgg ttggtttgaa     300
aaagccttag aacaggctgg taaatcatta aaagataaaa aagttatcgc agtatcaaaa     360
gatgttaaac ctatctattt aaacggtgaa gaaggcaaca agataaaca  agatccacac     420 gcatggttaa gtttagataa cggtattaaa tacgtaaaaa caattcaaca acatttatc     480 gataacgaca aaaaacataa agcagattat gaaaagcaag gtaacaaata cattgctcaa     540
ttggaaaaat taaataatga cagtaaagac aaatttaatg acrttccaaa agaacaacgt     600
gccatgatta caagtgaagg tgccttcaag tacttctcaa acaatacgg  tattacacca     660 ggttatattt gggaaattaa cactgaaaaa caaggtacac ctgaacaaat gagacaagct     720
attgagtttg ttaaaaagca caaattaaaa cacttattag tagaaacaag tgttgataag     780
aaagcaatgg aaagtttatc tgaagaaacg aagaaagata tctttggtga agtgtacaca     840
```

```
gattcaatcg gtaaagaagg cactaaaggt gactcttact acaaaatgat gaaatcaaat    900
attgatactg tacacggaag catgaaa                                         927
```

<210> SEQ ID NO 14
<211> LENGTH: 309
<212> TYPE: PRT
<213> ORGANISM: Staphylococcus aureus
<220> FEATURE:
<221> NAME/KEY: MOD_RES
<222> LOCATION: (195)..(195)
<223> OTHER INFORMATION: Any amino acid

<400> SEQUENCE: 14

```
Met Lys Lys Leu Val Pro Leu Leu Leu Ala Leu Leu Leu Val Ala
1               5                   10                  15

Ala Cys Gly Thr Gly Lys Gln Ser Ser Asp Lys Ser Asn Gly Lys
                20                  25                  30

Leu Lys Val Val Thr Thr Asn Ser Ile Leu Tyr Asp Met Ala Lys Asn
            35                  40                  45

Val Gly Gly Asp Asn Val Asp Ile His Ser Ile Val Pro Val Gly Gln
    50                  55                  60

Asp Pro His Glu Tyr Glu Val Lys Pro Lys Asp Ile Lys Lys Leu Thr
65                  70                  75                  80

Asp Ala Asp Val Ile Leu Tyr Asn Gly Leu Asn Leu Glu Thr Gly Asn
                85                  90                  95

Gly Trp Phe Glu Lys Ala Leu Glu Gln Ala Gly Lys Ser Leu Lys Asp
            100                 105                 110

Lys Lys Val Ile Ala Val Ser Lys Asp Val Lys Pro Ile Tyr Leu Asn
        115                 120                 125

Gly Glu Glu Gly Asn Lys Asp Lys Gln Asp Pro His Ala Trp Leu Ser
    130                 135                 140

Leu Asp Asn Gly Ile Lys Tyr Val Lys Thr Ile Gln Gln Thr Phe Ile
145                 150                 155                 160

Asp Asn Asp Lys Lys His Lys Ala Asp Tyr Glu Lys Gln Gly Asn Lys
                165                 170                 175

Tyr Ile Ala Gln Leu Glu Lys Leu Asn Asn Asp Ser Lys Asp Lys Phe
            180                 185                 190

Asn Asp Xaa Pro Lys Glu Gln Arg Ala Met Ile Thr Ser Glu Gly Ala
        195                 200                 205

Phe Lys Tyr Phe Ser Lys Gln Tyr Gly Ile Thr Pro Gly Tyr Ile Trp
    210                 215                 220

Glu Ile Asn Thr Glu Lys Gln Gly Thr Pro Glu Gln Met Arg Gln Ala
225                 230                 235                 240

Ile Glu Phe Val Lys Lys His Lys Leu Lys His Leu Leu Val Glu Thr
                245                 250                 255

Ser Val Asp Lys Lys Ala Met Glu Ser Leu Ser Glu Glu Thr Lys Lys
            260                 265                 270

Asp Ile Phe Gly Glu Val Tyr Thr Asp Ser Ile Gly Lys Glu Gly Thr
        275                 280                 285

Lys Gly Asp Ser Tyr Tyr Lys Met Met Lys Ser Asn Ile Asp Thr Val
    290                 295                 300

His Gly Ser Met Lys
305
```

<210> SEQ ID NO 15

```
<211> LENGTH: 1626
<212> TYPE: DNA
<213> ORGANISM: Staphylococcus aureus

<400> SEQUENCE: 15
ttgaaaaaaa gaattgatta tttgtcgaat aagcagaata agtattcgat tagacgtttt      60
acagtaggta ccacatcagt aatagtaggg gcaacgatac tatttgggat aggcaatcat     120
caagcacaag cttcagaaca atcgaacgat acaacgcaat cttcgaaaaa taatgcaagt     180
gcagattccg aaaaaaacaa tacgatagaa acacctcaat taaatacaac ggctaatgat     240
acatctgata ttagtgcaaa cacaaacagt gcgaatgtag atagcacagc aaaaccaatg     300
tctacacaaa cgagcaatac cactacaaca gagccagctt caacaaatga acacctcac      360
ccgacggcaa ttaaagatca agcaactgct gcaaaaatgc aagatcaaac tgttcctcaa     420
gaagcaaatt ctcaagtaga taataaaaca acgaatgatg ctaatagcat agcaacaaac     480
agtgagctta aaaatcctca acattagat ttaccacaat catcaccaca aacgatttcc      540
aatgcgcaag gaactagtaa accaagtgtt agaacgagag ctgtacgtag tcttgcagtt     600
actgaacctg tagtaaatgc tgctgatgct aaaggtacaa atgtaaatgg tcaagttacg     660
gcaagtgatt tcaagttaga aaagactaca tttgaccccta accaagtgg taacacattt      720
atggcggcaa attttaaagt ggcagggaaa gtgaaatcag gggattattt tacagcgaag     780
ttaccagata gtgtaactgg taatggagat gtggattact ctaactcgaa taatacgatg     840
ccaattgcag atattaaaag tacgaatggc gatgttgtag ctaaagcaac atatgatatc     900
ttgactaaga cgtatacatt tgtctttaca gattatgtaa atgataaaga aaatattaac     960
ggacaatttt cattaccatt atttacagac agagcaaagg cacctaaatc aggaacatat    1020
gatgcaaata ttaatattgc ggatgaaatg tttaataata aaattactta taactatagt    1080
tcaccaattg caggaattga taagccaaat ggcgcgaaca tttcttctca aattattggt    1140
gtagatacag cttcaggtca aaacacatac aagcaaacgg tatttgttaa ccctaagcaa    1200
cgagttttag gtaatacgtg ggtgtatatt aaaggttacc aagataaaat cgaagaaagt    1260
agcggtaaag taagtgctac agatacaaaa ctgagaattt ttgaagtgaa tgatacatct    1320
aaattatcag atagctacta tgcagaccca aatgactcta accttaaaga agtaactgat    1380
caattttaaag ataaaatttc atacaaatac gataacgtag caagtattaa ttttggtgat    1440
ataaataaaa cgtatgtcgt tttagtcgaa ggtcattatg ataatactgg taaaaacttg    1500
aaaacacagg ttattcaaga aaatattgac ccagcgacag gtaaagatta cagtattttc    1560
ggttggaata tgagaatgt tgtacgttat ggaggcggaa gtgctgatgg tgattcagca    1620
gtaaat                                                                1626

<210> SEQ ID NO 16
<211> LENGTH: 542
<212> TYPE: PRT
<213> ORGANISM: Staphylococcus aureus

<400> SEQUENCE: 16

Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
                20                  25                  30

Ile Leu Phe Gly Ile Gly Asn His Gln Ala Gln Ala Ser Glu Gln Ser
            35                  40                  45
```

```
Asn Asp Thr Thr Gln Ser Ser Lys Asn Asn Ala Ser Ala Asp Ser Glu
    50                  55                  60

Lys Asn Asn Thr Ile Glu Thr Pro Gln Leu Asn Thr Thr Ala Asn Asp
 65                  70                  75                  80

Thr Ser Asp Ile Ser Ala Asn Thr Asn Ser Ala Asn Val Asp Ser Thr
                 85                  90                  95

Ala Lys Pro Met Ser Thr Gln Thr Ser Asn Thr Thr Thr Thr Glu Pro
            100                 105                 110

Ala Ser Thr Asn Glu Thr Pro His Pro Thr Ala Ile Lys Asp Gln Ala
            115                 120                 125

Thr Ala Ala Lys Met Gln Asp Gln Thr Val Pro Gln Glu Ala Asn Ser
130                 135                 140

Gln Val Asp Asn Lys Thr Thr Asn Asp Ala Asn Ser Ile Ala Thr Asn
145                 150                 155                 160

Ser Glu Leu Lys Asn Pro Gln Thr Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Thr Glu Pro Val Val Asn Ala Ala
            195                 200                 205

Asp Ala Lys Gly Thr Asn Val Asn Gly Gln Val Thr Ala Ser Asp Phe
210                 215                 220

Lys Leu Glu Lys Thr Thr Phe Asp Pro Asn Gln Ser Gly Asn Thr Phe
225                 230                 235                 240

Met Ala Ala Asn Phe Lys Val Ala Gly Lys Val Lys Ser Gly Asp Tyr
                245                 250                 255

Phe Thr Ala Lys Leu Pro Asp Ser Val Thr Gly Asn Gly Asp Val Asp
            260                 265                 270

Tyr Ser Asn Ser Asn Asn Thr Met Pro Ile Ala Asp Ile Lys Ser Thr
            275                 280                 285

Asn Gly Asp Val Val Ala Lys Ala Thr Tyr Asp Ile Leu Thr Lys Thr
290                 295                 300

Tyr Thr Phe Val Phe Thr Asp Tyr Val Asn Asp Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
            340                 345                 350

Asn Lys Ile Thr Tyr Asn Tyr Ser Ser Pro Ile Ala Gly Ile Asp Lys
            355                 360                 365

Pro Asn Gly Ala Asn Ile Ser Ser Gln Ile Ile Gly Val Asp Thr Ala
370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
            420                 425                 430

Ile Phe Glu Val Asn Asp Thr Ser Lys Leu Ser Asp Ser Tyr Tyr Ala
            435                 440                 445

Asp Pro Asn Asp Ser Asn Leu Lys Glu Val Thr Asp Gln Phe Lys Asp
450                 455                 460

Lys Ile Ser Tyr Lys Tyr Asp Asn Val Ala Ser Ile Asn Phe Gly Asp
```

|     |     |     |     | 465 |     |     |     | 470 |     |     |     | 475 |     |     |     | 480 |     |
| --- | --- | --- | --- | --- | --- | --- | --- | --- | --- | --- | --- | --- | --- | --- | --- | --- | --- |
| Ile | Asn | Lys | Thr | Tyr | Val | Val | Leu | Val | Glu | Gly | His | Tyr | Asp | Asn | Thr |
|     |     |     |     |     |     | 485 |     |     |     | 490 |     |     |     | 495 |     |
| Gly | Lys | Asn | Leu | Lys | Thr | Gln | Val | Ile | Gln | Glu | Asn | Ile | Asp | Pro | Ala |
|     |     |     |     | 500 |     |     |     | 505 |     |     |     | 510 |     |     |     |
| Thr | Gly | Lys | Asp | Tyr | Ser | Ile | Phe | Gly | Trp | Asn | Asn | Glu | Asn | Val | Val |
|     |     |     | 515 |     |     |     | 520 |     |     |     | 525 |     |     |     |     |
| Arg | Tyr | Gly | Gly | Gly | Ser | Ala | Asp | Gly | Asp | Ser | Ala | Val | Asn |
|     |     | 530 |     |     |     | 535 |     |     |     | 540 |     |     |     |

<210> SEQ ID NO 17
<211> LENGTH: 1626
<212> TYPE: DNA
<213> ORGANISM: Staphylococcus aureus

<400> SEQUENCE: 17

```
ttgaaaaaaa gaattgatta tttgtcgaat aagcagaata agtattcgat tagacgtttt      60
acagtaggta ccacatcagt aatagtaggg gcaactatac tatttgggat aggcaatcat     120
caagcacaag cttcagaaca atcgaacgat acaacgcaat cttcgaaaaa taatgcaagt     180
gcagattccg aaaaaaacaa tacgatgaaa cacctcaat taaatacaac ggctaatgat     240
acatctgata ttagtgcaaa cacaaacagt gcgaatgtag atagcacagc aaaaacaatg     300
tctacacaaa cgagcaatac cactacaaca gagccagctt caacaaatga acacctcaa      360
ccgacggcaa ttaaagatca agcaactgct gcaaaaatgc aagatcaaac tgttcctcaa     420
gaagcaaatt ctcaagtaga taataaaaca acgaatgatg ctaataacat agcaacaaac     480
agtgagctta aaaatcctca acattagat ttaccacaat catcaccaca aacgatttcc      540
aatgcgcaag gaactagtaa accaagtgtt agaacgagag ctgtacgtag tcttgcagtt     600
gctgaacctg tagtaaatgc tgctgatgct aaaggtacaa atgtaaatga taaagttacg     660
gcaagtgatt tcaagttaga aaagactgca tttgaccta accaaagtgg taacacattt      720
atggcggcaa attttaaagt gactggacaa gtgaaatcag gggattattt tacagcgaag     780
ttaccagata gtgtaactgg taatggagac gtggattact ctaattcaaa taatacgatg     840
ccaattgcag acattaaaag tacgaatggc gatgttgtag ctaaagcaac atatgatatc     900
ttgactaaga cgtatacatt tgtctttaca gattatgtaa atgataaaga aaatattaac     960
ggacaatttt cattaccttt atttacagac cgagcaaagg cacctaaatc aggaacatat    1020
gatgcaaata ttaatattgc ggatgaaatg tttgataata aaattactta taactatagt    1080
tcgccaattg caggaattga taagccaaat ggcgcgaaca tttcttctca aattattggt    1140
gtagatacag cttcaggtca aaacacatac aagcaaacgg tatttgttaa ccctaagcaa    1200
cgagttttag gtaatacgtg ggtgtatatt aaaggttacc aagataaaat cgaagaaagt    1260
agcggtaaag taagtgctac agatacaaaa ctgagaattt ttgaagtgaa tgatacatct    1320
aaattatcag atagctacta tgcagaccca atgactctca accttaaaga agtgactggt    1380
gagtttaaag ataaaatttc atacaaatac gataacgtag caagtattaa ttttggtgat    1440
ataaataaaa cgtatgttgt attagtggaa ggtcactatg ataatactgg taaaaacttg    1500
aaaacacagg ttattcaaga aaatattgac ccagcgacag gtaaagacta cagtattttc    1560
ggttggaata tgagaatgt tgtacgttat ggaggcggaa gtgctgatgg tgattcagca    1620
gtaaat                                                              1626
```

<210> SEQ ID NO 18
<211> LENGTH: 542
<212> TYPE: PRT
<213> ORGANISM: Staphylococcus aureus

<400> SEQUENCE: 18

```
Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Thr Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Ala Lys Thr Met Ser Thr Gln Thr Ser Asn Thr Thr Thr Thr Glu Pro
            100                 105                 110

Ala Ser Thr Asn Glu Thr Pro Gln Pro Thr Ala Ile Lys Asp Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Asn Ile Ala Thr Asn
145                 150                 155                 160

Ser Glu Leu Lys Asn Pro Gln Thr Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Gly Thr Asn Val Asn Asp Lys Val Thr Ala Ser Asp Phe
    210                 215                 220

Lys Leu Glu Lys Thr Ala Phe Asp Pro Asn Gln Ser Gly Asn Thr Phe
225                 230                 235                 240

Met Ala Ala Asn Phe Lys Val Thr Gly Gln Val Lys Ser Gly Asp Tyr
                245                 250                 255

Phe Thr Ala Lys Leu Pro Asp Ser Val Thr Gly Asn Gly Asp Val Asp
            260                 265                 270

Tyr Ser Asn Ser Asn Asn Thr Met Pro Ile Ala Asp Ile Lys Ser Thr
        275                 280                 285

Asn Gly Asp Val Val Ala Lys Ala Thr Tyr Asp Ile Leu Thr Lys Thr
    290                 295                 300

Tyr Thr Phe Val Phe Thr Asp Tyr Val Asn Asp Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asp
            340                 345                 350

Asn Lys Ile Thr Tyr Asn Tyr Ser Ser Pro Ile Ala Gly Ile Asp Lys
        355                 360                 365

Pro Asn Gly Ala Asn Ile Ser Ser Gln Ile Ile Gly Val Asp Thr Ala
    370                 375                 380
```

-continued

```
Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
            420                 425                 430

Ile Phe Glu Val Asn Asp Thr Ser Lys Leu Ser Asp Ser Tyr Tyr Ala
        435                 440                 445

Asp Pro Asn Asp Ser Asn Leu Lys Glu Val Thr Gly Glu Phe Lys Asp
    450                 455                 460

Lys Ile Ser Tyr Lys Tyr Asp Asn Val Ala Ser Ile Asn Phe Gly Asp
465                 470                 475                 480

Ile Asn Lys Thr Tyr Val Val Leu Val Glu Gly His Tyr Asp Asn Thr
                485                 490                 495

Gly Lys Asn Leu Lys Thr Gln Val Ile Gln Glu Asn Ile Asp Pro Ala
            500                 505                 510

Thr Gly Lys Asp Tyr Ser Ile Phe Gly Trp Asn Asn Glu Asn Val Val
        515                 520                 525

Arg Tyr Gly Gly Gly Ser Ala Asp Gly Asp Ser Ala Val Asn
    530                 535                 540
```

<210> SEQ ID NO 19
<211> LENGTH: 1626
<212> TYPE: DNA
<213> ORGANISM: Staphylococcus aureus

<400> SEQUENCE: 19

| | | | | | |
|---|---|---|---|---|---|
| ttgaaaaaaa | gaattgatta | tttgtcgaat | aagcagaata | agtattcgat | tagacgtttt | 60 |
| acagtaggta | ccacatcagt | aatagtaggg | gcaactatac | tatttgggat | aggcaatcat | 120 |
| caagcacaag | cttcagaaca | atcgaacgat | acaacgcaat | cttcgaaaaa | taatgcaagt | 180 |
| gcagattccg | aaaaaaacaa | tacgatgaaa | acacctcaat | taaatacaac | ggctaatgat | 240 |
| acatctgata | ttagtgcaaa | cacaaacagt | gcgaatgtag | atagcacagc | aaaaccaatg | 300 |
| tctacacaaa | cgagcaatac | cactacaaca | gagccagctt | caacaaatga | acacctcaa | 360 |
| ccgacggcaa | ttaaagatca | agcaactgct | gcaaaaatgc | aagatcaaac | tgttcctcaa | 420 |
| gaagcaaatt | ctcaagtaga | taataaaaca | acgaatgatg | ctaatagcat | agcgacaaac | 480 |
| agcgagctta | aaaatcctca | atcattagat | ttaccacaat | catcaccaca | aacgatttcc | 540 |
| aatgcgcaag | gaactagtaa | accaagtgtt | agaacgagag | ctgtacgtag | tcttgcagtt | 600 |
| gctgaacctg | tagtaaatgc | tgctgatgct | aaaggtacaa | atgtaaatga | taaagttacg | 660 |
| gcaaaagatt | ttcaattaga | aaagactaca | tttgacccta | accaaagtgg | taatactttt | 720 |
| atggcggcaa | actttacagt | gactggacaa | gtgaaatcag | gggattattt | tacagcgaag | 780 |
| ttaccagata | gtgtaactgg | taatggagac | gtggattact | ctaattcaaa | taatacgatg | 840 |
| ccaattgcag | atatagtaaa | cgataaaaat | gaagttgtag | caaaagcgac | atatgatatt | 900 |
| ttgactaaga | catatacatt | tgtctttaca | gattatgtaa | atgataagca | aaatattaat | 960 |
| gggaaatttt | cattaccatt | atttacagac | cgagcaaagg | cacctaaatc | aggaatatat | 1020 |
| gatgcgaata | ttaatattgc | ggatgaaatg | tttaataata | aaattactta | taactatagt | 1080 |
| tcgccaattg | caggaattga | taagccaaat | ggcgcgaaca | tttcttctca | aattattggt | 1140 |
| gtagatacag | cttcaggtca | aaatacatac | aagcaaacgg | tatttgttaa | ccctaagcaa | 1200 |
| cgagttttag | gtaatacgtg | ggtgtatatt | aaaggttacc | aagataaaat | cgaagaaagt | 1260 |

```
agcggtaaag taagtgctac agatacaaaa ctgagaattt ttgaagtgaa tgatacatct    1320
aaattatcag atagctacta tgcggaccca aatgactcta accttaaaga agtgactggt    1380
gagtttaata atagaatttt ttatgaacat ccaaacgtag caagtattaa ttttggtgat    1440
ataaataaaa cgtatgtcgt tttagttgaa ggtcactatg ataatactgg taaaaacttg    1500
aaaacacagg ttattcaaga aatattgac  ccagcgacag gtaaagacta cagtattttc    1560
ggatggaata atgagaatgt tgtacgttat ggtggtggaa gtgctgatgg tgattcagca    1620
gtaaat                                                              1626

<210> SEQ ID NO 20
<211> LENGTH: 542
<212> TYPE: PRT
<213> ORGANISM: Staphylococcus aureus

<400> SEQUENCE: 20

Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Thr Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Ala Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asp Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Ser Ile Ala Thr Asn
145                 150                 155                 160

Ser Glu Leu Lys Asn Pro Gln Ser Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Gly Thr Asn Val Asn Asp Lys Val Thr Ala Lys Asp Phe
    210                 215                 220

Gln Leu Glu Lys Thr Thr Phe Asp Pro Asn Gln Ser Gly Asn Thr Phe
225                 230                 235                 240

Met Ala Ala Asn Phe Thr Val Thr Gly Gln Val Lys Ser Gly Asp Tyr
                245                 250                 255

Phe Thr Ala Lys Leu Pro Asp Ser Val Thr Gly Asn Gly Asp Val Asp
            260                 265                 270

Tyr Ser Asn Ser Asn Asn Thr Met Pro Ile Ala Asp Ile Val Asn Asp
        275                 280                 285

Lys Asn Glu Val Val Ala Lys Ala Thr Tyr Asp Ile Leu Thr Lys Thr
    290                 295                 300
```

```
Tyr Thr Phe Val Phe Thr Asp Tyr Val Asn Asp Lys Gln Asn Ile Asn
305                 310                 315                 320

Gly Lys Phe Ser Leu Pro Leu Phe Thr Asp Arg Ala Lys Ala Pro Lys
            325                 330                 335

Ser Gly Ile Tyr Asp Ala Asn Ile Asn Ile Ala Asp Glu Met Phe Asn
                340                 345                 350

Asn Lys Ile Thr Tyr Asn Tyr Ser Ser Pro Ile Ala Gly Ile Asp Lys
            355                 360                 365

Pro Asn Gly Ala Asn Ile Ser Ser Gln Ile Ile Gly Val Asp Thr Ala
370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
                420                 425                 430

Ile Phe Glu Val Asn Asp Thr Ser Lys Leu Ser Asp Ser Tyr Tyr Ala
            435                 440                 445

Asp Pro Asn Asp Ser Asn Leu Lys Glu Val Thr Gly Glu Phe Asn Asn
450                 455                 460

Arg Ile Phe Tyr Glu His Pro Asn Val Ala Ser Ile Asn Phe Gly Asp
465                 470                 475                 480

Ile Asn Lys Thr Tyr Val Val Leu Val Glu Gly His Tyr Asp Asn Thr
                485                 490                 495

Gly Lys Asn Leu Lys Thr Gln Val Ile Gln Glu Asn Ile Asp Pro Ala
                500                 505                 510

Thr Gly Lys Asp Tyr Ser Ile Phe Gly Trp Asn Asn Glu Asn Val Val
            515                 520                 525

Arg Tyr Gly Gly Gly Ser Ala Asp Gly Asp Ser Ala Val Asn
530                 535                 540

<210> SEQ ID NO 21
<211> LENGTH: 1626
<212> TYPE: DNA
<213> ORGANISM: Staphylococcus aureus

<400> SEQUENCE: 21
ttgaaaaaaa gaattgatta tttgtcgaat aagcagaata agtattcgat tagacgtttt      60
acagtaggta ccacatcagt aatagtaggg gcaactatac tatttgggat aggcaatcat     120
caagcacaag cttcagaaca atcgaacgat acaacgcaat cttcgaaaaa taatgcaagt     180
gcagattccg aaaaaaacaa tacgatgaaa cacctcaat taaatacaac ggctaatgat     240
acatctgata ttagtgcaaa cacaaacagt gcgaatgtag atagcacagc aaaaccaatg     300
tctacacaaa cgagcaatac cactacaaca gagccagctt caacaaatga acacctcaa     360 ccgacggcaa ttaaagatca agcaactgct gcaaaaatgc aagatcgaac tgttcctcaa     420
gaagcaaatt ctcaagtaga taataaaaca cgaatgatg ctaatagcat aacaacaaac     480
agtgagctta aaaatcctca aacattagat ttaccacaat catcaccaca aacgatttcc     540
aatgcgcaag gaactagtaa accaagtgtt agaacgagag ctgtacgtag tcttgcagtt     600
gctgaacctg tagtaaatgc tgctgatgct aaaggcacaa atgtaaatga taaagttacg     660
gcaaaagatt tcaattaga aaagactaca tttgacccta accaaagtgg taatactttt     720
atggcggcaa actttacagt gactggacaa gtgaaatcag gggattattt tacagcgaag     780
```

-continued

```
ttaccagaaa gtttaactgg taatggagac gtggattact ctaactcgaa taatacgatg      840
ccaattgcag atattaaaag tacgaatggc aatgttgtag ctaaagcaac atatgatatc      900
ttgactaaga cgtatacatt tgtctttaca gattatgtaa atgataaaga aaatattaac      960
ggacaatttt cattaccttt atttacagac cgagcaaagg cacctaaatc aggaacatat     1020
gatgcaaata ttaatattgc ggatgaaatg tttaacaata aaattactta taactatagt     1080
tcaccaattg caggaattga taagccaaat ggcgcgaaca tttcttctca aattattggt     1140
gtagatacag cttcaggtca aaacacatac aagcaaacgg tatttgttaa ccctaagcaa     1200
cgagttttag gtaatacgtg ggtgtatatt aaaggttacc aagataaaat cgaagaaagt     1260
agcggtaaag taagtgctac agatacaaaa ctgagaattt ttgaagtgaa tgatacatct     1320
aaattatcag atagctacta tgcggaccca aatgactcta atcttaaaga agtaactgat     1380
caatttaagg ataaaatcac ttataaatac caaaatgtag caagtattaa ttttggtgat     1440
attactaaaa cgtatgttgt attagtggaa ggtcactatg ataatactgg taaaaacttg     1500
aaaacacagg ttattcaaga aaatattgac ccagcgacag gtaaagacta cagtattttc     1560
ggatggaata atgagaatgt tgtacgttat ggtggtggaa gtgctgatgg tgattcagca     1620
gtaaat                                                                1626
```

<210> SEQ ID NO 22
<211> LENGTH: 542
<212> TYPE: PRT
<213> ORGANISM: Staphylococcus aureus

<400> SEQUENCE: 22

```
Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Ala Ser Ala Asp Ser Glu
    50                  55                  60

Lys Asn Asn Thr Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Ala Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asp Gln Ala
        115                 120                 125

Thr Ala Ala Lys Met Gln Asp Arg Thr Val Pro Gln Glu Ala Asn Ser
    130                 135                 140

Gln Val Asp Asn Lys Thr Thr Asn Asp Ala Asn Ser Ile Thr Thr Asn
145                 150                 155                 160

Ser Glu Leu Lys Asn Pro Gln Thr Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Gly Thr Asn Val Asn Asp Lys Val Thr Ala Lys Asp Phe
```

Gln Leu Glu Lys Thr Thr Phe Asp Pro Asn Gln Ser Gly Asn Thr Phe
225                 230                 235                 240

Met Ala Ala Asn Phe Thr Val Thr Gly Gln Val Lys Ser Gly Asp Tyr
            245                 250                 255

Phe Thr Ala Lys Leu Pro Glu Ser Leu Thr Gly Asn Gly Asp Val Asp
        260                 265                 270

Tyr Ser Asn Ser Asn Asn Thr Met Pro Ile Ala Asp Ile Lys Ser Thr
    275                 280                 285

Asn Gly Asn Val Val Ala Lys Ala Thr Tyr Asp Ile Leu Thr Lys Thr
290                 295                 300

Tyr Thr Phe Val Phe Thr Asp Tyr Val Asn Asp Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
            340                 345                 350

Asn Lys Ile Thr Tyr Asn Tyr Ser Ser Pro Ile Ala Gly Ile Asp Lys
        355                 360                 365

Pro Asn Gly Ala Asn Ile Ser Ser Gln Ile Ile Gly Val Asp Thr Ala
    370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
            420                 425                 430

Ile Phe Glu Val Asn Asp Thr Ser Lys Leu Ser Asp Ser Tyr Tyr Ala
        435                 440                 445

Asp Pro Asn Asp Ser Asn Leu Lys Glu Val Thr Asp Gln Phe Lys Asp
    450                 455                 460

Lys Ile Thr Tyr Lys Tyr Gln Asn Val Ala Ser Ile Asn Phe Gly Asp
465                 470                 475                 480

Ile Thr Lys Thr Tyr Val Val Leu Val Glu Gly His Tyr Asp Asn Thr
                485                 490                 495

Gly Lys Asn Leu Lys Thr Gln Val Ile Gln Glu Asn Ile Asp Pro Ala
            500                 505                 510

Thr Gly Lys Asp Tyr Ser Ile Phe Gly Trp Asn Asn Glu Asn Val Val
        515                 520                 525

Arg Tyr Gly Gly Gly Ser Ala Asp Gly Asp Ser Ala Val Asn
    530                 535                 540

<210> SEQ ID NO 23
<211> LENGTH: 1620
<212> TYPE: DNA
<213> ORGANISM: Staphylococcus aureus

<400> SEQUENCE: 23
ttgaaaaaaa gaattgatta tttgtcgaat aagcagaata agtattcgat tagacgtttt     60
acagtaggta ccacatcagt aatagtaggg gcaactatac tatttgggat aggcaatcat    120
caagcacaag cttcagaaca atcgaacgat acaacgcaat cttcgaaaaa taatgcaagt    180
gcagattccg aaaaaaacaa tacgatagaa acacctcaat taaatactaa tgatacatct    240
gatattagtg caaacacaaa cagtgcgaat gtagatagca cagcaaaacc aatgtctaca    300

```
caaacgagca ataccactac aacagagcca gcttcaacaa atgaaacacc tcaaccgacg    360
gcaattaaag atcaagcaac tgctgcaaaa atgcaagatc gaactgttcc tcaagaagca    420
aattctcaag tagataataa acaacgaat gatgctaata gcataacaac aaacagtgag    480
cttaaaaatc ctcaaacatt agatttacca caatcatcac cacaaacgat ttccaatgcg    540
caaggaacta gtaaccaag tgttagaacg agagctgtac gtagtcttgc agttgctgaa    600
cctgtagtaa atgctgctga tgctaaaggc acaaatgtaa atgataaagt tacggcaaaa    660
gattttcaat tagaaaagac tacatttgac cctaaccaaa gtggtaatac ttttatggcg    720
gcaaacttta cagtgactgg acaagtgaaa tcagggatt attttacagc gaagttacca    780
gaaagtttaa ctggtaatgg agacgtggat tactctaact cgaataatac gatgccaatt    840
gcagatatta aaagtacgaa tggcaatgtt gtagctaaag caacatatga tatcttgact    900
aagacgtata catttgtctt tacagattat gtaaatgata agaaaatat taacggacaa    960 ttttcattac ctttatttac agaccgagca aaggcaccta atcaggaac atatgatgca   1020 aatattaata ttgcggatga atgtttaac aataaaatta cttataacta tagttcacca   1080
attgcaggaa ttgataagcc aaatggcgcg aacatttctt ctcaaattat tggtgtagat   1140
acagcttcag gtcaaaacac atacaagcaa acggtatttg ttaaccctaa gcaacgagtt   1200
ttaggtaata cgtgggtgta tattaaaggt taccaagata aatcgaaga agtagcggt    1260 aaagtaagtg ctacagatac aaaactgaga attttttgaag tgaatgatac atctaaatta   1320
tcagatagct actatgcgga cccaaatgac tctaatctta agaagtaac tgatcaattt   1380 aaggataaaa tcacttataa ataccaaaat gtagcaagta ttaattttgg tgatattact   1440
aaaacgtatg ttgtattagt ggaaggtcac tatgataata ctggtaaaaa cttgaaaaca   1500
caggttattc aagaaaatat tgacccagcg acaggtaaag actacagtat tttcggatgg   1560
aataatgaga atgttgtacg ttatggtggt ggaagtgctg atggtgattc agcagtaaat   1620
```

<210> SEQ ID NO 24
<211> LENGTH: 540
<212> TYPE: PRT
<213> ORGANISM: Staphylococcus aureus

<400> SEQUENCE: 24

Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Thr Ile Glu Thr Pro Gln Leu Asn Thr Asn Asp Thr Ser
65                  70                  75                  80

Asp Ile Ser Ala Asn Thr Asn Ser Ala Asn Val Asp Ser Thr Ala Lys
                85                  90                  95

Pro Met Ser Thr Gln Thr Ser Asn Thr Thr Thr Thr Glu Pro Ala Ser
            100                 105                 110

Thr Asn Glu Thr Pro Gln Pro Thr Ala Ile Lys Asp Gln Ala Thr Ala
        115                 120                 125

Ala Lys Met Gln Asp Arg Thr Val Pro Gln Glu Ala Asn Ser Gln Val
    130                 135                 140

```
Asp Asn Lys Thr Thr Asn Asp Ala Asn Ser Ile Thr Asn Ser Glu
145                 150                 155                 160

Leu Lys Asn Pro Gln Thr Leu Asp Leu Pro Gln Ser Ser Pro Gln Thr
            165                 170                 175

Ile Ser Asn Ala Gln Gly Thr Ser Lys Pro Ser Val Arg Thr Arg Ala
        180                 185                 190

Val Arg Ser Leu Ala Val Ala Glu Pro Val Val Asn Ala Ala Asp Ala
    195                 200                 205

Lys Gly Thr Asn Val Asn Asp Lys Val Thr Ala Lys Asp Phe Gln Leu
    210                 215                 220

Glu Lys Thr Thr Phe Asp Pro Asn Gln Ser Gly Asn Thr Phe Met Ala
225                 230                 235                 240

Ala Asn Phe Thr Val Thr Gly Gln Val Lys Ser Gly Asp Tyr Phe Thr
                245                 250                 255

Ala Lys Leu Pro Glu Ser Leu Thr Gly Asn Gly Asp Val Asp Tyr Ser
            260                 265                 270

Asn Ser Asn Asn Thr Met Pro Ile Ala Asp Ile Lys Ser Thr Asn Gly
        275                 280                 285

Asn Val Val Ala Lys Ala Thr Tyr Asp Ile Leu Thr Lys Thr Tyr Thr
    290                 295                 300

Phe Val Phe Thr Asp Tyr Val Asn Asp Lys Glu Asn Ile Asn Gly Gln
305                 310                 315                 320

Phe Ser Leu Pro Leu Phe Thr Asp Arg Ala Lys Ala Pro Lys Ser Gly
                325                 330                 335

Thr Tyr Asp Ala Asn Ile Asn Ile Ala Asp Glu Met Phe Asn Asn Lys
            340                 345                 350

Ile Thr Tyr Asn Tyr Ser Ser Pro Ile Ala Gly Ile Asp Lys Pro Asn
        355                 360                 365

Gly Ala Asn Ile Ser Ser Gln Ile Ile Gly Val Asp Thr Ala Ser Gly
    370                 375                 380

Gln Asn Thr Tyr Lys Gln Thr Val Phe Val Asn Pro Lys Gln Arg Val
385                 390                 395                 400

Leu Gly Asn Thr Trp Val Tyr Ile Lys Gly Tyr Gln Asp Lys Ile Glu
                405                 410                 415

Glu Ser Ser Gly Lys Val Ser Ala Thr Asp Thr Lys Leu Arg Ile Phe
            420                 425                 430

Glu Val Asn Asp Thr Ser Lys Leu Ser Asp Ser Tyr Tyr Ala Asp Pro
        435                 440                 445

Asn Asp Ser Asn Leu Lys Glu Val Thr Asp Gln Phe Lys Asp Lys Ile
    450                 455                 460

Thr Tyr Lys Tyr Gln Asn Val Ala Ser Ile Asn Phe Gly Asp Ile Thr
465                 470                 475                 480

Lys Thr Tyr Val Val Leu Val Glu Gly His Tyr Asp Asn Thr Gly Lys
                485                 490                 495

Asn Leu Lys Thr Gln Val Ile Gln Glu Asn Ile Asp Pro Ala Thr Gly
            500                 505                 510

Lys Asp Tyr Ser Ile Phe Gly Trp Asn Asn Glu Asn Val Val Arg Tyr
        515                 520                 525

Gly Gly Gly Ser Ala Asp Gly Asp Ser Ala Val Asn
    530                 535                 540

<210> SEQ ID NO 25
<211> LENGTH: 1626
```

```
<212> TYPE: DNA
<213> ORGANISM: Staphylococcus aureus

<400> SEQUENCE: 25
ttgaaaaaaa gaattgatta tttgtcgaat aagcagaata agtattcgat tagacgtttt      60
acagtaggta ccacatcagt aatagtaggg gcaactatac tatttgggat aggcaatcat     120
caagcacaag cttcagaaca atcgaacgat acaacgcaat cttcgaaaaa taatgcaagt     180
gcagattccg aaaaaaacaa tatgatgaaa acacctcaat taaatacaac ggctaatgat     240
acatctgata ttagtgcaaa cacaaacagt gcgaatgtag atagcacaac aaaaccaatg     300
tctacacaaa cgagcaatac cactacaaca gagccagctt caacaaatga acacctcaa      360
ccgacggcaa ttaaaaatca agcaactgct gcaaaaatgc aagatcaaac tgttcctcaa     420
gaagcaaatt ctcaagtaga taataaaaca acgaatgatg ctaatagcat agcaacaaac     480
agtgagctta aaaattctca acattagat ttaccacaat catcaccaca acgatttcc       540
aatgcgcaag gaactagtaa accaagtgtt agaacgagag ctgtacgtag tttagctgtt     600
gctgaaccgg tagtaaatgc tgctgatgct aaaggtacaa atgtaaatga taaagttacg     660
gcaagtaatt tcaagttaga aaagactaca tttgaccta atcaaagtgg taacacattt      720
atggcggcaa attttacagt gacagataaa gtgaaatcag gggattattt tacagcgaag     780
ttaccagata gtttaactgg taatggagac gtggattatt ctaattcaaa taatacgatg     840
ccaattgcag acattaaaag tacgaatggc gatgttgtag ctaaagcaac atatgatatc     900
ttgactaaga cgtatacatt tgtctttaca gattatgtaa ataataaaga aaatattaac     960
ggacaatttt cattacctttt atttacagac cgagcaaagg cacctaaatc aggaacatat    1020
gatgcgaata ttaatattgc ggatgaaatg tttaataata aaattactta taactatagt    1080
tcgccaattg caggaattga taaaccaaat ggcgcgaaca tttcttctca aattattggt    1140
gtagatacag cttcaggtca aaacacatac aagcaaacag tatttgttaa ccctaagcaa    1200
cgagttttag gtaatacgtg ggtgtatatt aaaggctacc aagataaaat cgaagaaagt    1260
agcggtaaag taagtgctac agatacaaaa ctgagaattt ttgaagtgaa tgatacatct    1320
aaattatcag atagctacta tgcagatcca atgactcta accttaaaga agtaacagac     1380
caatttaaaa atagaatcta ttatgagcat ccaaatgtag ctagtattaa atttggtgat    1440
attactaaaa catatgtagt attagtagaa gggcattacg acaatacagg taagaactta    1500
aaaactcagg ttattcaaga aaatgttgat cctgtaacaa atagagacta cagtattttc    1560
ggttggaata atgagaatgt tgtacgttat ggtggtggaa gtgctgatgg tgattcagca    1620
gtaaat                                                                1626

<210> SEQ ID NO 26
<211> LENGTH: 542
<212> TYPE: PRT
<213> ORGANISM: Staphylococcus aureus

<400> SEQUENCE: 26

Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
```

```
            50                  55                  60
Lys Asn Asn Met Ile Glu Thr Pro Gln Leu Asn Thr Thr Ala Asn Asp
 65                  70                  75                  80

Thr Ser Asp Ile Ser Ala Asn Thr Asn Ser Ala Asn Val Asp Ser Thr
                     85                  90                  95

Thr Lys Pro Met Ser Thr Gln Thr Ser Asn Thr Thr Thr Thr Glu Pro
                    100                 105                 110

Ala Ser Thr Asn Glu Thr Pro Gln Pro Thr Ala Ile Lys Asn Gln Ala
                115                 120                 125

Thr Ala Ala Lys Met Gln Asp Gln Thr Val Pro Gln Glu Ala Asn Ser
            130                 135                 140

Gln Val Asp Asn Lys Thr Thr Asn Asp Ala Asn Ser Ile Ala Thr Asn
145                 150                 155                 160

Ser Glu Leu Lys Asn Ser Gln Thr Leu Asp Leu Pro Gln Ser Ser Pro
                165                 170                 175

Gln Thr Ile Ser Asn Ala Gln Gly Thr Ser Lys Pro Ser Val Arg Thr
                180                 185                 190

Arg Ala Val Arg Ser Leu Ala Val Ala Glu Pro Val Val Asn Ala Ala
                195                 200                 205

Asp Ala Lys Gly Thr Asn Val Asn Asp Lys Val Thr Ala Ser Asn Phe
            210                 215                 220

Lys Leu Glu Lys Thr Thr Phe Asp Pro Asn Gln Ser Gly Asn Thr Phe
225                 230                 235                 240

Met Ala Ala Asn Phe Thr Val Thr Asp Lys Val Lys Ser Gly Asp Tyr
                    245                 250                 255

Phe Thr Ala Lys Leu Pro Asp Ser Leu Thr Gly Asn Gly Asp Val Asp
                260                 265                 270

Tyr Ser Asn Ser Asn Asn Thr Met Pro Ile Ala Asp Ile Lys Ser Thr
                275                 280                 285

Asn Gly Asp Val Val Ala Lys Ala Thr Tyr Asp Ile Leu Thr Lys Thr
            290                 295                 300

Tyr Thr Phe Val Phe Thr Asp Tyr Val Asn Asn Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
                340                 345                 350

Asn Lys Ile Thr Tyr Asn Tyr Ser Ser Pro Ile Ala Gly Ile Asp Lys
                355                 360                 365

Pro Asn Gly Ala Asn Ile Ser Ser Gln Ile Ile Gly Val Asp Thr Ala
            370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                    405                 410                 415

Ile Glu Glu Ser Ser Gly Lys Val Ser Ala Thr Asp Thr Lys Leu Arg
                420                 425                 430

Ile Phe Glu Val Asn Asp Thr Ser Lys Leu Ser Asp Ser Tyr Tyr Ala
                435                 440                 445

Asp Pro Asn Asp Ser Asn Leu Lys Glu Val Thr Asp Gln Phe Lys Asn
            450                 455                 460

Arg Ile Tyr Tyr Glu His Pro Asn Val Ala Ser Ile Lys Phe Gly Asp
465                 470                 475                 480
```

```
Ile Thr Lys Thr Tyr Val Val Leu Val Glu Gly His Tyr Asp Asn Thr
            485                 490                 495

Gly Lys Asn Leu Lys Thr Gln Val Ile Gln Glu Asn Val Asp Pro Val
            500                 505                 510

Thr Asn Arg Asp Tyr Ser Ile Phe Gly Trp Asn Asn Glu Asn Val Val
            515                 520                 525

Arg Tyr Gly Gly Gly Ser Ala Asp Gly Asp Ser Ala Val Asn
            530                 535             540

<210> SEQ ID NO 27
<211> LENGTH: 1626
<212> TYPE: DNA
<213> ORGANISM: Staphylococcus aureus

<400> SEQUENCE: 27
```

| | | | | | |
|---|---|---|---|---|---|
| ttgaaaaaaa | gaattgatta | tttgtcgaat | aagcagaata | agtattcgat | tagacgtttt | 60 |
| acagtaggta | ccacatcagt | aatagtaggg | gcaactatac | tatttgggat | aggcaatcat | 120 |
| caagcacaag | cttcagaaca | atcgaacgat | acaacgcaat | cttcgaaaaa | taatgcaagt | 180 |
| gcagattccg | aaaaaaacaa | tatgatgaaa | acacctcaat | taaatacaac | ggctaatgat | 240 |
| acatctgata | ttagtgcaaa | cacaaacagt | gcgaatgtag | atagcacaac | aaaaccaatg | 300 |
| tctacacaaa | cgagcaatac | cactacaaca | gagccagctt | caacaaatga | acacctcaa | 360 |
| ccgacggcaa | ttaaaaatca | agcaactgct | gcaaaaatgc | aagatcaaac | tgttcctcaa | 420 |
| gaagcaaatt | ctcaagtaga | taataaaaca | acgaatgatg | ctaatagcat | agcaacaaac | 480 |
| agtgagctta | aaaattctca | acattagat | ttaccacaat | catcaccaca | aacgatttcc | 540 |
| aatgcgcaag | gaactagtaa | accaagtgtt | agaacgagag | ctgtacgtag | tttagctgtt | 600 |
| gctgaaccgg | tagtaaatgc | tgctgatgct | aaaggtacaa | atgtaaatga | taaagttacg | 660 |
| gcaagtaatt | tcaagttaga | aaagactaca | tttgaccta | atcaaagtgg | taacacattt | 720 |
| atggcggcaa | attttacagt | gacagataaa | gtgaaatcag | gggattattt | tacagcgaag | 780 |
| ttaccagata | gtttaactgg | taatggagac | gtggattatt | ctaattcaaa | taatacgatg | 840 |
| ccaattgcag | acattaaaag | tacgaatggc | gatgttgtag | ctaaagcaac | atatgatatc | 900 |
| ttgactaaga | cgtatacatt | tgtctttaca | gattatgtaa | ataataaaga | aaatattaac | 960 |
| ggacaatttt | cattaccttt | atttacagac | cgagcaaagg | cacctaaatc | aggaacatat | 1020 |
| gatgcgaata | ttaatattgc | ggatgaaatg | tttaataata | aaattactta | taactatagt | 1080 |
| tcgccaattg | caggaattga | taaaccaaat | ggcgcgaaca | tttcttctca | aattattggt | 1140 |
| gtagatacag | cttcaggtca | aaacacatac | aagcaaacag | tatttgttaa | ccctaagcaa | 1200 |
| cgagttttag | gtaatacgtg | ggtgtatatt | aaaggctacc | aagataaaat | cgaagaaagt | 1260 |
| agcggtaaag | taagtgctac | agatacaaaa | ctgagaattt | ttgaagtgaa | tgatatatct | 1320 |
| aaattatcag | atagctacta | tgcagatcca | aatgactcta | accttaaaga | agtaacagac | 1380 |
| caatttaaaa | atagaatcta | ttatgagcat | ccaaatgtag | ctagtattaa | atttggtgat | 1440 |
| attactaaaa | catatgtagt | attagtagaa | gggcattacg | acaatacagg | taagaactta | 1500 |
| aaaactcagg | ttattcaaga | aaatgttgat | cctgtaacaa | atagagacta | cagtattttc | 1560 |
| ggttggaata | atgagaatgt | tgtacgttat | ggtggtggaa | gtgctgatgg | tgattcagca | 1620 |
| gtaaat | | | | | | 1626 |

<210> SEQ ID NO 28

<211> LENGTH: 542
<212> TYPE: PRT
<213> ORGANISM: Staphylococcus aureus

<400> SEQUENCE: 28

```
Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Thr Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asn Gln Ala
        115                 120                 125

Thr Ala Ala Lys Met Gln Asp Gln Thr Val Pro Gln Glu Ala Asn Ser
130                 135                 140

Gln Val Asp Asn Lys Thr Thr Asn Asp Ala Asn Ser Ile Ala Thr Asn
145                 150                 155                 160

Ser Glu Leu Lys Asn Ser Gln Thr Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Gly Thr Asn Val Asn Asp Lys Val Thr Ala Ser Asn Phe
210                 215                 220

Lys Leu Glu Lys Thr Thr Phe Asp Pro Asn Gln Ser Gly Asn Thr Phe
225                 230                 235                 240

Met Ala Ala Asn Phe Thr Val Thr Asp Lys Val Lys Ser Gly Asp Tyr
                245                 250                 255

Phe Thr Ala Lys Leu Pro Asp Ser Leu Thr Gly Asn Gly Asp Val Asp
            260                 265                 270

Tyr Ser Asn Ser Asn Asn Thr Met Pro Ile Ala Asp Ile Lys Ser Thr
        275                 280                 285

Asn Gly Asp Val Val Ala Lys Ala Thr Tyr Asp Ile Leu Thr Lys Thr
290                 295                 300

Tyr Thr Phe Val Phe Thr Asp Tyr Val Asn Asn Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
            340                 345                 350

Asn Lys Ile Thr Tyr Asn Tyr Ser Pro Ile Ala Gly Ile Asp Lys
        355                 360                 365

Pro Asn Gly Ala Asn Ile Ser Ser Gln Ile Ile Gly Val Asp Thr Ala
370                 375                 380

Ser Gly Gln Asn Thr Tyr Lys Gln Thr Val Phe Val Asn Pro Lys Gln
```

```
                385              390                395              400
        Arg Val Leu Gly Asn Thr Trp Val Tyr Ile Lys Gly Tyr Gln Asp Lys
                        405              410              415

Ile Glu Glu Ser Ser Gly Lys Val Ser Ala Thr Asp Thr Lys Leu Arg
                        420              425              430

Ile Phe Glu Val Asn Asp Ile Ser Lys Leu Ser Asp Ser Tyr Tyr Ala
                        435              440              445

Asp Pro Asn Asp Ser Asn Leu Lys Glu Val Thr Asp Gln Phe Lys Asn
                450              455              460

Arg Ile Tyr Tyr Glu His Pro Asn Val Ala Ser Ile Lys Phe Gly Asp
        465              470              475              480

Ile Thr Lys Thr Tyr Val Leu Val Glu Gly His Tyr Asp Asn Thr
                        485              490              495

Gly Lys Asn Leu Lys Thr Gln Val Ile Gln Glu Asn Val Asp Pro Val
                        500              505              510

Thr Asn Arg Asp Tyr Ser Ile Phe Gly Trp Asn Asn Glu Asn Val Val
                        515              520              525

Arg Tyr Gly Gly Gly Ser Ala Asp Gly Asp Ser Ala Val Asn
                        530              535              540

<210> SEQ ID NO 29
<211> LENGTH: 1626
<212> TYPE: DNA
<213> ORGANISM: Staphylococcus aureus

<400> SEQUENCE: 29
ttgaaaaaaa gaattgatta tttgtcgaat aagcagaata agtattcgat tagacgtttt      60
acagtaggta ccacatcagt aatagtaggg gcaactatac tatttgggat aggcaatcat     120
caagcacaag cttcagaaca atcgaacgat acaacgcaat cttcgaaaaa taatgcaagt     180
gcagattccg aaaaaaacaa tatgatgaaa acacctcaat aaatacaac ggctaatgat      240 acatctgata ttagtgcaaa cacaaacagt gcgaatgtag atagcacagc aaaaccaatg     300
tctacacaaa cgagcaatac cactacaaca gagccagctt caacaaatga acacctcaa      360 ccgacggcaa ttaaagatca agcaactgct gcaaaaatgc aagatcaaac tgttcctcaa     420
gaagcaaatt ctcaagtaga taataaaaca cgaatgatg ctaatagcat agcgacaaac      480
agtgagctta aaaatcctca acattagat ttaccacaat catcaccaca aacgatttcc      540
aatgcgcaaa gaactagtaa accaagtgtt agaacgagag ctgtacgtag tttagctgtt     600
gctgaaccgg tagtaaatgc tgctgatgct aaaggtacaa atgtaaatgg tcaagttacg     660
gcaagtgatt tcaagttaga aaagactaca tttgacccta accaaagtgg taacacattt     720
atggcggtaa attttaaagt ggcagggaaa gtgaaatcag gggattatta tacagcgaag     780
ttaccagata gtttaactgg taatggagac gtggattact ctaattcaaa taatacgatg     840
ccaattgcag atattaaaag tacgaatggc gatgttgtag ctaaagcaac atatgatatc     900
ttgactaaga cgtatacatt tgtctttaca gattatgtaa atgataaaga aaatattaac     960
ggacaatttt cattacccttt atttacagac cgagcaaagg cacctaaatc aggaacatac    1020
gatgcaaata ttaatattgc ggatgaaatg tttaataata aaattactta taactatagt    1080
tcgccaattg caggaattga taagccaaat ggcgcgaaca tttcttctca aattattggt    1140
gtagatacag cttcaggtca aaacacatac aagcaaacgg tatttgttaa ccctaagcaa    1200
cgagttttag gtaatacgtg ggtgtatatt aaaggttacc aagataaaat cgaagaaagt    1260
```

-continued

```
agcggtaaag taagtgctac agatacaaaa ctgagaattt ttgaagtgaa tgatacatct    1320
aaattatcag atagctacta tgcagatcca aatgactcta accttaaaga agtaacgaat    1380
gagtttaagg ataaaatcac ttataaatac caaaatgtag caagtattaa ttttggcgat    1440
attactaaaa cgtatgttgt attagtggaa ggtcactatg ataatactgg taaaaacttg    1500
aaaacacagg ttattcaaga aaatattgac ccagcgacag gtaaagacta cagtattttc    1560
ggttggaata tgagaatgt tgtacgttat ggtggtggaa gtgctgatgg tgattcagca    1620
gtaaat                                                              1626
```

<210> SEQ ID NO 30
<211> LENGTH: 542
<212> TYPE: PRT
<213> ORGANISM: Staphylococcus aureus

<400> SEQUENCE: 30

```
Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Ala Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asp Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Ser Ile Ala Thr Asn
145                 150                 155                 160

Ser Glu Leu Lys Asn Pro Gln Thr Leu Asp Leu Pro Gln Ser Ser Pro
                165                 170                 175

Gln Thr Ile Ser Asn Ala Gln Arg Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Gly Thr Asn Val Asn Gly Gln Val Thr Ala Ser Asp Phe
    210                 215                 220

Lys Leu Glu Lys Thr Thr Phe Asp Pro Asn Gln Ser Gly Asn Thr Phe
225                 230                 235                 240

Met Ala Val Asn Phe Lys Val Ala Gly Lys Val Lys Ser Gly Asp Tyr
                245                 250                 255

Tyr Thr Ala Lys Leu Pro Asp Ser Leu Thr Gly Asn Gly Asp Val Asp
            260                 265                 270

Tyr Ser Asn Ser Asn Asn Thr Met Pro Ile Ala Asp Ile Lys Ser Thr
        275                 280                 285

Asn Gly Asp Val Val Ala Lys Ala Thr Tyr Asp Ile Leu Thr Lys Thr
    290                 295                 300
```

Tyr Thr Phe Val Phe Thr Asp Tyr Val Asn Asp Lys Glu Asn Ile Asn
305                 310                 315                 320

Gly Gln Phe Ser Leu Pro Leu Phe Thr Asp Arg Ala Lys Ala Pro Lys
            325                 330                 335

Ser Gly Thr Tyr Asp Ala Asn Ile Asn Ile Ala Asp Glu Met Phe Asn
            340                 345                 350

Asn Lys Ile Thr Tyr Asn Tyr Ser Ser Pro Ile Ala Gly Ile Asp Lys
            355                 360                 365

Pro Asn Gly Ala Asn Ile Ser Ser Gln Ile Ile Gly Val Asp Thr Ala
370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
            405                 410                 415

Ile Glu Glu Ser Ser Gly Lys Val Ser Ala Thr Asp Thr Lys Leu Arg
            420                 425                 430

Ile Phe Glu Val Asn Asp Thr Ser Lys Leu Ser Asp Ser Tyr Tyr Ala
            435                 440                 445

Asp Pro Asn Asp Ser Asn Leu Lys Glu Val Thr Asn Glu Phe Lys Asp
450                 455                 460

Lys Ile Thr Tyr Lys Tyr Gln Asn Val Ala Ser Ile Asn Phe Gly Asp
465                 470                 475                 480

Ile Thr Lys Thr Tyr Val Val Leu Val Glu Gly His Tyr Asp Asn Thr
            485                 490                 495

Gly Lys Asn Leu Lys Thr Gln Val Ile Gln Glu Asn Ile Asp Pro Ala
            500                 505                 510

Thr Gly Lys Asp Tyr Ser Ile Phe Gly Trp Asn Asn Glu Asn Val Val
            515                 520                 525

Arg Tyr Gly Gly Gly Ser Ala Asp Gly Asp Ser Ala Val Asn
530                 535                 540

<210> SEQ ID NO 31
<211> LENGTH: 1626
<212> TYPE: DNA
<213> ORGANISM: Staphylococcus aureus

<400> SEQUENCE: 31
ttgaaaaaaa gaattgatta tttgtcgaat aagcagaata agtattcgat tagacgtttt      60
acagtaggta ccacatcagt aatagtaggg gcaactatac tatttgggat aggcaatcat     120
caagcacaag cttcagaaca atcgaacgat acaacgcaat cttcgaaaaa taatgcaagt     180
gcagattccg aaaaaaacaa tatgatagaa cacctcaat taaatacaac ggctaatgat      240
acatctgata ttagtgcaaa cacaaacagt gcgaatgtag atagcacagc aaaaccaatg     300
tctacacaaa cgagcaatac cactacaaca gagccagctt caacaaatga acacctcaa      360 ctgacggcaa ttaaagatca agcaactgct gcaaaaatgc aagatcaaac tgttcctcaa     420
gaagcaaatt ctcaagtaga taataaaaca cgaatgatg ctaatagcat agcgacaaac      480
agtgagctta aaatcctca acattagat ttaccacaat catcaccaca aacaatttcc       540
aatgcgcaag gaactagtaa accaagtgtt agaacgagag ctgtacgtag tcttgcagtt     600
gctgaacctg tagtaaatgc tgctgatgct aaaggtacaa atgtaaatga taagttacg      660 gcaaaagatt tcaattaga aaagactaca tttgaccta accaaagtgg taatactttt       720
atggcggcaa actttacagt gactggacaa gtgaaatcag gggattattt tacagcgaag     780

```
ttaccagata gtgtaactgg taatggagac gtggattact ctaattcgaa taatacgatg      840
ccaattgcag atatagtaaa cgataaaaat gaagttgtag caaaagcgac atatgatatt      900
ttgactaaga catatacatt tgtctttaca gattatgtaa atgataagca aaatattaat      960
gggaaatttt cattaccact atttacagac agagcaaagg cacctaaatc aggaacatat     1020
gatgcaaata ttaatattgc ggatgaaatg tttaataata aaattactta taactatagt     1080
tcgccaattg caggaattga taagccaaat ggcgcgaaca tttcttctca aattattggt     1140
gtagatacag cttcaggtca aaatacatac aagcaaacgg tatttgttaa ccctaagcaa     1200
cgagttttag gtaatacgtg ggtgtatatt aaaggttacc aagataaaat cgaagaaagt     1260
agcggtaaag taagtgctac agatacaaaa ctgagaattt ttgaagtgaa tgatacatct     1320
aaattatcag atagctacta tgcagaccca aatgactcta atcttaaaga agtaactgat     1380
caatttaagg ataaaatcac ttataaatac caaaatgtag caagtattaa ttttggtgat     1440
ataaataaaa cgtatgtcgt tttagtcgaa ggtcattatg ataaaacagg taaaaacttg     1500
aaaacgcaag tcattcaaga aaatgttgac ccagcgacag gtaaagacta cagtattttc     1560
ggttggaata atgagaatgt tgtacgttat ggtggtggaa gtgctgatgg tgattcagca     1620
gtaaat                                                                1626

<210> SEQ ID NO 32
<211> LENGTH: 542
<212> TYPE: PRT
<213> ORGANISM: Staphylococcus aureus

<400> SEQUENCE: 32

Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Ala Lys Pro Met Ser Thr Gln Thr Ser Asn Thr Thr Thr Thr Glu Pro
            100                 105                 110

Ala Ser Thr Asn Glu Thr Pro Gln Leu Thr Ala Ile Lys Asp Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Ser Ile Ala Thr Asn
145                 150                 155                 160

Ser Glu Leu Lys Asn Pro Gln Thr Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Gly Thr Asn Val Asn Asp Lys Val Thr Ala Lys Asp Phe
    210                 215                 220
```

Gln Leu Glu Lys Thr Thr Phe Asp Pro Asn Gln Ser Gly Asn Thr Phe
225                 230                 235                 240

Met Ala Ala Asn Phe Thr Val Thr Gly Gln Val Lys Ser Gly Asp Tyr
            245                 250                 255

Phe Thr Ala Lys Leu Pro Asp Ser Val Thr Gly Asn Gly Asp Val Asp
            260                 265                 270

Tyr Ser Asn Ser Asn Asn Thr Met Pro Ile Ala Asp Ile Val Asn Asp
            275                 280                 285

Lys Asn Glu Val Val Ala Lys Ala Thr Tyr Asp Ile Leu Thr Lys Thr
290                 295                 300

Tyr Thr Phe Val Phe Thr Asp Tyr Val Asn Asp Lys Gln Asn Ile Asn
305                 310                 315                 320

Gly Lys Phe Ser Leu Pro Leu Phe Thr Asp Arg Ala Lys Ala Pro Lys
            325                 330                 335

Ser Gly Thr Tyr Asp Ala Asn Ile Asn Ile Ala Asp Glu Met Phe Asn
            340                 345                 350

Asn Lys Ile Thr Tyr Asn Tyr Ser Ser Pro Ile Ala Gly Ile Asp Lys
            355                 360                 365

Pro Asn Gly Ala Asn Ile Ser Ser Gln Ile Ile Gly Val Asp Thr Ala
            370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
            405                 410                 415

Ile Glu Glu Ser Ser Gly Lys Val Ser Ala Thr Asp Thr Lys Leu Arg
            420                 425                 430

Ile Phe Glu Val Asn Asp Thr Ser Lys Leu Ser Asp Ser Tyr Tyr Ala
            435                 440                 445

Asp Pro Asn Asp Ser Asn Leu Lys Glu Val Thr Asp Gln Phe Lys Asp
            450                 455                 460

Lys Ile Thr Tyr Lys Tyr Gln Asn Val Ala Ser Ile Asn Phe Gly Asp
465                 470                 475                 480

Ile Asn Lys Thr Tyr Val Val Leu Val Glu Gly His Tyr Asp Lys Thr
            485                 490                 495

Gly Lys Asn Leu Lys Thr Gln Val Ile Gln Glu Asn Val Asp Pro Ala
            500                 505                 510

Thr Gly Lys Asp Tyr Ser Ile Phe Gly Trp Asn Asn Glu Asn Val Val
            515                 520                 525

Arg Tyr Gly Gly Gly Ser Ala Asp Gly Asp Ser Ala Val Asn
            530                 535                 540

<210> SEQ ID NO 33
<211> LENGTH: 1626
<212> TYPE: DNA
<213> ORGANISM: Staphylococcus aureus

<400> SEQUENCE: 33
ttgaaaaaaa gaattgatta tttgtcgaat aagcagaata agtattcgat tagacgtttt        60
acagtaggta ccacatcagt aatagtaggg gcaactatac tatttgggat aggcaatcat       120
caagcacaag cttcagaaca atcgaacgat acaacgcaat cttcgaaaaa taatgcaagt       180
gcagattccg aaaaaaacaa tatgatgaaa cacctcaat taaatacaac ggctaatgat       240
acatctgata ttagtgcaaa cacaaacagt gcgaatgtag atagcacagc aaaaccaatg       300

```
tctacacaaa cgagcaatac cactacaaca gagccagctt caacaaatga aacacctcaa    360
ctgacggcaa ttaaagatca agcaactgct gcaaaaatgc aagatcaaac tgttcctcaa    420
gaagcaaatt ctcaagtaga taataaaaca acgaatgatg ctaatagcat agcgacaaac    480
agtgagctta aaaatcctca aacattagat ttaccacaat catcaccaca acaatttcc     540 aatgcgcaag gaactagtaa accaagtgtt agaacgagag ctgtacgtag tcttgcagtt    600
gctgaacctg tagtaaatgc tgctgatgct aaaggtacaa atgtaaatga taagttacg     660 gcaaaagatt ttcaattaga aaagactaca tttgacccta accaagtgg taatactttt     720 atggcggcaa actttacagt gactggacaa gtgaaatcag gggattattt tacagcgaag    780
ttaccagata gtgtaactgg taatggagac gtggattact ctaattcgaa taatacgatg    840
ccaattgcag atattaaaag cacgaatggt gatgttgtag ctaaagcaac atatgatatc    900
ttgactaaga catatacatt tgtctttaca gattatgtaa atgaaaaaga aaatattaac    960
ggacaatttt cattaccttt atttacagac agagcaaagg cacctaaatc aggaacatac   1020
gatgcaaata ttaatattgc ggatgaaatg tttgataata aaattactta taactatagt   1080
tcgcctattg caggaattga taaaccaaat ggcgcaaata tttcttctca aattattggt   1140
gtagatacag cttcaggtca aaacacatac aagcaaacag tatttgttaa ccctaagcaa   1200
cgagttttag gtaatacgtg ggtgtatatt aaaggttacc aagataaaat cgaagaaagt   1260
agcggtaaag taagtgctac agatacaaaa ctgagaattt ttgaagtgaa tgatacatct   1320
aaattatcag atagctacta tgcggaccca aatgactcta accttaaaga agtaacgaat   1380
gaatttaagg ataaaatcac ttataaatac caaaatgtag caagtattaa ttttggcgat   1440
attactaaaa cgtatgttgt attagtggaa ggtcactatg ataatactgg taaaaacttg   1500
aaaacacagg ttattcaaga aaatattgac ccagcgacag gtaaagacta cagtattttc   1560
ggttggaata atgagaatgt tgtacgttat ggtggtggaa gtgctgatgg tgattcagca   1620
gtaaat                                                              1626
```

<210> SEQ ID NO 34
<211> LENGTH: 542
<212> TYPE: PRT
<213> ORGANISM: Staphylococcus aureus

<400> SEQUENCE: 34

Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Ala Lys Pro Met Ser Thr Gln Thr Ser Asn Thr Thr Thr Thr Glu Pro
            100                 105                 110

Ala Ser Thr Asn Glu Thr Pro Gln Leu Thr Ala Ile Lys Asp Gln Ala
        115                 120                 125

Thr Ala Ala Lys Met Gln Asp Gln Thr Val Pro Gln Glu Ala Asn Ser

```
            130                 135                 140
Gln Val Asp Asn Lys Thr Thr Asn Asp Ala Asn Ser Ile Ala Thr Asn
145                 150                 155                 160

Ser Glu Leu Lys Asn Pro Gln Thr Leu Asp Leu Pro Gln Ser Ser Pro
                165                 170                 175

Gln Thr Ile Ser Asn Ala Gln Gly Thr Ser Lys Pro Ser Val Arg Thr
                180                 185                 190

Arg Ala Val Arg Ser Leu Ala Val Ala Glu Pro Val Val Asn Ala Ala
                195                 200                 205

Asp Ala Lys Gly Thr Asn Val Asn Asp Lys Val Thr Ala Lys Asp Phe
                210                 215                 220

Gln Leu Glu Lys Thr Thr Phe Asp Pro Asn Gln Ser Gly Asn Thr Phe
225                 230                 235                 240

Met Ala Ala Asn Phe Thr Val Thr Gly Gln Val Lys Ser Gly Asp Tyr
                245                 250                 255

Phe Thr Ala Lys Leu Pro Asp Ser Val Thr Gly Asn Gly Asp Val Asp
                260                 265                 270

Tyr Ser Asn Ser Asn Asn Thr Met Pro Ile Ala Asp Ile Lys Ser Thr
                275                 280                 285

Asn Gly Asp Val Val Ala Lys Ala Thr Tyr Asp Ile Leu Thr Lys Thr
                290                 295                 300

Tyr Thr Phe Val Phe Thr Asp Tyr Val Asn Glu Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asp
                340                 345                 350

Asn Lys Ile Thr Tyr Asn Tyr Ser Ser Pro Ile Ala Gly Ile Asp Lys
                355                 360                 365

Pro Asn Gly Ala Asn Ile Ser Ser Gln Ile Ile Gly Val Asp Thr Ala
                370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
                420                 425                 430

Ile Phe Glu Val Asn Asp Thr Ser Lys Leu Ser Asp Ser Tyr Tyr Ala
                435                 440                 445

Asp Pro Asn Asp Ser Asn Leu Lys Glu Val Thr Asn Glu Phe Lys Asp
                450                 455                 460

Lys Ile Thr Tyr Lys Tyr Gln Asn Val Ala Ser Ile Asn Phe Gly Asp
465                 470                 475                 480

Ile Thr Lys Thr Tyr Val Val Leu Val Glu Gly His Tyr Asp Asn Thr
                485                 490                 495

Gly Lys Asn Leu Lys Thr Gln Val Ile Gln Glu Asn Ile Asp Pro Ala
                500                 505                 510

Thr Gly Lys Asp Tyr Ser Ile Phe Gly Trp Asn Asn Glu Asn Val Val
                515                 520                 525

Arg Tyr Gly Gly Gly Ser Ala Asp Gly Asp Ser Ala Val Asn
                530                 535                 540

<210> SEQ ID NO 35
```

```
<211> LENGTH: 1626
<212> TYPE: DNA
<213> ORGANISM: Staphylococcus aureus

<400> SEQUENCE: 35
ttgaaaaaaa gaattgatta tttgtcgaat aagcagaata agtattcgat tagacgtttt        60
acagtaggta ccacatcagt aatagtaggg gcaactatac tatttgggat aggcaatcat       120
caagcacaag cttcagaaca atcgaacgat acaacgcaat cttcgaaaaa taatgcaagt       180
gcagattccg aaaaaaataa tatgatagaa acacctcaat taaatacaac ggctaatgat       240
acatctgata ttagtgcaaa cacaaacagt gcgaatgtag atagcacagc aaaaccaatg       300
tctacacaaa cgagcaatac cactacaaca gagccagctt caacaaatga acacctcaa        360
ccgacggcaa ttaaagatca agcaactgct gcaaaaatgc aagatcaaac tgttcctcaa       420
gaagcaaatt ctcaagtaga taataaaaca acgaatgatg ctaatagcat agcaacaaac       480
agtgaactta aaaatcctca acattagat ttaccacaat catcaccaca aacgatttcc        540
aatgcgcaag gaactagtaa accaagtgtt agaacgagag ctgtacgtag tcttgcagtt       600
gctgaacctg tagtaaatgc tgctgatgct aaaggtacaa atgtaaatga taaagttacg       660
gcaagtaatc tacagttgca aaagactaca tttgacccta accaaagtgg aaatacattt       720
atggcggcaa attttacagt gacagataaa gtgaaatcag gggattattt tacagcgaag       780
ttaccagata gtttaactgg taatggagac gtggattact ctaattcaaa taatacgatg       840
ccaattgcag atattaaaag tacgaatggc gatgttgtag ctaaagcaac atatgatatc       900
ttgactaaga cgtatacatt tgtctttaca gattatgtaa atgataaaga aaatattaac       960
gggcaatttt cattaccttt atttacagac cgagcaaagg cacctaaatc aggaacatat      1020
gatgcaaata ttaatattgc ggatgaaatg tttaataata aaattactta taactatagt      1080
tcgccaattg caggaattga taagccaaat ggcgcgaaca tttcttctca aattattggt      1140
gtagatacag cttcaggtca aaacacatac aagcaaacgg tatttgttaa ccctaagcaa      1200
cgagttttag gtaatacgtg ggtgtatatt aaaggttacc aagataaaat cgaagaaagt      1260
agcggtaaag taagtgctac agatacaaaa ctgagaattt ttgaagtgaa tgatacatct      1320
aaattatcag atagctacta tgcagaccca aatgactcta accttaaaga agtaactgat      1380
caatttaagg ataaaatcac ttataaatac caaaacgtag caagtattaa ttttggtgat      1440
ataaataaaa cgtatgtcgt tttagttgaa ggtcactatg ataatactgg aaaaaacttg      1500
aaaacacagg ttattcaaga aaatattgac ccagcgacag gtaaagacta cagtattttc      1560
ggatggaata atgagaatgt tgtacgttat ggtggtggaa gtgctgatgg tgattcagca      1620
gtaaat                                                                 1626

<210> SEQ ID NO 36
<211> LENGTH: 542
<212> TYPE: PRT
<213> ORGANISM: Staphylococcus aureus

<400> SEQUENCE: 36

Leu Lys Lys Arg Ile Asp Tyr Leu Ser Asn Lys Gln Asn Lys Tyr Ser
 1               5                  10                  15

Ile Arg Arg Phe Thr Val Gly Thr Thr Ser Val Ile Val Gly Ala Thr
                20                  25                  30

Ile Leu Phe Gly Ile Gly Asn His Gln Ala Gln Ala Ser Glu Gln Ser
            35                  40                  45
```

```
Asn Asp Thr Thr Gln Ser Ser Lys Asn Asn Ala Ser Ala Asp Ser Glu
    50              55                  60

Lys Asn Asn Met Ile Glu Thr Pro Gln Leu Asn Thr Thr Ala Asn Asp
65              70                  75                  80

Thr Ser Asp Ile Ser Ala Asn Thr Asn Ser Ala Asn Val Asp Ser Thr
                85                  90                  95

Ala Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asp Gln Ala
            115                 120                 125

Thr Ala Ala Lys Met Gln Asp Gln Thr Val Pro Gln Glu Ala Asn Ser
130                 135                 140

Gln Val Asp Asn Lys Thr Thr Asn Asp Ala Asn Ser Ile Ala Thr Asn
145                 150                 155                 160

Ser Glu Leu Lys Asn Pro Gln Thr Leu Asp Leu Pro Gln Ser Ser Pro
                165                 170                 175

Gln Thr Ile Ser Asn Ala Gln Gly Thr Ser Lys Pro Ser Val Arg Thr
                180                 185                 190

Arg Ala Val Arg Ser Leu Ala Val Ala Glu Pro Val Val Asn Ala Ala
            195                 200                 205

Asp Ala Lys Gly Thr Asn Val Asn Asp Lys Val Thr Ala Ser Asn Leu
210                 215                 220

Gln Leu Gln Lys Thr Thr Phe Asp Pro Asn Gln Ser Gly Asn Thr Phe
225                 230                 235                 240

Met Ala Ala Asn Phe Thr Val Thr Asp Lys Val Lys Ser Gly Asp Tyr
                245                 250                 255

Phe Thr Ala Lys Leu Pro Asp Ser Leu Thr Gly Asn Gly Asp Val Asp
                260                 265                 270

Tyr Ser Asn Ser Asn Asn Thr Met Pro Ile Ala Asp Ile Lys Ser Thr
            275                 280                 285

Asn Gly Asp Val Val Ala Lys Ala Thr Tyr Asp Ile Leu Thr Lys Thr
            290                 295                 300

Tyr Thr Phe Val Phe Thr Asp Tyr Val Asn Asp Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
            340                 345                 350

Asn Lys Ile Thr Tyr Asn Tyr Ser Ser Pro Ile Ala Gly Ile Asp Lys
            355                 360                 365

Pro Asn Gly Ala Asn Ile Ser Ser Gln Ile Ile Gly Val Asp Thr Ala
            370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
                420                 425                 430

Ile Phe Glu Val Asn Asp Thr Ser Lys Leu Ser Asp Ser Tyr Tyr Ala
            435                 440                 445

Asp Pro Asn Asp Ser Asn Leu Lys Glu Val Thr Asp Gln Phe Lys Asp
450                 455                 460

Lys Ile Thr Tyr Lys Tyr Gln Asn Val Ala Ser Ile Asn Phe Gly Asp
```

| | | | | | 465 | | | 470 | | | 475 | | | 480 | |
|---|---|---|---|---|---|---|---|---|---|---|---|---|---|---|---|

Ile Asn Lys Thr Tyr Val Val Leu Val Glu Gly His Tyr Asp Asn Thr
                        485                    490                    495

Gly Lys Asn Leu Lys Thr Gln Val Ile Gln Glu Asn Ile Asp Pro Ala
                   500                    505                    510

Thr Gly Lys Asp Tyr Ser Ile Phe Gly Trp Asn Asn Glu Asn Val Val
               515                    520                  525

Arg Tyr Gly Gly Gly Ser Ala Asp Gly Asp Ser Ala Val Asn
        530                    535                  540

<210> SEQ ID NO 37
<211> LENGTH: 1626
<212> TYPE: DNA
<213> ORGANISM: Staphylococcus aureus

<400> SEQUENCE: 37

```
ttgaaaaaaa gaattgatta tttgtcgaat aagcagaata agtattcgat tagacgtttt      60
acagtaggta ccacatcagt aatagtaggg gcaactatac tatttgggat aggcaatcat     120
caagcacaag cttcagaaca atcgaacgat acaacgcaat cttcgaaaaa taatgcaagt     180
gcagattccg aaaaaacaa tatgatgaa acacctcaat taaatacaac ggctaatgat     240
acatctgata ttagtgcaaa cacaaacagt gcgaatgtag atagcacaac aaaaccaatg     300
tctacacaaa cgagcaatac cactacaaca gagccagctt caacaaatga acacctcaa      360
ccgacggcaa ttaaagatca agcaactgct gcaaaaatgc aagatcaaac tgttcctcaa     420
gaagcaaatt ctcaagtaga taataaaaca acgaatgatg ctaatagcat agcgacaaac     480
agtgagctta aaaatcctca acattagat ttaccacaat catcaccaca aacaatttcc      540
aatgcgcaag gaactagtaa accaagtgtt agaacgagag ctgtacgtag tcttgcagtt     600
gctgaacctg tagtaaatgc tgctgatgct aaaggtacaa atgtaaatga taaagttacg     660
gcaaaagatt tcaattaga aaagactaca tttgaccta accaagtgg taatactttt      720
atggcggcaa actttacagt gactggacaa gtgaaatcag gggattattt tacagcgaag     780
ttaccagata gtgtaactgg taatggagac gtggattact ctaattcgaa taatacgatg     840
ccaattgcag atattaaaag cacgaatggt gatgttgtag ctaaagcaac atatgatatc     900
ttgactaaga catatacatt tgtctttaca gattatgtaa atgaaaaaga aaatattaac     960
ggacaatttt cattaccttt atttacagac agagcaaagg cacctaaatc aggaacatac    1020
gatgcaaata ttaatattgc ggatgaaatg tttgataata aaattactta taactatagt    1080
tcgcctattg caggaattga taaccaaat ggcgcaaata tttcttctca aattattggt    1140
gtagatacag cttcaggtca aaacacatac aagcaaacag tatttgttaa ccctaagcaa    1200
cgagttttag gtaatacgtg ggtgtatatt aaaggttacc aagataaaat cgaagaaagt    1260
agcggtaaag taagtgctac agatacaaaa ctgagaattt ttgaagtgaa tgatacatct    1320
aaattatcag atagctacta tgcggaccca aatgactcta accttaaaga agtaacgaat    1380
gaatttaagg ataaaatcac ttataaatac caaaatgtag caagtattaa ttttggcgat    1440
attactaaaa cgtatgttgt attagtggaa ggtcactatg ataatactgg taaaaacttg    1500
aaaacacagg ttattcaaga aaatattgac ccagcgacag gtaaagacta cagtattttc    1560
ggttggaata tgagaatgt tgtacgttat ggtggtggaa gtgctgatgg tgattcagca    1620
gtaaat                                                               1626
```

<210> SEQ ID NO 38
<211> LENGTH: 542
<212> TYPE: PRT
<213> ORGANISM: Staphylococcus aureus

<400> SEQUENCE: 38

```
Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Thr Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asp Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Ser Ile Ala Thr Asn
145                 150                 155                 160

Ser Glu Leu Lys Asn Pro Gln Thr Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Gly Thr Asn Val Asn Asp Lys Val Thr Ala Lys Asp Phe
    210                 215                 220

Gln Leu Glu Lys Thr Thr Phe Asp Pro Asn Gln Ser Gly Asn Thr Phe
225                 230                 235                 240

Met Ala Ala Asn Phe Thr Val Thr Gly Gln Val Lys Ser Gly Asp Tyr
                245                 250                 255

Phe Thr Ala Lys Leu Pro Asp Ser Val Thr Gly Asn Gly Asp Val Asp
            260                 265                 270

Tyr Ser Asn Ser Asn Asn Thr Met Pro Ile Ala Asp Ile Lys Ser Thr
        275                 280                 285

Asn Gly Asp Val Val Ala Lys Ala Thr Tyr Asp Ile Leu Thr Lys Thr
    290                 295                 300

Tyr Thr Phe Val Phe Thr Asp Tyr Val Asn Glu Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asp
            340                 345                 350

Asn Lys Ile Thr Tyr Asn Tyr Ser Ser Pro Ile Ala Gly Ile Asp Lys
        355                 360                 365

Pro Asn Gly Ala Asn Ile Ser Ser Gln Ile Ile Gly Val Asp Thr Ala
    370                 375                 380
```

```
Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
            405                 410                 415

Ile Glu Glu Ser Ser Gly Lys Val Ser Ala Thr Asp Thr Lys Leu Arg
            420                 425                 430

Ile Phe Glu Val Asn Asp Thr Ser Lys Leu Ser Asp Ser Tyr Tyr Ala
            435                 440                 445

Asp Pro Asn Asp Ser Asn Leu Lys Glu Val Thr Asn Glu Phe Lys Asp
        450                 455                 460

Lys Ile Thr Tyr Lys Tyr Gln Asn Val Ala Ser Ile Asn Phe Gly Asp
465                 470                 475                 480

Ile Thr Lys Thr Tyr Val Val Leu Val Glu Gly His Tyr Asp Asn Thr
            485                 490                 495

Gly Lys Asn Leu Lys Thr Gln Val Ile Gln Glu Asn Ile Asp Pro Ala
            500                 505                 510

Thr Gly Lys Asp Tyr Ser Ile Phe Gly Trp Asn Asn Glu Asn Val Val
            515                 520                 525

Arg Tyr Gly Gly Gly Ser Ala Asp Gly Asp Ser Ala Val Asn
            530                 535                 540

<210> SEQ ID NO 39
<211> LENGTH: 1626
<212> TYPE: DNA
<213> ORGANISM: Staphylococcus aureus

<400> SEQUENCE: 39
ttgaaaaaaa gaattgatta tttgtcgaat aagcagaata agtattcgat tagacgtttt      60
acagtaggta ccacatcagt aatagtaggg gcaactatac tatttgggat aggcaatcat    120
caagcacaag cttcagaaca atcgaacgat acaacacaat cttcgaaaaa taatgcaagt    180
gcagattccg aaaaaaacaa tatgatgaaa cacctcaat taaatacaac ggctaatgat    240
acatctgata ttagtgcaaa cacaaacagt gcgaatgtag atagcacagc aaaaccaatg    300
tctacacaaa cgagcaatac cactacaaca gagccagctt caacaaatga acaccctcaa    360
ccgacggcaa ttaaagatca agcaactgct gcaaaaatgc aagatcaaac tgttcctcaa    420
gaagcaaatt ctcaagtaga taataaaaca cgaatgatg ctaatagcat agcaacaaac    480
agtgagctta aaaatcctca aacattagat ttaccacaat catcaccaca acgatttcc    540 aatgcgcaag gaactagtaa accgagtgtt agaacgagag ctgtacgtag tcttgcagtt    600
gctgaacctg tagtaaatgc tgctgatgct aaaggtacaa atgtaaatgg tcaagttacg    660
gcaagtgatt tcaagttaga aaagactaca tttgaccta accaaagtgg taacacattt    720
atggcggcaa aatttacagt gactggacaa gtgaaagcag gggattattt tacagcgaag    780
ttaccagata gtgtaaatgg taatggagat gtggattact ctaattcaaa taatacgatg    840
ccaattgcag atattaaaag tacgaatggc gatgttgtag ctaaagcaac atatgatatc    900
ttgactaaga cgtatacatt tgtctttaca gattatgtaa ataataaaga aaatattaac    960
ggacaatttt cattaccttt atttacagac cgagcaaagg cacctaaatc aggaacatat   1020
gatgcgaata ttaatattgc ggatgaaatg tttaataata aaattactta taactatagt   1080
tcgccaattg caggaattga taaaccaaat ggcgcgaaca tttcttctca aattattggt   1140
gtagatacag cttcaggtca aaacacatac aagcaaacag tatatgttaa ccctaagcaa   1200
cgagttttag gtaatacgtg ggtgtatatt aaaggttacc aagataaaat cgaagaaagt   1260
```

```
agcggtaaag taagtgctac agatacaaaa ctgagaattt ttgaagtgaa tgatacatct   1320
aaattatcag atagctacta tgcagaccca aatgattcga atcttaaaga agtaacgaat   1380
gagtttaagg ataaaatcac ttataaatac caaaatgtag caagtattaa ttttggcgat   1440
attactaaaa cgtatgttgt attagtggaa ggtcactatg ataatactgg taaaaacttg   1500
aaaacacagg ttattcaaga aaatattgac ccagcgacag gtaaagacta cagtattttc   1560
ggttggaata atgagaatgt tgtacgttat ggtggtggaa gtgctgatgg tgattcagca   1620
gtaaat                                                              1626
```

<210> SEQ ID NO 40
<211> LENGTH: 542
<212> TYPE: PRT
<213> ORGANISM: Staphylococcus aureus

<400> SEQUENCE: 40

Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Ala Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asp Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Ser Ile Ala Thr Asn
145                 150                 155                 160

Ser Glu Leu Lys Asn Pro Gln Thr Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Gly Thr Asn Val Asn Gly Gln Val Thr Ala Ser Asp Phe
    210                 215                 220

Lys Leu Glu Lys Thr Thr Phe Asp Pro Asn Gln Ser Gly Asn Thr Phe
225                 230                 235                 240

Met Ala Ala Lys Phe Thr Val Thr Gly Gln Val Lys Ala Gly Asp Tyr
                245                 250                 255

Phe Thr Ala Lys Leu Pro Asp Ser Val Asn Gly Asn Gly Asp Val Asp
            260                 265                 270

Tyr Ser Asn Ser Asn Asn Thr Met Pro Ile Ala Asp Ile Lys Ser Thr
        275                 280                 285

Asn Gly Asp Val Val Ala Lys Ala Thr Tyr Asp Ile Leu Thr Lys Thr
    290                 295                 300

```
Tyr Thr Phe Val Phe Thr Asp Tyr Val Asn Asn Lys Glu Asn Ile Asn
305                 310                 315                 320

Gly Gln Phe Ser Leu Pro Leu Phe Thr Asp Arg Ala Lys Ala Pro Lys
            325                 330                 335

Ser Gly Thr Tyr Asp Ala Asn Ile Asn Ile Ala Asp Glu Met Phe Asn
        340                 345                 350

Asn Lys Ile Thr Tyr Asn Tyr Ser Ser Pro Ile Ala Gly Ile Asp Lys
    355                 360                 365

Pro Asn Gly Ala Asn Ile Ser Ser Gln Ile Ile Gly Val Asp Thr Ala
370                 375                 380

Ser Gly Gln Asn Thr Tyr Lys Gln Thr Val Tyr Val Asn Pro Lys Gln
385                 390                 395                 400

Arg Val Leu Gly Asn Thr Trp Val Tyr Ile Lys Gly Tyr Gln Asp Lys
            405                 410                 415

Ile Glu Glu Ser Ser Gly Lys Val Ser Ala Thr Asp Thr Lys Leu Arg
        420                 425                 430

Ile Phe Glu Val Asn Asp Thr Ser Lys Leu Ser Asp Ser Tyr Tyr Ala
    435                 440                 445

Asp Pro Asn Asp Ser Asn Leu Lys Glu Val Thr Asn Glu Phe Lys Asp
450                 455                 460

Lys Ile Thr Tyr Lys Tyr Gln Asn Val Ala Ser Ile Asn Phe Gly Asp
465                 470                 475                 480

Ile Thr Lys Thr Tyr Val Val Leu Val Glu Gly His Tyr Asp Asn Thr
            485                 490                 495

Gly Lys Asn Leu Lys Thr Gln Val Ile Gln Glu Asn Ile Asp Pro Ala
        500                 505                 510

Thr Gly Lys Asp Tyr Ser Ile Phe Gly Trp Asn Asn Glu Asn Val Val
    515                 520                 525

Arg Tyr Gly Gly Gly Ser Ala Asp Gly Asp Ser Ala Val Asn
530                 535                 540

<210> SEQ ID NO 41
<211> LENGTH: 1626
<212> TYPE: DNA
<213> ORGANISM: Staphylococcus aureus

<400> SEQUENCE: 41
ttgaaaaaaa gaattgatta tttgtcgaat aggcagaata agtattcgat tagacgtttt      60
acagtaggta ccacatcagt aatagtaggg gcaactatac tatttgggat aggcaatcat     120
caagcacaag cttcagaaca atcgaacgat acaacgcaat cttcgaaaaa taatgcaagt     180
gcagattccg aaaaaaacaa tatgatgaa acacctcaat taaatacaac ggctaatgat     240
acatctgata ttagtgcaaa cacaaacagt gcgaatgtag atagcacaac aaaaccaatg     300
tctacacaaa cgagcaatac cactacaaca gagccagctt caacaaatga acacctcaa      360 ccgacggcaa ttaaaaatca agcaactgct gcaaaaatgc aagatcaaac tgttcctcaa     420
gaagcaaatt ctcaagtaga taataaaaca acgaatgatg ctaatagcat agcaacaaac     480
agtgagctta aaaattctca acattagat ttaccacaat catcaccaca acgatttcc      540 aatgcgcaag gaactagtaa accaagtgtt agaacgagag ctgtacgtag tttagctgtt     600
gctgaaccgg tagtaaatgc tgctgatgct aaaggtacaa atgtaaatga taaagttacg     660
gcaagtaatt tcaagttaga aaagactaca tttgacccta tcaaagtgg taacacattt       720 atggcggcaa attttacagt gacagataaa gtgaaatcag gggattattt tacagcgaag     780
```

-continued

```
ttaccagata gtttaactgg taatggagac gtggattatt ctaattcaaa taatacgatg      840
ccaattgcag acattaaaag tacgaatggc gatgttgtag ctaaagcaac atatgatatc      900
ttgactaaga cgtatacatt tgtctttaca gattatgtaa ataataaaga aaatattaac      960
ggacaatttt cattaccttt atttacagac cgagcaaagg cacctaaatc aggaacatat     1020
gatgcgaata ttaatattgc ggatgaaatg tttaataata aaattactta taactatagt     1080
tcgccaattg caggaattga taaaccaaat ggcgcgaaca tttcttctca aattattggt     1140
gtagatacag cttcaggtca aaacacatac aagcaaacag tatttgttaa ccctaagcaa     1200
cgagttttag gtaatacgtg ggtgtatatt aaaggctacc aagataaaat cgaagaaagt     1260
agcggtaaag taagtgctac agatacaaaa ctgagaattt ttgaagtgaa tgatacatct     1320
aaattatcag atagctacta tgcagatcca atgactctaa accttaaaga agtaacagac     1380
caatttaaaa atagaatcta ttatgagcat ccaaatgtag ctagtattaa atttggtgat     1440
attactaaaa catatgtagt attagtagaa gggcattacg acaatacagg taagaactta     1500
aaaactcagg ttattcaaga aaatgttgat cctgtaacaa atagagacta cagtattttc     1560
ggttggaata atgagaatgt tgtacgttat ggtggtggaa gtgctgatgg tgattcagca     1620
gtaaat                                                                1626
```

<210> SEQ ID NO 42
<211> LENGTH: 542
<212> TYPE: PRT
<213> ORGANISM: Staphylococcus aureus

<400> SEQUENCE: 42

```
Leu Lys Lys Arg Ile Asp Tyr Leu Ser Asn Arg Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Thr Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asn Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Ser Ile Ala Thr Asn
145                 150                 155                 160

Ser Glu Leu Lys Asn Ser Gln Thr Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Gly Thr Asn Val Asn Asp Lys Val Thr Ala Ser Asn Phe
```

```
                210                 215                 220
Lys Leu Glu Lys Thr Thr Phe Asp Pro Asn Gln Ser Gly Asn Thr Phe
225                 230                 235                 240

Met Ala Ala Asn Phe Thr Val Thr Asp Lys Val Lys Ser Gly Asp Tyr
                245                 250                 255

Phe Thr Ala Lys Leu Pro Asp Ser Leu Thr Gly Asn Gly Asp Val Asp
                260                 265                 270

Tyr Ser Asn Ser Asn Asn Thr Met Pro Ile Ala Asp Ile Lys Ser Thr
                275                 280                 285

Asn Gly Asp Val Val Ala Lys Ala Thr Tyr Asp Ile Leu Thr Lys Thr
                290                 295                 300

Tyr Thr Phe Val Phe Thr Asp Tyr Val Asn Asn Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
                340                 345                 350

Asn Lys Ile Thr Tyr Asn Tyr Ser Ser Pro Ile Ala Gly Ile Asp Lys
                355                 360                 365

Pro Asn Gly Ala Asn Ile Ser Ser Gln Ile Ile Gly Val Asp Thr Ala
                370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
                420                 425                 430

Ile Phe Glu Val Asn Asp Thr Ser Lys Leu Ser Asp Ser Tyr Tyr Ala
                435                 440                 445

Asp Pro Asn Asp Ser Asn Leu Lys Glu Val Thr Asp Gln Phe Lys Asn
450                 455                 460

Arg Ile Tyr Tyr Glu His Pro Asn Val Ala Ser Ile Lys Phe Gly Asp
465                 470                 475                 480

Ile Thr Lys Thr Tyr Val Val Leu Val Glu Gly Tyr Tyr Asp Asn Thr
                485                 490                 495

Gly Lys Asn Leu Lys Thr Gln Val Ile Gln Glu Asn Val Asp Pro Val
                500                 505                 510

Thr Asn Arg Asp Tyr Ser Ile Phe Gly Trp Asn Asn Glu Asn Val Val
                515                 520                 525

Arg Tyr Gly Gly Gly Ser Ala Asp Gly Asp Ser Ala Val Asn
530                 535                 540

<210> SEQ ID NO 43
<211> LENGTH: 1626
<212> TYPE: DNA
<213> ORGANISM: Staphylococcus aureus

<400> SEQUENCE: 43
ttgaaaaaaa gaattgatta tttgtcgaat aagcagaata agtattcgat tagacgtttt      60
acagtaggta ccacatcagt aatagtaggg gcaactatac tatttgggat aggcaatcat     120
caagcacaag cttcagaaca atcgaacgat acaacgcaat cttcgaaaaa taatgcaagt     180
gcagattccg aaaaaacaa tatgatagaa acacctcaat taaatacaac ggctaatgat     240
acatctgata ttagtgcaaa cacaaacagt gcgaatgtag atagcacaac aaaaccaatg     300
```

-continued

```
tctacacaaa cgagcaatac cactacaaca gagccagctt caacaaatga aacacctcaa      360
ccgacggcaa ttaaaaatca agcaactgct gcaaaaatgc aagatcaaac tgttcctcaa      420
gaagcaaatt ctcaagtaga taataaaaca cgaatgatg  ctaatagcat agcaacaacc      480
agtgagctta aaaattctca acattagat  ttaccacaat catcaccaca aacgatttcc      540
aatgcgcaag gaactagtaa accaagtgtt agaacgagag ctgtacgtag tttagctgtt      600
gctgaaccgg tagtaaatgc tgctgatgct aaaggtacaa atgtaaatga taagttacg       660 gcaagtaatt tcaagttaga aaagactaca tttgaccta  atcaaagtgg taacacattt      720
atggcggcaa attttacagt gacagataaa gtgaaatcag gggattattt tacagcgaag      780
ttaccagata gtttaactgg taatggagac gtggattatt ctaattcaaa taatacgatg      840
ccaattgcag acattaaaag tacgaatggc gatgttgtag ctaaagcaac atatgatatc      900
ttgactaaga cgtatacatt tgtctttaca gattatgtaa ataataaaga aaatattaac      960
ggacaatttt cattaccttt atttacagac cgagcaaagg cacctaaatc aggaacatat     1020
gatgcgaata ttaatattgc ggatgaaatg tttaataata aaattactta taactatagt     1080
tcgccaattg caggaattga taaaccaaat ggcgcgaaca tttcttctca aattattggt     1140
gtagatacag cttcaggtca aaacacatac aagcaaacag tatttgttaa ccctaagcaa     1200
cgagttttag gtaatacgtg ggtgtatatt aaaggctacc aagataaaat cgaagaaagt     1260
agcggtaaag taagtgctac agatacaaaa ctgagaattt ttgaagtgaa tgatacatct     1320
aaattatcag atagctacta tgcagatcca aatgactcta accttaaaga agtaacagac     1380
caatttaaaa atagaatcta ttatgagcat ccaaatgtag ctagtattaa atttggtgat     1440
attactaaaa catatgtagt attagtagaa gggcattacg acaatacagg taagaactta     1500
aaaactcagg ttattcaaga aaatgttgat cctgtaacaa atagagacta cagtattttc     1560
ggttggaata tgagaatgt  tgtacgttat ggtggtggaa gtgctgatgg tgattcagca     1620
gtaaat                                                                1626
```

<210> SEQ ID NO 44
<211> LENGTH: 542
<212> TYPE: PRT
<213> ORGANISM: Staphylococcus aureus

<400> SEQUENCE: 44

```
Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Thr Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asn Gln Ala
        115                 120                 125
```

-continued

```
Thr Ala Ala Lys Met Gln Asp Gln Thr Val Pro Gln Glu Ala Asn Ser
    130                 135                 140
Gln Val Asp Asn Lys Thr Thr Asn Asp Ala Asn Ser Ile Ala Thr Thr
145                 150                 155                 160
Ser Glu Leu Lys Asn Ser Gln Thr Leu Asp Leu Pro Gln Ser Ser Pro
                165                 170                 175
Gln Thr Ile Ser Asn Ala Gln Gly Thr Ser Lys Pro Ser Val Arg Thr
            180                 185                 190
Arg Ala Val Arg Ser Leu Ala Val Ala Glu Pro Val Val Asn Ala Ala
        195                 200                 205
Asp Ala Lys Gly Thr Asn Val Asn Asp Lys Val Thr Ala Ser Asn Phe
    210                 215                 220
Lys Leu Glu Lys Thr Thr Phe Asp Pro Asn Gln Ser Gly Asn Thr Phe
225                 230                 235                 240
Met Ala Ala Asn Phe Thr Val Thr Asp Lys Val Lys Ser Gly Asp Tyr
                245                 250                 255
Phe Thr Ala Lys Leu Pro Asp Ser Leu Thr Gly Asn Gly Asp Val Asp
            260                 265                 270
Tyr Ser Asn Ser Asn Asn Thr Met Pro Ile Ala Asp Ile Lys Ser Thr
        275                 280                 285
Asn Gly Asp Val Val Ala Lys Ala Thr Tyr Asp Ile Leu Thr Lys Thr
    290                 295                 300
Tyr Thr Phe Val Phe Thr Asp Tyr Val Asn Asn Lys Glu Asn Ile Asn
305                 310                 315                 320
Gly Gln Phe Ser Leu Pro Leu Phe Thr Asp Arg Ala Lys Ala Pro Lys
                325                 330                 335
Ser Gly Thr Tyr Asp Ala Asn Ile Asn Ile Ala Asp Glu Met Phe Asn
            340                 345                 350
Asn Lys Ile Thr Tyr Asn Tyr Ser Ser Pro Ile Ala Gly Ile Asp Lys
        355                 360                 365
Pro Asn Gly Ala Asn Ile Ser Ser Gln Ile Ile Gly Val Asp Thr Ala
    370                 375                 380
Ser Gly Gln Asn Thr Tyr Lys Gln Thr Val Phe Val Asn Pro Lys Gln
385                 390                 395                 400
Arg Val Leu Gly Asn Thr Trp Val Tyr Ile Lys Gly Tyr Gln Asp Lys
                405                 410                 415
Ile Glu Glu Ser Ser Gly Lys Val Ser Ala Thr Asp Thr Lys Leu Arg
            420                 425                 430
Ile Phe Glu Val Asn Asp Thr Ser Lys Leu Ser Asp Ser Tyr Tyr Ala
        435                 440                 445
Asp Pro Asn Asp Ser Asn Leu Lys Glu Val Thr Asp Gln Phe Lys Asn
    450                 455                 460
Arg Ile Tyr Tyr Glu His Pro Asn Val Ala Ser Ile Lys Phe Gly Asp
465                 470                 475                 480
Ile Thr Lys Thr Tyr Val Val Leu Val Glu Gly His Tyr Asp Asn Thr
                485                 490                 495
Gly Lys Asn Leu Lys Thr Gln Val Ile Gln Glu Asn Val Asp Pro Val
            500                 505                 510
Thr Asn Arg Asp Tyr Ser Ile Phe Gly Trp Asn Asn Glu Asn Val Val
        515                 520                 525
Arg Tyr Gly Gly Gly Ser Ala Asp Gly Asp Ser Ala Val Asn
    530                 535                 540
```

```
<210> SEQ ID NO 45
<211> LENGTH: 1626
<212> TYPE: DNA
<213> ORGANISM: Staphylococcus aureus

<400> SEQUENCE: 45
ttgaaaaaaa gaattgatta tttgtcgaat aagcagaata agtattcgat tagacgtttt      60
acagtaggta ccacatcagt aatagtaggg gcaactatac tatttgggat aggcaatcat     120
caagcacaag cttcagaaca atcgaacgat acaacgcaat cttcgaaaaa taatgcaagt     180
gcagattccg aaaaaaacaa tatgatagaa cacctcaat taaatacaac ggctaatgat     240
acatctgata ttagtgcaaa cacaaacagt gcgaatgtag atagcacagc aaaaccaatg     300
tctacacaaa cgagcaatac cactacaaca gagccagctt caacaaatga acacctcaa     360 ccgacggcaa ttaaagatca agcaactgct gcaaaaatgc aagatcaaac tgttcctcaa     420
gaagcaaatt ctcaagtaga ataaaaaca cgaatgatg ctaatagcat agcgacaaac      480
tgtgagctta aaaatcctca aacattagat ttaccacaat catcaccaca aacaatttcc     540
aatgcgcaag gaactagtaa accaagtgtt agaacgagag ctgtacgtag tcttgcagtt     600
gctgaacctg tagtaaatgc tgctgatgct aaaggtacaa atgtaaatga taagttacg      660 gcaaaagatt ttcaattaga aaagaccaca tttgacccta accaaagtgg taatactttt      720
atggcggcaa actttacagt gactggacaa gtgaaatcag gggattattt tacagcgaag     780
ttaccagata gtgtaactgg taatggagac gtggattact ctaattcgaa taatacgatg     840
ccaattgcag atattaaaag tacgaatggc gatgttgtag ctaaagcaac atatgatatc     900
ttgactaaga cgtatacatt tgtctttaca gattatgtaa ataataaaga aaatattaac     960
ggacaatttt cattaccttt atttacagac cgagcaaagg cacctaaatc aggaacatat    1020
gatgcgaata ttaatattgc ggatgaaatg tttaataata aaattactta taactatagt    1080
tcgccaattg caggaattga taaaccaaat ggcgcgaaca tttcttctca aattattggt    1140
gtagatacag cttcaggtca aaacacatac aagcaaacag tatttgttaa ccctaagcaa    1200
cgagttttag gtaatacgtg ggtgtatatt aaaggttacc aagataaaat cgaagaaagt    1260
agcggtaaag taagtgctac agatacaaaa ctgagaattt ttgaagtgaa tgatacatct    1320
aaattatcag atagctacta tgcggaccca aatgactcta accttaaaga agtaacgaat    1380
gagtttaagg ataaaatcac ttataaatac caaaatgtag caagtattaa ttttggcgat    1440
attactaaaa cgtatgttgt attagtggaa ggtcactatg ataatactgg taaaaacttg    1500
aaaacacagg ttattcaaga aaatattgac ccagcgacag gtaaagacta cagtattttc    1560
ggttggaata atgagaatgt tgtacgttat ggtggtggaa gtgctgatgg tgattcagca    1620
gtaaat                                                                1626

<210> SEQ ID NO 46
<211> LENGTH: 542
<212> TYPE: PRT
<213> ORGANISM: Staphylococcus aureus

<400> SEQUENCE: 46

Leu Lys Lys Arg Ile Asp Tyr Leu Ser Asn Lys Gln Asn Lys Tyr Ser
1               5                  10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45
```

```
Asn Asp Thr Thr Gln Ser Ser Lys Asn Asn Ala Ser Ala Asp Ser Glu
     50                  55                  60

Lys Asn Asn Met Ile Glu Thr Pro Gln Leu Asn Thr Thr Ala Asn Asp
 65                  70                  75                  80

Thr Ser Asp Ile Ser Ala Asn Thr Asn Ser Ala Asn Val Asp Ser Thr
                 85                  90                  95

Ala Lys Pro Met Ser Thr Gln Thr Ser Asn Thr Thr Thr Glu Pro
            100                 105                 110

Ala Ser Thr Asn Glu Thr Pro Gln Pro Thr Ala Ile Lys Asp Gln Ala
            115                 120                 125

Thr Ala Ala Lys Met Gln Asp Gln Thr Val Pro Gln Glu Ala Asn Ser
            130                 135                 140

Gln Val Asp Asn Lys Thr Thr Asn Asp Ala Asn Ser Ile Ala Thr Asn
145                 150                 155                 160

Cys Glu Leu Lys Asn Pro Gln Thr Leu Asp Leu Pro Gln Ser Ser Pro
                165                 170                 175

Gln Thr Ile Ser Asn Ala Gln Gly Thr Ser Lys Pro Ser Val Arg Thr
                180                 185                 190

Arg Ala Val Arg Ser Leu Ala Val Ala Glu Pro Val Val Asn Ala Ala
            195                 200                 205

Asp Ala Lys Gly Thr Asn Val Asn Asp Lys Val Thr Ala Lys Asp Phe
            210                 215                 220

Gln Leu Glu Lys Thr Thr Phe Asp Pro Asn Gln Ser Gly Asn Thr Phe
225                 230                 235                 240

Met Ala Ala Asn Phe Thr Val Thr Gly Gln Val Lys Ser Gly Asp Tyr
                245                 250                 255

Phe Thr Ala Lys Leu Pro Asp Ser Val Thr Gly Asn Gly Asp Val Asp
                260                 265                 270

Tyr Ser Asn Ser Asn Asn Thr Met Pro Ile Ala Asp Ile Lys Ser Thr
            275                 280                 285

Asn Gly Asp Val Val Ala Lys Ala Thr Tyr Asp Ile Leu Thr Lys Thr
            290                 295                 300

Tyr Thr Phe Val Phe Thr Asp Tyr Val Asn Asn Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
            340                 345                 350

Asn Lys Ile Thr Tyr Asn Tyr Ser Ser Pro Ile Ala Gly Ile Asp Lys
            355                 360                 365

Pro Asn Gly Ala Asn Ile Ser Ser Gln Ile Ile Gly Val Asp Thr Ala
            370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
            420                 425                 430

Ile Phe Glu Val Asn Asp Thr Ser Lys Leu Ser Asp Ser Tyr Tyr Ala
            435                 440                 445

Asp Pro Asn Asp Ser Asn Leu Lys Glu Val Thr Asn Glu Phe Lys Asp
450                 455                 460
```

```
Lys Ile Thr Tyr Lys Tyr Gln Asn Val Ala Ser Ile Asn Phe Gly Asp
465                 470                 475                 480

Ile Thr Lys Thr Tyr Val Val Leu Val Glu Gly His Tyr Asp Asn Thr
                485                 490                 495

Gly Lys Asn Leu Lys Thr Gln Val Ile Gln Glu Asn Ile Asp Pro Ala
            500                 505                 510

Thr Gly Lys Asp Tyr Ser Ile Phe Gly Trp Asn Asn Glu Asn Val Val
        515                 520                 525

Arg Tyr Gly Gly Gly Ser Ala Asp Gly Asp Ser Ala Val Asn
    530                 535                 540

<210> SEQ ID NO 47
<211> LENGTH: 1626
<212> TYPE: DNA
<213> ORGANISM: Staphylococcus aureus

<400> SEQUENCE: 47
```

| | | | | | |
|---|---|---|---|---|---|
| ttgaaaaaaa | gaattgatta | tttgtcgaat | aagcagaata | agtattcgat | tagacgtttt | 60 |
| acagtaggta | ccacatcagt | aatagtaggg | gcaactatac | tatttgggat | aggcaatcat | 120 |
| caagcacaag | cttcagaaca | atcgaacgat | acaacgcaat | cttcgaaaaa | taatgcaagt | 180 |
| gcagattccg | aaaaaaacaa | tacgatagaa | acacctcaat | taaatacaac | ggctaatgat | 240 |
| acatctgata | ttagtgcaaa | cacaaacagt | gcgaatgtag | atagcacagc | aaaaccaatg | 300 |
| tctacacaaa | cgagcaatac | cactacaaca | gagccagctt | caacaaatga | aacacctcaa | 360 |
| ccgacggcaa | ttaaagatca | agcaactgct | gcaaaaatgc | aagatcaaac | tgttcctcaa | 420 |
| gaagcaaatt | ctcaagtaga | taataaaaca | acgaatgatg | ctaatagcat | agcgacaaac | 480 |
| agcgagctta | aaaatcctca | gacattagat | ttaccacaat | catcaccaca | aacgatttcc | 540 |
| aatgcgcaag | gaactagtga | accaagtgtt | agaacgagag | ctgtacgtag | tcttgcagtt | 600 |
| gctgaacctg | tagtaaatgc | tgctgatgct | aaaggtacaa | atgtaaatga | taaagttacg | 660 |
| gcaagtgatt | tcaagttaga | aaagactaca | tttgacccta | accaagtgg | taacacattt | 720 |
| atggcggcaa | attttaaagt | ggcagggaaa | gtgaaatcag | gggattattt | tacagcgaag | 780 |
| ttaccagata | gtgtaactgg | taatggagac | gtggattact | ctaattcaaa | taatacgatg | 840 |
| ccaattgcag | atatagtgaa | tgataaaaaa | gaagttgtag | ctaaagcaac | atatgatatc | 900 |
| ttgactaaga | cgtatacatt | tgtctttaca | gattatgtaa | atgataaaga | aaatattaac | 960 |
| ggacaatttt | cattaccttt | atttacagac | cgagcaaagg | cacctaaatc | aggaacatat | 1020 |
| gatgcaaata | ttaatattgc | ggatgaaatg | tttaacaatc | aaattactta | taactatagt | 1080 |
| tcaccaattg | caggaattga | taagccaaat | ggcgcgaaca | tttcttctca | aattattggt | 1140 |
| gtagatacag | cttcaggtca | aaacacatac | aagcaaacgg | tatttgttaa | ccctaagcaa | 1200 |
| cgagttttag | gtaatacgtg | ggtgtatatt | aaaggttacc | aagataaaat | cgaagaaagt | 1260 |
| agcggtaaag | taagtgctac | agatacaaaa | ctgagaattt | ttgaagtgaa | tgatacatct | 1320 |
| aaattatcag | atagctacta | tgcagaccca | aatgactcta | accttaaaga | agtaactaat | 1380 |
| gagtttaagg | ataaaatcac | ttataaatac | caaaacgtag | caagtattaa | ttttggtgat | 1440 |
| ataaataaaa | cgtatgtcgt | tttagtcgaa | ggtcattatg | ataatactgg | taaaaacttg | 1500 |
| aaaacacagg | ttattcaaga | aaatattgac | ccagcgacag | gtaaagatta | cagtattttc | 1560 |
| ggttggaata | atgagaatgt | tgtacgttat | ggaggcggaa | gtgctgatgg | tgattcagca | 1620 |
| gtaaat | | | | | | 1626 |

<210> SEQ ID NO 48
<211> LENGTH: 542
<212> TYPE: PRT
<213> ORGANISM: Staphylococcus aureus

<400> SEQUENCE: 48

| | | | | | | | | | | | | | | |
|---|---|---|---|---|---|---|---|---|---|---|---|---|---|---|
| Leu | Lys | Lys | Arg | Ile | Asp | Tyr | Leu | Ser | Asn | Lys | Gln | Asn | Lys | Tyr | Ser |
| 1 | | | | 5 | | | | | 10 | | | | | 15 | |
| Ile | Arg | Arg | Phe | Thr | Val | Gly | Thr | Thr | Ser | Val | Ile | Val | Gly | Ala | Thr |
| | | | 20 | | | | | 25 | | | | | 30 | | |
| Ile | Leu | Phe | Gly | Ile | Gly | Asn | His | Gln | Ala | Gln | Ala | Ser | Glu | Gln | Ser |
| | | 35 | | | | | 40 | | | | | 45 | | | |
| Asn | Asp | Thr | Thr | Gln | Ser | Ser | Lys | Asn | Asn | Ala | Ser | Ala | Asp | Ser | Glu |
| 50 | | | | | 55 | | | | | 60 | | | | | |
| Lys | Asn | Asn | Thr | Ile | Glu | Thr | Pro | Gln | Leu | Asn | Thr | Thr | Ala | Asn | Asp |
| 65 | | | | | 70 | | | | | 75 | | | | | 80 |
| Thr | Ser | Asp | Ile | Ser | Ala | Asn | Thr | Asn | Ser | Ala | Asn | Val | Asp | Ser | Thr |
| | | | | 85 | | | | | 90 | | | | | 95 | |
| Ala | Lys | Pro | Met | Ser | Thr | Gln | Thr | Ser | Asn | Thr | Thr | Thr | Thr | Glu | Pro |
| | | | 100 | | | | | 105 | | | | | 110 | | |
| Ala | Ser | Thr | Asn | Glu | Thr | Pro | Gln | Pro | Thr | Ala | Ile | Lys | Asp | Gln | Ala |
| | | 115 | | | | | 120 | | | | | 125 | | | |
| Thr | Ala | Ala | Lys | Met | Gln | Asp | Gln | Thr | Val | Pro | Gln | Glu | Ala | Asn | Ser |
| 130 | | | | | 135 | | | | | 140 | | | | | |
| Gln | Val | Asp | Asn | Lys | Thr | Thr | Asn | Asp | Ala | Asn | Ser | Ile | Ala | Thr | Asn |
| 145 | | | | | 150 | | | | | 155 | | | | | 160 |
| Ser | Glu | Leu | Lys | Asn | Pro | Gln | Thr | Leu | Asp | Leu | Pro | Gln | Ser | Ser | Pro |
| | | | | 165 | | | | | 170 | | | | | 175 | |
| Gln | Thr | Ile | Ser | Asn | Ala | Gln | Gly | Thr | Ser | Glu | Pro | Ser | Val | Arg | Thr |
| | | | 180 | | | | | 185 | | | | | 190 | | |
| Arg | Ala | Val | Arg | Ser | Leu | Ala | Val | Ala | Glu | Pro | Val | Val | Asn | Ala | Ala |
| | | 195 | | | | | 200 | | | | | 205 | | | |
| Asp | Ala | Lys | Gly | Thr | Asn | Val | Asn | Asp | Lys | Val | Thr | Ala | Ser | Asp | Phe |
| 210 | | | | | 215 | | | | | 220 | | | | | |
| Lys | Leu | Glu | Lys | Thr | Thr | Phe | Asp | Pro | Asn | Gln | Ser | Gly | Asn | Thr | Phe |
| 225 | | | | | 230 | | | | | 235 | | | | | 240 |
| Met | Ala | Ala | Asn | Phe | Lys | Val | Ala | Gly | Lys | Val | Lys | Ser | Gly | Asp | Tyr |
| | | | | 245 | | | | | 250 | | | | | 255 | |
| Phe | Thr | Ala | Lys | Leu | Pro | Asp | Ser | Val | Thr | Gly | Asn | Gly | Asp | Val | Asp |
| | | | 260 | | | | | 265 | | | | | 270 | | |
| Tyr | Ser | Asn | Ser | Asn | Asn | Thr | Met | Pro | Ile | Ala | Asp | Ile | Val | Asn | Asp |
| | | | 275 | | | | | 280 | | | | | 285 | | |
| Lys | Lys | Glu | Val | Val | Ala | Lys | Ala | Thr | Tyr | Asp | Ile | Leu | Thr | Lys | Thr |
| 290 | | | | | 295 | | | | | 300 | | | | | |
| Tyr | Thr | Phe | Val | Phe | Thr | Asp | Tyr | Val | Asn | Asp | Lys | Glu | Asn | Ile | Asn |
| 305 | | | | | 310 | | | | | 315 | | | | | 320 |
| Gly | Gln | Phe | Ser | Leu | Pro | Leu | Phe | Thr | Asp | Arg | Ala | Lys | Ala | Pro | Lys |
| | | | | 325 | | | | | 330 | | | | | 335 | |
| Ser | Gly | Thr | Tyr | Asp | Ala | Asn | Ile | Asn | Ile | Ala | Asp | Glu | Met | Phe | Asn |
| | | | 340 | | | | | 345 | | | | | 350 | | |
| Asn | Gln | Ile | Thr | Tyr | Asn | Tyr | Ser | Ser | Pro | Ile | Ala | Gly | Ile | Asp | Lys |
| | | | 355 | | | | | 360 | | | | | 365 | | |
| Pro | Asn | Gly | Ala | Asn | Ile | Ser | Ser | Gln | Ile | Ile | Gly | Val | Asp | Thr | Ala |
| 370 | | | | | 375 | | | | | 380 | | | | | |

```
Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
            405                 410                 415

Ile Glu Glu Ser Ser Gly Lys Val Ser Ala Thr Asp Thr Lys Leu Arg
        420                 425                 430

Ile Phe Glu Val Asn Asp Thr Ser Lys Leu Ser Asp Ser Tyr Tyr Ala
    435                 440                 445

Asp Pro Asn Asp Ser Asn Leu Lys Glu Val Thr Asn Glu Phe Lys Asp
    450                 455                 460

Lys Ile Thr Tyr Lys Tyr Gln Asn Val Ala Ser Ile Asn Phe Gly Asp
465                 470                 475                 480

Ile Asn Lys Thr Tyr Val Val Leu Val Glu Gly His Tyr Asp Asn Thr
            485                 490                 495

Gly Lys Asn Leu Lys Thr Gln Val Ile Gln Glu Asn Ile Asp Pro Ala
        500                 505                 510

Thr Gly Lys Asp Tyr Ser Ile Phe Gly Trp Asn Asn Glu Asn Val Val
    515                 520                 525

Arg Tyr Gly Gly Gly Ser Ala Asp Gly Asp Ser Ala Val Asn
    530                 535                 540

<210> SEQ ID NO 49
<211> LENGTH: 1626
<212> TYPE: DNA
<213> ORGANISM: Staphylococcus aureus

<400> SEQUENCE: 49
ttgaaaaaaa gaattgatta tttgtcgaat aagcagaata agtattcgat tagacgtttt      60
acagtaggta ccacatcagt aatagtaggg gcaactatac tatttgggat aggcaatcat    120
caagcacaag cttcagaaca atcgaacgat acaacgcaat cttcgaaaaa taatgcaagt    180
gcagattccg aaaaaaacaa tatgatagaa acacctcaat taaatacaac ggctaatgat    240
acatctgata ttagtgcaaa cacaaacagt gcgaatgtag atagcacagc aaaaccaatg    300
tctacacaaa cgagcaatac cactacaaca gagccagctt caacaaatga acacctcaa     360 ccgacggcaa ttaaagatca agcaactgct gcaaaaatgc aagatcaaac tgttcctcaa    420
gaagcaaatt ctcaagtaga taataaaaca cgaatgatg ctaatagcat agcgacaaac     480
agtgagctta aaaatcctca aacattagat ttaccacaat catcaccaca aacgatttcc    540
aatgcgcaaa gaactagtaa accaagtgtt agaaccagac tgtacgtag tttagctgtt     600 gctgaaccgg tagtaaatgc tgctgatgct aaaggtacaa atgtaaatga taaagttacg    660
gcaagtaatc tacagttgca aaagactacg tttgacccta accaaagtgg taacacattt    720
atggcggcaa attttacagt gacagataaa gtgaaatcag gagattattt tacagcgaag    780
ttaccagata gttaactgg taatggagac gtggattact ctaattcaaa taatacgatg     840
ccaattgcag atattaaaag tacgaatggc gatgttgtag ctaaagcaac atatgatatc    900
ttgactaaga cgtatacatt tgtctttaca gattatgtaa atgataaaga aaatattaac    960
ggacaatttt cattaccttt atttacagac cgagcaaagg cacctaaatc aggaacatac   1020
gatgcaaata ttaatattgc ggatgaaatg tttaataata aaattactta taactatagt   1080
tcgccaattg caggaattga taagccaaat ggcgcgaaca tttcttctca gattattggt   1140
gtagatacag cttcaggtca aaacacatac aagcaaacgg tatttgttaa ccctaagcaa   1200
```

-continued

```
cgagttttag gtaatacgtg ggtgtatatt aaaggctacc aagataaaat cgaagaaagt    1260
agcggtaaag taagtgctaa agatacaaaa ctgagaattt ttgaagtgaa tgatacatct    1320
aaattatcag atagctacta tgcagaccca atgattcga atcttaaaga agtaacagac     1380
caatttaaaa atagaatcta ttatgagcat ccaaatgtag ctagtattaa ttttggcgat    1440
attactaaaa cgtatgttgt attagtggaa ggtcactatg ataatactgg taaaaacttg    1500
aaaacacagg ttattcaaga aaatattgac ccagcgacag gtaaagacta cagtattttc    1560
ggttggaata atgagaatgt tgtacgttat ggtggtggaa gtgctgatgg tgattcagca    1620
gtaaat                                                               1626
```

<210> SEQ ID NO 50
<211> LENGTH: 542
<212> TYPE: PRT
<213> ORGANISM: Staphylococcus aureus

<400> SEQUENCE: 50

```
Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Ala Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asp Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Ser Ile Ala Thr Asn
145                 150                 155                 160

Ser Glu Leu Lys Asn Pro Gln Thr Leu Asp Leu Pro Gln Ser Ser Pro
                165                 170                 175

Gln Thr Ile Ser Asn Ala Gln Arg Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Gly Thr Asn Val Asn Asp Lys Val Thr Ala Ser Asn Leu
    210                 215                 220

Gln Leu Gln Lys Thr Thr Phe Asp Pro Asn Gln Ser Gly Asn Thr Phe
225                 230                 235                 240

Met Ala Ala Asn Phe Thr Val Thr Asp Lys Val Lys Ser Gly Asp Tyr
                245                 250                 255

Phe Thr Ala Lys Leu Pro Asp Ser Leu Thr Gly Asn Gly Asp Val Asp
            260                 265                 270

Tyr Ser Asn Ser Asn Asn Thr Met Pro Ile Ala Asp Ile Lys Ser Thr
        275                 280                 285

Asn Gly Asp Val Val Ala Lys Ala Thr Tyr Asp Ile Leu Thr Lys Thr
```

```
                   290                 295                 300
Tyr Thr Phe Val Phe Thr Asp Tyr Val Asn Asp Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
                340                 345                 350

Asn Lys Ile Thr Tyr Asn Tyr Ser Ser Pro Ile Ala Gly Ile Asp Lys
            355                 360                 365

Pro Asn Gly Ala Asn Ile Ser Ser Gln Ile Ile Gly Val Asp Thr Ala
        370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Lys Asp Thr Lys Leu Arg
            420                 425                 430

Ile Phe Glu Val Asn Asp Thr Ser Lys Leu Ser Asp Ser Tyr Tyr Ala
        435                 440                 445

Asp Pro Asn Asp Ser Asn Leu Lys Glu Val Thr Asp Gln Phe Lys Asn
    450                 455                 460

Arg Ile Tyr Tyr Glu His Pro Asn Val Ala Ser Ile Asn Phe Gly Asp
465                 470                 475                 480

Ile Thr Lys Thr Tyr Val Val Leu Val Glu Gly His Tyr Asp Asn Thr
                485                 490                 495

Gly Lys Asn Leu Lys Thr Gln Val Ile Gln Glu Asn Ile Asp Pro Ala
            500                 505                 510

Thr Gly Lys Asp Tyr Ser Ile Phe Gly Trp Asn Asn Glu Asn Val Val
        515                 520                 525

Arg Tyr Gly Gly Gly Ser Ala Asp Gly Asp Ser Ala Val Asn
    530                 535                 540

<210> SEQ ID NO 51
<211> LENGTH: 1626
<212> TYPE: DNA
<213> ORGANISM: Staphylococcus aureus

<400> SEQUENCE: 51
ttgaaaaaaa gaattgatta tttgtcgaat aagcagaata agtattcgat tagacgtttt      60
acagtaggta ccacatcagt aatagtaggg gcaactatac tatttgggat aggcaatcat     120
caagcacaag cttcagaaca atcgaacgat acaacgcaat cttcgaaaaa taatgcaagt     180
gcagattccg aaaaaacaa tatgatgaa acacctcaat taaatacaac ggctaatgat      240
acatctgata ttagtgcaaa cacaaacagt gcgaatgtag atagcacagc aaaaccaatg     300
tctacacaaa cgagcaatac cactacaaca gagccagctt caacaaatga acacctcaa      360 ccgacggcaa ttaaagatca agcaactgct gcaaaaatgc aagatcaaac tgttcctcaa     420
gaagcaaatt ctcaagtaga taataaaaca acgaatgatg ctaataacat agcaacaaac     480
agtgggctta aaaatcctca acattagat ttaccacaat catcaccaca acgatttcc      540 aatgcgcaag gaactagtaa accaagtgtt agaacgagag ctgtacgtag tcttgcagtt     600
gctgaacctg tagtaaatgc tgctgatgct aaaggtacaa atgtaaatga taaagttacg     660
gcaagtgatt tcaagttaga aaagactaca ttcgacccta ccaaagtgg taacacattt     720
```

```
atggcggcaa attttacagt gacagataaa gtgaaatcag gggattattt tacagcgaag    780
ttaccagata gtttaactgg taatggagac gtggattact ctaattcaaa taatacgatg    840
ccaattgcag acattaaaag tacgaatggt gatgttgtag cgacagcgac ttataatatc    900
ttgactaaga cgtatacatt tgtctttaca gattatgtaa atgataaaga aaatattaac    960
ggacaatttt cattaccttt atttacagac cgagcaaagg cacctaaatc aggaacatat   1020
gatgcaaata ttaatattgc ggatgaaatg tttaataata aaattactta taactatagt   1080
tcgccaattg caggaattga taagccaaat ggcgcgaaca tttcttctca aattattggt   1140
gtagatacag cttcaggcca aaacacatac aagcaaacgg tatttgttaa ccctaagcaa   1200
cgagttttag gtaatacgtg ggtgtatatt aaaggctacc aagataaaat cgaagaaagt   1260
agcggtaaag taagtgctac agatacaaaa ctgagaattt ttgaagtgaa tgatacatct   1320
aaattatcag atagctacta tgcggaccca aatgactcta atcttaaaga agtaacgaat   1380
gagtttaagg ataaaatcac ttataaatac caaaatgtag caagtattaa ttttggcgat   1440
attactaaaa cgtatgttgt attagtggaa ggtcactatg ataatactgg taaaaacttg   1500
aaaacacagg ttattcaaga aaatattgac ccagcgacag gtaaagatta cagtattttc   1560
ggttggaata atgagaatgt tgtacgttat ggaggcggaa gtgctgatgg tgattcagca   1620
gtaaat                                                               1626
```

<210> SEQ ID NO 52
<211> LENGTH: 542
<212> TYPE: PRT
<213> ORGANISM: Staphylococcus aureus

<400> SEQUENCE: 52

```
Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Ala Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asp Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Ile Ala Thr Asn
145                 150                 155                 160

Ser Gly Leu Lys Asn Pro Gln Thr Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205
```

```
Asp Ala Lys Gly Thr Asn Val Asn Asp Lys Val Thr Ala Ser Asp Phe
    210                 215                 220
Lys Leu Glu Lys Thr Thr Phe Asp Pro Asn Gln Ser Gly Asn Thr Phe
225                 230                 235                 240
Met Ala Ala Asn Phe Thr Val Thr Asp Lys Val Lys Ser Gly Asp Tyr
                245                 250                 255
Phe Thr Ala Lys Leu Pro Asp Ser Leu Thr Gly Asn Gly Asp Val Asp
            260                 265                 270
Tyr Ser Asn Ser Asn Asn Thr Met Pro Ile Ala Asp Ile Lys Ser Thr
        275                 280                 285
Asn Gly Asp Val Val Ala Thr Ala Thr Tyr Asn Ile Leu Thr Lys Thr
    290                 295                 300
Tyr Thr Phe Val Phe Thr Asp Tyr Val Asn Asp Lys Glu Asn Ile Asn
305                 310                 315                 320
Gly Gln Phe Ser Leu Pro Leu Phe Thr Asp Arg Ala Lys Ala Pro Lys
                325                 330                 335
Ser Gly Thr Tyr Asp Ala Asn Ile Asn Ile Ala Asp Glu Met Phe Asn
            340                 345                 350
Asn Lys Ile Thr Tyr Asn Tyr Ser Ser Pro Ile Ala Gly Ile Asp Lys
        355                 360                 365
Pro Asn Gly Ala Asn Ile Ser Ser Gln Ile Ile Gly Val Asp Thr Ala
    370                 375                 380
Ser Gly Gln Asn Thr Tyr Lys Gln Thr Val Phe Val Asn Pro Lys Gln
385                 390                 395                 400
Arg Val Leu Gly Asn Thr Trp Val Tyr Ile Lys Gly Tyr Gln Asp Lys
                405                 410                 415
Ile Glu Glu Ser Ser Gly Lys Val Ser Ala Thr Asp Thr Lys Leu Arg
            420                 425                 430
Ile Phe Glu Val Asn Asp Thr Ser Lys Leu Ser Asp Ser Tyr Tyr Ala
        435                 440                 445
Asp Pro Asn Asp Ser Asn Leu Lys Glu Val Thr Asn Glu Phe Lys Asp
    450                 455                 460
Lys Ile Thr Tyr Lys Tyr Gln Asn Val Ala Ser Ile Asn Phe Gly Asp
465                 470                 475                 480
Ile Thr Lys Thr Tyr Val Val Leu Val Glu Gly His Tyr Asp Asn Thr
                485                 490                 495
Gly Lys Asn Leu Lys Thr Gln Val Ile Gln Glu Asn Ile Asp Pro Ala
            500                 505                 510
Thr Gly Lys Asp Tyr Ser Ile Phe Gly Trp Asn Asn Glu Asn Val Val
        515                 520                 525
Arg Tyr Gly Gly Gly Ser Ala Asp Gly Asp Ser Ala Val Asn
    530                 535                 540

<210> SEQ ID NO 53
<211> LENGTH: 1626
<212> TYPE: DNA
<213> ORGANISM: Staphylococcus aureus

<400> SEQUENCE: 53
ttgaaaaaaa gaattgatta tttgtcgaat aagcagaata agtattcgat tagacgtttt      60
acagtaggta ccacatcagt aatagtaggg gcaactatac tatttgggat aggcaatcat     120
caagcacaag cttcagaaca atcgaacgat acaacgcaat cttcgaaaaa taatgcaagt     180
gcagattccg aaaaaaacaa tatgatagaa acacctcaat taaatacaac ggctaatgat     240
```

```
acatctgata ttagtgcaaa cacaaacagt gcgaatgtag atagcacagc aaaaccaatg    300
tctacacaaa cgagcaatac cactacaaca gagccagctt caacaaatga acacctcaa    360 ccgacggcaa ttaaagatca agcaactgct gcaaaaatgc aagatcaaac tgttcctcaa    420
gaagcaaatt ctcaagtaga taataaaaca acgaatgatg ctaataacat agcaacaaac    480
agtgagctta aaaatcctca aacattagat ttaccacaat catcaccaca aacgatttcc    540
aatgcgcaag gaactagtaa accaagtgtt agaacgagag ctgtacgtag tcttgcagtt    600
gctgaacctg tagtaaatgc tgctgatgct aaaggtacaa atgtaaatga taaagttacg    660
gcaagtgatt tcaagttaga aaagactaca ttcgacccta accaaagtgg taacacattt    720
atggcggcaa attttacagt gacagataaa gtgaaatcag gggattattt tacagcgaag    780
ttaccagata gtttaactgg taatggagac gtggattact ctaattcaaa taatacgatg    840
ccaattgcag acattaaaag tacgaatggt gatgttgtag cgacagcgac ttataatatc    900
ttgactaaga cgtatacatt tgtctttaca gattatgtaa atgataaaga aaatattaac    960
ggacaatttt cattaccttt atttacagac cgagcaaagg cacctaaatc aggaacatat   1020
gatgcaaata ttaatattgc ggatgaaatg tttaataata aaattactta taactatagt   1080
tcgccaattg caggaattga taagccaaat ggcgcgaaca tttcttctca aattattggt   1140
gtagatacag cttcaggcca aaacacatac aagcaaacgg tatttgttaa ccctaagcaa   1200
cgagttttag gtaatacgtg ggtgtatatt aaaggctacc aagataaaat cgaagaaagt   1260
agcggtaaag taagtgctac agatacaaaa ctgagaattt ttgaagtgaa tgatacatct   1320
aaattatcag atagctacta tgcggaccca atgactctaa tcttaaaga agtaacgaat   1380 gagtttaagg ataaaatcac ttataaatac caaaatgtag caagtattaa ttttggcgat   1440
attactaaaa cgtatgttgt attagtggaa ggtcactatg ataatactgg taaaaacttg   1500
aaaacacagg ttattcaaga aaatattgac ccagcgacag gtaaagatta cagtattttc   1560
ggttggaata atgagaatgt tgtacgttat ggaggcggaa gtgctgatgg tgattcagca   1620
gtaaat                                                             1626
```

<210> SEQ ID NO 54
<211> LENGTH: 542
<212> TYPE: PRT
<213> ORGANISM: Staphylococcus aureus
<400> SEQUENCE: 54

```
Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Ala Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asp Gln Ala
        115                 120                 125
```

```
Thr Ala Ala Lys Met Gln Asp Gln Thr Val Pro Gln Glu Ala Asn Ser
    130                 135                 140

Gln Val Asp Asn Lys Thr Thr Asn Asp Ala Asn Asn Ile Ala Thr Asn
145                 150                 155                 160

Ser Glu Leu Lys Asn Pro Gln Thr Leu Asp Leu Pro Gln Ser Ser Pro
                165                 170                 175

Gln Thr Ile Ser Asn Ala Gln Gly Thr Ser Lys Pro Ser Val Arg Thr
                180                 185                 190

Arg Ala Val Arg Ser Leu Ala Val Ala Glu Pro Val Val Asn Ala Ala
                195                 200                 205

Asp Ala Lys Gly Thr Asn Val Asn Asp Lys Val Thr Ala Ser Asp Phe
    210                 215                 220

Lys Leu Glu Lys Thr Thr Phe Asp Pro Asn Gln Ser Gly Asn Thr Phe
225                 230                 235                 240

Met Ala Ala Asn Phe Thr Val Thr Asp Lys Val Lys Ser Gly Asp Tyr
                245                 250                 255

Phe Thr Ala Lys Leu Pro Asp Ser Leu Thr Gly Asn Gly Asp Val Asp
                260                 265                 270

Tyr Ser Asn Ser Asn Asn Thr Met Pro Ile Ala Asp Ile Lys Ser Thr
    275                 280                 285

Asn Gly Asp Val Val Ala Thr Ala Thr Tyr Asn Ile Leu Thr Lys Thr
    290                 295                 300

Tyr Thr Phe Val Phe Thr Asp Tyr Val Asn Asp Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
                340                 345                 350

Asn Lys Ile Thr Tyr Asn Tyr Ser Ser Pro Ile Ala Gly Ile Asp Lys
    355                 360                 365

Pro Asn Gly Ala Asn Ile Ser Ser Gln Ile Ile Gly Val Asp Thr Ala
    370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
                420                 425                 430

Ile Phe Glu Val Asn Asp Thr Ser Lys Leu Ser Asp Ser Tyr Tyr Ala
    435                 440                 445

Asp Pro Asn Asp Ser Asn Leu Lys Glu Val Thr Asn Glu Phe Lys Asp
450                 455                 460

Lys Ile Thr Tyr Lys Tyr Gln Asn Val Ala Ser Ile Asn Phe Gly Asp
465                 470                 475                 480

Ile Thr Lys Thr Tyr Val Val Leu Val Glu Gly His Tyr Asp Asn Thr
                485                 490                 495

Gly Lys Asn Leu Lys Thr Gln Val Ile Gln Glu Asn Ile Asp Pro Ala
                500                 505                 510

Thr Gly Lys Asp Tyr Ser Ile Phe Gly Trp Asn Asn Glu Asn Val Val
    515                 520                 525

Arg Tyr Gly Gly Gly Ser Ala Asp Gly Asp Ser Ala Val Asn
    530                 535                 540
```

<210> SEQ ID NO 55
<211> LENGTH: 1626
<212> TYPE: DNA
<213> ORGANISM: Staphylococcus aureus

<400> SEQUENCE: 55

| | | | | | |
|---|---|---|---|---|---|
| ttgaaaaaaa | gaattgatta | tttgtcgaat | aagcagaata | agtattcgat | tagacgtttt | 60 |
| acagtaggta | ccacatcagt | aatagtaggg | gcaactatac | tatttgggat | aggcaatcat | 120 |
| caagcacaag | cttcagaaca | atcgaacgat | acaacgcaat | cttcgaaaaa | taatgcaagt | 180 |
| gcagattccg | aaaaaaacaa | tatgatgaaa | cacctcaat | taaatacaac | ggctaatgat | 240 |
| acatctgata | ttagtgcaaa | cacaaacagt | gcgaatgtag | atagcacagc | aaaaccaatg | 300 |
| tctacacaaa | cgagcaatac | cactacaaca | gagccagctt | caacaaatga | acacctcaa | 360 |
| ccgacggcaa | ttaaagatca | agcaactgct | gcaaaaatgc | aagatcaaac | tgttcctcaa | 420 |
| gaagcaaatt | ctcaagtaga | taataaaaca | acgaatgatg | ctaatagcat | agcgacaaac | 480 |
| agtgagctta | aaaatcctca | aacattagat | ttaccacaat | catcaccaca | aacaatttcc | 540 |
| aatgcgcaag | gaactagtaa | accaagtgtt | agaacgagag | ctgtacgtag | tcttgcagtt | 600 |
| gctgaacctg | tagtaaatgc | tgctgatgct | aaaggtacaa | atgtaaatga | taagttacg | 660 |
| gcaaagatt | tcaattaga | aaagaccaca | tttgaccccta | accaaagtgg | taatactttt | 720 |
| atggcggcaa | actttacagt | gactggacaa | gtgaaatcag | gggattattt | tacagcgaag | 780 |
| ttaccagata | gtgtaactgg | taatggagac | gtggattact | ctaattcgaa | taatacgatg | 840 |
| ccaattgcag | atattaaaag | tacgaatggc | gatgttgtag | ctaaagcaac | atatgatatc | 900 |
| ttgactaaga | cgtatacatt | tgtctttaca | gattatgtaa | ataataaaga | aaatattaac | 960 |
| ggacaatttt | cattacccttt | atttacagac | cgagcaaagg | cacctaaatc | aggaacatat | 1020 |
| gatgcgaata | ttaatattgc | ggatgaaatg | tttaataata | aaattactta | taactatagt | 1080 |
| tcgccaattg | caggaattga | taaaccaaat | ggcgcgaaca | tttcttctca | aattattggt | 1140 |
| gtagatacag | cttcaggtca | aaacacatac | aagcaaacag | tatttgttaa | ccctaagcaa | 1200 |
| cgagttttag | gtaatacgtg | ggtgtatatt | aaaggttacc | aagataaaat | cgaagaaagt | 1260 |
| agcggtaaag | taagtgctac | agatacaaaa | ctgagaattt | tgaagtgaa | tgatacatct | 1320 |
| aaattatcag | atagctacta | tgcggaccca | aatgactcta | accttaaaga | agtaacgaat | 1380 |
| gagtttaagg | ataaaatcac | ttataaatac | caaaatgtag | caagtattaa | ttttggcgat | 1440 |
| attactaaaa | cgtatgttgt | attagtggaa | ggtcactatg | ataatactgg | taaaaacttg | 1500 |
| aaaacacagg | ttattcaaga | aaatattgac | ccagcgacag | gtaaagacta | cagtattttc | 1560 |
| ggttggaata | atgagaatgt | tgtacgttat | ggtggtggaa | gtgctgatgg | tgattcagca | 1620 |
| gtaaat | | | | | | 1626 |

<210> SEQ ID NO 56
<211> LENGTH: 542
<212> TYPE: PRT
<213> ORGANISM: Staphylococcus aureus

<400> SEQUENCE: 56

Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser

```
                35                  40                  45
Asn Asp Thr Thr Gln Ser Ser Lys Asn Asn Ala Ser Ala Asp Ser Glu
 50                  55                  60

Lys Asn Asn Met Ile Glu Thr Pro Gln Leu Asn Thr Thr Ala Asn Asp
 65                  70                  75                  80

Thr Ser Asp Ile Ser Ala Asn Thr Asn Ser Ala Asn Val Asp Ser Thr
                 85                  90                  95

Ala Lys Pro Met Ser Thr Gln Thr Ser Asn Thr Thr Thr Glu Pro
                100                 105                 110

Ala Ser Thr Asn Glu Thr Pro Gln Pro Thr Ala Ile Lys Asp Gln Ala
                115                 120                 125

Thr Ala Ala Lys Met Gln Asp Gln Thr Val Pro Gln Glu Ala Asn Ser
                130                 135                 140

Gln Val Asp Asn Lys Thr Thr Asn Asp Ala Asn Ser Ile Ala Thr Asn
145                 150                 155                 160

Ser Glu Leu Lys Asn Pro Gln Thr Leu Asp Leu Pro Gln Ser Ser Pro
                165                 170                 175

Gln Thr Ile Ser Asn Ala Gln Gly Thr Ser Lys Pro Ser Val Arg Thr
                180                 185                 190

Arg Ala Val Arg Ser Leu Ala Val Ala Glu Pro Val Asn Ala Ala
                195                 200                 205

Asp Ala Lys Gly Thr Asn Val Asn Asp Lys Val Thr Ala Lys Asp Phe
210                 215                 220

Gln Leu Glu Lys Thr Thr Phe Asp Pro Asn Gln Ser Gly Asn Thr Phe
225                 230                 235                 240

Met Ala Ala Asn Phe Thr Val Thr Gly Gln Val Lys Ser Gly Asp Tyr
                245                 250                 255

Phe Thr Ala Lys Leu Pro Asp Ser Val Thr Gly Asn Gly Asp Val Asp
                260                 265                 270

Tyr Ser Asn Ser Asn Asn Thr Met Pro Ile Ala Asp Ile Lys Ser Thr
                275                 280                 285

Asn Gly Asp Val Val Ala Lys Ala Thr Tyr Asp Ile Leu Thr Lys Thr
290                 295                 300

Tyr Thr Phe Val Phe Thr Asp Tyr Val Asn Asn Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
                340                 345                 350

Asn Lys Ile Thr Tyr Asn Tyr Ser Ser Pro Ile Ala Gly Ile Asp Lys
                355                 360                 365

Pro Asn Gly Ala Asn Ile Ser Ser Gln Ile Ile Gly Val Asp Thr Ala
                370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
                420                 425                 430

Ile Phe Glu Val Asn Asp Thr Ser Lys Leu Ser Asp Ser Tyr Tyr Ala
                435                 440                 445

Asp Pro Asn Asp Ser Asn Leu Lys Glu Val Thr Asn Glu Phe Lys Asp
                450                 455                 460
```

```
Lys Ile Thr Tyr Lys Tyr Gln Asn Val Ala Ser Ile Asn Phe Gly Asp
465                 470                 475                 480

Ile Thr Lys Thr Tyr Val Val Leu Val Glu Gly His Tyr Asp Asn Thr
            485                 490                 495

Gly Lys Asn Leu Lys Thr Gln Val Ile Gln Glu Asn Ile Asp Pro Ala
        500                 505                 510

Thr Gly Lys Asp Tyr Ser Ile Phe Gly Trp Asn Asn Glu Asn Val Val
            515                 520                 525

Arg Tyr Gly Gly Gly Ser Ala Asp Gly Asp Ser Ala Val Asn
530                 535                 540
```

<210> SEQ ID NO 57
<211> LENGTH: 1626
<212> TYPE: DNA
<213> ORGANISM: Staphylococcus aureus

<400> SEQUENCE: 57

```
ttgaaaaaaa gaattgatta tttgtcgaat aagcagaata agtattcgat tagacgtttt    60
acagtaggta ccacatcagt aatagtaggg gcaactatac tatttgggat aggcaatcat   120
caagcacaag cttcagaaca atcgaacgat acaacgcaat cttcgaaaaa taatgcaagt   180
gcagattccg aaaaaaacaa tacgataaga cacctcaat taaatacaac ggctaatgat   240
acatctgata ttagtgcaaa cacaaacagt gcgaatgtga atagcacagc aaaaacaatg   300
tctacacaaa cgagcaatac cactacaaca gagccagctt caacaaatga aacacctcaa   360
ccgacggcaa ttaaagatca agcaactgct gcaaaaatgc aagatcaaac tgttcctcaa   420
gaagcaaatt ctcaagtaga taataaaaca cgaatgatg ctaataacat agcaacaaac   480
agtgagctta aaaatcctca acattagat ttaccacaat catcaccaca aacgatttcc   540
aatgcgcaag gaactagtaa accaagtgtt agaacgagag ctgtacgtag tcttgcagtt   600
gctgaacctg tagtaaatgc tgctgatgct aaaggtacaa atgtaaatga taagttacg    660
gcaagtgatc tcaagttaga aaagactgca tttgacccta ccaaagtgg taacacattt    720
atggcggcaa attttaaagt gactggacaa gtgaaatcag gggattattt tacagcgaag   780
ttaccagata gtgtaactgg taatggagac gtggattact ctaattcaaa taatacgatg   840
ccaattgcag acattaaaag tacgaatggc gatgttgtag ctaaagcaac atatgatatc   900
ttgactaaga cgtatacatt tgtctttaca gattatgtaa atgataaaga aaatattaac   960
ggacaatttt cattacctt atttacagac cgagcaaagg cacctaaatc aggaacatat  1020
gatgcaaata ttaatattgc ggatgaaatg tttgataata aaattactta taactatagt  1080
tcgccaattg caggaattga taagccaaat ggcgcgaaca tttcttctca aattattggt  1140
gtagatacag cttcaggtca aaacacatac aagcaaacgg tatttgttaa ccctaagcaa  1200
cgagttttag gtaatacgtg ggtgtatatt aaaggttacc aagataaaat cgaagaaagt  1260
agcggtaaag taagtgctac agatacaaaa ctgagaattt ttgaagtgaa tgatacatct  1320
aaattatcag atagctacta tgcagaccca aatgactcta accttaaaga agtgactggt  1380
gagtttaaag ataaaatttc atacaaatac gataacgtag caagtattaa ttttggtgat  1440
ataaataaaa cgtatgttgt attagtggaa ggtcactatg ataatactgg taaaaacttg  1500
aaaacacagg ttattcaaga aaatattgac tcagcgacag gtaaagacta cagtattttc  1560
ggttggaata tgagaatgt tgtacgttat ggaggcggaa gtgctgatgg tgattcagca  1620
gtaaat                                                              1626
```

<210> SEQ ID NO 58
<211> LENGTH: 542
<212> TYPE: PRT
<213> ORGANISM: Staphylococcus aureus

<400> SEQUENCE: 58

Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Thr Ile Glu Thr Pro Gln Leu Asn Thr Ala Asn Asp
65                  70                  75                  80

Thr Ser Asp Ile Ser Ala Asn Thr Asn Ser Ala Asn Val Asp Ser Thr
                85                  90                  95

Ala Lys Thr Met Ser Thr Gln Thr Ser Asn Thr Thr Thr Thr Glu Pro
            100                 105                 110

Ala Ser Thr Asn Glu Thr Pro Gln Pro Thr Ala Ile Lys Asp Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Asn Ile Ala Thr Asn
145                 150                 155                 160

Ser Glu Leu Lys Asn Pro Gln Thr Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Gly Thr Asn Val Asn Asp Lys Val Thr Ala Ser Asp Leu
    210                 215                 220

Lys Leu Glu Lys Thr Ala Phe Asp Pro Asn Gln Ser Gly Asn Thr Phe
225                 230                 235                 240

Met Ala Ala Asn Phe Lys Val Thr Gly Gln Val Lys Ser Gly Asp Tyr
                245                 250                 255

Phe Thr Ala Lys Leu Pro Asp Ser Val Thr Gly Asn Gly Asp Val Asp
            260                 265                 270

Tyr Ser Asn Ser Asn Asn Thr Met Pro Ile Ala Asp Ile Lys Ser Thr
        275                 280                 285

Asn Gly Asp Val Val Ala Lys Ala Thr Tyr Asp Ile Leu Thr Lys Thr
    290                 295                 300

Tyr Thr Phe Val Phe Thr Asp Tyr Val Asn Asp Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asp
            340                 345                 350

Asn Lys Ile Thr Tyr Asn Tyr Ser Ser Pro Ile Ala Gly Ile Asp Lys
        355                 360                 365

Pro Asn Gly Ala Asn Ile Ser Ser Gln Ile Ile Gly Val Asp Thr Ala

```
          370            375              380
Ser Gly Gln Asn Thr Tyr Lys Gln Thr Val Phe Val Asn Pro Lys Gln
385              390              395              400

Arg Val Leu Gly Asn Thr Trp Val Tyr Ile Lys Gly Tyr Gln Asp Lys
             405              410              415

Ile Glu Glu Ser Ser Gly Lys Val Ser Ala Thr Asp Thr Lys Leu Arg
             420              425              430

Ile Phe Glu Val Asn Asp Thr Ser Lys Leu Ser Asp Ser Tyr Tyr Ala
         435              440              445

Asp Pro Asn Asp Ser Asn Leu Lys Glu Val Thr Gly Glu Phe Lys Asp
    450              455              460

Lys Ile Ser Tyr Lys Tyr Asp Asn Val Ala Ser Ile Asn Phe Gly Asp
465              470              475              480

Ile Asn Lys Thr Tyr Val Val Leu Val Glu Gly His Tyr Asp Asn Thr
             485              490              495

Gly Lys Asn Leu Lys Thr Gln Val Ile Gln Glu Asn Ile Asp Ser Ala
             500              505              510

Thr Gly Lys Asp Tyr Ser Ile Phe Gly Trp Asn Asn Glu Asn Val Val
             515              520              525

Arg Tyr Gly Gly Gly Ser Ala Asp Gly Asp Ser Ala Val Asn
         530              535              540
```

<210> SEQ ID NO 59
<211> LENGTH: 1626
<212> TYPE: DNA
<213> ORGANISM: Staphylococcus aureus

<400> SEQUENCE: 59

| | | | | | |
|---|---|---|---|---|---|
| ttgaaaaaaa | gaattgatta | tttgtcgaat | aagcagaata | agtattcgat | tagacgtttt | 60 |
| acagtaggta | ccacatcagt | aatagtaggg | gcaactatac | tatttgggat | aggcaatcat | 120 |
| caagcacaag | cttcagaaca | atcgaacgat | acaacgcaat | cttcgaaaaa | taatgcaagt | 180 |
| gcagattccg | aaaaaaacaa | tatgatagaa | acacctcaat | taaatacaac | ggctaatgat | 240 |
| acatctgata | ttagtgcaaa | cacaaacagt | gcgaatgtag | atagcacaac | aaaaccaatg | 300 |
| tctacacaaa | cgagcaatac | cactacaaca | gagccagctt | caacaaatga | acacctcaa  | 360 |
| ccgacggcaa | ttaaaaatca | agcaactgct | gcaaaaatgc | aagatcaaac | tgttcctcaa | 420 |
| gaagcaaatt | ctcaagtaga | taataaaaca | acgaatgatg | ctaatagcat | agcaacaaac | 480 |
| agtgagctta | aaaattctca | aacattagat | ttaccacaat | catcaccaca | aacgatttcc | 540 |
| aatgcgcaag | gaactagtaa | accaagtgtt | agaacgagag | ctgtacgtag | tttagctgtt | 600 |
| gctgaaccgg | tagtaaatgc | tgctgatgct | aaagatacaa | atgtaaatga | taaagttacg | 660 |
| gcaagtaatt | tcaagttaga | aaagactaca | tttgacccta | atcaaagtgg | taacacattt | 720 |
| atggcggcaa | attttacagt | gacagataaa | gtgaaatcag | gggattattt | tacagcgaag | 780 |
| ttaccagata | gtttaactgg | taatggagac | gtggattatt | ctaattcaaa | taatacgatg | 840 |
| ccaattgcag | acattaaaag | tacgaatggc | gatgttgtag | ctaaagcaac | atatgatatc | 900 |
| ttgactaaga | cgtatacatt | tgtctttaca | gattatgtaa | ataataaaga | aaatattaac | 960 |
| ggacaatttt | cattaccttt | atttacagac | cgagcaaagg | cacctaaatc | aggaacatat | 1020 |
| gatgcgaata | ttaatattgc | ggatgaaatg | tttaataata | aaattactta | taactatagt | 1080 |
| tcgccaattg | caggaattga | taaaccaaat | ggcgcgaaca | tttcttctca | aattattggt | 1140 |
| gtagatacag | cttcaggtca | aaacacatac | aagcaaacag | tatttgttaa | ccctaagcaa | 1200 |

```
cgagttttag gtaatacgtg ggtgtatatt aaaggctacc aagataaaat cgaagaaagt    1260
agcggtaaag taagtgctac agatacaaaa ctgagaattt ttgaagtgaa tgatacatct    1320
aaattatcag atagctacta tgcagatcca aatgactcta accttaaaga agtaacagac    1380
caatttaaaa atagaatcta ttatgagcat ccaaatgtag ctagtattaa atttggtgat    1440
attactaaaa catatgtagt attagtagaa gggcattacg acaatacagg taagaactta    1500
aaaactcagg ttattcaaga aaatgttgat cctgtaacaa atagagacta cagtattttc    1560
ggttggaata atgagaatgt tgtacgttat ggtggtggaa gtgctgatgg tgattcagca    1620
gtaaat                                                                1626
```

<210> SEQ ID NO 60
<211> LENGTH: 542
<212> TYPE: PRT
<213> ORGANISM: Staphylococcus aureus

<400> SEQUENCE: 60

```
Leu Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Thr Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asn Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Ser Ile Ala Thr Asn
145                 150                 155                 160

Ser Glu Leu Lys Asn Ser Gln Thr Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Asp Thr Asn Val Asn Asp Lys Val Thr Ala Ser Asn Phe
    210                 215                 220

Lys Leu Glu Lys Thr Thr Phe Asp Pro Asn Gln Ser Gly Asn Thr Phe
225                 230                 235                 240

Met Ala Ala Asn Phe Thr Val Thr Asp Lys Val Lys Ser Gly Asp Tyr
                245                 250                 255

Phe Thr Ala Lys Leu Pro Asp Ser Leu Thr Gly Asn Gly Asp Val Asp
            260                 265                 270

Tyr Ser Asn Ser Asn Asn Thr Met Pro Ile Ala Asp Ile Lys Ser Thr
        275                 280                 285
```

```
Asn Gly Asp Val Val Ala Lys Ala Thr Tyr Asp Ile Leu Thr Lys Thr
    290                 295                 300

Tyr Thr Phe Val Phe Thr Asp Tyr Val Asn Asn Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
                340                 345                 350

Asn Lys Ile Thr Tyr Asn Tyr Ser Pro Ile Ala Gly Ile Asp Lys
                355                 360                 365

Pro Asn Gly Ala Asn Ile Ser Ser Gln Ile Ile Gly Val Asp Thr Ala
    370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
                420                 425                 430

Ile Phe Glu Val Asn Asp Thr Ser Lys Leu Ser Asp Ser Tyr Tyr Ala
                435                 440                 445

Asp Pro Asn Asp Ser Asn Leu Lys Glu Val Thr Asp Gln Phe Lys Asn
    450                 455                 460

Arg Ile Tyr Tyr Glu His Pro Asn Val Ala Ser Ile Lys Phe Gly Asp
465                 470                 475                 480

Ile Thr Lys Thr Tyr Val Val Leu Val Glu Gly His Tyr Asp Asn Thr
                485                 490                 495

Gly Lys Asn Leu Lys Thr Gln Val Ile Gln Glu Asn Val Asp Pro Val
                500                 505                 510

Thr Asn Arg Asp Tyr Ser Ile Phe Gly Trp Asn Asn Glu Asn Val Val
                515                 520                 525

Arg Tyr Gly Gly Gly Ser Ala Asp Gly Asp Ser Ala Val Asn
    530                 535                 540

<210> SEQ ID NO 61
<211> LENGTH: 1677
<212> TYPE: DNA
<213> ORGANISM: Staphylococcus aureus

<400> SEQUENCE: 61
atgaatatga agaaaaaaga aaacacgca attcggaaaa aatcgattgg cgtggcttca      60
gtgcttgtag gtacgttaat cggttttgga ctactcagca gtaaagaagc agatgcaagt     120 gaaatagtg ttacgcaatc tgatagcgca agtaacgaaa gcaaagtaa tgattcaagt      180 agcgttagtg ctgcacctaa acagacgac acaaacgtga gtgatactaa acatcgtca      240 aacactaata tggcgaaac gagtgtggcg caaaatccag cacaacagga acgacacaa      300 tcatcatcaa caaatgcaac tacggaagaa acgccggtaa ctggtgaagc tactactacg     360
acaacgaatc aagctaatac accggcaaca actcaatcaa gcaatacaaa tgcggaggaa     420
ttagtgaatc aaacaagtaa tgaaacgact tctaatgata ctaatacagt atcatctgta     480
aattcacctc aaaattctac aaatgcggaa atgtttcaa caacgcaaga tacttcaact     540
gaagcaacac cttcaaacaa tgaatcagct ccacagagta cagatgcaag taataaagat     600
gtagttaatc aagcggttaa tacaagtgcg cctagaatga gagcatttag tttagcggca     660
gtagctgcag atgcaccggc agctggcaca gatattacga atcagttgac gaatgtgaca     720
```

-continued

```
gttggtattg actctggtac gactgtgtat ccgcaccaag caggttatgt caaactgaat    780
tatggttttt cagtgcctaa ttctgctgtt aaaggtgaca cattcaaaat aactgtacct    840
aaagaattaa acttaaatgg tgtaacttca actgctaaag tgccaccaat tatggctgga    900
gatcaagtat tggcaaatgg tgtaatcgat agtgatggta atgttattta cacatttaca    960
gactatgtaa atactaaaga tgatgtaaaa gcaactttga ccatgcccgc ttatattgac   1020
cctgaaaatg ttaaaaagac aggtaatgtg acattggcta ctggcatagg tagtacaaca   1080
gcaaacaaaa cagtattagt agattatgaa aaatatggta agttttataa cttatctatt   1140
aaaggtacaa ttgaccaaat cgataaaaca aataatacgt atcgtcagac aatttatgtc   1200
aatccaagtg gagataacgt tattgcgccg gttttaacag gtaatttaaa accaaatacg   1260
gatagtaatg cattaataga tcagcaaaat acaagtatta agtatataa agtagataat   1320 gcagctgatt tatctgaaag ttactttgtg aatccagaaa actttgagga tgtcactaat   1380
agtgtgaata ttacattccc aaatccaaat caatataaag tagagtttaa tacgcctgat   1440
gatcaaatta caacaccgta tatagtagtt gttaatggtc atattgatcc gaatagcaaa   1500
ggtgatttag ctttacgttc aactttatat gggtataact cgaatataat ttggcgctct   1560
atgtcatggg acaacgaagt agcatttaat aacggatcag gttctggtga cggtatcgat   1620
aaaccagttg ttcctgaaca acctgatgag cctggtgaaa ttgaaccaat tccagag     1677
```

<210> SEQ ID NO 62
<211> LENGTH: 559
<212> TYPE: PRT
<213> ORGANISM: Staphylococcus aureus

<400> SEQUENCE: 62

| | | | | | | | | | | | | | | |
|---|---|---|---|---|---|---|---|---|---|---|---|---|---|---|
| Met | Asn | Met | Lys | Lys | Lys | Glu | Lys | His | Ala | Ile | Arg | Lys | Lys | Ser | Ile |
| 1 | | | | 5 | | | | | 10 | | | | | 15 | |
| Gly | Val | Ala | Ser | Val | Leu | Val | Gly | Thr | Leu | Ile | Gly | Phe | Gly | Leu | Leu |
| | | | 20 | | | | | 25 | | | | | 30 | | |
| Ser | Ser | Lys | Glu | Ala | Asp | Ala | Ser | Glu | Asn | Ser | Val | Thr | Gln | Ser | Asp |
| | | 35 | | | | | 40 | | | | | 45 | | | |
| Ser | Ala | Ser | Asn | Glu | Ser | Lys | Ser | Asn | Asp | Ser | Ser | Ser | Val | Ser | Ala |
| | 50 | | | | | 55 | | | | | 60 | | | | |
| Ala | Pro | Lys | Thr | Asp | Asp | Thr | Asn | Val | Ser | Asp | Thr | Lys | Thr | Ser | Ser |
| 65 | | | | | 70 | | | | | 75 | | | | | 80 |
| Asn | Thr | Asn | Asn | Gly | Glu | Thr | Ser | Val | Ala | Gln | Asn | Pro | Ala | Gln | Gln |
| | | | | 85 | | | | | 90 | | | | | 95 | |
| Glu | Thr | Thr | Gln | Ser | Ser | Ser | Thr | Asn | Ala | Thr | Thr | Glu | Glu | Thr | Pro |
| | | | 100 | | | | | 105 | | | | | 110 | | |
| Val | Thr | Gly | Glu | Ala | Thr | Thr | Thr | Thr | Thr | Asn | Gln | Ala | Asn | Thr | Pro |
| | | | | 115 | | | | | 120 | | | | | 125 | |
| Ala | Thr | Thr | Gln | Ser | Ser | Asn | Thr | Asn | Ala | Glu | Glu | Leu | Val | Asn | Gln |
| | | 130 | | | | | 135 | | | | | 140 | | | |
| Thr | Ser | Asn | Glu | Thr | Thr | Ser | Asn | Asp | Thr | Asn | Thr | Val | Ser | Ser | Val |
| 145 | | | | | 150 | | | | | 155 | | | | | 160 |
| Asn | Ser | Pro | Gln | Asn | Ser | Thr | Asn | Ala | Glu | Asn | Val | Ser | Thr | Thr | Gln |
| | | | | 165 | | | | | 170 | | | | | 175 | |
| Asp | Thr | Ser | Thr | Glu | Ala | Thr | Pro | Ser | Asn | Asn | Glu | Ser | Ala | Pro | Gln |
| | | | 180 | | | | | 185 | | | | | 190 | | |
| Ser | Thr | Asp | Ala | Ser | Asn | Lys | Asp | Val | Val | Asn | Gln | Ala | Val | Asn | Thr |
| | | | | 195 | | | | | 200 | | | | | 205 | |

Ser Ala Pro Arg Met Arg Ala Phe Ser Leu Ala Ala Val Ala Ala Asp
210                 215                 220

Ala Pro Ala Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
            245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
            275                 280                 285

Thr Ser Thr Ala Lys Val Pro Pro Ile Met Ala Gly Asp Gln Val Leu
290                 295                 300

Ala Asn Gly Val Ile Asp Ser Asp Gly Asn Val Ile Tyr Thr Phe Thr
305                 310                 315                 320

Asp Tyr Val Asn Thr Lys Asp Val Lys Ala Thr Leu Thr Met Pro
            325                 330                 335

Ala Tyr Ile Asp Pro Glu Asn Val Lys Lys Thr Gly Asn Val Thr Leu
            340                 345                 350

Ala Thr Gly Ile Gly Ser Thr Thr Ala Asn Lys Thr Val Leu Val Asp
            355                 360                 365

Tyr Glu Lys Tyr Gly Lys Phe Tyr Asn Leu Ser Ile Lys Gly Thr Ile
370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
            405                 410                 415

Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
            435                 440                 445

Phe Val Asn Pro Glu Asn Phe Glu Asp Val Thr Asn Ser Val Asn Ile
450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
            485                 490                 495

Pro Asn Ser Lys Gly Asp Leu Ala Leu Arg Ser Thr Leu Tyr Gly Tyr
            500                 505                 510

Asn Ser Asn Ile Ile Trp Arg Ser Met Ser Trp Asp Asn Glu Val Ala
            515                 520                 525

Phe Asn Asn Gly Ser Gly Ser Gly Asp Gly Ile Asp Lys Pro Val Val
            530                 535                 540

Pro Glu Gln Pro Asp Glu Pro Gly Glu Ile Glu Pro Ile Pro Glu
545                 550                 555

<210> SEQ ID NO 63
<211> LENGTH: 1677
<212> TYPE: DNA
<213> ORGANISM: Staphylococcus aureus

<400> SEQUENCE: 63
atgaatatga agaaaaaaga aaaacacgca attcggaaaa aatcgattgg cgtggcttca      60
gtgcttgtag gtacgttaat cggttttgga ctactcagca gtaaagaagc agatgcaagt     120

```
gaaaatagtg ttacgcaatc tgatagcgca agtaacgaaa gcaaaagtaa tgattcaagt    180
agcgttagtg ctgcacctaa aacagacgac acaaacgtga gtgatactaa acatcgtca     240
aacactaata atggcgaaac gagtgtggcg caaaatccag cacaacagga aacgacacaa    300
tcatcatcaa caaatgcaac tacgaagaa acgccggtaa ctggtgaagc tactactacg     360
acaacgaatc aagctaatac accggcaaca actcaatcaa gcaatacaaa tgcggaggaa    420
ttagtgaatc aaacaagtaa tgaaacgact tctaatgata ctaatacagt atcatctgta    480
aattcacctc aaaattctac aaatgcggaa aatgtttcaa caacgcaaga tacttcaact    540
gaagcaacac cttcaaacaa tgaatcagct ccacagaata cagatgcaag taataaagat    600
gtagttagtc aagcggttaa tccaagtacg cctagaatga gagcatttag tttagcggca    660
gtagctgcag atgcaccggc agctggcaca gatattacga atcagttgac agatgtgaaa    720
gttactattg actctggtac gactgtgtat ccgcaccaag caggttatgt caaactgaat    780
tatggttttt cagtgcctaa ttctgctgtt aaaggtgaca cattcaaaat aactgtacct    840
aaagaattaa acttaaatgg tgtaacttca actgctaaag tgccaccaat tatggctgga    900
gatcaagtat tggcaaatgg tgtaatcgat agtgatggta atgttattta tacatttaca    960
gactatgttg ataataaaga aaatgtaaca gctaatatta ctatgccagc ttatattgac   1020
cctgaaaatg ttacaaagac aggtaatgtg acattgacaa ctggcatagg aaccaatact   1080
gctagtaaga cagtattaat cgactatgag aaatatggac aattccataa tttatcaatt   1140
aaaggtacga ttgatcaaat cgataaaaca aataatacgt atcgccaaac aatttatgtc   1200
aatccaagcg gagataacgt tgtgttacct gccttaacag gtaatttaat tcctaataca   1260
aagagtaatg cgttaataga tgcaaaaaac actgatatta agtttatag agtcgataat   1320
gctaatgatt tatctgaaag ttattatgtg aatcctagcg attttgaaga tgtaactaat   1380
caagttagaa tttcatttcc aaatgctaat caatacaaag tagaatttcc tacggacgat   1440
gaccaaatta caacaccgta tattgtagtt gttaatggcc atattgatcc tgctagtaca   1500
ggtgatttag cactacgttc gacatttat ggttatgatt ctaatttat atggagatct    1560
atgtcatggg acaacgaagt agcatttaat aacggatcag gttctggtga cggtatcgat   1620
aaaccagttg ttcctgaaca acctgatgag cctggtgaaa ttgaaccaat tccagag      1677
```

<210> SEQ ID NO 64
<211> LENGTH: 559
<212> TYPE: PRT
<213> ORGANISM: Staphylococcus aureus

<400> SEQUENCE: 64

```
Met Asn Met Lys Lys Glu Lys His Ala Ile Arg Lys Lys Ser Ile
1               5                  10                  15

Gly Val Ala Ser Val Leu Val Gly Thr Leu Ile Gly Phe Gly Leu Leu
                20                  25                  30

Ser Ser Lys Glu Ala Asp Ala Ser Glu Asn Ser Val Thr Gln Ser Asp
            35                  40                  45

Ser Ala Ser Asn Glu Ser Lys Ser Asn Asp Ser Ser Val Ser Ala
        50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
```

-continued

```
                100                 105                 110
Val Thr Gly Glu Ala Thr Thr Thr Thr Asn Gln Ala Asn Thr Pro
            115                 120                 125
Ala Thr Thr Gln Ser Ser Asn Thr Asn Ala Glu Glu Leu Val Asn Gln
130                 135                 140
Thr Ser Asn Glu Thr Thr Ser Asn Asp Thr Asn Thr Val Ser Ser Val
145                 150                 155                 160
Asn Ser Pro Gln Asn Ser Thr Asn Ala Glu Asn Val Ser Thr Thr Gln
                165                 170                 175
Asp Thr Ser Thr Glu Ala Thr Pro Ser Asn Asn Glu Ser Ala Pro Gln
            180                 185                 190
Asn Thr Asp Ala Ser Asn Lys Asp Val Val Ser Gln Ala Val Asn Pro
            195                 200                 205
Ser Thr Pro Arg Met Arg Ala Phe Ser Leu Ala Ala Val Ala Ala Asp
            210                 215                 220
Ala Pro Ala Ala Gly Thr Asp Ile Thr Asn Gln Leu Thr Asp Val Lys
225                 230                 235                 240
Val Thr Ile Asp Ser Gly Thr Thr Val Tyr Pro His Gln Ala Gly Tyr
                245                 250                 255
Val Lys Leu Asn Tyr Gly Phe Ser Val Pro Asn Ser Ala Val Lys Gly
                260                 265                 270
Asp Thr Phe Lys Ile Thr Val Pro Lys Glu Leu Asn Leu Asn Gly Val
            275                 280                 285
Thr Ser Thr Ala Lys Val Pro Pro Ile Met Ala Gly Asp Gln Val Leu
            290                 295                 300
Ala Asn Gly Val Ile Asp Ser Asp Gly Asn Val Ile Tyr Thr Phe Thr
305                 310                 315                 320
Asp Tyr Val Asp Asn Lys Glu Asn Val Thr Ala Asn Ile Thr Met Pro
                325                 330                 335
Ala Tyr Ile Asp Pro Glu Asn Val Thr Lys Thr Gly Asn Val Thr Leu
            340                 345                 350
Thr Thr Gly Ile Gly Thr Asn Thr Ala Ser Lys Thr Val Leu Ile Asp
            355                 360                 365
Tyr Glu Lys Tyr Gly Gln Phe His Asn Leu Ser Ile Lys Gly Thr Ile
            370                 375                 380
Asp Gln Ile Asp Lys Thr Asn Asn Thr Tyr Arg Gln Thr Ile Tyr Val
385                 390                 395                 400
Asn Pro Ser Gly Asp Asn Val Val Leu Pro Ala Leu Thr Gly Asn Leu
                405                 410                 415
Ile Pro Asn Thr Lys Ser Asn Ala Leu Ile Asp Ala Lys Asn Thr Asp
            420                 425                 430
Ile Lys Val Tyr Arg Val Asp Asn Ala Asn Asp Leu Ser Glu Ser Tyr
            435                 440                 445
Tyr Val Asn Pro Ser Asp Phe Glu Asp Val Thr Asn Gln Val Arg Ile
            450                 455                 460
Ser Phe Pro Asn Ala Asn Gln Tyr Lys Val Glu Phe Pro Thr Asp Asp
465                 470                 475                 480
Asp Gln Ile Thr Thr Pro Tyr Ile Val Val Asn Gly His Ile Asp
                485                 490                 495
Pro Ala Ser Thr Gly Asp Leu Ala Leu Arg Ser Thr Phe Tyr Gly Tyr
            500                 505                 510
Asp Ser Asn Phe Ile Trp Arg Ser Met Ser Trp Asp Asn Glu Val Ala
            515                 520                 525
```

Phe Asn Asn Gly Ser Gly Ser Gly Asp Gly Ile Asp Lys Pro Val Val
    530                 535                 540

Pro Glu Gln Pro Asp Glu Pro Gly Glu Ile Glu Pro Ile Pro Glu
545                 550                 555

<210> SEQ ID NO 65
<211> LENGTH: 1677
<212> TYPE: DNA
<213> ORGANISM: Staphylococcus aureus

<400> SEQUENCE: 65

```
atgaatatga agaaaaaaga aaaacacgca attcggaaaa aatcgattgg cgtggcttca      60
gtgcttgtag gtacgttaat cggttttgga ctactcagca gtaaagaagc agatgcaagt     120
gaaaatagtg ttacgcaatc tgatagcgca agtaacgaaa gcaaaagtaa tgattcaagt     180
agcgttagtg ctgcacctaa acagacgac acaaacgtga gtgatactaa acatcgtca      240
aacactaata tggcgaaac gagtgtggcg caaaatccag cacaacagga aacgacacaa     300
tcatcatcaa caaatgcaac tacggaagaa acgccggtaa ctggtgaagc tactactacg     360
acaacgaatc aagctaatac accggcaaca actcaatcaa gcaatacaaa tgcggaggaa     420
ttagtgaatc aaacaagtaa tgaaacgact tctaatgata ctaatacagt atcatctgta     480
aattcacctc aaaattctac aaatgcggaa atgtttcaa caacgcaaga tacttcaact     540
gaagcaacac cttcaaacaa tgaatcagct ccacagagta cagatgcaag taataaagat     600
gtagttaatc aagcggttaa tacaagtgcg cctagaatga gagcatttag tttagcggca     660
gtagctgcag atgcaccggc agctggcaca gatattacga atcagttgac gaatgtgaca     720
gttggtattg actctggtac gactgtgtat ccgcaccaag caggttatgt caaactgaat     780
tatggttttt cagtgcctaa ttctgctgtt aaaggtgaca cattcaaaat aactgtacct     840
aaagaattaa acttaaatgg tgtaacttca actgctaaag tgccaccaat tatggctgga     900
gatcaagtat tggcaaatgg tgtaatcgat agtgatggta atgttatta tacatttaca     960
gactatgtaa atactaaaga tgatgtaaaa gcaactttga ccatgcccgc ttatattaac    1020
cctgaaaatg ttaaaaagac aggtaatgtg acattggcta ctggcatagg tagtacaaca    1080
gcaaacaaaa cagtattagt agattatgaa aaatatggta agttttataa cttatctatt    1140
aaaggtacaa ttgaccaaat cgataaaaca ataatacgt atcgtcagac aatttatgtc    1200
aatccaagtg gagataacgt tattgcgccg gttttaacag gtaatttaaa accaaatacg    1260
gatagtaatg cattaataga tcagcaaaat acaagtatta agtatataa agtagataat    1320
gcagctgatt tatctgaaag ttactttgtg aatccagaaa actttgagga tgtcactaat    1380
agtgtgaata ttacattccc aaatccaaat caatataaag tagagtttaa tacgcctgat    1440
gatcaaatta caacaccgta tatagtagtt gttaatggtc atattgatcc gaatagcaaa    1500
ggtgatttag ctttacgttc aacttttatat gggtataact cgaatataat ttggcgctct    1560
atgtcatggg acaacgaagt agcatttaat aacggatcag gttctggtga cggtatcgat    1620
aaaccagttg ttcctgaaca acctgatgag cctggtgaaa ttgaaccaat tccagag      1677
```

<210> SEQ ID NO 66
<211> LENGTH: 559
<212> TYPE: PRT
<213> ORGANISM: Staphylococcus aureus

<400> SEQUENCE: 66

```
Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Asn Gln Ala Asn Thr Pro
            115                 120                 125

Ala Thr Thr Gln Ser Ser Asn Thr Asn Ala Glu Glu Leu Val Asn Gln
    130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Gln Ala Val Asn Thr
    195                 200                 205

Ser Ala Pro Arg Met Arg Ala Phe Ser Leu Ala Ala Val Ala Ala Asp
210                 215                 220

Ala Pro Ala Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
    275                 280                 285

Thr Ser Thr Ala Lys Val Pro Pro Ile Met Ala Gly Asp Gln Val Leu
290                 295                 300

Ala Asn Gly Val Ile Asp Ser Asp Gly Asn Val Ile Tyr Thr Phe Thr
305                 310                 315                 320

Asp Tyr Val Asn Thr Lys Asp Asp Val Lys Ala Thr Leu Thr Met Pro
                325                 330                 335

Ala Tyr Ile Asn Pro Glu Asn Val Lys Lys Thr Gly Asn Val Thr Leu
            340                 345                 350

Ala Thr Gly Ile Gly Ser Thr Thr Ala Asn Lys Thr Val Leu Val Asp
    355                 360                 365

Tyr Glu Lys Tyr Gly Lys Phe Tyr Asn Leu Ser Ile Lys Gly Thr Ile
370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
```

```
              420            425            430
Ile Lys Val Tyr Lys Val Asp Asn Ala Ala Asp Leu Ser Glu Ser Tyr
            435            440            445

Phe Val Asn Pro Glu Asn Phe Glu Asp Val Thr Asn Ser Val Asn Ile
450            455            460

Thr Phe Pro Asn Pro Asn Gln Tyr Lys Val Glu Phe Asn Thr Pro Asp
465            470            475            480

Asp Gln Ile Thr Thr Pro Tyr Ile Val Val Asn Gly His Ile Asp
            485            490            495

Pro Asn Ser Lys Gly Asp Leu Ala Leu Arg Ser Thr Leu Tyr Gly Tyr
            500            505            510

Asn Ser Asn Ile Ile Trp Arg Ser Met Ser Trp Asp Asn Glu Val Ala
            515            520            525

Phe Asn Asn Gly Ser Gly Ser Gly Asp Gly Ile Asp Lys Pro Val Val
            530            535            540

Pro Glu Gln Pro Asp Glu Pro Gly Glu Ile Glu Pro Ile Pro Glu
545            550            555

<210> SEQ ID NO 67
<211> LENGTH: 1677
<212> TYPE: DNA
<213> ORGANISM: Staphylococcus aureus

<400> SEQUENCE: 67
atgaatatga agaaacaaga aaaacacgca attcgtaaaa aatcgattgg cgtggcttca      60
gtgcttgtag gtacgttaat cggttttgga ctactcagca gtaaagaagc agatgcaagt     120
gaaaatagta tgcacaaaac ggaaaatacg agtaatgaga gcaaaagtaa tgatccaagt     180
agcgttaatg ctgcacctaa aacagacaac acaaacgtga gtgattctaa tacaacgaca     240
aacactaata gtgacgaaac gaatgtagcg caaaatccag cacaacagga acgacacaa     300 tcagcatcaa caaatgcaac tacagaagaa acaccggtaa ctggtgaagt tactactacg     360
gcaacgaatc aagctaatac accggcaaca actcaatcaa gcaatacaaa tgcggaagaa     420
tcagtgaatc aaacaagtaa tgaaacgact tctaatgata ctaatacagt atcatctgta     480
aattcacctc aaaattctac aaatgcggaa atgtttcaa caacgcaaga catttcaact     540
gaagcaacac cttcaaacaa tgaatcagct ccacagagta cagatgcaag taataaagat     600
gtagttaatc aagcggttaa tacaagtgcg cctagaatga gagcatttag tttagcggct     660
gtagctgcag atgcaccggc tgctggcaaa gatattacga atcagttgac gaatgtgaca     720
gttggtattg actctggaga tacagtttat ccgcaccaag caggctatgt caaactgaat     780
tatgggttct cagtaccaaa tgaggctgtt caaggtgaca cattcaaaat aactgtgccc     840
aaagaattaa acttaaatgg tgtaacttca actgctaaag tgccaccaat tatggccgga     900
gatcaagtat tggcaaatgg tgtaatcgat agtgatggta atgttatta cacatttaca     960 gactatgtaa atactaaaga tgatgttaaa gcaactttga ccatgcccgc ttatattgac    1020
cctgaaaatg ttacaaagac aggtaatgtg acattggcta ctggcatagg tagtacaaca    1080
gcaaacaaaa cagtattagt agattatgaa aaatatggta gttttataa cttatctatt    1140 aaaggtacaa ttgaccaaat cgataaaaca ataatacgt atcgtcagac aattttatgtc    1200 aatccaagtg gagataacgt tattgcgccg gtttaacag gtaatttaaa accaaatacg    1260
gatagtaatg cattaataga tgcacaaaat actagtatta agtatataa agttgataat    1320 gcatcagact tgtctgaaag ttattatgtg aatccagata actttgaaga tgtcactgat    1380
```

-continued

```
agtgtgaata ttacattccc aaatccaaat caatataaag tagagttcaa tacgcctgat      1440
gatcaaataa caacaccata tattgtagtt gttaatgggc atattgatcc taatagtaaa      1500
ggtgatttag ctttacgttc aactttatat ggatataatt cgaatataat ttggcgatca      1560
atgtcatggg ataatgaagt agcatttaat aacggatcag gttctggtga cggtatcgat      1620
aaacctgttg ttcctgaaca acctgatgag ccgggtgaaa ttgaaccaat tccagag        1677
```

<210> SEQ ID NO 68
<211> LENGTH: 559
<212> TYPE: PRT
<213> ORGANISM: Staphylococcus aureus

<400> SEQUENCE: 68

```
Met Asn Met Lys Lys Gln Glu Lys His Ala Ile Arg Lys Lys Ser Ile
  1               5                  10                  15

Gly Val Ala Ser Val Leu Val Gly Thr Leu Ile Gly Phe Gly Leu Leu
             20                  25                  30

Ser Ser Lys Glu Ala Asp Ala Ser Glu Asn Ser Met Thr Gln Thr Glu
         35                  40                  45

Asn Thr Ser Asn Glu Ser Lys Ser Asn Asp Pro Ser Ser Val Asn Ala
     50                  55                  60

Ala Pro Lys Thr Asp Asn Thr Asn Val Ser Asp Ser Asn Thr Thr Thr
 65                  70                  75                  80

Asn Thr Asn Ser Asp Glu Thr Asn Val Ala Gln Asn Pro Ala Gln Gln
                 85                  90                  95

Glu Thr Thr Gln Ser Ala Ser Thr Asn Ala Thr Thr Glu Glu Thr Pro
            100                 105                 110

Val Thr Gly Glu Val Thr Thr Thr Ala Thr Asn Gln Ala Asn Thr Pro
        115                 120                 125

Ala Thr Thr Gln Ser Ser Asn Thr Asn Ala Glu Glu Ser Val Asn Gln
    130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Ile Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
    210                 215                 220

Ala Pro Ala Ala Gly Lys Asp Ile Thr Asn Gln Leu Thr Asn Val Thr
225                 230                 235                 240

Val Gly Ile Asp Ser Gly Asp Thr Val Tyr Pro His Gln Ala Gly Tyr
                245                 250                 255

Val Lys Leu Asn Tyr Gly Phe Ser Val Pro Asn Glu Ala Val Gln Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
305                 310                 315                 320
```

```
Asp Tyr Val Asn Thr Lys Asp Val Lys Ala Thr Leu Thr Met Pro
                325                 330                 335

Ala Tyr Ile Asp Pro Glu Asn Val Thr Lys Thr Gly Asn Val Thr Leu
            340                 345                 350

Ala Thr Gly Ile Gly Ser Thr Thr Ala Asn Lys Thr Val Leu Val Asp
            355                 360                 365

Tyr Glu Lys Tyr Gly Lys Phe Tyr Asn Leu Ser Ile Lys Gly Thr Ile
370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Ala Gln Asn Thr Ser
                420                 425                 430

Ile Lys Val Tyr Lys Val Asp Asn Ala Ser Asp Leu Ser Glu Ser Tyr
            435                 440                 445

Tyr Val Asn Pro Asp Asn Phe Glu Asp Val Thr Asp Ser Val Asn Ile
        450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Val Asn Gly His Ile Asp
                485                 490                 495

Pro Asn Ser Lys Gly Asp Leu Ala Leu Arg Ser Thr Leu Tyr Gly Tyr
                500                 505                 510

Asn Ser Asn Ile Ile Trp Arg Ser Met Ser Trp Asp Asn Glu Val Ala
            515                 520                 525

Phe Asn Asn Gly Ser Gly Ser Gly Asp Gly Ile Asp Lys Pro Val Val
        530                 535                 540

Pro Glu Gln Pro Asp Glu Pro Gly Glu Ile Glu Pro Ile Pro Glu
545                 550                 555
```

<210> SEQ ID NO 69
<211> LENGTH: 1677
<212> TYPE: DNA
<213> ORGANISM: Staphylococcus aureus

<400> SEQUENCE: 69

```
atgaatatga agaaaaaga aaaacacgca attcggaaaa aatcgattgg cgtggcttca      60
gtgcttgtag gtacgttaat cggttttgga ctactcagca gtaaagaagc agatgcaagt    120
gaaaatagtg ttacgcaatc tgatagcgca agtaacgaaa gcaaaagtaa tgattcaagt    180
agcattaatg ctgcacctaa acagacaaac acaaacgtga gtgatactaa accaacgtca    240
aacactaata tggcgaaaac gagtgtggcg caaaatccag cacaacagga aacgacacaa    300
tcagcatcaa caaatgcaac tacggaagaa acgccggtaa ctggtgaagc tactactacg    360
acaacgaatc aagctaatac accggcaaca actcaatcaa gcaatacaaa tgcggaggaa    420
ttagtgaatc aaacaagtaa tgaaacgact tctaatgata ctaatacagt atcatctgta    480
aattcacctc aaaattctac aaatgcggaa aatgtttcaa caacgcaaga tacttcaact    540
gaagcaacac cttcaaacaa tgaatcagct ccacagagta cagatgcaag taataaagat    600
gtagttaatc aagcggttaa tacaagtgcg cctagaaaga gagcatttag tttagcggct    660
gtagctgcag atgcaccggc agctggcaca gatattacga atcagttgac agatgtgaaa    720
gttactattg actctggtac gactgtgtat ccgcaccaag caggttatgt caaactgaat    780
```

-continued

```
tatggttttt cagtgcctaa ttctgctgtt aaaggtgaca cattcaaaat aactgtacct    840
aaagaattaa acttaaatgg tgtaacttca actgctaaag tgccaccaat tatggctgga    900
gatcaagtat tggcaaatgg tgtaatcgat agtgatggta atgttattta tacatttaca    960
gactatgttg ataataaaga aaatgtaaca gctaatatta ctatgccagc ttatattgac   1020
cctgaaaatg ttacaaagac aggtaatgtg acattgacaa ctggcatagg aaccaatact   1080
gctagtaaga cagtattaat cgactatgag aaatatggac aattccataa tttatcaatt   1140
aaaggtacga ttgatcaaat cgataaaaca aataatacgt atcgccaaac aatttatgtc   1200
aatccaagcg gagataacgt tgtgttacct gccttaacag gtaatttaat tcctaataca   1260
aagagtaatg cgttaataga tgcaaaaaac actgatatta aagtttatag agtcgataat   1320
gctaatgatt tatctgaaag ttattatgtg aatcctagcg attttgaaga tgtaactaat   1380
caagttagaa tttcatttcc aaatgctaat caatacaaag tagaatttcc tacggacgat   1440
gaccaaatta caacaccgta tattgtagtt gttaatggcc atattgatcc tgctagtaca   1500
ggtgatttag cactacgttc gacattttat ggttatgatt ctaattttat atggagatct   1560
atgtcatggg acaacgaagt agcatttaat aacggatcag gttctggtga cggtatcgat   1620
aaaccagttg ttcctgaaca acctgatgag cctggtgaaa ttgaaccaat tccagag     1677
```

<210> SEQ ID NO 70
<211> LENGTH: 559
<212> TYPE: PRT
<213> ORGANISM: Staphylococcus aureus

<400> SEQUENCE: 70

```
Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Ile Asn Ala
    50                  55                  60

Ala Pro Lys Thr Asp Asn Thr Asn Val Ser Asp Thr Lys Pro Thr Ser
65                  70                  75                  80

Asn Thr Asn Asn Gly Glu Thr Ser Val Ala Gln Asn Pro Ala Gln Gln
                85                  90                  95

Glu Thr Thr Gln Ser Ala Ser Thr Asn Ala Thr Thr Glu Glu Thr Pro
            100                 105                 110

Val Thr Gly Glu Ala Thr Thr Thr Thr Thr Asn Gln Ala Asn Thr Pro
        115                 120                 125

Ala Thr Thr Gln Ser Ser Asn Thr Asn Ala Glu Glu Leu Val Asn Gln
    130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Lys Arg Ala Phe Ser Leu Ala Ala Val Ala Ala Asp
    210                 215                 220
```

Ala Pro Ala Ala Gly Thr Asp Ile Thr Asn Gln Leu Thr Asp Val Lys
225                 230                 235                 240

Val Thr Ile Asp Ser Gly Thr Thr Val Tyr Pro His Gln Ala Gly Tyr
            245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
            275                 280                 285

Thr Ser Thr Ala Lys Val Pro Pro Ile Met Ala Gly Asp Gln Val Leu
290                 295                 300

Ala Asn Gly Val Ile Asp Ser Asp Gly Asn Val Ile Tyr Thr Phe Thr
305                 310                 315                 320

Asp Tyr Val Asp Asn Lys Glu Asn Val Thr Ala Asn Ile Thr Met Pro
                325                 330                 335

Ala Tyr Ile Asp Pro Glu Asn Val Thr Lys Thr Gly Asn Val Thr Leu
            340                 345                 350

Thr Thr Gly Ile Gly Thr Asn Thr Ala Ser Lys Thr Val Leu Ile Asp
            355                 360                 365

Tyr Glu Lys Tyr Gly Gln Phe His Asn Leu Ser Ile Lys Gly Thr Ile
370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Val Leu Pro Ala Leu Thr Gly Asn Leu
            405                 410                 415

Ile Pro Asn Thr Lys Ser Asn Ala Leu Ile Asp Ala Lys Asn Thr Asp
            420                 425                 430

Ile Lys Val Tyr Arg Val Asp Asn Ala Asn Asp Leu Ser Glu Ser Tyr
            435                 440                 445

Tyr Val Asn Pro Ser Asp Phe Glu Asp Val Thr Asn Gln Val Arg Ile
450                 455                 460

Ser Phe Pro Asn Ala Asn Gln Tyr Lys Val Glu Phe Pro Thr Asp Asp
465                 470                 475                 480

Asp Gln Ile Thr Thr Pro Tyr Ile Val Val Asn Gly His Ile Asp
            485                 490                 495

Pro Ala Ser Thr Gly Asp Leu Ala Leu Arg Ser Thr Phe Tyr Gly Tyr
            500                 505                 510

Asp Ser Asn Phe Ile Trp Arg Ser Met Ser Trp Asp Asn Glu Val Ala
            515                 520                 525

Phe Asn Asn Gly Ser Gly Ser Gly Asp Gly Ile Asp Lys Pro Val Val
530                 535                 540

Pro Glu Gln Pro Asp Glu Pro Gly Glu Ile Glu Pro Ile Pro Glu
545                 550                 555

<210> SEQ ID NO 71
<211> LENGTH: 1677
<212> TYPE: DNA
<213> ORGANISM: Staphylococcus aureus

<400> SEQUENCE: 71
atgaatatga agaaaaaga aaaacacgca attcggaaaa aatcgattgg cgtggcttca      60
gtgcttgtag gtacgttaat cggttttgga ctactcagca gtaaagaagc agatgcaagt     120 gaaatagtg ttacgcaatc tgatagcgca agtaacgaaa gcaaaagtaa tgattcaagt     180
agcgttagtg ctgcacctaa aacagacgac acaaacgtga gtgatactaa acatcgtca     240

```
aacactaata atggcgaaac gagtgtggcg caaaatccag cacaacagga aacgacacaa      300
tcatcatcaa caaatgcaac tacgaagaa acgccggtaa ctggtgaagc tactactacg      360
acaacgaatc aagctaatac accggcaaca actcaatcaa gcaatacaaa tgcggaggaa      420
ttagtgaatc aaacaagtaa tgaaacgact tctaatgata ctaatacagt atcatctgta      480
aattcacctc aaaattctac aaatgcggaa aatgtttcaa caacgcaaga tacttcaact      540
gaagcaacac cttcaaacaa tgaatcagct ccacagaata cagatgcaag taataaagat      600
gtagttagtc aagcggttaa tccaagtacg cctagaatga gagcatttag tttagcggca      660
gtagctgcag atgcaccggc agctggcaca gatattacga atcagttgac agatgtgaaa      720
gttactattg actctggtac gactgtgtat ccgcaccaag caggttatgt caaactgaat      780
tatggttttt cagtgcctaa ttctcctgtt aaaggtgaca cattcaaaat aactgtacct      840
aaagaattaa acttaaatgg tgtaacttca actgctaaag tgccaccaat tatggctgga      900
gatcaagtat tggcaaatgg tgtaatcgat agtgatggta atgttattta tacatttaca      960
gactatgttg ataataaaga aaatgtaaca gctaatatta ctatgccagc ttatattgac     1020
cctgaaaatg ttacaaagac aggtaatgtg acattgacaa ctggcatagg aaccaatact     1080
gctagtaaga cagtattaat cgactatgag aaatatggac aattccataa tttatcaatt     1140
aaaggtacga ttgatcaaat cgataaaaca aataatacgt atcgccaaac aatttatgtc     1200
aatccaagcg gagataacgt tgtgttacct gccttaacag gtaatttaat tcctaataca     1260
aagagtaatg cgttaataga tgcaaaaaac actgatatta agtttatag agtcgataat      1320 gctaatgatt tatctgaaag ttattatgtg aatcctagcg attttgaaga tgtaactaat     1380
caagttagaa tttcatttcc aaatgctaat caatacaaag tagaatttcc tacgacgat      1440 gaccaaatta caacaccgta tattgtagtt gttaatggcc atattgatcc tgctagtaca     1500
ggtgatttag cactacgttc gacattttat ggttatgatt ctaattttat atggagatct     1560
atgtcatggg acaacgaagt agcatttaat aacggatcag gttctggtga cggtatcgat     1620
aaaccagttg ttcctgaaca acctgatgag cctggtgaaa ttgaaccaat tccagag       1677
```

<210> SEQ ID NO 72
<211> LENGTH: 559
<212> TYPE: PRT
<213> ORGANISM: Staphylococcus aureus

<400> SEQUENCE: 72

```
Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
                20                  25                  30

Ser Ser Lys Glu Ala Asp Ala Ser Glu Asn Ser Val Thr Gln Ser Asp
            35                  40                  45

Ser Ala Ser Asn Glu Ser Lys Ser Asn Asp Ser Ser Val Ser Ala
        50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Thr Asn Gln Ala Asn Thr Pro
```

```
            115                 120                 125
Ala Thr Thr Gln Ser Ser Asn Thr Asn Ala Glu Glu Leu Val Asn Gln
130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Asn Thr Asp Ala Ser Asn Lys Asp Val Val Ser Gln Ala Val Asn Pro
        195                 200                 205

Ser Thr Pro Arg Met Arg Ala Phe Ser Leu Ala Ala Val Ala Ala Asp
210                 215                 220

Ala Pro Ala Ala Gly Thr Asp Ile Thr Asn Gln Leu Thr Asp Val Lys
225                 230                 235                 240

Val Thr Ile Asp Ser Gly Thr Thr Val Tyr Pro His Gln Ala Gly Tyr
                245                 250                 255

Val Lys Leu Asn Tyr Gly Phe Ser Val Pro Asn Ser Pro Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
290                 295                 300

Ala Asn Gly Val Ile Asp Ser Asp Gly Asn Val Ile Tyr Thr Phe Thr
305                 310                 315                 320

Asp Tyr Val Asp Asn Lys Glu Asn Val Thr Ala Asn Ile Thr Met Pro
                325                 330                 335

Ala Tyr Ile Asp Pro Glu Asn Val Thr Lys Thr Gly Asn Val Thr Leu
            340                 345                 350

Thr Thr Gly Ile Gly Thr Asn Thr Ala Ser Lys Thr Val Leu Ile Asp
        355                 360                 365

Tyr Glu Lys Tyr Gly Gln Phe His Asn Leu Ser Ile Lys Gly Thr Ile
370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Val Leu Pro Ala Leu Thr Gly Asn Leu
                405                 410                 415

Ile Pro Asn Thr Lys Ser Asn Ala Leu Ile Asp Ala Lys Asn Thr Asp
            420                 425                 430

Ile Lys Val Tyr Arg Val Asp Asn Ala Asn Asp Leu Ser Glu Ser Tyr
        435                 440                 445

Tyr Val Asn Pro Ser Asp Phe Glu Asp Val Thr Asn Gln Val Arg Ile
450                 455                 460

Ser Phe Pro Asn Ala Asn Gln Tyr Lys Val Glu Phe Pro Thr Asp Asp
465                 470                 475                 480

Asp Gln Ile Thr Thr Pro Tyr Ile Val Val Asn Gly His Ile Asp
                485                 490                 495

Pro Ala Ser Thr Gly Asp Leu Ala Leu Arg Ser Thr Phe Tyr Gly Tyr
            500                 505                 510

Asp Ser Asn Phe Ile Trp Arg Ser Met Ser Trp Asp Asn Glu Val Ala
        515                 520                 525

Phe Asn Asn Gly Ser Gly Ser Gly Asp Gly Ile Asp Lys Pro Val Val
530                 535                 540
```

Pro Gln Pro Asp Glu Pro Gly Glu Ile Glu Pro Ile Pro Glu
545             550             555

<210> SEQ ID NO 73
<211> LENGTH: 1677
<212> TYPE: DNA
<213> ORGANISM: Staphylococcus aureus

<400> SEQUENCE: 73

| | |
|---|---:|
| atgaatatga agaaaaaga aaaacacgca attcggaaaa aatcgattgg cgtggcttca | 60 |
| gtgcttgtag gtacgttaat cggttttgga ctactcagca gtaaagaagc agatgcaagt | 120 |
| gaaaatagtg ttacgcaatc tgatagcgca agtaacgaaa gcaaaagtaa tgattcaagt | 180 |
| agcattaatg ctgcacctaa acagacaac acaaacgtga gtgatactaa acaacgtca | 240 |
| aacactaata atggcgaaac gagtgtggcg caaaatccag cacaacagga aacgacacaa | 300 |
| tcagcatcaa caaatgcaac tacgaagaa acgccggtaa ctggtgaaac tactactacg | 360 |
| gcaacgaatc aagctaatac accggcaaca actcaatcaa gcaatacaaa tgcggaggaa | 420 |
| ttagtgaatc aaacaagtaa tgaaacgact tctaatgata ctaatacagt atcatctgta | 480 |
| aattcacctc aaaattctac aaatgcggaa atgtttcaa caacgcaaga tacttcaact | 540 |
| gaagcaacac cttcaaacaa tgaatcagct ccacagagta cagatgcaag taataaagat | 600 |
| gtagttaatc aagcggttaa tacaagtgcg cctagaatga gagcattag tttagcggca | 660 |
| gtagctgcag atgcaccggc agctggcaca gatattacga atcagttgac agatgtgaaa | 720 |
| gttactattg actctggtac gactgtgtat ccgcaccaag caggttatgt caaactgaat | 780 |
| tatggttttt cagtgcctaa ttctgctgtt aaaggtgaca cattcaaaat aactgtacct | 840 |
| aaagaattaa acttaaatgg tgtaacttca actgctaaag tgccaccaat tatggctgga | 900 |
| gatcaagtat tggcaaatgg tgtaatcgat agtgatggta atgttattta cattttaca | 960 |
| gactatgttg ataataaaga aaatgtaaca gctaatatta ctatgccagc ttatattgac | 1020 |
| cctgaaaatg ttacaaagac aggtaatgtg acattgacaa ctggcatagg aaccaatact | 1080 |
| gctagtaaga cagtattaat cgactatgag aaatatggac aattccataa tttatcaatt | 1140 |
| aaaggtacga ttgatcaaat cgataaaaca ataatacgt atcgccaaac aatttatgtc | 1200 |
| aatccaagcg gagataacgt tgtgttacct gccttaacag taatttaat tcctaataca | 1260 |
| aagagtaatg cgttaataga tgcaaaaaac actgatatta agtttatag agtcgataat | 1320 |
| gctaatgatt tatctgaaag ttattatgtg aatcctagcg attttgaaga tgtaactaat | 1380 |
| caagttagaa tttcatttcc aaatgctaat caatacaaag tagaatttcc tacggacgat | 1440 |
| gaccaaatta caacaccgta tattgtagtt gttaatggcc atattgatcc tgctagtaca | 1500 |
| ggtgatttag cactacgttc gacattttat ggttatgatt ctaattttat atggagatct | 1560 |
| atgtcatggg acaacgaagt agcatttaat aacggatcag ttctggtga cggtatcgat | 1620 |
| aaaccagttg ttcctgaaca acctgatgag cctggtgaaa ttgaaccaat tccagag | 1677 |

<210> SEQ ID NO 74
<211> LENGTH: 559
<212> TYPE: PRT
<213> ORGANISM: Staphylococcus aureus

<400> SEQUENCE: 74

Met Asn Met Lys Lys Lys Glu Lys His Ala Ile Arg Lys Lys Ser Ile
1               5                   10                  15

```
Gly Val Ala Ser Val Leu Val Gly Thr Leu Ile Gly Phe Gly Leu Leu
            20                  25                  30
Ser Ser Lys Glu Ala Asp Ala Ser Glu Asn Ser Val Thr Gln Ser Asp
        35                  40                  45
Ser Ala Ser Asn Glu Ser Lys Ser Asn Asp Ser Ser Ser Ile Asn Ala
    50                  55                  60
Ala Pro Lys Thr Asp Asn Thr Asn Val Ser Asp Thr Lys Thr Thr Ser
65                  70                  75                  80
Asn Thr Asn Asn Gly Glu Thr Ser Val Ala Gln Asn Pro Ala Gln Gln
                85                  90                  95
Glu Thr Thr Gln Ser Ala Ser Thr Asn Ala Thr Thr Glu Glu Thr Pro
            100                 105                 110
Val Thr Gly Glu Thr Thr Thr Ala Thr Asn Gln Ala Asn Thr Pro
        115                 120                 125
Ala Thr Thr Gln Ser Ser Asn Thr Asn Ala Glu Glu Leu Val Asn Gln
    130                 135                 140
Thr Ser Asn Glu Thr Thr Ser Asn Asp Thr Asn Thr Val Ser Ser Val
145                 150                 155                 160
Asn Ser Pro Gln Asn Ser Thr Asn Ala Glu Asn Val Ser Thr Thr Gln
                165                 170                 175
Asp Thr Ser Thr Glu Ala Thr Pro Ser Asn Asn Glu Ser Ala Pro Gln
            180                 185                 190
Ser Thr Asp Ala Ser Asn Lys Asp Val Val Asn Gln Ala Val Asn Thr
        195                 200                 205
Ser Ala Pro Arg Met Arg Ala Phe Ser Leu Ala Ala Val Ala Ala Asp
    210                 215                 220
Ala Pro Ala Ala Gly Thr Asp Ile Thr Asn Gln Leu Thr Asp Val Lys
225                 230                 235                 240
Val Thr Ile Asp Ser Gly Thr Thr Val Tyr Pro His Gln Ala Gly Tyr
                245                 250                 255
Val Lys Leu Asn Tyr Gly Phe Ser Val Pro Asn Ser Ala Val Lys Gly
            260                 265                 270
Asp Thr Phe Lys Ile Thr Val Pro Lys Glu Leu Asn Leu Asn Gly Val
        275                 280                 285
Thr Ser Thr Ala Lys Val Pro Pro Ile Met Ala Gly Asp Gln Val Leu
    290                 295                 300
Ala Asn Gly Val Ile Asp Ser Asp Gly Asn Val Ile Tyr Thr Phe Thr
305                 310                 315                 320
Asp Tyr Val Asp Asn Lys Glu Asn Val Thr Ala Asn Ile Thr Met Pro
                325                 330                 335
Ala Tyr Ile Asp Pro Glu Asn Val Thr Lys Thr Gly Asn Val Thr Leu
            340                 345                 350
Thr Thr Gly Ile Gly Thr Asn Thr Ala Ser Lys Thr Val Leu Ile Asp
        355                 360                 365
Tyr Glu Lys Tyr Gly Gln Phe His Asn Leu Ser Ile Lys Gly Thr Ile
    370                 375                 380
Asp Gln Ile Asp Lys Thr Asn Asn Thr Tyr Arg Gln Thr Ile Tyr Val
385                 390                 395                 400
Asn Pro Ser Gly Asp Asn Val Val Leu Pro Ala Leu Thr Gly Asn Leu
                405                 410                 415
Ile Pro Asn Thr Lys Ser Asn Ala Leu Ile Asp Ala Lys Asn Thr Asp
            420                 425                 430
Ile Lys Val Tyr Arg Val Asp Asn Ala Asn Asp Leu Ser Glu Ser Tyr
```

|  | 435 |  |  | 440 |  |  |  | 445 |  |  |  |
|---|---|---|---|---|---|---|---|---|---|---|---|

Tyr Val Asn Pro Ser Asp Phe Glu Asp Val Thr Asn Gln Val Arg Ile
450                455                460

Ser Phe Pro Asn Ala Asn Gln Tyr Lys Val Glu Phe Pro Thr Asp Asp
465                470                475                480

Asp Gln Ile Thr Thr Pro Tyr Ile Val Val Asn Gly His Ile Asp
                    485                490                495

Pro Ala Ser Thr Gly Asp Leu Ala Leu Arg Ser Thr Phe Tyr Gly Tyr
            500                505                510

Asp Ser Asn Phe Ile Trp Arg Ser Met Ser Trp Asp Asn Glu Val Ala
515                520                525

Phe Asn Asn Gly Ser Gly Ser Gly Asp Gly Ile Asp Lys Pro Val Val
530                535                540

Pro Glu Gln Pro Asp Glu Pro Gly Glu Ile Glu Pro Ile Pro Glu
545                550                555

```
<210> SEQ ID NO 75
<211> LENGTH: 1677
<212> TYPE: DNA
<213> ORGANISM: Staphylococcus aureus

<400> SEQUENCE: 75
```

| | | | | |
|---|---|---|---|---|
| atgaatatga agaaaaaga aaacacgca attcggaaaa aatcgattgg cgtggcttca | 60 |
| gtgcttgtag gtacgttaat cggtttcgga ttacttagca gtaaagaagc agatgcaagt | 120 |
| gaaaatagtg ttacgcaatc tgatagcgca agtaacgaaa gcaaaagtaa tgattcaagt | 180 |
| agcgttaatg ctgcacctaa acagacaac acaaacgtga gtgatactaa acaacgtca | 240 |
| aacactaata tggcgaaac gagtgtggcg caaaatccag cacaacagga acgatacaa | 300 |
| tcagcatcaa caaatgcaac tacggaagaa acaccggtaa ctggtgaagc tactactacg | 360 |
| gcaacgaagc aagctaatac accggcaaca actcaatcaa gcaatacaaa tgcggaggaa | 420 |
| ttagtgaatc aaacaagtaa tgaaacgact tctaatgata ctaatacagt atcatctgta | 480 |
| aattcacctc aaaattctac aaatgcggaa atgtttcaa caacgcaaga tacttcaact | 540 |
| gaagcaacac cttcaaacaa tgaatcagct ccacagagta cagatgcaag taataaagat | 600 |
| gtagttaatc aagcggttaa tacaagtgcg cctagaatga gagcatttag tttagcggct | 660 |
| gtagctgcag atgcaccggc tgctggcaca gatattacga atcagttgac agatgtgaaa | 720 |
| gttactattg actctggtac gactgtgtat ccgcaccaag caggttatgt caaactgaat | 780 |
| tatggttttt cagtgcctaa ttctgctgtt aaaggtgaca cattcaaaat aactgtacct | 840 |
| aaagaattaa acttaaatgg tgtaacttca actgctaaag tgccaccaat tatggccgga | 900 |
| gatcaagtat tggcaaatgg tgtaatcgat agtgatggta tgttattta acatttaca | 960 |
| gactatgtaa atactaaaga tgatgttaaa gcaactttga ccatgcccgc ttatattgac | 1020 |
| cctgaaaatg ttcaaagac aggtaatgtg acattggcta ctggcatagg tagtacaaca | 1080 |
| gcaaacaaaa cagtattagt agattatgaa aaatatggta gttttataa cttatctatt | 1140 |
| aaaggtacaa ttgaccaaat cgataaaaca ataatacgt atcgtcagac aatttatgtc | 1200 |
| aatccaagtg gagataacgt tattgcgccg gttttaacag gtaatttaaa accaaatacg | 1260 |
| gatagtaatg cattaataga tcagcaaaat acaagtatta agtatataa agtagataat | 1320 |
| gcagctgatt tatctgaaag ttactttgtg aatccagaaa actttgagga tgtcactaat | 1380 |
| agtgtgaata ttacattccc aaatccaaat caatataaag tagagtttaa tacgcctgat | 1440 |

```
gatcaaatta caacaccgta tattgtagtt gttaatggtc atattgatcc gaatagcaaa      1500
ggtgatttag ctttacgttc aactttatat gggtatgact caaggtttgt atggagatct      1560
atgtcatggg acaacgaagt agcatttaat aacggatcag gttctggtga cggtatcgat      1620
aaaccagttg ttcctgaaca acctgatgag cctggtgaaa ttgaaccaat tccagag         1677
```

<210> SEQ ID NO 76
<211> LENGTH: 559
<212> TYPE: PRT
<213> ORGANISM: Staphylococcus aureus

<400> SEQUENCE: 76

```
Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Ser Val Asn Ala
    50                  55                  60

Ala Pro Lys Thr Asp Asn Thr Asn Val Ser Asp Thr Lys Thr Thr Ser
65                  70                  75                  80

Asn Thr Asn Asn Gly Glu Thr Ser Val Ala Gln Asn Pro Ala Gln Gln
                85                  90                  95

Glu Thr Ile Gln Ser Ala Ser Thr Asn Ala Thr Thr Glu Glu Thr Pro
            100                 105                 110

Val Thr Gly Glu Ala Thr Thr Thr Ala Thr Lys Gln Ala Asn Thr Pro
        115                 120                 125

Ala Thr Thr Gln Ser Ser Asn Thr Asn Ala Glu Glu Leu Val Asn Gln
    130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
    210                 215                 220

Ala Pro Ala Ala Gly Thr Asp Ile Thr Asn Gln Leu Thr Asp Val Lys
225                 230                 235                 240

Val Thr Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
305                 310                 315                 320

Asp Tyr Val Asn Thr Lys Asp Asp Val Lys Ala Thr Leu Thr Met Pro
                325                 330                 335
```

Ala Tyr Ile Asp Pro Glu Asn Val Thr Lys Thr Gly Asn Val Thr Leu
                340                 345                 350

Ala Thr Gly Ile Gly Ser Thr Thr Ala Asn Lys Thr Val Leu Val Asp
            355                 360                 365

Tyr Glu Lys Tyr Gly Lys Phe Tyr Asn Leu Ser Ile Lys Gly Thr Ile
        370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
        435                 440                 445

Phe Val Asn Pro Glu Asn Phe Glu Asp Val Thr Asn Ser Val Asn Ile
    450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly Tyr
            500                 505                 510

Asp Ser Arg Phe Val Trp Arg Ser Met Ser Trp Asp Asn Glu Val Ala
        515                 520                 525

Phe Asn Asn Gly Ser Gly Ser Gly Asp Gly Ile Asp Lys Pro Val Val
    530                 535                 540

Pro Glu Gln Pro Asp Glu Pro Gly Glu Ile Glu Pro Ile Pro Glu
545                 550                 555

<210> SEQ ID NO 77
<211> LENGTH: 1677
<212> TYPE: DNA
<213> ORGANISM: Staphylococcus aureus

<400> SEQUENCE: 77
atgaatatga agaaacaaga aaaacacgca attcgtaaaa aatcgattgg cgtggcttca      60
gtgcttgtag gtacgttaat cggttttgga ctactcagca gtaaagaagc agatgcaagt     120
gaaaatagtg ttacgcaaac ggaaaatacg agtaatgaga gcaaaagtaa tgattcgagt     180
agcgttaatg ctgcacctaa acagacaaca caaacgtgag gtgattctaa tacaacgaca     240
aacactaata gtgacgaaac gaatgtagcg caaaatccag cacaacagga aacgacacaa     300
tcagcatcaa caaatgcaac tacagaagaa acaccggtaa ctggtgaagt tactactacg     360
gcaacgaatc aagctaatac accggcaaca actcaatcaa gcaatacaaa tgcggaaaaa     420
tcagtgaatc aaacaagtaa tgaaacgact tctaatgata ctaatacagt atcatctgta     480 aattcaccte aaaattctac aaatgcggaa atgtttcaa caacgcaaga tacttcaact     540
gaagcaaaac cttcaaacaa tgaatcagct ccacagagta cagatgcaag taataaagat     600
gtagttaatc aagcggttaa tacaagtgcg cctagaatga gagcatttag tttagcggct     660
gtagctgcag atgcaccggc tgctggcaca gatattacga atcagttgac gaatgtgaca     720
gttggtattg actctggaga tacagtttat ccgcaccaag caggctatgt caaactgaat     780
tatgggttct cagtacccaa ttctgcggtt caaggtgaca catttaaaat aactgtacct     840
aaagaattaa acttaaatgg tgtaacctca actgctaaag tgccaccaat tatggccgga     900

```
gatcaagtat tggcaaatgg tgtaatcgat agtgatggta atgttattta tacatttaca    960
gactatgtaa atactaaaga tgatgttaaa gcaacattaa ctgtgccggc ttatattgac   1020
cctgaatatg ttacacatac tggtaatgtg acattggcta ctggcatagg aaatacaaca   1080
gcaaacaaaa cagtattagt agattatgaa aaatatggta gtttttataa cttatctatt   1140
aaaggtacaa ttgaccaaat cgataaaaca ataatacgt atcgtcagac aatttatgtc    1200
aatccaagtg gagataacgt tattgcaccg gttttaacag gtaatttaaa accaaatacg   1260
gaaagtaatg cattaataga tcagcaaaat acaagtatta aagtatataa agtagataat   1320
gcagctgatt tatctgaaag ttactttgtg aatccagaaa actttgagga tgtcactaat   1380
agtgtaaata ttacattccc aaatccaaat caatataaag tagagtttaa tacgcctgat   1440
gatcaaataa caacaccata tattgtagtt gttaatgggc atattgatcc taatagtaaa   1500
ggtgatttag ctttacgttc aactttatat ggatataatt cgaatataat ttggagatct   1560
atgtcatggg acaacgaagt agcatttaat aacggatcag ttctggtga cggtatcgat    1620 aaacctgttg ttcctgaaca acctgatgag cctggtgaaa ttgaaccaat tccagag      1677
```

<210> SEQ ID NO 78
<211> LENGTH: 559
<212> TYPE: PRT
<213> ORGANISM: Staphylococcus aureus

<400> SEQUENCE: 78

```
Met Asn Met Lys Lys Gln Glu Lys His Ala Ile Arg Lys Lys Ser Ile
1               5                  10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Thr Glu
        35                  40                  45

Asn Thr Ser Asn Glu Ser Lys Ser Asn Asp Ser Ser Val Asn Ala
    50                  55                  60

Ala Pro Lys Thr Asp Asn Thr Asn Val Ser Asp Ser Asn Thr Thr Thr
65                  70                  75                  80

Asn Thr Asn Ser Asp Glu Thr Asn Val Ala Gln Asn Pro Ala Gln Gln
                85                  90                  95

Glu Thr Thr Gln Ser Ala Ser Thr Asn Ala Thr Thr Glu Glu Thr Pro
            100                 105                 110

Val Thr Gly Glu Val Thr Thr Thr Ala Thr Asn Gln Ala Asn Thr Pro
        115                 120                 125

Ala Thr Thr Gln Ser Ser Asn Thr Asn Ala Glu Lys Ser Val Asn Gln
    130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Lys Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
    210                 215                 220

Ala Pro Ala Ala Gly Thr Asp Ile Thr Asn Gln Leu Thr Asn Val Thr
225                 230                 235                 240
```

Val Gly Ile Asp Ser Gly Asp Thr Val Tyr Pro His Gln Ala Gly Tyr
            245                 250                 255

Val Lys Leu Asn Tyr Gly Phe Ser Val Pro Asn Ser Ala Val Gln Gly
            260                 265                 270

Asp Thr Phe Lys Ile Thr Val Pro Lys Glu Leu Asn Leu Asn Gly Val
            275                 280                 285

Thr Ser Thr Ala Lys Val Pro Pro Ile Met Ala Gly Asp Gln Val Leu
            290                 295                 300

Ala Asn Gly Val Ile Asp Ser Asp Gly Asn Val Ile Tyr Thr Phe Thr
305                 310                 315                 320

Asp Tyr Val Asn Thr Lys Asp Val Lys Ala Thr Leu Thr Val Pro
            325                 330                 335

Ala Tyr Ile Asp Pro Glu Tyr Val Thr His Thr Gly Asn Val Thr Leu
            340                 345                 350

Ala Thr Gly Ile Gly Asn Thr Thr Ala Asn Lys Thr Val Leu Val Asp
            355                 360                 365

Tyr Glu Lys Tyr Gly Lys Phe Tyr Asn Leu Ser Ile Lys Gly Thr Ile
            370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
            405                 410                 415

Lys Pro Asn Thr Glu Ser Asn Ala Leu Ile Asp Gln Asn Thr Ser
            420                 425                 430

Ile Lys Val Tyr Lys Val Asp Asn Ala Ala Asp Leu Ser Glu Ser Tyr
            435                 440                 445

Phe Val Asn Pro Glu Asn Phe Glu Asp Val Thr Asn Ser Val Asn Ile
            450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
            485                 490                 495

Pro Asn Ser Lys Gly Asp Leu Ala Leu Arg Ser Thr Leu Tyr Gly Tyr
            500                 505                 510

Asn Ser Asn Ile Ile Trp Arg Ser Met Ser Trp Asp Asn Glu Val Ala
            515                 520                 525

Phe Asn Asn Gly Ser Gly Ser Gly Asp Gly Ile Asp Lys Pro Val Val
            530                 535                 540

Pro Glu Gln Pro Asp Glu Pro Gly Glu Ile Glu Pro Ile Pro Glu
545                 550                 555

<210> SEQ ID NO 79
<211> LENGTH: 1677
<212> TYPE: DNA
<213> ORGANISM: Staphylococcus aureus

<400> SEQUENCE: 79
atgaatatga agaaaaaaga aaaacacgca attcggaaaa aatcgattgg cgtggcttca    60
gtgcttgtag gtacgttaat cggttttgga ctactcagca gtaaagaagc agatgcaagt   120
gaaaatagtg ttacgcaatc tgatagcgca agtaacgaaa gcaaagtaa tgattcaagt   180 agcgttagtg ctgcacctaa acagacgac acaaacgtga gtgatactaa acatcgtca   240 aacactaata atggcgaaac gagtgtggcg caaaatccag cacaacagga aacgacacaa   300

|  |  |
|---|---|
| tcatcatcaa caaatgcaac tacggaagaa acgccggtaa ctggtgaagc tactactacg | 360 |
| acaacgaatc aagctaatac accggcaaca actcaatcaa gcaatacaaa tgcggaggaa | 420 |
| ttagtgaatc aaacaagtaa tgaaacgact tctaatgata ctaatacagt atcatctgta | 480 |
| aattcacctc aaaattctac aaatgcggaa atgtttcaa caacgcaaga tacttcaact | 540 |
| gaagcaacac cttcaaacaa tgaatcagct ccacagagta cagatgcaag taataaagat | 600 |
| gtagttaatc aagcggttaa tacaagtgcg cctagaatga gagcatttag tttagcggca | 660 |
| gtagctgcag atgcaccggt agctggcaca gatattacga atcagttgac gaatgtgaca | 720 |
| gttggtattg actctggtac gactgtgtat ccgcaccaag caggttatgt caaactgaat | 780 |
| tatggttttt cagtgcctaa ttctgctgtt aaaggtgaca cattcaaaat aactgtacct | 840 |
| aaagaattaa acttaaatgg tgtaacttca actgctaaag tgccaccaat tatggctgga | 900 |
| gatcaagtat tggcaaatgg tgtaatcgat agtgatggta atgttattta acatttaca | 960 |
| gactatgtaa atactaaaga tgatgtaaaa gcaactttga ccatgcccgc ttatattgac | 1020 |
| cctgaaaatg ttaaaaagac aggtaatgtg acattggcta ctggcatagg tagtacaaca | 1080 |
| gcaaacaaaa cagtattagt agattatgaa aaatatggta gttttataa cttatctatt | 1140 |
| aaaggtacaa ttgaccaaat cgataaaaca ataatacgt atcgtcagac aatttatgtc | 1200 |
| aatccaagtg gagataacgt tattgcgccg gttttaacag gtaatttaaa accaaatacg | 1260 |
| gatagtaatg cattaataga tcagcaaaat acaagtatta agtatataa agtagataat | 1320 |
| gcagctgatt tatctgaaag ttactttgtg aatccagaaa actttgagga tgtcactaat | 1380 |
| agtgtgaata ttcattccc aaatccaaat caatataaag tagagtttaa tacgcctgat | 1440 |
| gatcaaatta caacaccgta tatagtagtt gttaatggtc atattgatcc gaatagcaaa | 1500 |
| ggtgatttag ctttacgttc aactttatat gggtataact cgaatataat ttggcgctct | 1560 |
| atgtcatggg acaacgaagt agcatttaat aacggatcag gttctggtga cggtatcgat | 1620 |
| aaaccagttg ttcctgaaca acctgatgag cctggtgaaa ttgaaccaat tccagag | 1677 |

<210> SEQ ID NO 80
<211> LENGTH: 559
<212> TYPE: PRT
<213> ORGANISM: Staphylococcus aureus

<400> SEQUENCE: 80

Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Glu Glu Thr Pro
            100                 105                 110

Val Thr Gly Glu Ala Thr Thr Thr Thr Thr Asn Gln Ala Asn Thr Pro
        115                 120                 125

Ala Thr Thr Gln Ser Ser Asn Thr Asn Ala Glu Glu Leu Val Asn Gln

```
              130                 135                 140
Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
                180                 185                 190

Ser Thr Asp Ala Ser Asn Lys Asp Val Val Asn Gln Ala Val Asn Thr
                195                 200                 205

Ser Ala Pro Arg Met Arg Ala Phe Ser Leu Ala Ala Val Ala Ala Asp
210                 215                 220

Ala Pro Val Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
                260                 265                 270

Asp Thr Phe Lys Ile Thr Val Pro Lys Glu Leu Asn Leu Asn Gly Val
                275                 280                 285

Thr Ser Thr Ala Lys Val Pro Pro Ile Met Ala Gly Asp Gln Val Leu
290                 295                 300

Ala Asn Gly Val Ile Asp Ser Asp Gly Asn Val Ile Tyr Thr Phe Thr
305                 310                 315                 320

Asp Tyr Val Asn Thr Lys Asp Asp Val Lys Ala Thr Leu Thr Met Pro
                325                 330                 335

Ala Tyr Ile Asp Pro Glu Asn Val Lys Lys Thr Gly Asn Val Thr Leu
                340                 345                 350

Ala Thr Gly Ile Gly Ser Thr Thr Ala Asn Lys Thr Val Leu Val Asp
                355                 360                 365

Tyr Glu Lys Tyr Gly Lys Phe Tyr Asn Leu Ser Ile Lys Gly Thr Ile
                370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
                420                 425                 430

Ile Lys Val Tyr Lys Val Asp Asn Ala Ala Asp Leu Ser Glu Ser Tyr
                435                 440                 445

Phe Val Asn Pro Glu Asn Phe Glu Asp Val Thr Asn Ser Val Asn Ile
450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly Tyr
                500                 505                 510

Asn Ser Asn Ile Ile Trp Arg Ser Met Ser Trp Asp Asn Glu Val Ala
                515                 520                 525

Phe Asn Asn Gly Ser Gly Ser Gly Asp Gly Ile Asp Lys Pro Val Val
                530                 535                 540

Pro Glu Gln Pro Asp Glu Pro Gly Glu Ile Glu Pro Ile Pro Glu
545                 550                 555
```

<210> SEQ ID NO 81
<211> LENGTH: 1677
<212> TYPE: DNA
<213> ORGANISM: Staphylococcus aureus

<400> SEQUENCE: 81

```
atgaatatga agaaaaaaga aaaacacgca attcggaaaa aatcgattgg cgtggcttca      60
gtgcttgtag gtacgttaat cggttttgga ctactcagca gtaaagaagc agatgcaagt     120
gaaaatagtg ttacgcaatc tgatagcgca gtaacgaaa gcaaaagtaa tgattcaagt     180
agcgttagtg ctgcacctaa acagacgac acaaacgtga gtgatactaa acatcgtca     240
aacactaata atggcgaaac gagtgtggcg caaaatccag cacaacagga acgacacaa     300
tcatcatcaa caaatgcaac tacggaagaa acgccggtaa ctggtgaagc tactactacg     360
acaacgaatc aagctaatac accggcaaca actcaatcaa gcaatacaaa tgcggaggaa     420
ttagtgaatc aaacaagtaa tgaaacgact tttaatgata ctaatacagt atcatctgta     480
aattcacctc aaaattctac aaatgcggaa atgtttcaa caacgcaaga tacttcaact     540
gaagcaacac cttcaaacaa tgaatcagct ccacagagta cagatgcaag taataaagat     600
gtagttaatc aagcggttaa tacaagtgcg cctagaatga gagcatttag tttagcggca     660
gtagctgcag atgcaccggc agctggcaca gatattacga atcagttgac gaatgtgaca     720
gttggtattg actctggtac gactgtgtat ccgcaccaag caggttatgt caaactgaat     780
tatggttttt cagtgcctaa ttctgctgtt aaaggtgaca cattcaaaat aactgtacct     840
aaagaattaa acttaaatgg tgtaacttca actgctaaag tgccaccaat tatggctgga     900
gatcaagtat tggcaaatgg tgtaatcgat agtgatggta atgttattta cactttaca     960
gactatgtaa atactaaaga tgatgtaaaa gcaactttga ccatgcccgc ttatattgac    1020
cctgaaaatg ttaaaaagac aggtaatgtg acattggcta ctggcatagg tagtacaaca    1080
gcaaacaaaa cagtattagt agattatgaa aaatatggta agttttataa cttatctatt    1140
aaaggtacaa ttgaccaaat cgataaaaca ataatacgt atcgtcagac aatttatgtc    1200
aatccaagtg gagataacgt tattgcgccg gttttaacag gtaatttaaa accaaatacg    1260
gatagtaatg cattaataga tcagcaaaat acaagtatta agtatataa agtagataat    1320
gcagctgatt tatctgaaag ttactttgtg aatccagaaa actttgagga tgtcactaat    1380
agtgtgaata ttacattccc aaatccaaat caatataaag tagagtttaa tacgcctgat    1440
gatcaaatta caacaccgta tagtagtt gttaatggtc atattgatcc gaatagcaaa    1500
ggtgatttag ctttacgttc aactttatat gggtataact cgaatataat ttggcgctct    1560
atgtcatggg acaacgaagt agcatttaat aacggatcag ttctggtga cggtatcgat    1620
aaaccagttg ttcctgaaca acctgatgag cctggtgaaa ttgaaccaat tccagag    1677
```

<210> SEQ ID NO 82
<211> LENGTH: 559
<212> TYPE: PRT
<213> ORGANISM: Staphylococcus aureus

<400> SEQUENCE: 82

```
Met Asn Met Lys Lys Lys Glu Lys His Ala Ile Arg Lys Lys Ser Ile
1               5                  10                  15

Gly Val Ala Ser Val Leu Val Gly Thr Leu Ile Gly Phe Gly Leu Leu
            20                  25                  30
```

```
Ser Ser Lys Glu Ala Asp Ala Ser Glu Asn Ser Val Thr Gln Ser Asp
         35                  40                  45

Ser Ala Ser Asn Glu Ser Lys Ser Asn Asp Ser Ser Val Ser Ala
 50                  55                  60

Ala Pro Lys Thr Asp Asp Thr Asn Val Ser Asp Thr Lys Thr Ser Ser
 65                  70                  75                  80

Asn Thr Asn Asn Gly Glu Thr Ser Val Ala Gln Asn Pro Ala Gln Gln
                 85                  90                  95

Glu Thr Thr Gln Ser Ser Ser Thr Asn Ala Thr Glu Glu Thr Pro
             100                 105                 110

Val Thr Gly Glu Ala Thr Thr Thr Thr Asn Gln Ala Asn Thr Pro
         115                 120                 125

Ala Thr Thr Gln Ser Ser Asn Thr Asn Ala Glu Glu Leu Val Asn Gln
         130                 135                 140

Thr Ser Asn Glu Thr Thr Phe Asn Asp Thr Asn Thr Val Ser Ser Val
145                 150                 155                 160

Asn Ser Pro Gln Asn Ser Thr Asn Ala Glu Asn Val Ser Thr Thr Gln
                 165                 170                 175

Asp Thr Ser Thr Glu Ala Thr Pro Ser Asn Asn Glu Ser Ala Pro Gln
             180                 185                 190

Ser Thr Asp Ala Ser Asn Lys Asp Val Val Asn Gln Ala Val Asn Thr
         195                 200                 205

Ser Ala Pro Arg Met Arg Ala Phe Ser Leu Ala Ala Val Ala Ala Asp
         210                 215                 220

Ala Pro Ala Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                 245                 250                 255

Val Lys Leu Asn Tyr Gly Phe Ser Val Pro Asn Ser Ala Val Lys Gly
             260                 265                 270

Asp Thr Phe Lys Ile Thr Val Pro Lys Glu Leu Asn Leu Asn Gly Val
         275                 280                 285

Thr Ser Thr Ala Lys Val Pro Pro Ile Met Ala Gly Asp Gln Val Leu
         290                 295                 300

Ala Asn Gly Val Ile Asp Ser Asp Gly Asn Val Ile Tyr Thr Phe Thr
305                 310                 315                 320

Asp Tyr Val Asn Thr Lys Asp Val Lys Ala Thr Leu Thr Met Pro
                 325                 330                 335

Ala Tyr Ile Asp Pro Glu Asn Val Lys Lys Thr Gly Asn Val Thr Leu
             340                 345                 350

Ala Thr Gly Ile Gly Ser Thr Thr Ala Asn Lys Thr Val Leu Val Asp
         355                 360                 365

Tyr Glu Lys Tyr Gly Lys Phe Tyr Asn Leu Ser Ile Lys Gly Thr Ile
         370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                 405                 410                 415

Lys Pro Asn Thr Asp Ser Asn Ala Leu Ile Asp Gln Asn Thr Ser
             420                 425                 430

Ile Lys Val Tyr Lys Val Asp Asn Ala Ala Asp Leu Ser Glu Ser Tyr
         435                 440                 445

Phe Val Asn Pro Glu Asn Phe Glu Asp Val Thr Asn Ser Val Asn Ile
```

```
                    450                 455                 460
Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
            485                 490                 495

Pro Asn Ser Lys Gly Asp Leu Ala Leu Arg Ser Thr Leu Tyr Gly Tyr
                500                 505                 510

Asn Ser Asn Ile Ile Trp Arg Ser Met Ser Trp Asp Asn Glu Val Ala
            515                 520                 525

Phe Asn Asn Gly Ser Gly Ser Gly Asp Gly Ile Asp Lys Pro Val Val
            530                 535                 540

Pro Glu Gln Pro Asp Glu Pro Gly Glu Ile Glu Pro Ile Pro Glu
545                 550                 555
```

<210> SEQ ID NO 83
<211> LENGTH: 1674
<212> TYPE: DNA
<213> ORGANISM: Staphylococcus aureus

<400> SEQUENCE: 83

```
atgaatatga agaaaaaaga aaaacacgca attcggaaaa atcgattgg cgtggcttca      60
gtgcttgtag gtacgttaat cggttttgga ctactcagca gtaaagaagc agatgcaagt    120
gaaaatagtg ttacgcaatc tgatagcgca agtaacgaaa gcaaaagtaa tgattcaagt    180
agcgttagtg ctgcacctaa acagacgac acaaacgtga gtgatactaa acatcgtca     240
aacactaata tggcgaaaac gagtgtggcg caaaatccag cacaacagga acgacacaa    300
tcagcattaa caaatgcaac tacggaagaa actccggtaa ctggtgaagc tactacggca    360
acgaatcaag ctaatacacc ggcaacaact caatcaagca atacaaatgc ggaggaatta    420
gtgaatcaaa caagtaatga acgacttct aatgatacta atacagtatc atctgtaaat     480
tcacctcaaa attctacaaa tgcggaaaat gtttcaacaa cgcaagatac ttcaactgaa    540
gcaacaccttcaaacaatga atcagctcca cagagtacag atgcaagtaa taagatgta    600
gttaatcaag cggttaatac aagtgcgcct agaatgagag catttagttt atcggcagta    660
gctgcagatg caccggcagc tggcaaagat attacgaatc agttgacgaa tgtgacagtt    720
ggtattgact ctggagatac agtttatccg caccaagcag gctatgtcaa actgaattat    780
ggttttttcag tgcctaattc tgctgttaaa ggtgacacat tcaaaataac tgtacctaaa    840
gaattaaact aaatggtgt aacttcaact gctaaagtgc ctccaattat ggccggagat    900
caagtattgg caaatggtgt aatcgatagt gatggtaatg ttatttatac atttacagac    960
tatgttgata ctaaagaaaa tgtaacagct aatattacta tgccagctta tattgaccct   1020
gaaaatgtta caaagacagg taatgtaaca ttgacaactg gcataggtag tacaacagca   1080
aacaaaacag tattagtaga ttatgaaaaa tatggtaagt tttataactt atctattaaa   1140
ggtacaattg accaaatcga taaaacaaat aatacgtatc gtcagacaat ttatgtcaat   1200
ccaagtggag ataatgttat tgcgccggtt ttaacaggta atttaaaacc aaatacggat   1260
agtaatgcat taatagatca gcaaaataca agtattaaag tatataaagt agataatgca   1320
gctgatttat ctgaaagtta ctttgtgaat ccagaaaact ttgaggatgt cactaatagt   1380
gtgaatatta cattcccaaa tccaaatcaa tataaagtag agtttaatac gcctgatgat   1440
caaattacaa caccgtatat tgtagttgtt aatggtcata ttgatccgaa tagcaaaggt   1500
gatttagctt tacgttcaac tttatatgga tatgactcaa ggtttgtatg gagatctatg   1560
```

```
tcatgggaca acgaagtagc atttaataac ggatcaggtt ctggtgacgg tatcgataaa    1620
ccagttgttc ctgaacaacc tgatgagcct ggtgaaattg aaccaattcc agag          1674
```

<210> SEQ ID NO 84
<211> LENGTH: 558
<212> TYPE: PRT
<213> ORGANISM: Staphylococcus aureus

<400> SEQUENCE: 84

```
Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Val Ser Ala
50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ala Leu Thr Asn Ala Thr Glu Glu Thr Pro
            100                 105                 110

Val Thr Gly Glu Ala Thr Thr Ala Thr Asn Gln Ala Asn Thr Pro Ala
        115                 120                 125

Thr Thr Gln Ser Ser Asn Thr Asn Ala Glu Glu Leu Val Asn Gln Thr
130                 135                 140

Ser Asn Glu Thr Thr Ser Asn Asp Thr Asn Thr Val Ser Ser Val Asn
145                 150                 155                 160

Ser Pro Gln Asn Ser Thr Asn Ala Glu Asn Val Ser Thr Thr Gln Asp
                165                 170                 175

Thr Ser Thr Glu Ala Thr Pro Ser Asn Asn Glu Ser Ala Pro Gln Ser
            180                 185                 190

Thr Asp Ala Ser Asn Lys Asp Val Val Asn Gln Ala Val Asn Thr Ser
        195                 200                 205

Ala Pro Arg Met Arg Ala Phe Ser Leu Ser Ala Val Ala Ala Asp Ala
210                 215                 220

Pro Ala Ala Gly Lys Asp Ile Thr Asn Gln Leu Thr Asn Val Thr Val
225                 230                 235                 240

Gly Ile Asp Ser Gly Asp Thr Val Tyr Pro His Gln Ala Gly Tyr Val
                245                 250                 255

Lys Leu Asn Tyr Gly Phe Ser Val Pro Asn Ser Ala Val Lys Gly Asp
            260                 265                 270

Thr Phe Lys Ile Thr Val Pro Lys Glu Leu Asn Leu Asn Gly Val Thr
        275                 280                 285

Ser Thr Ala Lys Val Pro Pro Ile Met Ala Gly Asp Gln Val Leu Ala
290                 295                 300

Asn Gly Val Ile Asp Ser Asp Gly Asn Val Ile Tyr Thr Phe Thr Asp
305                 310                 315                 320

Tyr Val Asp Thr Lys Glu Asn Val Thr Ala Asn Ile Thr Met Pro Ala
                325                 330                 335

Tyr Ile Asp Pro Glu Asn Val Thr Lys Thr Gly Asn Val Thr Leu Thr
            340                 345                 350
```

```
Thr Gly Ile Gly Ser Thr Thr Ala Asn Lys Thr Val Leu Val Asp Tyr
        355                 360                 365
Glu Lys Tyr Gly Lys Phe Tyr Asn Leu Ser Ile Lys Gly Thr Ile Asp
    370                 375                 380
Gln Ile Asp Lys Thr Asn Asn Thr Tyr Arg Gln Thr Ile Tyr Val Asn
385                 390                 395                 400
Pro Ser Gly Asp Asn Val Ile Ala Pro Val Leu Thr Gly Asn Leu Lys
                405                 410                 415
Pro Asn Thr Asp Ser Asn Ala Leu Ile Asp Gln Gln Asn Thr Ser Ile
            420                 425                 430
Lys Val Tyr Lys Val Asp Asn Ala Ala Asp Leu Ser Glu Ser Tyr Phe
        435                 440                 445
Val Asn Pro Glu Asn Phe Glu Asp Val Thr Asn Ser Val Asn Ile Thr
    450                 455                 460
Phe Pro Asn Pro Asn Gln Tyr Lys Val Glu Phe Asn Thr Pro Asp Asp
465                 470                 475                 480
Gln Ile Thr Thr Pro Tyr Ile Val Val Asn Gly His Ile Asp Pro
                485                 490                 495
Asn Ser Lys Gly Asp Leu Ala Leu Arg Ser Thr Leu Tyr Gly Tyr Asp
            500                 505                 510
Ser Arg Phe Val Trp Arg Ser Met Ser Trp Asp Asn Glu Val Ala Phe
        515                 520                 525
Asn Asn Gly Ser Gly Ser Asp Gly Ile Asp Lys Pro Val Val Pro
    530                 535                 540
Glu Gln Pro Asp Glu Pro Gly Glu Ile Glu Pro Ile Pro Glu
545                 550                 555
```

<210> SEQ ID NO 85
<211> LENGTH: 1674
<212> TYPE: DNA
<213> ORGANISM: Staphylococcus aureus

<400> SEQUENCE: 85

```
atgaatatga agaaaaaaga aaaacacgca attcggaaaa aatcgattgg cgtggcttca      60
gtgcttgtag gtacgttaat cggttttgga ctactcagca gtaaagaagc agatgcaagt     120
gaaaatagtg ttacgcaatc tgatagcgca agtaacgaaa gcaaaagtaa tgattcaagt     180
agcgttagtg ctgcacctaa aacagacgac acaaacgtga gtgatactaa acatcgtca      240
aacactaata tggcgaaac gagtgtggcg caaaatccag cacaacagga acgacacaa       300
tcagcattaa caaatgcaac tacgaagaa actccgttaa ctggtgaagc tactacggca      360
acgaatcaag ctaatacacc ggcaacaact caatcaagca atacaaatgc ggaggaatta     420
gtgaatcaaa caagtaatga aacgacttct aatgatacta atacagtatc atctgtaaat     480
tcacctcaaa attctacaaa tgcggaaaat gtttcaacaa cgcaagatac ttcaactgaa     540
gcaacacctt caaacaatga atcagctcca cagagtacga tgcaagtaa taaagatgta      600
gttaatcaag cggttaatac aagtgcgcct agaatgagag catttagttt agcggcagta     660
gctgcagatg caccggcagc tggcacagat attacgaatc agttgacaga tgtgaaagtt     720
actattgact ctggtacgac tgtgtatccg caccaagcag ttatgtcaa actgaattat      780
ggttttcag tgcctaattc tgctgttaaa ggtgacacat tcaaaataac tgtacctaaa      840
gaattaaact taaatggtgt aacttcaact gctaaagtgc ctccaattat ggccggagat     900
caagtattgg caaatggtgt aatcgatagt gatggtaatg ttatttatac atttacagac     960
```

```
tatgttgata ctaaaaatga tgttaaagca acactaactg tgcctgcata cattgatcca    1020
gaaaatgtta caaagacggg taatgtaaca ttgaaaactg gcataggaac caatactgat    1080
agtaagacag ttttaatcga ctatgagaaa tatggacaat tccataattt atcaattaaa    1140
ggtacgattg atcaaatcga taaaacaaat aatacgtatc gtcaaacaat ttatgtcaat    1200
ccaagcggag ataacgttgt gttacctgcc ttaacaggta atttaattcc taatacaaag    1260
agtaatgcgt taatagatgc aaaaaacact gatattaaag tttatagagt agataatgct    1320
aatgatttat ctgaaagtta ttatgtgaat cctagcgatt ttgaagatgt aactaatcaa    1380
gttagaattt catttccaaa tgctaatcaa tacaaagtag aatttcctac ggacgatgat    1440
caaattacaa caccgtatat tgtagttgtt aatggccata ttgatcctgc tagcacaggt    1500
gatttagcac tacgttcgac attttatggt tatgattcta attttatatg gagatctatg    1560
tcatgggaca acgaagtagc atttaataac ggatcaggtt caggtgacgg tatcgataaa    1620
cctgttgttc ctgaacaacc tgatgagcct ggtgaaattg aaccaattcc agag           1674
```

<210> SEQ ID NO 86
<211> LENGTH: 558
<212> TYPE: PRT
<213> ORGANISM: Staphylococcus aureus

<400> SEQUENCE: 86

```
Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ala Leu Thr Asn Ala Thr Glu Glu Thr Pro
            100                 105                 110

Leu Thr Gly Glu Ala Thr Thr Ala Thr Asn Gln Ala Asn Thr Pro Ala
        115                 120                 125

Thr Thr Gln Ser Ser Asn Thr Asn Ala Glu Glu Leu Val Asn Gln Thr
    130                 135                 140

Ser Asn Glu Thr Thr Ser Asn Asp Thr Asn Thr Val Ser Ser Val Asn
145                 150                 155                 160

Ser Pro Gln Asn Ser Thr Asn Ala Glu Asn Val Ser Thr Thr Gln Asp
                165                 170                 175

Thr Ser Thr Glu Ala Thr Pro Ser Asn Asn Glu Ser Ala Pro Gln Ser
            180                 185                 190

Thr Asp Ala Ser Asn Lys Asp Val Val Asn Gln Ala Val Asn Thr Ser
        195                 200                 205

Ala Pro Arg Met Arg Ala Phe Ser Leu Ala Ala Val Ala Ala Asp Ala
    210                 215                 220

Pro Ala Ala Gly Thr Asp Ile Thr Asn Gln Leu Thr Asp Val Lys Val
225                 230                 235                 240

Thr Ile Asp Ser Gly Thr Thr Val Tyr Pro His Gln Ala Gly Tyr Val
                245                 250                 255
```

Lys Leu Asn Tyr Gly Phe Ser Val Pro Asn Ser Ala Val Lys Gly Asp
                260                 265                 270

Thr Phe Lys Ile Thr Val Pro Lys Glu Leu Asn Leu Asn Gly Val Thr
            275                 280                 285

Ser Thr Ala Lys Val Pro Pro Ile Met Ala Gly Asp Gln Val Leu Ala
    290                 295                 300

Asn Gly Val Ile Asp Ser Asp Gly Asn Val Ile Tyr Thr Phe Thr Asp
305                 310                 315                 320

Tyr Val Asp Thr Lys Asn Asp Val Lys Ala Thr Leu Thr Val Pro Ala
                325                 330                 335

Tyr Ile Asp Pro Glu Asn Val Thr Lys Thr Gly Asn Val Thr Leu Lys
            340                 345                 350

Thr Gly Ile Gly Thr Asn Thr Asp Ser Lys Thr Val Leu Ile Asp Tyr
    355                 360                 365

Glu Lys Tyr Gly Gln Phe His Asn Leu Ser Ile Lys Gly Thr Ile Asp
370                 375                 380

Gln Ile Asp Lys Thr Asn Asn Thr Tyr Arg Gln Thr Ile Tyr Val Asn
385                 390                 395                 400

Pro Ser Gly Asp Asn Val Val Leu Pro Ala Leu Thr Gly Asn Leu Ile
                405                 410                 415

Pro Asn Thr Lys Ser Asn Ala Leu Ile Asp Ala Lys Asn Thr Asp Ile
            420                 425                 430

Lys Val Tyr Arg Val Asp Asn Ala Asn Asp Leu Ser Glu Ser Tyr Tyr
    435                 440                 445

Val Asn Pro Ser Asp Phe Glu Asp Val Thr Asn Gln Val Arg Ile Ser
450                 455                 460

Phe Pro Asn Ala Asn Gln Tyr Lys Val Glu Phe Pro Thr Asp Asp
465                 470                 475                 480

Gln Ile Thr Thr Pro Tyr Ile Val Val Asn Gly His Ile Asp Pro
                485                 490                 495

Ala Ser Thr Gly Asp Leu Ala Leu Arg Ser Thr Phe Tyr Gly Tyr Asp
            500                 505                 510

Ser Asn Phe Ile Trp Arg Ser Met Ser Trp Asp Asn Glu Val Ala Phe
    515                 520                 525

Asn Asn Gly Ser Gly Ser Gly Asp Gly Ile Asp Lys Pro Val Val Pro
530                 535                 540

Glu Gln Pro Asp Glu Pro Gly Glu Ile Glu Pro Ile Pro Glu
545                 550                 555

<210> SEQ ID NO 87
<211> LENGTH: 1674
<212> TYPE: DNA
<213> ORGANISM: Staphylococcus aureus

<400> SEQUENCE: 87
atgaatatga agaaaaaga aaaacacgca attcggaaaa aatcgattgg cgtggcttca      60
gtgcttgtag gtacgttaat cggttttgga ctactcagca gtaaagaagc agatgcaagt     120 gaaatagtg ttacgcaatc tgatagcgca agtaacgaaa gcaaaagtaa tgattcaagt     180
agcgttaatg ctgcacctaa acagacaac acaaacgtga gtgatactaa aacaacgtca     240
aacactaata atggcgaaac gagtgtggcg caatatctag cacaacagga aacgacacaa     300
tcagtatcaa caaatgcaac tacgaagaa acaccggtaa ctggtgaagc tactacggca     360
acgaatcaag ctaatacacc ggcaacaact caatcaagca atacaaatgc ggaggaatta     420

```
gtgaatcaaa caagtaatga aacgacttct aatgatacta atacagtatc atctgtaaat    480
tcacctcaaa attctacaaa tgcggaaaat gtttcaacaa cgcaagatac ttcaactgaa    540
gcaacacctt caaacaatga atcagctcca cagagtacag atgcaagtaa taaagatgta    600
gttaatcaag cggttaatac aagtgcgcct agaatgagag catttagttt agcggctgta    660
gctgcagatg caccggcagc tggcacagat attacgaatc agttgacgaa tgtgacagtt    720
ggtattgact ctggtacgac tgtgtatccg caccaagcag ttatgtcaa actgaattat    780 ggtttttcag tgcctaattc tgctgttaaa ggtgacacat caaaataac tgtacctaaa    840 gaattaaact taaatggtgt aacttcaact gctaaagtgc ctccaattat ggctggagat    900
caagtattgg caaatggtgt aatcgataat gatggtaatg ttatttatac atttacagac    960
tatgtaaata ctaagatga tgttaaagca actttgacta tgcccgctta tattgaccct   1020
gaaaatgtta caaagacagg taatgtgaca ttggctactg gcataggtag tacaacagca   1080
aacaaaacag tattagtaga ttatgaaaaa tatggtaagt tttataactt atctattaaa   1140
ggtacaattg accaaatcga taaaacaaat aatacgtatc gtcagacaat ttatgtcaat   1200
ccaagtggag ataacgttat tgcgccggtt ttaacaggta atttaaaacc aaatacggat   1260
agtaatgcat taatagatca gcaaaataca agtattaaag tatataaagt agataatgca   1320
gctgatttat ctgaaagtta ctttgtgaat ccagaaaaact ttgaggatgt cactaatagt   1380
gtgaatatta cattcccaaa tccaaatcaa tataaagtag agtttccaac agacgatgat   1440
caaattacaa caccgtatat tgtagttgtt aatggtcata ttgatccgaa tagcaaaggt   1500
gatttagctt tacgttcaac tttatatggg tataactcga atataatttg gcgctctatg   1560
tcatgggaca acgaagtagc atttaataac ggatcaggtt ctggtgacgg tatcgataaa   1620
cctgttgttc ctgaacaacc tgatgagcct ggtgaaattg aaccaattcc agag         1674
```

<210> SEQ ID NO 88
<211> LENGTH: 558
<212> TYPE: PRT
<213> ORGANISM: Staphylococcus aureus

<400> SEQUENCE: 88

```
Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
                20                  25                  30

Ser Ser Lys Glu Ala Asp Ala Ser Glu Asn Ser Val Thr Gln Ser Asp
            35                  40                  45

Ser Ala Ser Asn Glu Ser Lys Ser Asn Asp Ser Ser Val Asn Ala
        50                  55                  60

Ala Pro Lys Thr Asp Asn Thr Asn Val Ser Asp Thr Lys Thr Thr Ser
65                  70                  75                  80

Asn Thr Asn Asn Gly Glu Thr Ser Val Ala Gln Tyr Leu Ala Gln Gln
                85                  90                  95

Glu Thr Thr Gln Ser Val Ser Thr Asn Ala Thr Thr Glu Glu Thr Pro
            100                 105                 110

Val Thr Gly Glu Ala Thr Thr Ala Thr Asn Gln Ala Asn Thr Pro Ala
        115                 120                 125

Thr Thr Gln Ser Ser Asn Thr Asn Ala Glu Glu Leu Val Asn Gln Thr
    130                 135                 140

Ser Asn Glu Thr Thr Ser Asn Asp Thr Asn Thr Val Ser Ser Val Asn
```

```
            145                 150                 155                 160
        Ser Pro Gln Asn Ser Thr Asn Ala Glu Asn Val Ser Thr Thr Gln Asp
                        165                 170                 175

Thr Ser Thr Glu Ala Thr Pro Ser Asn Asn Glu Ser Ala Pro Gln Ser
                        180                 185                 190

Thr Asp Ala Ser Asn Lys Asp Val Val Asn Gln Ala Val Asn Thr Ser
                        195                 200                 205

Ala Pro Arg Met Arg Ala Phe Ser Leu Ala Ala Val Ala Ala Asp Ala
        210                 215                 220

Pro Ala Ala Gly Thr Asp Ile Thr Asn Gln Leu Thr Asn Val Thr Val
        225                 230                 235                 240

Gly Ile Asp Ser Gly Thr Thr Val Tyr Pro His Gln Ala Gly Tyr Val
                        245                 250                 255

Lys Leu Asn Tyr Gly Phe Ser Val Pro Asn Ser Ala Val Lys Gly Asp
                        260                 265                 270

Thr Phe Lys Ile Thr Val Pro Lys Glu Leu Asn Leu Asn Gly Val Thr
                        275                 280                 285

Ser Thr Ala Lys Val Pro Pro Ile Met Ala Gly Asp Gln Val Leu Ala
                        290                 295                 300

Asn Gly Val Ile Asp Asn Asp Gly Asn Val Ile Tyr Thr Phe Thr Asp
        305                 310                 315                 320

Tyr Val Asn Thr Lys Asp Asp Val Lys Ala Thr Leu Thr Met Pro Ala
                        325                 330                 335

Tyr Ile Asp Pro Glu Asn Val Thr Lys Thr Gly Asn Val Thr Leu Ala
                        340                 345                 350

Thr Gly Ile Gly Ser Thr Thr Ala Asn Lys Thr Val Leu Val Asp Tyr
                        355                 360                 365

Glu Lys Tyr Gly Lys Phe Tyr Asn Leu Ser Ile Lys Gly Thr Ile Asp
                        370                 375                 380

Gln Ile Asp Lys Thr Asn Asn Thr Tyr Arg Gln Thr Ile Tyr Val Asn
        385                 390                 395                 400

Pro Ser Gly Asp Asn Val Ile Ala Pro Val Leu Thr Gly Asn Leu Lys
                        405                 410                 415

Pro Asn Thr Asp Ser Asn Ala Leu Ile Asp Gln Gln Asn Thr Ser Ile
                        420                 425                 430

Lys Val Tyr Lys Val Asp Asn Ala Ala Asp Leu Ser Glu Ser Tyr Phe
                        435                 440                 445

Val Asn Pro Glu Asn Phe Glu Asp Val Thr Asn Ser Val Asn Ile Thr
        450                 455                 460

Phe Pro Asn Pro Asn Gln Tyr Lys Val Glu Phe Pro Thr Asp Asp
        465                 470                 475                 480

Gln Ile Thr Thr Pro Tyr Ile Val Val Asn Gly His Ile Asp Pro
                        485                 490                 495

Asn Ser Lys Gly Asp Leu Ala Leu Arg Ser Thr Leu Tyr Gly Tyr Asn
                        500                 505                 510

Ser Asn Ile Ile Trp Arg Ser Met Ser Trp Asp Asn Glu Val Ala Phe
                        515                 520                 525

Asn Asn Gly Ser Gly Ser Gly Asp Gly Ile Asp Lys Pro Val Val Pro
                        530                 535                 540

Glu Gln Pro Asp Glu Pro Gly Glu Ile Glu Pro Ile Pro Glu
        545                 550                 555

<210> SEQ ID NO 89
```

<211> LENGTH: 1674
<212> TYPE: DNA
<213> ORGANISM: Staphylococcus aureus

<400> SEQUENCE: 89

| | | | | | |
|---|---|---|---|---|---|
| atgaatatga | agaaaaaaga | aaaacacgca | attcggaaaa | aatcgattgg cgtggcttca | 60 |
| gtgcttgtag | gtacgttaat | cggttttgga | ctactcagca | gtaaagaagc agatgcaagt | 120 |
| gaaaatagtg | ttacgcaatc | tgatagcgca | agtaacgaaa | gcaaaagtaa tgattcaagt | 180 |
| agcgttagtg | ctgcacctaa | aacagacgac | acaaacgtga | gtgatactaa acatcgtca | 240 |
| aacactaata | atggcgaaac | gagtgtggcg | caaaatccag | cacaacagga acgacacaa | 300 |
| tcagcattaa | caaatgcaac | tacggaagaa | actccggtaa | ctggtgaagc tactacggca | 360 |
| acgaatcaag | ctaatacacc | ggcaacaact | caatcaagca | atacaaatgc ggaggaatta | 420 |
| gtgaatcaaa | caagtaatga | aacgacttct | aatgatacta | atacagtatc atctgtaaat | 480 |
| tcacctcaaa | attctacaaa | tgcggaaaat | gtttcaacaa | cgcaagatac ttcaactgaa | 540 |
| gcaacacctt | caaacaatga | atcagctcca | cagaatacag | atgcaagtaa taagatgta | 600 |
| gttaatcaag | cggttaatac | aagtgcgcct | agaaagagag | catttagttt agcggctgta | 660 |
| gctgcagatg | caccggcagc | tggcacagat | attacgaatc | agttgacaga tgtgaaagtt | 720 |
| actattgact | ctggtacgac | tgtgtatccg | caccaagcag | gttatgtcaa actgaattat | 780 |
| ggtttttcag | tgcctaattc | tgctgttaaa | ggtgacacat | tcaaataac tgtacctaaa | 840 |
| gaattaaact | taaatggtgt | aacttcaact | gctaaagtgc | caccaattat ggctggagat | 900 |
| caagtattgg | caaatggtgt | aatcgatagt | gatggtaatg | ttatttatac atttacagac | 960 |
| tatgttgata | taaagaaaa | tgtaacagct | aatattacta | tgccagctta tattgaccct | 1020 |
| gaaaatgtta | caaagacagg | taatgtgaca | ttgacaactg | gcataggaac caatactgct | 1080 |
| agtaagacag | tattaatcga | ctatgagaaa | tatggacaat | tccataattt atcaattaaa | 1140 |
| ggtacgattg | atcaaatcga | taaacaaat | aatacgtatc | gccaaacaat ttatgtcaat | 1200 |
| ccaagcggag | ataacgttgt | gttacctgcc | ttaacaggta | atttaattcc taatacaaag | 1260 |
| agtaatgcgt | taatagatgc | aaaaaacact | gatattaaag | tttatagagt cgataatgct | 1320 |
| aatgatttat | ctgaaagtta | ttatgtgaat | cctagcgatt | ttgaagatgt aactaatcaa | 1380 |
| gttagaattt | catttccaaa | tgctaatcaa | tacaaagtag | aatttcctac ggacgatgac | 1440 |
| caaattacaa | caccgtatat | tgtagttgtt | aatggccata | ttgatcctgc tagtacaggt | 1500 |
| gatttagcac | tacgttcgac | attttatggt | tatgattcta | attttatatg gagatctatg | 1560 |
| tcatgggaca | acgaagtagc | atttaataac | ggatcaggtt | ctggtgacgg tatcgataaa | 1620 |
| ccagttgttc | ctgaacaacc | tgatgagcct | ggtgaaattg | aaccaattcc agag | 1674 |

<210> SEQ ID NO 90
<211> LENGTH: 558
<212> TYPE: PRT
<213> ORGANISM: Staphylococcus aureus

<400> SEQUENCE: 90

Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

```
Ser Ala Ser Asn Glu Ser Lys Ser Asn Asp Ser Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ala Leu Thr Asn Ala Thr Thr Glu Glu Thr Pro
            100                 105                 110

Val Thr Gly Glu Ala Thr Thr Ala Thr Asn Gln Ala Asn Thr Pro Ala
            115                 120                 125

Thr Thr Gln Ser Ser Asn Thr Asn Ala Glu Glu Leu Val Asn Gln Thr
    130                 135                 140

Ser Asn Glu Thr Thr Ser Asn Asp Thr Asn Thr Val Ser Ser Val Asn
145                 150                 155                 160

Ser Pro Gln Asn Ser Thr Asn Ala Glu Asn Val Ser Thr Thr Gln Asp
                165                 170                 175

Thr Ser Thr Glu Ala Thr Pro Ser Asn Asn Glu Ser Ala Pro Gln Asn
            180                 185                 190

Thr Asp Ala Ser Asn Lys Asp Val Val Asn Gln Ala Val Asn Thr Ser
            195                 200                 205

Ala Pro Arg Lys Arg Ala Phe Ser Leu Ala Ala Val Ala Ala Asp Ala
    210                 215                 220

Pro Ala Ala Gly Thr Asp Ile Thr Asn Gln Leu Thr Asp Val Lys Val
225                 230                 235                 240

Thr Ile Asp Ser Gly Thr Thr Val Tyr Pro His Gln Ala Gly Tyr Val
                245                 250                 255

Lys Leu Asn Tyr Gly Phe Ser Val Pro Asn Ser Ala Val Lys Gly Asp
            260                 265                 270

Thr Phe Lys Ile Thr Val Pro Lys Glu Leu Asn Leu Asn Gly Val Thr
            275                 280                 285

Ser Thr Ala Lys Val Pro Pro Ile Met Ala Gly Asp Gln Val Leu Ala
    290                 295                 300

Asn Gly Val Ile Asp Ser Asp Gly Asn Val Ile Tyr Thr Phe Thr Asp
305                 310                 315                 320

Tyr Val Asp Asn Lys Glu Asn Val Thr Ala Asn Ile Thr Met Pro Ala
                325                 330                 335

Tyr Ile Asp Pro Glu Asn Val Thr Lys Thr Gly Asn Val Thr Leu Thr
            340                 345                 350

Thr Gly Ile Gly Thr Asn Thr Ala Ser Lys Thr Val Leu Ile Asp Tyr
            355                 360                 365

Glu Lys Tyr Gly Gln Phe His Asn Leu Ser Ile Lys Gly Thr Ile Asp
    370                 375                 380

Gln Ile Asp Lys Thr Asn Asn Thr Tyr Arg Gln Thr Ile Tyr Val Asn
385                 390                 395                 400

Pro Ser Gly Asp Asn Val Val Leu Pro Ala Leu Thr Gly Asn Leu Ile
                405                 410                 415

Pro Asn Thr Lys Ser Asn Ala Leu Ile Asp Ala Lys Asn Thr Asp Ile
            420                 425                 430

Lys Val Tyr Arg Val Asp Asn Ala Asn Asp Leu Ser Glu Ser Tyr Tyr
            435                 440                 445

Val Asn Pro Ser Asp Phe Glu Asp Val Thr Asn Gln Val Arg Ile Ser
    450                 455                 460

Phe Pro Asn Ala Asn Gln Tyr Lys Val Glu Phe Pro Thr Asp Asp Asp
```

```
            465                 470                 475                 480
Gln Ile Thr Thr Pro Tyr Ile Val Val Asn Gly His Ile Asp Pro
                485                 490                 495

Ala Ser Thr Gly Asp Leu Ala Leu Arg Ser Thr Phe Tyr Gly Tyr Asp
            500                 505                 510

Ser Asn Phe Ile Trp Arg Ser Met Ser Trp Asp Asn Glu Val Ala Phe
            515                 520                 525

Asn Asn Gly Ser Gly Ser Gly Asp Gly Ile Asp Lys Pro Val Val Pro
        530                 535                 540

Glu Gln Pro Asp Glu Pro Gly Glu Ile Glu Pro Ile Pro Glu
545                 550                 555

<210> SEQ ID NO 91
<211> LENGTH: 1674
<212> TYPE: DNA
<213> ORGANISM: Staphylococcus aureus

<400> SEQUENCE: 91
atgaatatga agaaaaaaga aaaacacgca attcggaaaa aatcgattgg cgtggcttca      60
gtgcttgtag gtacgttaat cggttttgga ctactcagca gtaaagaagc agatgcaagt     120
gaaaatagtg ttacgcaatc tgatagcgca agtaacgaaa gcaaaagtaa tgattcaagt     180
agcgttagtg ctgcacctaa aacagacgac acaaacgtga gtgatactaa acatcgtca      240 aacactaata atggcgaaac gagtgtggcg caaaatccag cacaacagga aacgacacaa     300
tcatcattaa caaatgcaac tacgaagaa actccggtaa ctggtgaagc tactacggca     360
acgaatcaag ctaatacacc ggcaacaact caatcaagca atacaaatgc ggaggaatta     420
gtgaatcaaa caagtaatga aacgacttct aatgatacta atacagtatc atctgtaaat     480
tcacctcaaa attctacaaa tgcggaaaat gtttcaacaa cgcaagatac ttcaactgaa     540
gcaacacctt caaacaatga atcagctcca cagagtacag atgcaagtaa taagatttta     600
gttaatcaag cggttaatac aagtgcgcct agaatgagag catttagttt agcggcagta     660
gctgcagatg cacctgcagc tggcacagat attacgaatc agttgacaga tgttaaagtt     720
actattgact ctggtacgac tgtgtatccg caccaagcag gttatgtcaa actgaattat     780 ggttttcag tgcctaattc tgctgttaaa ggtgacacat tcaaaataac tgtacctaaa     840
gaattaaact taaatggtgt aacttcaact gctaaagtgc caccaattat ggctggagat     900
caagtattgg caaatggtgt aatcgatagt gatggtaatg ttatttatac atttacagac     960
tatgttgata taaaaacga tgttaaagca actttgacca tgcccgctta tattgatcca    1020
gaaaatgtaa cgaaaacagg taatgtaaca ttgacaactg gcataggtag tacaacagca    1080
aacaaaacag tattagtaga ttatgaaaaa tatggtaagt tttataactt atctattaaa    1140
ggtacaattg accaaatcga taaacaaat aatacgtatc gtcagacaat ttatgtcaat    1200
ccaagtggag ataacgttat tgcgccggtt taacaggta attaaaacc aaatacggat    1260 agtaatgcat taatagatca gcaaaataca agtattaaag tatataaagt agataatgca    1320
gctgatttat ctgaaagtta ctttgtaaat ccagaaaact ttgaggatgt cactaatagt    1380
gtgaatatta cattcccaaa tccaaatcaa tataagtag agttaatac gcctgatgat    1440 caaattacaa caccgtatat tgtagttgtt aatggtcata ttgatccgaa tagcaaaggt    1500
gatttagctt tacgttcaac tttatatggg tataactcga atataatttg gcgctctatg    1560
tcatgggaca acgaagtagc atttaataac ggatcaggtt ctggtgacgg tatcgataaa    1620
```
cctgttgtcc ctgaacaacc tgatgagcct ggtgaaattg aaccaattcc agag    1674

<210> SEQ ID NO 92
<211> LENGTH: 558
<212> TYPE: PRT
<213> ORGANISM: Staphylococcus aureus

<400> SEQUENCE: 92

```
Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Val Ser Ala
    50                  55                  60

Ala Pro Lys Thr Asp Asp Thr Asn Val Ser Asp Thr Lys Thr Ser Ser
65              70                  75                  80

Asn Thr Asn Asn Gly Glu Thr Ser Val Ala Gln Asn Pro Ala Gln Gln
                85                  90                  95

Glu Thr Thr Gln Ser Ser Leu Thr Asn Ala Thr Glu Glu Thr Pro
        100                 105                 110

Val Thr Gly Glu Ala Thr Thr Ala Thr Asn Gln Ala Asn Thr Pro Ala
        115                 120                 125

Thr Thr Gln Ser Ser Asn Thr Asn Ala Glu Glu Leu Val Asn Gln Thr
    130                 135                 140

Ser Asn Glu Thr Thr Ser Asn Asp Thr Asn Thr Val Ser Ser Val Asn
145                 150                 155                 160

Ser Pro Gln Asn Ser Thr Asn Ala Glu Asn Val Ser Thr Thr Gln Asp
                165                 170                 175

Thr Ser Thr Glu Ala Thr Pro Ser Asn Asn Glu Ser Ala Pro Gln Ser
            180                 185                 190

Thr Asp Ala Ser Asn Lys Asp Leu Val Asn Gln Ala Val Asn Thr Ser
        195                 200                 205

Ala Pro Arg Met Arg Ala Phe Ser Leu Ala Ala Val Ala Ala Asp Ala
    210                 215                 220

Pro Ala Ala Gly Thr Asp Ile Thr Asn Gln Leu Thr Asp Val Lys Val
225                 230                 235                 240

Thr Ile Asp Ser Gly Thr Thr Val Tyr Pro His Gln Ala Gly Tyr Val
                245                 250                 255

Lys Leu Asn Tyr Gly Phe Ser Val Pro Asn Ser Ala Val Lys Gly Asp
            260                 265                 270

Thr Phe Lys Ile Thr Val Pro Lys Glu Leu Asn Leu Asn Gly Val Thr
        275                 280                 285

Ser Thr Ala Lys Val Pro Pro Ile Met Ala Gly Asp Gln Val Leu Ala
    290                 295                 300

Asn Gly Val Ile Asp Ser Asp Gly Asn Val Ile Tyr Thr Phe Thr Asp
305                 310                 315                 320

Tyr Val Asp Asn Lys Asn Asp Val Lys Ala Thr Leu Thr Met Pro Ala
                325                 330                 335

Tyr Ile Asp Pro Glu Asn Val Thr Lys Thr Gly Asn Val Thr Leu Thr
            340                 345                 350

Thr Gly Ile Gly Ser Thr Thr Ala Asn Lys Thr Val Leu Val Asp Tyr
        355                 360                 365
```

```
Glu Lys Tyr Gly Lys Phe Tyr Asn Leu Ser Ile Lys Gly Thr Ile Asp
    370             375                 380

Gln Ile Asp Lys Thr Asn Asn Thr Tyr Arg Gln Thr Ile Tyr Val Asn
385             390                 395                 400

Pro Ser Gly Asp Asn Val Ile Ala Pro Val Leu Thr Gly Asn Leu Lys
                405                 410                 415

Pro Asn Thr Asp Ser Asn Ala Leu Ile Asp Gln Gln Asn Thr Ser Ile
                420                 425                 430

Lys Val Tyr Lys Val Asp Asn Ala Ala Asp Leu Ser Glu Ser Tyr Phe
                435                 440                 445

Val Asn Pro Glu Asn Phe Glu Asp Val Thr Asn Ser Val Asn Ile Thr
450                 455                 460

Phe Pro Asn Pro Asn Gln Tyr Lys Val Glu Phe Asn Thr Pro Asp Asp
465                 470                 475                 480

Gln Ile Thr Thr Pro Tyr Ile Val Val Asn Gly His Ile Asp Pro
                485                 490                 495

Asn Ser Lys Gly Asp Leu Ala Leu Arg Ser Thr Leu Tyr Gly Tyr Asn
                500                 505                 510

Ser Asn Ile Ile Trp Arg Ser Met Ser Trp Asp Asn Glu Val Ala Phe
                515                 520                 525

Asn Asn Gly Ser Gly Ser Gly Asp Gly Ile Asp Lys Pro Val Val Pro
                530                 535                 540

Glu Gln Pro Asp Glu Pro Gly Glu Ile Glu Pro Ile Pro Glu
545                 550                 555

<210> SEQ ID NO 93
<211> LENGTH: 1674
<212> TYPE: DNA
<213> ORGANISM: Staphylococcus aureus

<400> SEQUENCE: 93
atgaatatga agaaaaaaga aaaacacgca attcggaaaa aatcgattgg cgtggcttca      60
gtgcttgtag gtacgttaat cggttttgga ctactcagca gtaaagaagc agatgcaagt     120
gaaaatagtg ttacgcaatc tgatagcgca agtaacgaaa gcaaaagtaa tgatccaagt     180
agcgttaatg ctgcacctaa acagacaaac acaaacgtga gtgatactaa acatcgtca      240 aacactaata tggcgaaac gagtgtggcg caaaatccag cacaacagga acgacacaa       300 tcatcattaa caaatgcaac tacggaagaa actccggtaa ctggtgaagc tactacggca     360
acgaatcaag ctaatacacc ggcaacaact caatcaagca atacaaatgc ggaggaatta     420
gtgaatcaaa caagtaatga aacgacttct aatgatacta atacagtatc atctgtaaat     480
tcacctcaaa attctacaaa tgcggaaaat gtttcaacaa cgcaagatac ttcaactgaa     540 gcaacaccctt caaacaatga atcagctcca cagagtacag atgcaagtaa taagatttta     600
gttaatcaag cggttaatac aagtgcgcct agaatgagag catttagttt agcggcagta     660
gctgcagatg cacctgcagc tggcacagat attacgaatc agttgacaga tgttaaagtt     720
actattgact ctggtacgac tgtgtatccg caccaagcag ttatgtcaa actgaattat      780 ggttttcag tgcctaattc tgctgttaaa ggtgacacat tcaaaataac tgtacctaaa     840 gaattaaaact taaatggtgt aacttcaact gctaaagtgc ctccaattat ggccggagat    900
caagtattgg caaatggtgt aatcgatagt gatggtaatg ttattatac atttacagac      960 tatgttgata ctaaagaaaa tgtaacagct aatattacta tgccagctta tattgaccct    1020
gaaaatgtta caaagacagg taatgtaaca ttgacaactg gcataggtag tacaacagca   1080
```

-continued

```
aacaaaacag tattagtaga ttatgaaaaa tatggtaagt tttataactt atctattaaa   1140
ggtacaattg accaaatcga taaaacaaat aatacgtatc gtcagacaat ttatgtcaat   1200
ccaagtggag ataacgttat tgcgccggtt ttaacaggta atttaaaacc caatacggat   1260
agtaatgcat taatagatca gcaaaataca agtattaaag tatataaagt agataatgca   1320
gctgatttat ctgaaagtta ctttgtaaat ccagaaaact ttgaggatgt cactaatagt   1380
gtgaatatta cattcccaaa tccaaatcaa tataaagtag agtttaatac gcctgatgat   1440
caaattacaa caccgtatat tgtagttgtt aatggtcata ttgatccgaa tagcaaaggt   1500
gatttagctt tacgttcaac tttatatggg tataactcga atataatttg gcgctctatg   1560
tcatgggaca acgaagtagc atttaataac ggatcaggtt ctggtgacgg tatcgataaa   1620
cctgttgtcc ctgaacaacc tgatgagcct ggtgaaattg aaccaattcc agag         1674
```

<210> SEQ ID NO 94
<211> LENGTH: 558
<212> TYPE: PRT
<213> ORGANISM: Staphylococcus aureus

<400> SEQUENCE: 94

```
Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Pro Ser Ser Val Asn Ala
    50                  55                  60

Ala Pro Lys Thr Asp Asn Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Leu Thr Asn Ala Thr Thr Glu Glu Thr Pro
            100                 105                 110

Val Thr Gly Glu Ala Thr Thr Ala Thr Asn Gln Ala Asn Thr Pro Ala
        115                 120                 125

Thr Thr Gln Ser Ser Asn Thr Asn Ala Glu Glu Leu Val Asn Gln Thr
    130                 135                 140

Ser Asn Glu Thr Thr Ser Asn Asp Thr Asn Thr Val Ser Ser Val Asn
145                 150                 155                 160

Ser Pro Gln Asn Ser Thr Asn Ala Glu Asn Val Ser Thr Thr Gln Asp
                165                 170                 175

Thr Ser Thr Glu Ala Thr Pro Ser Asn Asn Glu Ser Ala Pro Gln Ser
            180                 185                 190

Thr Asp Ala Ser Asn Lys Asp Leu Val Asn Gln Ala Val Asn Thr Ser
        195                 200                 205

Ala Pro Arg Met Arg Ala Phe Ser Leu Ala Ala Val Ala Ala Asp Ala
    210                 215                 220

Pro Ala Ala Gly Thr Asp Ile Thr Asn Gln Leu Thr Asp Val Lys Val
225                 230                 235                 240

Thr Ile Asp Ser Gly Thr Thr Val Tyr Pro His Gln Ala Gly Tyr Val
                245                 250                 255

Lys Leu Asn Tyr Gly Phe Ser Val Pro Asn Ser Ala Val Lys Gly Asp
            260                 265                 270
```

-continued

```
Thr Phe Lys Ile Thr Val Pro Lys Glu Leu Asn Leu Asn Gly Val Thr
        275                 280                 285
Ser Thr Ala Lys Val Pro Pro Ile Met Ala Gly Asp Gln Val Leu Ala
    290                 295                 300
Asn Gly Val Ile Asp Ser Asp Gly Asn Val Ile Tyr Thr Phe Thr Asp
305                 310                 315                 320
Tyr Val Asp Thr Lys Glu Asn Val Thr Ala Asn Ile Thr Met Pro Ala
                325                 330                 335
Tyr Ile Asp Pro Glu Asn Val Thr Lys Thr Gly Asn Val Thr Leu Thr
                340                 345                 350
Thr Gly Ile Gly Ser Thr Thr Ala Asn Lys Thr Val Leu Val Asp Tyr
        355                 360                 365
Glu Lys Tyr Gly Lys Phe Tyr Asn Leu Ser Ile Lys Gly Thr Ile Asp
    370                 375                 380
Gln Ile Asp Lys Thr Asn Asn Thr Tyr Arg Gln Thr Ile Tyr Val Asn
385                 390                 395                 400
Pro Ser Gly Asp Asn Val Ile Ala Pro Val Leu Thr Gly Asn Leu Lys
                405                 410                 415
Pro Asn Thr Asp Ser Asn Ala Leu Ile Asp Gln Gln Asn Thr Ser Ile
                420                 425                 430
Lys Val Tyr Lys Val Asp Asn Ala Ala Asp Leu Ser Glu Ser Tyr Phe
        435                 440                 445
Val Asn Pro Glu Asn Phe Glu Asp Val Thr Asn Ser Val Asn Ile Thr
    450                 455                 460
Phe Pro Asn Pro Asn Gln Tyr Lys Val Glu Phe Asn Thr Pro Asp Asp
465                 470                 475                 480
Gln Ile Thr Thr Pro Tyr Ile Val Val Asn Gly His Ile Asp Pro
                485                 490                 495
Asn Ser Lys Gly Asp Leu Ala Leu Arg Ser Thr Leu Tyr Gly Tyr Asn
                500                 505                 510
Ser Asn Ile Ile Trp Arg Ser Met Ser Trp Asp Asn Glu Val Ala Phe
        515                 520                 525
Asn Asn Gly Ser Gly Ser Gly Asp Gly Ile Asp Lys Pro Val Val Pro
    530                 535                 540
Glu Gln Pro Asp Glu Pro Gly Glu Ile Glu Pro Ile Pro Glu
545                 550                 555
```

<210> SEQ ID NO 95
<211> LENGTH: 1677
<212> TYPE: DNA
<213> ORGANISM: Staphylococcus aureus

<400> SEQUENCE: 95

```
atgaatatga agaaaaaga aaaacacgca attcggaaaa aatcgattgg cgtggcttca      60
gtgcttgtag gtacgttaat cggttttgga ctactcagca gtaaagaagc agatgcaagt    120
gaaaatagtg ttacgcaatc tgatagcgca agtaacgaaa gcaaaagtaa tgattcaagt    180
agcgttagtg ctgcacctaa acagacgac acaaacgtga gtgatactaa acatcgtca     240
aacactaata tggcgaaac gagtgtggcg caaaatctag cacaacagga acgacacaa     300
tcatcatcaa caaatgcaac tacggaagaa acgccggtaa ctggtgaagc tactactacg    360
acaacgaatc aagctaatac accggcaaca actcaatcaa gcaatacaaa tgcggaggaa    420
ttagtgaatc aaacaagtaa tgaaacgact tctaatgata ctaatacagt atcatctgta    480
```

```
aattcacctc aaaattctac aaatgcggaa aatgtttcaa caacgcaaga tacttcaact    540
gaagcaacac cttcaaacaa tgaatcagct ccacagagta cagatgcaag taataaagat    600
gtagttaatc aagcggttaa tacaagtgcg cctagaatga gagcatttag tttagcggca    660
gtagctgcag atgcaccggc agctggcaca gatattacga atcagttgac gaatgtgaca    720
gttggtattg actctggtac gactgtgtat ccgcaccaag caggttatgt caaactgaat    780
tatggttttt cagtgcctaa ttctgctgtt aaaggtgaca cattcaaaat aactgtacct    840
aaagaattaa acttaaatgg tgtaacttca actgctaaag tgccaccaat tatggctgga    900
gatcaagtat tggcaaatgg tgtaatcgat agtgatggta atgttattta cacatttaca    960
gactatgtaa atactaaaga tgatgttaaa gcaactttga ccatgcccgc ttatattgac   1020
cctgaaaatg ttacaaagac aggtaatgtg acattggcta ctggcatagg aaatacaaca   1080
gcaaacaaaa cagtattagt agattatgaa aaatatggta agttttataa cttatctatt   1140
aaaggtacaa ttgaccaaat cgataaaaca ataatacgt atcgtcagac aatttatgtc   1200
aatccaagtg gagataacgt tattgcgccg gttttaacag gtaatttaaa accaaatacg   1260
gatagtaatg cattaataga tcagcaaaat acaagtatta agtatataa agtagataat   1320
gcagctgatt tatctgaaag ttactttgtg aatccagaaa actttgagga tgtcactaat   1380
agtgtgaata ttacattccc aaatccaaat caatataaag tagagtttaa tacgcctgat   1440
gatcaaatta caacaccgta tatagtagtt gttaatggtc atattgatcc gaatagcaaa   1500
ggtgatttag ctttacgttc aactttatat gggtataact cgaatataat ttggcgctct   1560
atgtcatggg acaacgaagt agcatttaat aacggatcag ttctggtga cggtatcgat   1620
aaacctgttg ttcctgaaca acctgatgag cctggtgaaa ttgaaccaat tccagag     1677
```

<210> SEQ ID NO 96
<211> LENGTH: 559
<212> TYPE: PRT
<213> ORGANISM: Staphylococcus aureus

<400> SEQUENCE: 96

```
Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Leu Ala Gln Gln
                85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Asn Gln Ala Asn Thr Pro
        115                 120                 125

Ala Thr Thr Gln Ser Ser Asn Thr Asn Ala Glu Glu Leu Val Asn Gln
    130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
```

```
                    165                 170                 175
Asp Thr Ser Thr Glu Ala Thr Pro Ser Asn Asn Glu Ser Ala Pro Gln
                180                 185                 190

Ser Thr Asp Ala Ser Asn Lys Asp Val Val Asn Gln Ala Val Asn Thr
            195                 200                 205

Ser Ala Pro Arg Met Arg Ala Phe Ser Leu Ala Ala Val Ala Ala Asp
        210                 215                 220

Ala Pro Ala Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
305                 310                 315                 320

Asp Tyr Val Asn Thr Lys Asp Val Lys Ala Thr Leu Thr Met Pro
                325                 330                 335

Ala Tyr Ile Asp Pro Glu Asn Val Thr Lys Thr Gly Asn Val Thr Leu
            340                 345                 350

Ala Thr Gly Ile Gly Asn Thr Thr Ala Asn Lys Thr Val Leu Val Asp
        355                 360                 365

Tyr Glu Lys Tyr Gly Lys Phe Tyr Asn Leu Ser Ile Lys Gly Thr Ile
    370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
        435                 440                 445

Phe Val Asn Pro Glu Asn Phe Glu Asp Val Thr Asn Ser Val Asn Ile
    450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly Tyr
            500                 505                 510

Asn Ser Asn Ile Ile Trp Arg Ser Met Ser Trp Asp Asn Glu Val Ala
        515                 520                 525

Phe Asn Asn Gly Ser Gly Ser Gly Asp Gly Ile Asp Lys Pro Val Val
    530                 535                 540

Pro Glu Gln Pro Asp Glu Pro Gly Glu Ile Glu Pro Ile Pro Glu
545                 550                 555

<210> SEQ ID NO 97
<211> LENGTH: 1674
<212> TYPE: DNA
<213> ORGANISM: Staphylococcus aureus
```

<400> SEQUENCE: 97

```
atgaatatga agaaaaaga aaaacacgca attcggaaaa aatcgattgg cgtggcttca      60
gtgcttgtag gtacgttaat cggttttgga ctactcagca gtaaagaagc agatgcaagt     120
gaaaatagtg ttacgcaatc tgatagcgca agtaacgaaa gcaaaagtaa tgattcaagt     180
agcgttagtg ctgcacctaa acagacgac acaaacgtga gtgatactaa acatcgtca      240
aacactaata tggcgaaac gagtgtggcg caaaatccag cacaacagga acgacacaa      300
tcagcattaa caaatgcaac tacggaagaa actccgttaa ctggtgaagc tactacggca     360
acgaatcaag ctaatacacc ggcaacaact caatcaagca atacaaatgc ggaggaatta     420
gtgaatcaaa caagtaatga acgacttct aatgatacta atacagtatc atctgtaaat     480
tcacctcaaa attctacaaa tgcggaaaat gtttcaacaa cgcaagatac ttcaactgaa     540
gcaacacctt caaacaatga atcagctcca cagagtacag atgcaagtaa taagatgta     600
gttaatcaag cggttaatac aagtgcgcct agaatgagag catttagttt agcggcagta     660
gctgcagatg caccggcagc tggcacagat attacgaatc agttgacaga tgtgaaagtt     720
actattgact ctggtacgac tgtgtatccg caccaagcag ttatgtcaa actgaattat     780
ggttttcag tgcctaattc tgctgttaaa ggtgacacat tcaaaataac tgtacctaaa     840
gaattaaact taaatggtgt aacttcaact gctaaagtgc ctccaattat ggccggagat     900
caagtattgg caaatggtgt aatcgatagt gatggtaatg ttatttatac atttacagac     960
tatgttgata taaaaacga tgttaaagca acactaactg ttcctgcata cattgatcca    1020
gaaaatgtaa cgaaaacagg taatgtaaca ttgacaactg gcataggaac caatactgct    1080
agtaagacag ttttaatcga ctatgagaaa tatggacaat tccataattt atcaattaaa    1140
ggtacaattg atcaaatcga caaacaaac aatacgtatc gtcaaacgat ttatgtcaat    1200
ccaagtggag acaatgttgt attaccagtg ttaactggta atctaattcc taagagtaat    1260
agtaatgctt aatagatgc caacaatact aatattaaag tttataaagt ggataatgct    1320
aatgatttat ctgaaagtta ttatgtgaat cctagcgatt ttgaagatgt aactaatcaa    1380
gttagaattt catttccaaa tgctaatcaa tacaaagtag aatttcctac ggacgatgac    1440
caaattacaa caccgtatat tgtagttgtt aatggccata ttgatcctgc tagtacaggt    1500
gatttagcac tacgttcgac atttttatggt tatgattcta ttttatatg gagatctatg    1560
tcatgggaca acgaagtagc atttaataac ggatcaggtt ctggtgacgg tatcgataaa    1620
ccagttgttc ctgaacaacc tgatgagcct ggtgaaattg aaccaattcc agag         1674
```

<210> SEQ ID NO 98
<211> LENGTH: 558
<212> TYPE: PRT
<213> ORGANISM: Staphylococcus aureus

<400> SEQUENCE: 98

```
Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Val Ser Ala
    50                  55                  60
```

-continued

```
Ala Pro Lys Thr Asp Asp Thr Asn Val Ser Asp Thr Lys Thr Ser Ser
 65                  70                  75                  80

Asn Thr Asn Asn Gly Glu Thr Ser Val Ala Gln Asn Pro Ala Gln Gln
                 85                  90                  95

Glu Thr Thr Gln Ser Ala Leu Thr Asn Ala Thr Glu Glu Thr Pro
            100                 105                 110

Leu Thr Gly Glu Ala Thr Thr Ala Thr Asn Gln Ala Asn Thr Pro Ala
            115                 120                 125

Thr Thr Gln Ser Ser Asn Thr Asn Ala Glu Glu Leu Val Asn Gln Thr
        130                 135                 140

Ser Asn Glu Thr Thr Ser Asn Asp Thr Asn Thr Val Ser Ser Val Asn
145                 150                 155                 160

Ser Pro Gln Asn Ser Thr Asn Ala Glu Asn Val Ser Thr Thr Gln Asp
                165                 170                 175

Thr Ser Thr Glu Ala Thr Pro Ser Asn Asn Glu Ser Ala Pro Gln Ser
            180                 185                 190

Thr Asp Ala Ser Asn Lys Asp Val Val Asn Gln Ala Val Asn Thr Ser
        195                 200                 205

Ala Pro Arg Met Arg Ala Phe Ser Leu Ala Ala Val Ala Ala Asp Ala
210                 215                 220

Pro Ala Ala Gly Thr Asp Ile Thr Asn Gln Leu Thr Asp Val Lys Val
225                 230                 235                 240

Thr Ile Asp Ser Gly Thr Thr Val Tyr Pro His Gln Ala Gly Tyr Val
                245                 250                 255

Lys Leu Asn Tyr Gly Phe Ser Val Pro Asn Ser Ala Val Lys Gly Asp
            260                 265                 270

Thr Phe Lys Ile Thr Val Pro Lys Glu Leu Asn Leu Asn Gly Val Thr
        275                 280                 285

Ser Thr Ala Lys Val Pro Pro Ile Met Ala Gly Asp Gln Val Leu Ala
290                 295                 300

Asn Gly Val Ile Asp Ser Asp Gly Asn Val Ile Tyr Thr Phe Thr Asp
305                 310                 315                 320

Tyr Val Asp Asn Lys Asn Asp Val Lys Ala Thr Leu Thr Val Pro Ala
                325                 330                 335

Tyr Ile Asp Pro Glu Asn Val Thr Lys Thr Gly Asn Val Thr Leu Thr
            340                 345                 350

Thr Gly Ile Gly Thr Asn Thr Ala Ser Lys Thr Val Leu Ile Asp Tyr
        355                 360                 365

Glu Lys Tyr Gly Gln Phe His Asn Leu Ser Ile Lys Gly Thr Ile Asp
    370                 375                 380

Gln Ile Asp Lys Thr Asn Asn Thr Tyr Arg Gln Thr Ile Tyr Val Asn
385                 390                 395                 400

Pro Ser Gly Asp Asn Val Val Leu Pro Val Leu Thr Gly Asn Leu Ile
                405                 410                 415

Pro Lys Ser Asn Ser Asn Ala Leu Ile Asp Ala Asn Asn Thr Asn Ile
            420                 425                 430

Lys Val Tyr Lys Val Asp Asn Ala Asn Asp Leu Ser Glu Ser Tyr Tyr
        435                 440                 445

Val Asn Pro Ser Asp Phe Glu Asp Val Thr Asn Gln Val Arg Ile Ser
    450                 455                 460

Phe Pro Asn Ala Asn Gln Tyr Lys Val Glu Phe Pro Thr Asp Asp
465                 470                 475                 480

Gln Ile Thr Thr Pro Tyr Ile Val Val Asn Gly His Ile Asp Pro
```

```
                  485              490              495
Ala Ser Thr Gly Asp Leu Ala Leu Arg Ser Thr Phe Tyr Gly Tyr Asp
            500              505              510

Ser Asn Phe Ile Trp Arg Ser Met Ser Trp Asp Asn Glu Val Ala Phe
            515              520              525

Asn Asn Gly Ser Gly Ser Gly Asp Gly Ile Asp Lys Pro Val Val Pro
            530              535              540

Glu Gln Pro Asp Glu Pro Gly Glu Ile Glu Pro Ile Pro Glu
545              550              555

<210> SEQ ID NO 99
<211> LENGTH: 1674
<212> TYPE: DNA
<213> ORGANISM: Staphylococcus aureus

<400> SEQUENCE: 99
```

| | | | | | |
|---|---|---|---|---|---|
| atgaatatga | agaaaaaaga | aaaacacgca | attcggaaaa | aatcgattgg cgtggcttca | 60 |
| gtgcttgtag | gtacgttaat | cggttttgga | ctactcagca | gtaaagaagc agatgcaagt | 120 |
| gaaaatagtg | ttacgcaatc | tgatagcgca | agtaacgaaa | gcaaaagtaa tgattcaagt | 180 |
| agcgttagtg | ctgcacctaa | aacagacgac | acaaacgtga | gtgatactaa acatcgtca | 240 |
| aacactaata | atggcgaaac | gagtgtggcg | caaaatccag | cacaacaaga aacgacacaa | 300 |
| tcagcattaa | caaatgcaac | tacggaagaa | actccggtaa | ctggtgaagc tactacggca | 360 |
| acgaatcaag | ctaatacacc | ggcaacaact | caatcaagca | atacaaatgc ggaggaatta | 420 |
| gtgaatcaaa | caagtaatga | aacgacttct | aatgatacta | tacagtatc atctgtaaat | 480 |
| tcacctcaaa | attctacaaa | tgcggaaaat | gtttcaacaa | cgcaagatac ttcaactgaa | 540 |
| gcaacacctt | caaacaatga | atcagctcca | cagaatacag | atgcaagtaa taagatgta | 600 |
| gttaatcaag | cggttaatac | aagtgcgcct | agaaagagag | catttagttt agcggctgta | 660 |
| gctgcagatg | caccggcagc | tggcacagat | attacgaatc | agttgacaga tgtgaaagtt | 720 |
| actattgact | ctggtacgac | tgtgtatccg | caccaagcag | gttatgtcaa actgaattat | 780 |
| ggttttcag | tgcctaattc | tgctgttaaa | ggtgacacat | tcaaaataac tgtacctaaa | 840 |
| gaattaaact | taaatggtgt | aacttcaact | gctaaagcgc | caccaattat ggctggagat | 900 |
| caagtattgg | caaatggtgt | aatcgatagt | gatggtaatg | ttattatac atttacagac | 960 |
| tatgttgata | ataaagaaaa | tgtaacagct | aatattacta | tgccagctta tattgaccct | 1020 |
| gaaaatgtta | caaagacagg | taatgtgaca | ttgacaactg | gcataggaac caatactgct | 1080 |
| agtaagacag | tattaatcga | ctatgagaaa | tatggacaat | tccataattt atcaattaaa | 1140 |
| ggtacgattg | atcaaatcga | taaaacaaat | aatacgtatc | gccaaacaat ttatgtcaat | 1200 |
| ccaagcggag | ataacgttgt | gttacctgcc | ttaacaggta | atttaattcc taatacaaag | 1260 |
| agtaatgcgt | taatagatgc | aaaaaacact | gatattaaag | tttatagagt cgataatgct | 1320 |
| aatgatttat | ctgaaagtta | ttatgtgaat | cctagcgatt | tgaagatgt aactaatcaa | 1380 |
| gttagaattt | catttccaaa | tgctaatcaa | tacaaagtag | aatttcctac ggacgatgac | 1440 |
| caaattacaa | caccgtatat | tgtagttgtt | aatggccata | ttgatcctgc tagtacaggt | 1500 |
| gatttagcac | tacgttcgac | atttatggt | tatgattcta | attttatatg gagatctatg | 1560 |
| tcatgggaca | acgaagtagc | atttaataac | ggatcaggtt | ctggtgacgg tatcgataaa | 1620 |
| ccagttgttc | ctgaacaacc | tgatgagcct | ggtgaaattg | aaccaattcc agag | 1674 |

<210> SEQ ID NO 100
<211> LENGTH: 558
<212> TYPE: PRT
<213> ORGANISM: Staphylococcus aureus

<400> SEQUENCE: 100

| | | | | | | | | | | | | | | | |
|---|---|---|---|---|---|---|---|---|---|---|---|---|---|---|---|
| Met | Asn | Met | Lys | Lys | Glu | Lys | His | Ala | Ile | Arg | Lys | Lys | Ser | Ile | |
| 1 | | | | 5 | | | | | 10 | | | | | 15 | |
| Gly | Val | Ala | Ser | Val | Leu | Val | Gly | Thr | Leu | Ile | Gly | Phe | Gly | Leu | Leu |
| | | | 20 | | | | | 25 | | | | | 30 | | |
| Ser | Ser | Lys | Glu | Ala | Asp | Ala | Ser | Glu | Asn | Ser | Val | Thr | Gln | Ser | Asp |
| | | 35 | | | | | 40 | | | | | 45 | | | |
| Ser | Ala | Ser | Asn | Glu | Ser | Lys | Ser | Asn | Asp | Ser | Ser | Val | Ser | Ala | |
| | 50 | | | | | 55 | | | | | 60 | | | | |
| Ala | Pro | Lys | Thr | Asp | Asp | Thr | Asn | Val | Ser | Asp | Thr | Lys | Thr | Ser | Ser |
| 65 | | | | | 70 | | | | | 75 | | | | | 80 |
| Asn | Thr | Asn | Asn | Gly | Glu | Thr | Ser | Val | Ala | Gln | Asn | Pro | Ala | Gln | Gln |
| | | | | 85 | | | | | 90 | | | | | 95 | |
| Glu | Thr | Thr | Gln | Ser | Ala | Leu | Thr | Asn | Ala | Thr | Thr | Glu | Glu | Thr | Pro |
| | | | 100 | | | | | 105 | | | | | 110 | | |
| Val | Thr | Gly | Glu | Ala | Thr | Thr | Ala | Thr | Asn | Gln | Ala | Asn | Thr | Pro | Ala |
| | | | 115 | | | | | 120 | | | | | 125 | | |
| Thr | Thr | Gln | Ser | Ser | Asn | Thr | Asn | Ala | Glu | Glu | Leu | Val | Asn | Gln | Thr |
| | 130 | | | | | 135 | | | | | 140 | | | | |
| Ser | Asn | Glu | Thr | Thr | Ser | Asn | Asp | Thr | Asn | Thr | Val | Ser | Ser | Val | Asn |
| 145 | | | | | 150 | | | | | 155 | | | | | 160 |
| Ser | Pro | Gln | Asn | Ser | Thr | Asn | Ala | Glu | Asn | Val | Ser | Thr | Thr | Gln | Asp |
| | | | | 165 | | | | | 170 | | | | | 175 | |
| Thr | Ser | Thr | Glu | Ala | Thr | Pro | Ser | Asn | Asn | Glu | Ser | Ala | Pro | Gln | Asn |
| | | | 180 | | | | | 185 | | | | | 190 | | |
| Thr | Asp | Ala | Ser | Asn | Lys | Asp | Val | Val | Asn | Gln | Ala | Val | Asn | Thr | Ser |
| | | | 195 | | | | | 200 | | | | | 205 | | |
| Ala | Pro | Arg | Lys | Arg | Ala | Phe | Ser | Leu | Ala | Ala | Val | Ala | Ala | Asp | Ala |
| | 210 | | | | | 215 | | | | | 220 | | | | |
| Pro | Ala | Ala | Gly | Thr | Asp | Ile | Thr | Asn | Gln | Leu | Thr | Asp | Val | Lys | Val |
| 225 | | | | | 230 | | | | | 235 | | | | | 240 |
| Thr | Ile | Asp | Ser | Gly | Thr | Thr | Val | Tyr | Pro | His | Gln | Ala | Gly | Tyr | Val |
| | | | | 245 | | | | | 250 | | | | | 255 | |
| Lys | Leu | Asn | Tyr | Gly | Phe | Ser | Val | Pro | Asn | Ser | Ala | Val | Lys | Gly | Asp |
| | | | 260 | | | | | 265 | | | | | 270 | | |
| Thr | Phe | Lys | Ile | Thr | Val | Pro | Lys | Glu | Leu | Asn | Leu | Asn | Gly | Val | Thr |
| | | 275 | | | | | 280 | | | | | 285 | | | |
| Ser | Thr | Ala | Lys | Ala | Pro | Pro | Ile | Met | Ala | Gly | Asp | Gln | Val | Leu | Ala |
| | 290 | | | | | 295 | | | | | 300 | | | | |
| Asn | Gly | Val | Ile | Asp | Ser | Asp | Gly | Asn | Val | Ile | Tyr | Thr | Phe | Thr | Asp |
| 305 | | | | | 310 | | | | | 315 | | | | | 320 |
| Tyr | Val | Asp | Asn | Lys | Glu | Asn | Val | Thr | Ala | Asn | Ile | Thr | Met | Pro | Ala |
| | | | | 325 | | | | | 330 | | | | | 335 | |
| Tyr | Ile | Asp | Pro | Glu | Asn | Val | Thr | Lys | Thr | Gly | Asn | Val | Thr | Leu | Thr |
| | | | 340 | | | | | 345 | | | | | 350 | | |
| Thr | Gly | Ile | Gly | Thr | Asn | Thr | Ala | Ser | Lys | Thr | Val | Leu | Ile | Asp | Tyr |
| | | 355 | | | | | 360 | | | | | 365 | | | |
| Glu | Lys | Tyr | Gly | Gln | Phe | His | Asn | Leu | Ser | Ile | Lys | Gly | Thr | Ile | Asp |
| | 370 | | | | | 375 | | | | | 380 | | | | |

Gln Ile Asp Lys Thr Asn Asn Thr Tyr Arg Gln Thr Ile Tyr Val Asn
385                 390                 395                 400

Pro Ser Gly Asp Asn Val Val Leu Pro Ala Leu Thr Gly Asn Leu Ile
            405                 410                 415

Pro Asn Thr Lys Ser Asn Ala Leu Ile Asp Ala Lys Asn Thr Asp Ile
            420                 425                 430

Lys Val Tyr Arg Val Asp Asn Ala Asn Asp Leu Ser Glu Ser Tyr Tyr
            435                 440                 445

Val Asn Pro Ser Asp Phe Glu Asp Val Thr Asn Gln Val Arg Ile Ser
        450                 455                 460

Phe Pro Asn Ala Asn Gln Tyr Lys Val Glu Phe Pro Thr Asp Asp
465                 470                 475                 480

Gln Ile Thr Thr Pro Tyr Ile Val Val Asn Gly His Ile Asp Pro
            485                 490                 495

Ala Ser Thr Gly Asp Leu Ala Leu Arg Ser Thr Phe Tyr Gly Tyr Asp
            500                 505                 510

Ser Asn Phe Ile Trp Arg Ser Met Ser Trp Asp Asn Glu Val Ala Phe
            515                 520                 525

Asn Asn Gly Ser Gly Ser Gly Asp Gly Ile Asp Lys Pro Val Val Pro
530                 535                 540

Glu Gln Pro Asp Glu Pro Gly Glu Ile Glu Pro Ile Pro Glu
545                 550                 555

<210> SEQ ID NO 101
<211> LENGTH: 1677
<212> TYPE: DNA
<213> ORGANISM: Staphylococcus aureus

<400> SEQUENCE: 101
atgaatatga agaaaaaaga aaacacgca attcggaaaa aatcgattgg cgtggcttca    60
gtgcttgtag gtacgttaat cggttttgga ctactcagca gtaaagaagc agatgcaagt   120
gaaaatagtg ttacgcaatc tgatagcgca agtaacgaaa gcaaagtaa tgattcaagt   180 agcgttagtg ctgcacctaa aacagacgac acaaacgtga gtgatactaa acatcgtca   240 aacactaata tggcgaaac gagtgtggcg caaaatccag cacaacagga aacgacacaa   300
tcatcatcaa caaatgcaac tacggaagaa acgccggtaa ctggtgaagc tactactacg   360
acaacgaatc aagctaatac accggcaaca actcaatcaa gcaatacaaa tgcggaggaa   420
ttagtgaatc aaacaagtaa tgaaacgact tctaatgata ctaatacagt atcatctgta   480
aattcacctc aaaattctac aaatgcggaa atgtttcaa caacgcaaga tacttcaact   540
gaagcaacac cttcaaacaa tgaatcagct ccacagagta cagatgcaag taataaagat   600
gtagttaatc aagcggttaa tacaagtgcg cctagaatga gagcatttag tttagcggca   660
gtagctgcag atgcaccggc agctggcaca gatattacga atcagttgac gaatgtgaca   720
gttggtattg actctggaga tacagtttat ccgcaccaag caggctatgt caaactgaat   780
tatggttttt cagtgcctaa ttctgctgtt aaaggtgaca cattcaaaat aactgtacct   840
aaagaattaa acttaaatgg tgtaacttca actgctaaag tgccaccaat tatggctgga   900
gatcaagtat tggcaaatgg tgtaatcgat agtgatggta tgttattta acatttaca   960 gactatgtaa atactaaaga tgatgttaaa gcaactttga ccatgcccgc ttatattgac  1020
cctgaaaatg ttacaaagac aggtaatgtg acattggcta ctggcatagg aaatacaaca  1080
gcaaacaaaa cagtattagt agattatgaa aaatatggta agtttataa cttatctatt  1140

```
aaaggtacaa ttgaccaaat cgataaaaca aataatacgt atcgtcagac aatttatgtc    1200
aatccaagtg gagataacgt tattgcgccg gttttaacag gtaatttaaa accaaatacg    1260
gatagtaatg cattaataga tcagcaaaat acaagtatta agtatataa agtagataat     1320 gcagctgatt tatctgaaag ttactttgtg aatccagaaa actttgagga tgtcactaat    1380
agtgtgaata ttacattccc aaatccaaat caatataaag tagagtttaa tacgcctgat    1440
gatcaaatta caacaccgta tatagtagtt gttaatggtc atattgatcc gaatagcaaa    1500
ggtgatttag ctttacgttc aactttatat gggtatgact caaggtttgt atggagatct    1560
atgtcatggg acaacgaagt agcatttaat aacggatcag gttctggtga cggtatcgat    1620
aaaccagttg ttcctgaaca acctgatgag cctggtgaaa ttgaaccaat tccagag      1677
```

<210> SEQ ID NO 102
<211> LENGTH: 559
<212> TYPE: PRT
<213> ORGANISM: Staphylococcus aureus

<400> SEQUENCE: 102

```
Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
                20                  25                  30

Ser Ser Lys Glu Ala Asp Ala Ser Glu Asn Ser Val Thr Gln Ser Asp
                35                  40                  45

Ser Ala Ser Asn Glu Ser Lys Ser Asn Asp Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Asn Gln Ala Asn Thr Pro
            115                 120                 125

Ala Thr Thr Gln Ser Ser Asn Thr Asn Ala Glu Glu Leu Val Asn Gln
            130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
            195                 200                 205

Ser Ala Pro Arg Met Arg Ala Phe Ser Leu Ala Ala Val Ala Ala Asp
            210                 215                 220

Ala Pro Ala Ala Gly Thr Asp Ile Thr Asn Gln Leu Thr Asn Val Thr
225                 230                 235                 240

Val Gly Ile Asp Ser Gly Asp Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
            275                 280                 285
```

```
Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
305                 310                 315                 320

Asp Tyr Val Asn Thr Lys Asp Ser Val Lys Ala Thr Leu Thr Met Pro
                325                 330                 335

Ala Tyr Ile Asp Pro Glu Asn Val Thr Lys Thr Gly Asn Val Thr Leu
                340                 345                 350

Ala Thr Gly Ile Gly Asn Thr Thr Ala Asn Lys Thr Val Leu Val Asp
            355                 360                 365

Tyr Glu Lys Tyr Gly Lys Phe Tyr Asn Leu Ser Ile Lys Gly Thr Ile
    370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
                420                 425                 430

Ile Lys Val Tyr Lys Val Asp Asn Ala Ala Asp Leu Ser Glu Ser Tyr
            435                 440                 445

Phe Val Asn Pro Glu Asn Phe Glu Asp Val Thr Asn Ser Val Asn Ile
    450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly Tyr
                500                 505                 510

Asp Ser Arg Phe Val Trp Arg Ser Met Ser Trp Asp Asn Glu Val Ala
            515                 520                 525

Phe Asn Asn Gly Ser Gly Ser Gly Asp Gly Ile Asp Lys Pro Val Val
    530                 535                 540

Pro Glu Gln Pro Asp Glu Pro Gly Glu Ile Glu Pro Ile Pro Glu
545                 550                 555

<210> SEQ ID NO 103
<211> LENGTH: 1677
<212> TYPE: DNA
<213> ORGANISM: Staphylococcus aureus

<400> SEQUENCE: 103
atgaatatga agaaaaaaga aaaacacgca attcggaaaa aatcgattgg cgtggcttca      60
gtgcttgtag gtacgttaat cggttttgga ctactcagca gtaaagaagc agatgcaagt     120
gaaaatagtg ttacgcaatc cgatagcgca agtaacgaaa gcaaaagtaa tgattcaagt     180
agcgttagtg ctgcacctaa aacagtcgac acaaacgtga gtgatactaa acaacgtca      240 aacactaata gtggcgaaac aagtgtggcg caaaatccgg cacaacagga aacgacacaa     300
tcagcatcaa caaatgcaac tacgaagaa actccggcaa ctggtgaagc tactactacg     360
gcaacgaatc aagctaatac accggcaaca actcaatcaa gcaatacaaa tgcggaggaa     420
ttagtgaatc aaacaaataa tgaaacgact tctaatgata ctaatacagt atcatctgta     480
aattcacctc aaaattctac aaatgcggaa atgtttcaa caacgcaaga tacttcaact     540
gaagcaacac cttcaaacaa tgaatcagct ccacagagta cagatgcaag taataaagat     600
```

-continued

```
gtagttaatc aagcggttaa tacaagtgcg cctagaatga gagcatttag tttagcggca    660
gtagctgcag atgcaccggc tgctggcaca gatattacga atcagttgac agatgtgaaa    720
gttactattg actctggtac gactgtgtat ccgcaccaag caggttatgt caaactgaat    780
tatggttttt cagtccctaa ttctgctgtt aaaggtgaca cattcaaaat aactgtacct    840
aaagaattaa acttaaatgg tgtaacttca actgctaagg tgccaccaat tatggccgga    900
gatcaagtat tggcaaatgg tgtaatcgat agtgatggta atgttattta cattttaca     960 gactatgttg ataataaaga aaatgtaaca gctaatatta ctatgccagc ttatattgac   1020
cctgaaaatg ttacaaagac aggtaatgtg acattgacaa ctggcatagg aaccaatact   1080
gctagtaaga cagtattaat cgactatgag aaatatggac aattccataa tttatcaatt   1140
aaaggtacga ttgatcaaat cgataaaaca ataatacgt atcgccaaac aatttatgtc     1200
aatccaagcg gagataacgt tgtgttacct gccttaacag gtaatttaat tcctaataca   1260
aagagtaatg cgttaataga tgcaaaaaac actgatatta aagttatag agtcgataat    1320 gctaatgatt tatctgaaag ttattatgtg aatcctagcg attttgaaga tgtaactaat   1380
caagttagaa tttcatttcc aaatgctaat caatacaaag tagaatttcc tacgacgat    1440 gaccaaatta caacaccgta tattgtagtt gttaatggcc atattgatcc tgctagtaca   1500
ggtgatttag cactacgttc gacattttat ggttatgatt ctaatttat atggagatct    1560 atgtcatggg acaacgaagt agcatttaat aacggatcag gctctggtga cggtatcgat   1620
aaaccagttg ttcctgaaca acctgatgag cctggtgaaa ttgaaccaat tccagag      1677
```

```
<210> SEQ ID NO 104
<211> LENGTH: 559
<212> TYPE: PRT
<213> ORGANISM: Staphylococcus aureus

<400> SEQUENCE: 104

Met Asn Met Lys Lys Glu Lys His Ala Ile Arg Lys Lys Ser Ile
1               5                  10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Ser Val Ser Ala
    50                  55                  60

Ala Pro Lys Thr Val Asp Thr Asn Val Ser Asp Thr Lys Thr Thr Ser
65                  70                  75                  80

Asn Thr Asn Ser Gly Glu Thr Ser Val Ala Gln Asn Pro Ala Gln Gln
                85                  90                  95

Glu Thr Thr Gln Ser Ala Ser Thr Asn Ala Thr Thr Glu Glu Thr Pro
            100                 105                 110

Ala Thr Gly Glu Ala Thr Thr Thr Ala Thr Asn Gln Ala Asn Thr Pro
        115                 120                 125

Ala Thr Thr Gln Ser Ser Asn Thr Asn Ala Glu Glu Leu Val Asn Gln
    130                 135                 140

Thr Asn Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
```

```
                180                 185                 190
Ser Thr Asp Ala Ser Asn Lys Asp Val Val Asn Gln Ala Val Asn Thr
            195                 200                 205

Ser Ala Pro Arg Met Arg Ala Phe Ser Leu Ala Ala Val Ala Ala Asp
        210                 215                 220

Ala Pro Ala Ala Gly Thr Asp Ile Thr Asn Gln Leu Thr Asp Val Lys
225                 230                 235                 240

Val Thr Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
305                 310                 315                 320

Asp Tyr Val Asp Asn Lys Glu Asn Val Thr Ala Asn Ile Thr Met Pro
                325                 330                 335

Ala Tyr Ile Asp Pro Glu Asn Val Thr Lys Thr Gly Asn Val Thr Leu
            340                 345                 350

Thr Thr Gly Ile Gly Thr Asn Thr Ala Ser Lys Thr Val Leu Ile Asp
        355                 360                 365

Tyr Glu Lys Tyr Gly Gln Phe His Asn Leu Ser Ile Lys Gly Thr Ile
    370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Val Leu Pro Ala Leu Thr Gly Asn Leu
                405                 410                 415

Ile Pro Asn Thr Lys Ser Asn Ala Leu Ile Asp Ala Lys Asn Thr Asp
            420                 425                 430

Ile Lys Val Tyr Arg Val Asp Asn Ala Asn Asp Leu Ser Glu Ser Tyr
        435                 440                 445

Tyr Val Asn Pro Ser Asp Phe Glu Asp Val Thr Asn Gln Val Arg Ile
    450                 455                 460

Ser Phe Pro Asn Ala Asn Gln Tyr Lys Val Glu Phe Pro Thr Asp Asp
465                 470                 475                 480

Asp Gln Ile Thr Thr Pro Tyr Ile Val Val Asn Gly His Ile Asp
                485                 490                 495

Pro Ala Ser Thr Gly Asp Leu Ala Leu Arg Ser Thr Phe Tyr Gly Tyr
            500                 505                 510

Asp Ser Asn Phe Ile Trp Arg Ser Met Ser Trp Asp Asn Glu Val Ala
        515                 520                 525

Phe Asn Asn Gly Ser Gly Ser Gly Asp Gly Ile Asp Lys Pro Val Val
    530                 535                 540

Pro Glu Gln Pro Asp Glu Pro Gly Glu Ile Glu Pro Ile Pro Glu
545                 550                 555

<210> SEQ ID NO 105
<211> LENGTH: 1677
<212> TYPE: DNA
<213> ORGANISM: Staphylococcus aureus

<400> SEQUENCE: 105
```

```
atgaatatga agaaaaaaga aaaacacgca attcggaaaa aatcgattgg cgtggcttca      60
gtgcttgtag gtacgttaat cggttttgga ctactcagca gtaaagaagc agatgcaagt     120
gaaaatagtg ttacgcaatc cgatagcgca agtaacgaaa gcaaaagtaa taatccaagt     180
agcgttaacg ctgcacctaa aacagacaac acaaacgtga gtgatactaa aacaacgtca     240
aacactaata atagcgaaac gagtgtgtgca caaaatccag cacaacagga aacgacacaa     300
tcagcatcaa caaatgcaac tacgaagaa acaccggtaa ctggtgaagg tactactacg     360
gcaacgaatc aagctaatac accggcagca actcaatcaa acaatacaaa tgcggaggaa     420
ttagtgaatc aaacaagtaa tgaaacgact tctaatgata ctaatacagt atcatctgta     480
aattcaccto aaaattctac aaatgcggaa atgtttcaa caacgcaaga cacttcaact     540
gaagcaacac cttcaaacaa tgaatcagct ccacagagta cagatgcaag taataaagat     600
gtagttagtc aagccgttaa tccaagtgcg cctagaatga gagcatttag tttagcggct     660
gtagctgcag atgcaccggc tgctggcaca gatattacga atcagttgac agatgttact     720
gttggtattg aatctggaga tacagtttat ccgcaccaag caggttatgt caaactgaat     780
tatggttttt ccgtgcctaa ttctgctgtt aaaggtgaca cattcaaaat aactgtacct     840
aaagaattaa acttaaatgg tgtaacttca actgctaaag ttcctccaat tatggctgga     900
gatcaagtat tagctaatgg tgtaatcgat agtgatggta atgttattta cactttaca     960
gactatgtaa atactaaaga tgatgttaaa gcaacactaa ctgtgcctgc atacattgac    1020
cctgaatatg ttacacatac tggtaatgtg acattggcta ctggcatagg aaatacaaca    1080
gcaaacaaaa cagtattagt agattatgaa aaatatggta agtttataa cttatctatt    1140
aaaggtacaa ttgaccaagt cgataaaaca aataatacgt atcgtcagac aattatgtc    1200
aatccaagtg gagataacgt tattgcaccg gttttaacag gtaatttaaa accaaatacg    1260
gatagtaatg cattaataga tcagcaaaat acaagtatta agtatataa agtagataat    1320
gcagctgatt tatctgaaag ttactttgtg aatccagaaa actttgagga tgtcactaat    1380
agtgtaaata ttacattccc aaatccaaat caatataaag tagagtttaa tacgcctgat    1440
gatcaaatta caacaccgta tattgtagtt gttaatggtc atattgatcc gaatagcaaa    1500
ggtgatttag ctttacgttc aactttatat ggatataact caaatataat ttggcgctct    1560
atgtcatggg acaacgaagt agcatttaat aacggatcag gttctggtga cggtatcgat    1620
aaacctgttg ttcctgaaca acctgatgag ccgggtgaaa ttgaaccaat tccagag      1677
```

<210> SEQ ID NO 106
<211> LENGTH: 559
<212> TYPE: PRT
<213> ORGANISM: Staphylococcus aureus

<400> SEQUENCE: 106

```
Met Asn Met Lys Lys Glu Lys His Ala Ile Arg Lys Lys Ser Ile
1               5                  10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asn Pro Ser Ser Val Asn Ala
    50                  55                  60

Ala Pro Lys Thr Asp Asn Thr Asn Val Ser Asp Thr Lys Thr Thr Ser
65                  70                  75                  80
```

```
Asn Thr Asn Asn Ser Glu Thr Ser Val Ala Gln Asn Pro Ala Gln Gln
                85                  90                  95

Glu Thr Thr Gln Ser Ala Ser Thr Asn Ala Thr Thr Glu Glu Thr Pro
            100                 105                 110

Val Thr Gly Glu Gly Thr Thr Ala Thr Asn Gln Ala Asn Thr Pro
        115                 120                 125

Ala Ala Thr Gln Ser Asn Asn Thr Asn Ala Glu Glu Leu Val Asn Gln
    130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Ser Gln Ala Val Asn Pro
        195                 200                 205

Ser Ala Pro Arg Met Arg Ala Phe Ser Leu Ala Ala Val Ala Ala Asp
    210                 215                 220

Ala Pro Ala Ala Gly Thr Asp Ile Thr Asn Gln Leu Thr Asp Val Thr
225                 230                 235                 240

Val Gly Ile Glu Ser Gly Asp Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
305                 310                 315                 320

Asp Tyr Val Asn Thr Lys Asp Asp Val Lys Ala Thr Leu Thr Val Pro
                325                 330                 335

Ala Tyr Ile Asp Pro Glu Tyr Val Thr His Thr Gly Asn Val Thr Leu
            340                 345                 350

Ala Thr Gly Ile Gly Asn Thr Thr Ala Asn Lys Thr Val Leu Val Asp
        355                 360                 365

Tyr Glu Lys Tyr Gly Lys Phe Tyr Asn Leu Ser Ile Lys Gly Thr Ile
    370                 375                 380

Asp Gln Val Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
        435                 440                 445

Phe Val Asn Pro Glu Asn Phe Glu Asp Val Thr Asn Ser Val Asn Ile
    450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly Tyr
```

```
                   500               505                510
Asn Ser Asn Ile Ile Trp Arg Ser Met Ser Trp Asp Asn Glu Val Ala
            515                 520                525

Phe Asn Asn Gly Ser Gly Ser Gly Asp Gly Ile Asp Lys Pro Val Val
        530                 535                540

Pro Glu Gln Pro Asp Glu Pro Gly Glu Ile Glu Pro Ile Pro Glu
545                 550                 555

<210> SEQ ID NO 107
<211> LENGTH: 1677
<212> TYPE: DNA
<213> ORGANISM: Staphylococcus aureus

<400> SEQUENCE: 107
atgaatatga agaaacaaga aaaacacgca attcgtaaaa aatcgattgg cgtggcttca      60
gtgcttgtag gtacgttaat cggttttgga ctactcagca gtaaagaagc agatgcaagt     120
gaaaatagta tgcacaaaac ggaaaatacg agtaatgaga gcaaaagtaa tgatccaagt     180
agcgttaatg ctgcacctaa acagacaaac acaaacgtga gtgattctaa tacaacgaca     240
aacactaata gtgacgaaac gaatgtagcg caaaatccag cacaacagga aacgacacaa     300
tcagcatcaa caaatgcaac tacagaagaa acaccggtaa ctggtgaagt tactactacg     360
gcaacgaatc aagctaatac accggcaaca actcaatcaa gcaatacaaa tgcggaagaa     420
tcagtgaatc aaacaagtaa tgaaacgact tctaatgata ctaatacagt atcatctgta     480
aattcacctc aaaattctac aaatgcggaa aatgtttcaa caacgcaaga catttcaact     540
gaagcaacac cttcaaacaa tgaatcagct ccacagagta cagatgcaag taataaagat     600
gtagttaatc aagcggttaa tacaagtgcg cctagaatga gagcatttag tttagcggct     660
gtagctgcag atgcaccggc tgctggcaaa gatattacga atcagttgac gaatgtgaca     720
gttggtattg actctggaga tacagtttat ccgcaccaag caggctatgt caaactgaat     780
tatgggttct cagtaccaaa tgaggctgtt caaggtgaca cattcaaaat aactgtgccc     840
aaagaattaa acttaaatgg tgtaacttca actgctaaag tgccaccaat tatggccgga     900
gatcaagtat tggcaaatgg tgtaatcgat agtgatggta atgttatta cattttaca     960 gactatgtaa atactaaaga tgatgttaaa gcaactttga ccatgcccgc ttatattgac    1020
cctgaaaatg ttacaaagac aggtaatgtg acattggcta ctggcatagg tagtacaaca    1080
gcaaacaaaa cagtattagt agattatgaa aaatatggta gttttataa cttatctatt    1140 aaaggtacaa ttgaccaaat cgataaaaca ataatacgt atcgtcagac aatttatgtc    1200
aatccaagtg gagataacgt tattgcgccg gttttaacag gtaatttaaa accaaatacg    1260
gatagtaatg cattaataga tgcacaaaat actagtatta agtatataa agttgataat    1320 gcatcagact tgtctgaaag ttattatgtg aatccagata actttgaaga tgtcactgat    1380
agtgtgaata ttacattccc aaatccaaat caatataaag tagagttcaa tacgcctgat    1440
gatcaaataa caacaccata tattgtagtt gttaatgggc atattgatcc taatagtaaa    1500
ggtgatttag ctttacgttc aactttatat ggatataatt cgaatataat ttggcgatca    1560
atgtcatggg ataatgaagt agcatttaat aacggatcag gttttggtga cggtatcgat    1620
aaacctgttg ttcctgaaca acctgatgag ccgggtgaaa ttgaaccaat tccagag       1677

<210> SEQ ID NO 108
<211> LENGTH: 559
<212> TYPE: PRT
```

<213> ORGANISM: Staphylococcus aureus

<400> SEQUENCE: 108

| | | | | | | | | | | | | | | |
|---|---|---|---|---|---|---|---|---|---|---|---|---|---|---|
| Met<br>1 | Asn | Met | Lys | Lys<br>5 | Gln | Glu | Lys | His | Ala<br>10 | Ile | Arg | Lys | Lys | Ser<br>15 | Ile |
| Gly | Val | Ala | Ser<br>20 | Val | Leu | Val | Gly | Thr<br>25 | Leu | Ile | Gly | Phe | Gly<br>30 | Leu | Leu |
| Ser | Ser | Lys<br>35 | Glu | Ala | Asp | Ala | Ser<br>40 | Glu | Asn | Ser | Met | Thr<br>45 | Gln | Thr | Glu |
| Asn | Thr<br>50 | Ser | Asn | Glu | Ser | Lys<br>55 | Ser | Asn | Asp | Pro | Ser<br>60 | Ser | Val | Asn | Ala |
| Ala<br>65 | Pro | Lys | Thr | Asp | Asn<br>70 | Thr | Asn | Val | Ser | Asp<br>75 | Ser | Asn | Thr | Thr | Thr<br>80 |
| Asn | Thr | Asn | Ser | Asp<br>85 | Glu | Thr | Asn | Val | Ala<br>90 | Gln | Asn | Pro | Ala | Gln<br>95 | Gln |
| Glu | Thr | Thr | Gln<br>100 | Ser | Ala | Ser | Thr | Asn<br>105 | Ala | Thr | Thr | Glu | Glu<br>110 | Thr | Pro |
| Val | Thr | Gly<br>115 | Glu | Val | Thr | Thr | Thr<br>120 | Ala | Thr | Asn | Gln | Ala<br>125 | Asn | Thr | Pro |
| Ala | Thr<br>130 | Thr | Gln | Ser | Ser | Asn<br>135 | Thr | Asn | Ala | Glu | Glu<br>140 | Ser | Val | Asn | Gln |
| Thr<br>145 | Ser | Asn | Glu | Thr | Thr<br>150 | Ser | Asn | Asp | Thr | Asn<br>155 | Thr | Val | Ser | Ser | Val<br>160 |
| Asn | Ser | Pro | Gln | Asn<br>165 | Ser | Thr | Asn | Ala | Glu<br>170 | Asn | Val | Ser | Thr | Thr<br>175 | Gln |
| Asp | Ile | Ser | Thr<br>180 | Glu | Ala | Thr | Pro | Ser<br>185 | Asn | Asn | Glu | Ser | Ala<br>190 | Pro | Gln |
| Ser | Thr | Asp<br>195 | Ala | Ser | Asn | Lys | Asp<br>200 | Val | Val | Asn | Gln | Ala<br>205 | Val | Asn | Thr |
| Ser | Ala<br>210 | Pro | Arg | Met | Arg | Ala<br>215 | Phe | Ser | Leu | Ala | Ala<br>220 | Val | Ala | Ala | Asp |
| Ala<br>225 | Pro | Ala | Ala | Gly | Lys<br>230 | Asp | Ile | Thr | Asn | Gln<br>235 | Leu | Thr | Asn | Val | Thr<br>240 |
| Val | Gly | Ile | Asp | Ser<br>245 | Gly | Asp | Thr | Val | Tyr<br>250 | Pro | His | Gln | Ala | Gly<br>255 | Tyr |
| Val | Lys | Leu | Asn<br>260 | Tyr | Gly | Phe | Ser | Val<br>265 | Pro | Asn | Glu | Ala | Val<br>270 | Gln | Gly |
| Asp | Thr | Phe<br>275 | Lys | Ile | Thr | Val | Pro<br>280 | Lys | Glu | Leu | Asn | Leu<br>285 | Asn | Gly | Val |
| Thr | Ser<br>290 | Thr | Ala | Lys | Val | Pro<br>295 | Pro | Ile | Met | Ala | Gly<br>300 | Asp | Gln | Val | Leu |
| Ala<br>305 | Asn | Gly | Val | Ile | Asp<br>310 | Ser | Asp | Gly | Asn | Val<br>315 | Ile | Tyr | Thr | Phe | Thr<br>320 |
| Asp | Tyr | Val | Asn | Thr<br>325 | Lys | Asp | Asp | Val | Lys<br>330 | Ala | Thr | Leu | Thr | Met<br>335 | Pro |
| Ala | Tyr | Ile | Asp<br>340 | Pro | Glu | Asn | Val | Lys<br>345 | Thr | Gly | Asn | Val | Thr<br>350 | Leu | |
| Ala | Thr | Gly<br>355 | Ile | Gly | Ser | Thr | Thr<br>360 | Ala | Asn | Lys | Thr | Val<br>365 | Leu | Val | Asp |
| Tyr | Glu<br>370 | Lys | Tyr | Gly | Lys | Phe<br>375 | Tyr | Asn | Leu | Ser | Ile<br>380 | Lys | Gly | Thr | Ile |
| Asp<br>385 | Gln | Ile | Asp | Lys | Thr<br>390 | Asn | Asn | Thr | Tyr | Arg<br>395 | Gln | Thr | Ile | Tyr | Val<br>400 |

```
Asn Pro Ser Gly Asp Asn Val Ile Ala Pro Val Leu Thr Gly Asn Leu
            405                 410                 415

Lys Pro Asn Thr Asp Ser Asn Ala Leu Ile Asp Ala Gln Asn Thr Ser
        420                 425                 430

Ile Lys Val Tyr Lys Val Asp Asn Ala Ser Asp Leu Ser Glu Ser Tyr
    435                 440                 445

Tyr Val Asn Pro Asp Asn Phe Glu Asp Val Thr Asp Ser Val Asn Ile
450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly Tyr
            500                 505                 510

Asn Ser Asn Ile Ile Trp Arg Ser Met Ser Trp Asp Asn Glu Val Ala
        515                 520                 525

Phe Asn Asn Gly Ser Gly Phe Gly Asp Gly Ile Asp Lys Pro Val Val
    530                 535                 540

Pro Glu Gln Pro Asp Glu Pro Gly Glu Ile Glu Pro Ile Pro Glu
545                 550                 555

<210> SEQ ID NO 109
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cacaaaattt acgaatagaa agaaacgag                                    29

<210> SEQ ID NO 110
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
aaaatattgg agataccaat attttaggtt g                                 31

<210> SEQ ID NO 111
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
tttcttggat ccggtactgg tggtaaacaa agcagtg                           37

<210> SEQ ID NO 112
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
```

```
tttcttgcat gcttatttca tgcttccgtg tacagtttc                                39
```

<210> SEQ ID NO 113
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113

```
tttcttccat gggtactggt ggtaaacaaa gcag                                     34
```

<210> SEQ ID NO 114
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114

```
tttcttgctc agcattattt catgcttccg tgtacag                                  37
```

<210> SEQ ID NO 115
<211> LENGTH: 309
<212> TYPE: PRT
<213> ORGANISM: Staphylococcus epidermidis

<400> SEQUENCE: 115

```
Val Lys Lys Ile Leu Ala Leu Ala Ile Ala Phe Leu Ile Ile Leu Ala
1               5                   10                  15

Ala Cys Gly Asn His Ser Asn His Glu His His Ser His Glu Gly Lys
            20                  25                  30

Leu Lys Val Val Thr Thr Asn Ser Ile Leu Tyr Asp Met Val Lys Arg
        35                  40                  45

Val Gly Gly Asn Lys Val Asp Val His Ser Ile Val Pro Val Gly Gln
    50                  55                  60

Asp Pro His Glu Tyr Glu Val Lys Pro Lys Asp Ile Lys Ala Leu Thr
65                  70                  75                  80

Asp Ala Asp Val Val Phe Tyr Asn Gly Leu Asn Leu Glu Thr Gly Asn
                85                  90                  95

Gly Trp Phe Glu Lys Ala Leu Asp Gln Ala Gly Lys Ser Thr Lys Asp
            100                 105                 110

Lys Asn Val Ile Ala Ala Ser Asn Asn Val Lys Pro Ile Tyr Leu Asn
        115                 120                 125

Gly Glu Glu Gly Asn Lys Asn Lys Gln Asp Pro His Ala Trp Leu Ser
    130                 135                 140

Leu Glu Asn Gly Ile Lys Tyr Val Lys Thr Ile Gln Lys Ser Leu Glu
145                 150                 155                 160

His His Asp Lys Lys Asp Lys Ser Thr Tyr Glu Lys Gln Gly Asn Ala
                165                 170                 175

Tyr Ile Ser Lys Leu Glu Glu Leu Asn Lys Asp Ser Lys Asn Lys Phe
            180                 185                 190

Asp Asp Ile Pro Lys Asn Gln Arg Ala Met Met Thr Ser Glu Gly Ala
        195                 200                 205

Phe Lys Tyr Phe Ala Gln Gln Phe Asp Val Lys Pro Gly Tyr Ile Trp
    210                 215                 220
```

Glu Ile Asn Thr Glu Lys Gln Gly Thr Pro Gly Gln Met Lys Gln Ala
225                 230                 235                 240

Ile Lys Phe Val Lys Asp Asn His Leu Lys His Leu Leu Val Glu Thr
            245                 250                 255

Ser Val Asp Lys Lys Ala Met Gln Ser Leu Ser Glu Glu Thr Lys Lys
        260                 265                 270

Asp Ile Tyr Gly Glu Val Phe Thr Asp Ser Ile Gly Lys Ala Gly Thr
    275                 280                 285

Lys Gly Asp Ser Tyr Tyr Lys Met Met Lys Ser Asn Ile Asp Thr Ile
    290                 295                 300

His Gly Ser Met Lys
305

<210> SEQ ID NO 116
<211> LENGTH: 930
<212> TYPE: DNA
<213> ORGANISM: Staphylococcus epidermidis

<400> SEQUENCE: 116

```
gtgaaaaaaa ttctcgcttt agcaatagca tttttaatta ccttgccgc atgtgggaat      60
cacagtaacc atgaacatca ctcacatgaa ggaaaattaa agttgtaac tacaaactct     120
attctctatg acatggttaa acgtgtcggt ggaaataagg tcgatgttca tagcatcgtt     180
ccagtaggac aagatccaca tgaatatgag gttaaaccta agatattaa agcattaaca     240
gatgctgacg ttgtatttta taatggttta aacctagaaa ctggaaatgg ttggtttgaa     300
aaagcacttg accaagcagg aaaatcaaca aaagataaaa atgtgatagc agcatcaaat     360
aatgttaaac caatatactt aaatggtgag gaaggtaaca aaaacaaaca agatccacat     420
gcatggttaa gtttagagaa tggaattaaa tacgtaaaaa caatacaaaa atcactagaa     480
catcatgata aaaagataa gtctacatat gaaaaacaag ggaatgcata tatatcaaaa     540
ttagaagaac ttaataaaga tagtaaaaat aaatttgatg acatacccaa aaatcaacgt     600
gccatgatga caagtgaagg tgcatttaaa tattttgctc aacaattcga tgttaaacca     660
ggttatattt gggagataaa cacagaaaaa caaggtacac ctggtcaaat gaaacaagcc     720
attaaatttg ttaaagataa tcatttaaaa catttattag tcgaaacaag cgtagataaa     780
aaagctatgc aaagtttatc agaagaaact aagaaagata tttatggtga agtatttacc     840
gactctatag gtaaggcagg tactaaaggt gactcatact ataaaatgat gaaatctaat     900
attgatacaa tacatggtag tatgaaataa                                     930
```

<210> SEQ ID NO 117
<211> LENGTH: 510
<212> TYPE: PRT
<213> ORGANISM: Staphylococcus aureus

<400> SEQUENCE: 117

Met Ala Ser Met Thr Gly Gly Gln Gln Met Gly Ala Ser Glu Gln Ser
1               5                   10                  15

Asn Asp Thr Thr Gln Ser Ser Lys Asn Asn Ala Ser Ala Asp Ser Glu
            20                  25                  30

Lys Asn Asn Met Ile Glu Thr Pro Gln Leu Asn Thr Thr Ala Asn Asp
        35                  40                  45

Thr Ser Asp Ile Ser Ala Asn Thr Asn Ser Ala Asn Val Asp Ser Thr
    50                  55                  60

Thr Lys Pro Met Ser Thr Gln Thr Ser Asn Thr Thr Thr Thr Glu Pro

```
                65                  70                  75                  80
Ala Ser Thr Asn Glu Thr Pro Gln Pro Thr Ala Ile Lys Asn Gln Ala
                    85                  90                  95
Thr Ala Ala Lys Met Gln Asp Gln Thr Val Pro Gln Glu Ala Asn Ser
                    100                 105                 110
Gln Val Asp Asn Lys Thr Thr Asn Asp Ala Asn Ser Ile Ala Thr Asn
                    115                 120                 125
Ser Glu Leu Lys Asn Ser Gln Thr Leu Asp Leu Pro Gln Ser Ser Pro
                    130                 135                 140
Gln Thr Ile Ser Asn Ala Gln Gly Thr Ser Lys Pro Ser Val Arg Thr
145                 150                 155                 160
Arg Ala Val Arg Ser Leu Ala Val Ala Glu Pro Val Val Asn Ala Ala
                    165                 170                 175
Asp Ala Lys Gly Thr Asn Val Asn Asp Lys Val Thr Ala Ser Asn Phe
                    180                 185                 190
Lys Leu Glu Lys Thr Thr Phe Asp Pro Asn Gln Ser Gly Asn Thr Phe
                    195                 200                 205
Met Ala Ala Asn Phe Thr Val Thr Asp Lys Val Lys Ser Gly Asp Tyr
                    210                 215                 220
Phe Thr Ala Lys Leu Pro Asp Ser Leu Thr Gly Asn Gly Asp Val Asp
225                 230                 235                 240
Tyr Ser Asn Ser Asn Asn Thr Met Pro Ile Ala Asp Ile Lys Ser Thr
                    245                 250                 255
Asn Gly Asp Val Val Ala Lys Ala Thr Tyr Asp Ile Leu Thr Lys Thr
                    260                 265                 270
Tyr Thr Phe Val Phe Thr Asp Tyr Val Asn Asn Lys Glu Asn Ile Asn
                    275                 280                 285
Gly Gln Phe Ser Leu Pro Leu Phe Thr Asp Arg Ala Lys Ala Pro Lys
                    290                 295                 300
Ser Gly Thr Tyr Asp Ala Asn Ile Asn Ile Ala Asp Glu Met Phe Asn
305                 310                 315                 320
Asn Lys Ile Thr Tyr Asn Tyr Ser Ser Pro Ile Ala Gly Ile Asp Lys
                    325                 330                 335
Pro Asn Gly Ala Asn Ile Ser Ser Gln Ile Ile Gly Val Asp Thr Ala
                    340                 345                 350
Ser Gly Gln Asn Thr Tyr Lys Gln Thr Val Phe Val Asn Pro Lys Gln
                    355                 360                 365
Arg Val Leu Gly Asn Thr Trp Val Tyr Ile Lys Gly Tyr Gln Asp Lys
                    370                 375                 380
Ile Glu Glu Ser Ser Gly Lys Val Ser Ala Thr Asp Thr Lys Leu Arg
385                 390                 395                 400
Ile Phe Glu Val Asn Asp Thr Ser Lys Leu Ser Asp Ser Tyr Tyr Ala
                    405                 410                 415
Asp Pro Asn Asp Ser Asn Leu Lys Glu Val Thr Asp Gln Phe Lys Asn
                    420                 425                 430
Arg Ile Tyr Tyr Glu His Pro Asn Val Ala Ser Ile Lys Phe Gly Asp
                    435                 440                 445
Ile Thr Lys Thr Tyr Val Val Leu Val Glu Gly His Tyr Asp Asn Thr
                    450                 455                 460
Gly Lys Asn Leu Lys Thr Gln Val Ile Gln Glu Asn Val Asp Pro Val
465                 470                 475                 480
Thr Asn Arg Asp Tyr Ser Ile Phe Gly Trp Asn Asn Glu Asn Val Val
                    485                 490                 495
```

Arg Tyr Gly Gly Gly Ser Ala Asp Gly Asp Ser Ala Val Asn
            500             505             510

<210> SEQ ID NO 118
<211> LENGTH: 1533
<212> TYPE: DNA
<213> ORGANISM: Staphylococcus aureus

<400> SEQUENCE: 118

| | | | | | |
|---|---|---|---|---|---|
| atggctagca | tgactggtgg | acagcaaatg | ggtgcttcag | aacaatcgaa | cgatacaacg | 60 |
| caatcttcga | aaataatgc | aagtgcagat | tccgaaaaaa | acaatatgat | agaaacacct | 120 |
| caattaaata | caacggctaa | tgatacatct | gatattagtg | caaacacaaa | cagtgcgaat | 180 |
| gtagatagca | aacaaaaacc | aatgtctaca | caaacgagca | ataccactac | aacagagcca | 240 |
| gcttcaacaa | atgaaacacc | tcaaccgacg | gcaattaaaa | atcaagcaac | tgctgcaaaa | 300 |
| atgcaagatc | aaactgttcc | tcaagaagca | aattctcaag | tagataataa | acaacgaat | 360 |
| gatgctaata | gcatagcaac | aaacagtgag | cttaaaaatt | ctcaaacatt | agatttacca | 420 |
| caatcatcac | cacaaacgat | ttccaatgcg | caaggaacta | gtaaaccaag | tgttagaacg | 480 |
| agagctgtac | gtagtttagc | tgttgctgaa | ccggtagtaa | atgctgctga | tgctaaaggt | 540 |
| acaaatgtaa | atgataaagt | tacggcaagt | aatttcaagt | tagaaaagac | tacatttgac | 600 |
| cctaatcaaa | gtggtaacac | atttatggcg | gcaaattta | cagtgacaga | taaagtgaaa | 660 |
| tcagggatt | attttacagc | gaagttacca | gatagtttaa | ctggtaatgg | agacgtggat | 720 |
| tattctaatt | caaataatac | gatgccaatt | gcagacatta | aaagtacgaa | tggcgatgtt | 780 |
| gtagctaaag | caacatatga | tatcttgact | aagacgtata | catttgtctt | tacagattat | 840 |
| gtaaataata | agaaaatat | taacggacaa | ttttcattac | ctttatttac | agaccgagca | 900 |
| aaggcaccta | atcaggaac | atatgatgcg | aatattaata | ttgcggatga | aatgtttaat | 960 |
| aataaaatta | cttataacta | tagttcgcca | attgcaggaa | ttgataaacc | aaatggcgcg | 1020 |
| aacatttctt | ctcaaattat | tggtgtagat | acagcttcag | gtcaaaacac | atacaagcaa | 1080 |
| acagtatttg | ttaaccctaa | gcaacgagtt | ttaggtaata | cgtgggtgta | tattaaaggc | 1140 |
| taccaagata | aaatcgaaga | agtagcggt | aaagtaagtg | ctacagatac | aaaactgaga | 1200 |
| attttttgaag | tgaatgatac | atctaaatta | tcagatagct | actatgcaga | tccaaatgac | 1260 |
| tctaaccttta | aagaagtaac | agaccaattt | aaaaatagaa | tctattatga | gcatccaaat | 1320 |
| gtagctagta | ttaaattgg | tgatattact | aaaacatatg | tagtattagt | agaagggcat | 1380 |
| tacgacaata | caggtaagaa | cttaaaaact | caggttattc | aagaaaatgt | tgatcctgta | 1440 |
| acaaatagag | actacagtat | tttcggttgg | aataatgaga | atgttgtacg | ttatggtggt | 1500 |
| ggaagtgctg | atggtgattc | agcagtaaat | taa | | | 1533 |

<210> SEQ ID NO 119
<211> LENGTH: 292
<212> TYPE: PRT
<213> ORGANISM: Staphylococcus aureus

<400> SEQUENCE: 119

Met Gly Thr Gly Gly Lys Gln Ser Ser Asp Lys Ser Asn Gly Lys Leu
1               5                   10                  15

Lys Val Val Thr Thr Asn Ser Ile Leu Tyr Asp Met Ala Lys Asn Val
            20                  25                  30

Gly Gly Asp Asn Val Asp Ile His Ser Ile Val Pro Val Gly Gln Asp

```
              35                  40                  45
Pro His Glu Tyr Glu Val Lys Pro Lys Asp Ile Lys Lys Leu Thr Asp
             50                  55                  60
Ala Asp Val Ile Leu Tyr Asn Gly Leu Asn Leu Glu Thr Gly Asn Gly
 65                  70                  75                  80
Trp Phe Glu Lys Ala Leu Glu Gln Ala Gly Lys Ser Leu Lys Asp Lys
                 85                  90                  95
Lys Val Ile Ala Val Ser Lys Asp Val Lys Pro Ile Tyr Leu Asn Gly
                100                 105                 110
Glu Glu Gly Asn Lys Asp Lys Gln Asp Pro His Ala Trp Leu Ser Leu
                115                 120                 125
Asp Asn Gly Ile Lys Tyr Val Lys Thr Ile Gln Gln Thr Phe Ile Asp
            130                 135                 140
Asn Asp Lys Lys His Lys Ala Asp Tyr Glu Lys Gln Gly Asn Lys Tyr
145                 150                 155                 160
Ile Ala Gln Leu Glu Lys Leu Asn Asn Asp Ser Lys Asp Lys Phe Asn
                165                 170                 175
Asp Ile Pro Lys Glu Gln Arg Ala Met Ile Thr Ser Glu Gly Ala Phe
                180                 185                 190
Lys Tyr Phe Ser Lys Gln Tyr Gly Ile Thr Pro Gly Tyr Ile Trp Glu
                195                 200                 205
Ile Asn Thr Glu Lys Gln Gly Thr Pro Glu Gln Met Arg Gln Ala Ile
210                 215                 220
Glu Phe Val Lys Lys His Lys Leu Lys His Leu Leu Val Glu Thr Ser
225                 230                 235                 240
Val Asp Lys Lys Ala Met Glu Ser Leu Ser Glu Thr Lys Lys Asp
                245                 250                 255
Ile Phe Gly Glu Val Tyr Thr Asp Ser Ile Gly Lys Glu Gly Thr Lys
                260                 265                 270
Gly Asp Ser Tyr Tyr Lys Met Met Lys Ser Asn Ile Glu Thr Val His
            275                 280                 285
Gly Ser Met Lys
        290

<210> SEQ ID NO 120
<211> LENGTH: 879
<212> TYPE: DNA
<213> ORGANISM: Staphylococcus aureus

<400> SEQUENCE: 120
atgggtactg gtggtaaaca aagcagtgat aagtcaaatg gcaaattaaa agtagtaacg      60
acgaattcaa tttatatga tatggctaaa aatgttggtg gagacaacgt cgatattcat     120
agtattgtac ctgttggtca agatcctcat gaatatgaag ttaaacctaa agatattaaa     180
aagttaactg acgctgacgt tatttatac aacggattaa atttagagac tggtaacggt     240
tggtttgaaa aagccttaga acaggctggt aaatcattaa agataaaaa agttatcgca     300 gtatcaaaag atgttaaacc tatctatta aacggtgaag aaggcaacaa agataaacaa     360
gatccacacg catggttaag tttagataat ggtattaaat acgtaaaaac aattcaacaa     420
acatttatcg ataacgacaa aaaacataaa gcagattatg aaaagcaagg taacaaatac     480
attgctcaat tggaaaaatt aaataatgac agtaaagaca atttaatga cattccaaaa     540 gaacaacgtg ccatgattac aagtgaaggt gccttcaagt acttctcaaa acaatacggt     600
attacaccag gttatatttg ggaaattaac actgaaaaac aaggtacacc tgaacaaatg     660
```

```
agacaagcta ttgagtttgt taaaaagcac aaattaaaac acttattagt agaaacaagt      720
gttgataaga aagcaatgga aagtttatct gaagaaacga agaaagatat ctttggtgaa      780
gtgtacacag attcaatcgg taagaaggc actaaaggtg actcttacta caaaatgatg       840
aaatcaaata ttgaaactgt acacggaagc atgaaataa                             879
```

<210> SEQ ID NO 121
<211> LENGTH: 292
<212> TYPE: PRT
<213> ORGANISM: Staphylococcus epidermidis

<400> SEQUENCE: 121

```
Met Gly Asn His Ser Asn His Glu His His Ser His Glu Gly Lys Leu
1               5                   10                  15

Lys Val Val Thr Thr Asn Ser Ile Leu Tyr Asp Met Val Lys Arg Val
            20                  25                  30

Gly Gly Asn Lys Val Asp Val His Ser Ile Val Pro Val Gly Gln Asp
        35                  40                  45

Pro His Glu Tyr Glu Val Lys Pro Lys Asp Ile Lys Ala Leu Thr Asp
    50                  55                  60

Ala Asp Val Val Phe Tyr Asn Gly Leu Asn Leu Glu Thr Gly Asn Gly
65                  70                  75                  80

Trp Phe Glu Lys Ala Leu Asp Gln Ala Gly Lys Ser Thr Lys Asp Lys
                85                  90                  95

Asn Val Ile Ala Ala Ser Asn Asn Val Lys Pro Ile Tyr Leu Asn Gly
            100                 105                 110

Glu Glu Gly Asn Lys Asn Lys Gln Asp Pro His Ala Trp Leu Ser Leu
        115                 120                 125

Glu Asn Gly Ile Lys Tyr Val Lys Thr Ile Gln Lys Ser Leu Glu His
    130                 135                 140

His Asp Lys Lys Asp Lys Ser Thr Tyr Glu Lys Gln Gly Asn Ala Tyr
145                 150                 155                 160

Ile Ser Lys Leu Glu Glu Leu Asn Lys Asp Ser Lys Asn Lys Phe Asp
                165                 170                 175

Asp Ile Pro Lys Asn Gln Arg Ala Met Met Thr Ser Glu Gly Ala Phe
            180                 185                 190

Lys Tyr Phe Ala Gln Gln Phe Asp Val Lys Pro Gly Tyr Ile Trp Glu
        195                 200                 205

Ile Asn Thr Glu Lys Gln Gly Thr Pro Gly Gln Met Lys Gln Ala Ile
    210                 215                 220

Lys Phe Val Lys Asp Asn His Leu Lys His Leu Leu Val Glu Thr Ser
225                 230                 235                 240

Val Asp Lys Lys Ala Met Gln Ser Leu Ser Glu Glu Thr Lys Lys Asp
                245                 250                 255

Ile Tyr Gly Glu Val Phe Thr Asp Ser Ile Gly Lys Glu Gly Thr Lys
            260                 265                 270

Gly Asp Ser Tyr Tyr Lys Met Met Lys Ser Asn Ile Asp Thr Ile His
        275                 280                 285

Gly Ser Met Lys
    290
```

<210> SEQ ID NO 122
<211> LENGTH: 879
<212> TYPE: DNA
<213> ORGANISM: Staphylococcus epidermidis

<400> SEQUENCE: 122

```
atggggaatc acagtaacca tgaacatcac tcacatgaag gaaaattaaa agttgtaact      60
acaaactcta ttctctatga catggttaaa cgtgtcggtg gaaataaggt cgatgttcat     120
agcatcgttc cagtaggaca agatccacat gaatatgagg ttaaacctaa agatattaaa     180
gcattaacag atgctgacgt tgtatttat aatggtttaa acctagaaac tggaaatggt      240
tggtttgaaa agcacttga ccaagcagga aatcaacaa agataaaaa tgtgatagca        300
gcatcaaata atgttaaacc aatatactta aatggtgagg aaggtaacaa aaacaaacaa     360
gatccacatg catggttaag tttagagaat ggaattaaat acgtaaaaac aatacaaaaa     420
tcactagaac atcatgataa aaagataag tctacatatg aaaaacaagg gaatgcatat      480
atatcaaaat tagaagaact taataaagat agtaaaaata aatttgatga catacccaaa     540
aatcaacgtg ccatgatgac aagtgaaggt gcatttaaat attttgctca acaattcgat     600
gttaaaccag ttatatttg ggagataaac acagaaaaac aaggtacacc tggtcaaatg      660
aaacaagcca ttaaatttgt taaagataat catttaaaac atttattagt cgaaacaagc     720
gtagataaaa aagctatgca agtttatca gaagaaacta agaaagatat ttatggtgaa      780
gtatttaccg actctatagg taaggaaggt actaaaggtg actcatacta taaaatgatg     840
aaatctaata ttgatacaat acatggtagt atgaaataa                            879
```

<210> SEQ ID NO 123
<211> LENGTH: 531
<212> TYPE: PRT
<213> ORGANISM: Staphylococcus aureus

<400> SEQUENCE: 123

```
Met Ala Ser Met Thr Gly Gly Gln Gln Met Gly Ser Glu Asn Ser Val
 1               5                  10                  15

Thr Gln Ser Asp Ser Ala Ser Asn Glu Ser Lys Ser Asn Asp Ser Ser
            20                  25                  30

Ser Val Ser Ala Ala Pro Lys Thr Asp Asp Thr Asn Val Ser Asp Thr
        35                  40                  45

Lys Thr Ser Ser Asn Thr Asn Asn Gly Glu Thr Ser Val Ala Gln Asn
    50                  55                  60

Pro Ala Gln Gln Glu Thr Thr Gln Ser Ser Thr Asn Ala Thr Thr
65                  70                  75                  80

Glu Glu Thr Pro Val Thr Gly Glu Ala Thr Thr Thr Thr Asn Gln
                85                  90                  95

Ala Asn Thr Pro Ala Thr Thr Gln Ser Ser Asn Thr Asn Ala Glu Glu
            100                 105                 110

Leu Val Asn Gln Thr Ser Asn Glu Thr Thr Phe Asn Asp Thr Asn Thr
        115                 120                 125

Val Ser Ser Val Asn Ser Pro Gln Asn Ser Thr Asn Ala Glu Asn Val
    130                 135                 140

Ser Thr Thr Gln Asp Thr Ser Thr Glu Ala Thr Pro Ser Asn Asn Glu
145                 150                 155                 160

Ser Ala Pro Gln Ser Thr Asp Ala Ser Asn Lys Asp Val Val Asn Gln
                165                 170                 175

Ala Val Asn Thr Ser Ala Pro Arg Met Arg Ala Phe Ser Leu Ala Ala
            180                 185                 190

Val Ala Ala Asp Ala Pro Ala Ala Gly Thr Asp Ile Thr Asn Gln Leu
        195                 200                 205
```

```
Thr Asn Val Thr Val Gly Ile Asp Ser Gly Thr Thr Val Tyr Pro His
    210                 215                 220

Gln Ala Gly Tyr Val Lys Leu Asn Tyr Gly Phe Ser Val Pro Asn Ser
225                 230                 235                 240

Ala Val Lys Gly Asp Thr Phe Lys Ile Thr Val Pro Lys Glu Leu Asn
                245                 250                 255

Leu Asn Gly Val Thr Ser Thr Ala Lys Val Pro Pro Ile Met Ala Gly
            260                 265                 270

Asp Gln Val Leu Ala Asn Gly Val Ile Asp Ser Asp Gly Asn Val Ile
        275                 280                 285

Tyr Thr Phe Thr Asp Tyr Val Asn Thr Lys Asp Val Lys Ala Thr
290                 295                 300

Leu Thr Met Pro Ala Ala Ile Asp Pro Glu Asn Val Lys Lys Thr Gly
305                 310                 315                 320

Asn Val Thr Leu Ala Thr Gly Ile Gly Ser Thr Thr Ala Asn Lys Thr
                325                 330                 335

Val Leu Val Asp Tyr Glu Lys Tyr Gly Lys Phe Tyr Asn Leu Ser Ile
            340                 345                 350

Lys Gly Thr Ile Asp Gln Ile Asp Lys Thr Asn Asn Thr Tyr Arg Gln
        355                 360                 365

Thr Ile Tyr Val Asn Pro Ser Gly Asp Asn Val Ile Ala Pro Val Leu
370                 375                 380

Thr Gly Asn Leu Lys Pro Asn Thr Asp Ser Asn Ala Leu Ile Asp Gln
385                 390                 395                 400

Gln Asn Thr Ser Ile Lys Val Tyr Lys Val Asp Asn Ala Ala Asp Leu
                405                 410                 415

Ser Glu Ser Tyr Phe Val Asn Pro Glu Asn Phe Glu Asp Val Thr Asn
            420                 425                 430

Ser Val Asn Ile Thr Phe Pro Asn Pro Asn Gln Tyr Lys Val Glu Phe
        435                 440                 445

Asn Thr Pro Asp Asp Gln Ile Thr Thr Pro Tyr Ile Val Val Val Asn
450                 455                 460

Gly His Ile Asp Pro Asn Ser Lys Gly Asp Leu Ala Leu Arg Ser Thr
465                 470                 475                 480

Leu Tyr Gly Tyr Asn Ser Asn Ile Ile Trp Arg Ser Met Ser Trp Asp
                485                 490                 495

Asn Glu Val Ala Phe Asn Asn Gly Ser Gly Ser Gly Asp Gly Ile Asp
            500                 505                 510

Lys Pro Val Val Pro Glu Gln Pro Asp Glu Pro Gly Glu Ile Glu Pro
        515                 520                 525

Ile Pro Glu
    530

<210> SEQ ID NO 124
<211> LENGTH: 1596
<212> TYPE: DNA
<213> ORGANISM: Staphylococcus aureus

<400> SEQUENCE: 124
atggctagca tgactggtgg acagcaaatg ggtagtgaaa atagtgttac gcaatctgat      60
agcgcaagta cgaaagcaa aagtaatgat tcaagtagcg ttagtgctgc acctaaaaca     120
gacgacacaa acgtgagtga tactaaaaca tcgtcaaaca ctaataatgg cgaaacgagt     180
gtggcgcaaa atccagcaca acaggaaacg acacaatcat catcaacaaa tgcaactacg     240
```

```
gaagaaacgc cggtaactgg tgaagctact actacgacaa cgaatcaagc taatacaccg    300
gcaacaactc aatcaagcaa tacaaatgct gaagaattag tgaatcaaac aagtaatgaa    360 acgacttta  atgatactaa tacagtatca tctgtaaatt cacctcaaaa ttctacaaat    420
gcggaaaatg tttcaacaac gcaagatact tcaactgaag caacaccttc aaacaatgaa    480
tcagctccac agagtacaga tgcaagtaat aaagatgtag ttaatcaagc ggttaataca    540
agtgcgccta gaatgagagc atttagttta gcggcagtag ctgcagatgc accggcagct    600
ggcacagata ttacgaatca gttgacgaat gtgacagttg gtattgactc tggtacgact    660
gtgtatccac accaagcagg ttatgtcaaa ctgaattatg ttttttcagt gcctaattct    720
gctgttaaag gtgacacatt caaataact gtacctaaag aattaaactt aaatggtgta    780
acttcaactg ctaaagtgcc accaattatg gctggagatc aagtattggc aaatggtgta    840
atcgatagtg atggtaatgt tatttataca tttacagact atgtaaatac taaagatgat    900
gtaaaagcaa ctttgaccat gcccgctgct attgaccctg aaaatgttaa aaagacaggt    960
aatgtgacat tggctactgg cataggtagt acaacagcaa acaaaacagt attagtagat   1020
tatgaaaaat atggtaagtt ttataactta tctattaaag gtacaattga ccaaatcgat   1080
aaaacaaata atacgtatcg tcagacaatt tatgtcaatc caagtggaga taacgttatt   1140
gcgccggttt taacaggtaa tttaaaacca aatacggata gtaatgcatt aatagatcag   1200
caaaatacaa gtattaaagt atataaagta gataatgcag ctgatttatc tgaaagttac   1260
tttgtgaatc cagaaaactt tgaggatgtc actaatagtg tgaatattac attcccaaat   1320
ccaaatcaat ataaagtaga gtttaatacg cctgatgatc aaattacaac accgtatata   1380
gtagttgtta atggtcatat tgatccgaat agcaaaggtg atttagcttt acgttcaact   1440
ttatatgggt ataactcgaa tataatttgg cgctctatgt catgggacaa cgaagtagca   1500
tttaataacg gatcaggttc tggtgacggt atcgataaac cagttgttcc tgaacaacct   1560
gatgagcctg gtgaaattga accaattcca gagtag                              1596
```

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 125

Leu Pro Xaa Thr Gly
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Thr Tyr Thr Phe Thr Asp Tyr Val Asp
1               5

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Met Arg Gly Ser His His His His His His Gly Ser
1               5                   10

<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Met Ala Ser Met Thr Gly Gly Gln Gln Met Gly Arg Gly Ser
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Met Ala Ser Met Thr Gly Gly Gln Gln Met Gly
1               5                   10

<210> SEQ ID NO 130
<211> LENGTH: 933
<212> TYPE: PRT
<213> ORGANISM: Staphylococcus aureus

<400> SEQUENCE: 130

Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
                20                  25                  30

Ser Ser Lys Glu Ala Asp Ala Ser Glu Asn Ser Val Thr Gln Ser Asp
            35                  40                  45

Ser Ala Ser Asn Glu Ser Lys Ser Asn Asp Ser Ser Ser Val Ser Ala
        50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Thr Asn Gln Ala Asn Thr Pro
        115                 120                 125

Ala Thr Thr Gln Ser Ser Asn Thr Asn Ala Glu Glu Leu Val Asn Gln
    130                 135                 140

Thr Ser Asn Glu Thr Thr Phe Asn Asp Thr Asn Thr Val Ser Ser Val
145                 150                 155                 160

```
Asn Ser Pro Gln Asn Ser Thr Asn Ala Glu Asn Val Ser Thr Thr Gln
            165                 170                 175

Asp Thr Ser Thr Glu Ala Thr Pro Ser Asn Asn Glu Ser Ala Pro Gln
        180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
    210                 215                 220

Ala Pro Ala Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
305                 310                 315                 320

Asp Tyr Val Asn Thr Lys Asp Asp Val Lys Ala Thr Leu Thr Met Pro
                325                 330                 335

Ala Tyr Ile Asp Pro Glu Asn Val Lys Lys Thr Gly Asn Val Thr Leu
            340                 345                 350

Ala Thr Gly Ile Gly Ser Thr Thr Ala Asn Lys Thr Val Leu Val Asp
        355                 360                 365

Tyr Glu Lys Tyr Gly Lys Phe Tyr Asn Leu Ser Ile Lys Gly Thr Ile
    370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
        435                 440                 445

Phe Val Asn Pro Glu Asn Phe Glu Asp Val Thr Asn Ser Val Asn Ile
    450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly Tyr
            500                 505                 510

Asn Ser Asn Ile Ile Trp Arg Ser Met Ser Trp Asp Asn Glu Val Ala
        515                 520                 525

Phe Asn Asn Gly Ser Gly Ser Gly Asp Gly Ile Asp Lys Pro Val Val
    530                 535                 540

Pro Glu Gln Pro Asp Glu Pro Gly Glu Ile Glu Pro Ile Pro Glu Asp
545                 550                 555                 560

Ser Asp Ser Asp Pro Gly Ser Asp Ser Gly Ser Asp Ser Asn Ser Asp
                565                 570                 575
```

```
Ser Gly Ser Asp Ser Gly Ser Asp Ser Thr Ser Asp Ser Gly Ser Asp
            580                 585                 590

Ser Ala Ser Asp Ser Asp Ser Ala Ser Asp Ser Asp Ser Ala Ser Asp
    595                 600                 605

Ser Asp Ser Ala Ser Asp Ser Ala Ser Asp Ser Asp Ser Asp
610                 615                 620

Asn Asp Ser Asp Ser Asp Ser Asp Ser Asp Ser Asp Ser Asp Ser Asp
625                 630                 635                 640

Ser Asp Ser Asp Ser Asp Ser Asp Ser Asp Ser Asp Ser Asp
            645                 650                 655

Ser Asp Ser Asp Ser Asp Ser Asp Ser Asp Ser Asp Ser Asp
    660                 665                 670

Ser Asp Ser Asp Ser Asp Ser Asp Ser Asp Ser Asp Ser Asp
            675                 680                 685

Ser Asp Ser Asp Ser Asp Ser Asp Ser Asp Ser Asp Ser Asp
    690                 695                 700

Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp
            725                 730                 735

Ser Asp Ser Asp Ser Asp Ser Asp Ser Asp Ser Asp Ser Asp
    740                 745                 750

Ser Asp Ser Asp Ser Asp Ser Asp Ser Asp Ser Asp Ser Ala
            755                 760                 765

Ser Asp Ser Asp Ser Asp Ser Asp Ser Asp Ser Asp Ser Asp
    770                 775                 780

Ser Asp Ser Asp Ser Asp Ser Asp Ser Asp Ser Asp Ser Asp
785                 790                 795                 800

Ser Asp Ser Asp Ser Asp Ser Glu Ser Asp Ser Asp Ser Glu Ser Asp
            805                 810                 815

Ser Asp Ser Asp Ser Asp Ser Asp Ser Asp Ser Asp Ser Asp
    820                 825                 830

Ser Asp Ser Asp Ser Ala Ser Asp Ser Asp Ser Gly Ser Asp Ser Asp
            835                 840                 845

Ser Ser Ser Asp Ser Asp Ser Glu Ser Asp Ser Asn Ser Asp Ser Glu
850                 855                 860

Ser Gly Ser Asn Asn Asn Val Val Pro Pro Asn Ser Pro Lys Asn Gly
865                 870                 875                 880

Thr Asn Ala Ser Asn Lys Asn Glu Ala Lys Asp Ser Lys Glu Pro Leu
                885                 890                 895

Pro Asp Thr Gly Ser Glu Asp Glu Ala Asn Thr Ser Leu Ile Trp Gly
            900                 905                 910

Leu Leu Ala Ser Ile Gly Ser Leu Leu Leu Phe Arg Arg Lys Lys Glu
        915                 920                 925

Asn Lys Asp Lys Lys
    930
```

<210> SEQ ID NO 131
<211> LENGTH: 2802
<212> TYPE: DNA
<213> ORGANISM: Staphylococcus aureus

<400> SEQUENCE: 131

```
atgaatatga agaaaaaga aaaacacgca attcggaaaa aatcgattgg cgtggcttca    60
```

-continued

```
gtgcttgtag gtacgttaat cggttttgga ctactcagca gtaaagaagc agatgcaagt      120
gaaaatagtg ttacgcaatc tgatagcgca agtaacgaaa gcaaaagtaa tgattcaagt      180
agcgttagtg ctgcacctaa aacagacgac acaaacgtga gtgatactaa acatcgtca      240 aacactaata atggcgaaac gagtgtggcg caaaatccag cacaacagga aacgacacaa      300
tcatcatcaa caaatgcaac tacggaagaa acgccggtaa ctggtgaagc tactactacg      360
acaacgaatc aagctaatac accggcaaca actcaatcaa gcaatacaaa tgcggaggaa      420
ttagtgaatc aaacaagtaa tgaaacgact tttaatgata ctaatacagt atcatctgta      480
aattcacctc aaaattctac aaatgcggaa aatgtttcaa caacgcaaga tacttcaact      540
gaagcaacac cttcaaacaa tgaatcagct ccacagagta cagatgcaag taataaagat      600
gtagttaatc aagcggttaa tacaagtgcg cctagaatga gagcatttag tttagcggca      660
gtagctgcag atgcaccggc agctggcaca gatattacga atcagttgac gaatgtgaca      720
gttggtattg actctggtac gactgtgtat ccgcaccaag caggttatgt caaactgaat      780
tatggttttt cagtgcctaa ttctgctgtt aaaggtgaca cattcaaaat aactgtacct      840
aaagaattaa acttaaatgg tgtaacttca actgctaaag tgccaccaat tatggctgga      900
gatcaagtat tggcaaatgg tgtaatcgat agtgatggta atgttattta acatttaca       960 gactatgtaa atactaaaga tgatgtaaaa gcaactttga ccatgcccgc ttatattgac     1020
cctgaaaatg ttaaaaagac aggtaatgtg acattggcta ctggcatagg tagtacaaca     1080
gcaaacaaaa cagtattagt agattatgaa aaatatggta agttttataa cttatctatt     1140
aaaggtacaa ttgaccaaat cgataaaaca ataatacgt atcgtcagac aatttatgtc      1200
aatccaagtg gagataacgt tattgcgccg gttttaacag gtaatttaaa accaaatacg     1260
gatagtaatg cattaataga tcagcaaaat acaagtatta agtatataa agtagataat      1320 gcagctgatt tatctgaaag ttactttgtg aatccagaaa actttgagga tgtcactaat     1380
agtgtgaata ttacattccc aaatccaaat caatataaag tagagtttaa tacgcctgat     1440
gatcaaatta caacaccgta tatagtagtt gttaatggtc atattgatcc gaatagcaaa     1500
ggtgatttag ctttacgttc aactttatat gggtataact cgaatataat ttggcgctct     1560
atgtcatggg acaacgaagt agcatttaat aacggatcag gttctggtga cggtatcgat     1620
aaaccagttt tcctgaaca acctgatgag cctggtgaaa ttgaaccaat tccagaggat     1680
tcagattctg acccaggttc agattctggc agcgattcta attcagatag cggttcagat     1740
tcgggtagtg attctacatc agatagtggt tcagattcag cgagtgattc agattcagca     1800
agtgattcag actcagcgag tgattcagat tcagcaagcg attccgactc agcgagcgat     1860
tccgactcag acaatgactc ggattcagat agcgattctg actcagacag tgactcagat     1920
tccgacagtg actcagattc agatagcgat tctgactcag acagtgactc agattcagat     1980
agcgattcag attcagatag cgattcagat tccgacagtg attccgactc agacagcgat     2040
tctgactccg acagtgattc cgactcagac agcgattcag attccgacag tgattccgac     2100
tcagatagcg attccgactc agatagcgac tcagattcag acagcgattc agattcagac     2160
agcgattcag attcagatag cgattcagat tccgacagtg actcagattc cgacagtgac     2220
tcggattcag atagcgattc agattccgac agtgactcag attccgacag tgactcagac     2280
tcagacagtg attcggattc agcgagtgat tcggattcag atagtgattc cgactccgac     2340
agtgactcgg attcagatag cgactcagac tcggatagcg actcggattc agatagcgat     2400
tcggactcag atagcgattc agaatcagac agcgattcag aatcagacag cgattcagat     2460
```

```
tcagacagcg actcagacag tgactcagat tcagatagtg actcggattc agcgagtgat    2520
tcagactcag gtagtgactc cgattcatca agtgattccg actcagaaag tgattcaaat    2580
agcgattccg agtcaggttc taacaataat gtagttccgc ctaattcacc taaaaatggt    2640
actaatgctt ctaataaaaa tgaggctaaa gatagtaaag aaccattacc agatacaggt    2700
tctgaagatg aagcaaatac gtcactaatt tggggattat tagcatcaat aggttcatta    2760
ctacttttca gaagaaaaaa agaaaataaa gataagaaat aa                       2802
```

IMMUNOGENIC COMPOSITIONS OF *STAPHYLOCOCCUS AUREUS* ANTIGENS

CROSS REFERENCE TO RELATED APPLICATION

This application is a divisional of U.S. application Ser. No. 13/379,216, filed Dec. 19, 2011, now issued as U.S. Pat. No. 8,568,735 which is the national stage entry of International Application No. PCT/US10/39510, filed Jun. 22, 2010, which claims the priority benefit of U.S. Provisional Patent Application No. 61/219,134, filed Jun. 22, 2009, the entirety of which are hereby incorporated by reference herein.

FIELD OF THE INVENTION

The present invention relates to immunogenic compositions, comprising polypeptides and capsular polysaccharides isolated from *Staphylococcus aureus*. In addition, the invention relates to methods of inducing an immune response in subjects against *Staphylococcus aureus* using immunogenic compositions of the *Staphylococcus aureus* polypeptides, and capsular polysaccharides. The resulting antibodies can also be used to treat or prevent *Staphylococcus aureus* infection via passive immunotherapy.

BACKGROUND OF THE INVENTION

Humans are the natural reservoirs for *Staphylococcus aureus* (*S. aureus*). Healthy individuals can be colonized by *S. aureus* on the skin, in the nares and the throat either persistently (10-35%), intermittently (20-75%) or be in a non-carriage state (5-70%) with no associated disease. See Vandenbergh et al., *J. Clin. Micro.* 37:3133-3140 (1999). Disease subsequently occurs when individuals become immunocompromised due to breaches in immune barriers, such as during surgery, placement of indwelling catheters or other devices, trauma, or wounds. The resulting *S. aureus* infection can cause a wide range of different diseases that range from mild skin infections to endocarditis, osteomyelitis, bacteremia, sepsis, and other forms of disease with accompanying high mortality rates. The large human reservoir enhances opportunity for evolution and spread of adapted pathogenic clonal types.

Invasive staphylococcal infections from the Gram positive cocci *S. aureus* and *S. epidermidis* are of particular concern because they are an increasing public health problem worldwide. Specifically, *S. aureus* is responsible for the majority of hospital-acquired (nosocomial) infections and its prevalence in community-onset infections is increasing. For example, the incidence of invasive methicillin-resistant *S. aureus* (MRSA) was estimated at 31.8 per 100,000 persons, including 18,650 deaths in the United States in 2005. See Klevens R. M. et al., *JAMA*, 298:1763-71 (2007).

Staphylococcal diseases have seen a dramatic increase in the last 20 years, this increase parallels the use of intravascular devices and invasive procedures. This rise in disease incidence is made more troubling because of the parallel rise of antibiotic resistance, therefore, there is an urgent need for immunogenic compositions for use in vaccines or to elicit polyclonal or monoclonal antibodies to confer passive immunity as a means to prevent or treat staphylococcal infection and associated diseases.

SUMMARY OF THE INVENTION

The present invention is directed towards a multi-antigen or multicomponent immunogenic composition comprising at least three antigens isolated from a staphylococcal bacterium. The antigens, which are polypeptides and polysaccharides, may be obtained, inter alia, directly from the bacterium using isolation procedures known to those skilled in the art, or they may be produced using synthetic protocols, or they may be recombinantly produced using genetic engineering procedures also known to those skilled in the art, or through a combination of any of the foregoing. In certain embodiments, an immunogenic composition of the invention comprises three or more antigens selected from an isolated *S. aureus* clumping factor A (ClfA) polypeptide, an isolated *S. aureus* clumping factor B (ClfB) polypeptide, an isolated *S. aureus* capsular polysaccharide type 5 (CP5) conjugated to a carrier protein, an isolated *S. aureus* capsular polysaccharide type 8 (CP8) conjugated to a carrier protein and an isolated *S. aureus* MntC protein. In addition, the present invention provides methods for inducing an immune response against a staphylococcal bacterium, methods for preventing, reducing the severity, or delaying onset of a disease caused by a staphylococcal bacterium, and methods for preventing, reducing the severity, or delaying onset of at least one symptom of a disease caused by infection with a staphylococcal bacterium.

Accordingly, in one embodiment, the invention provides an immunogenic composition comprising: an isolated *S. aureus* clumping factor A (ClfA) polypeptide, an isolated *S. aureus* capsular polysaccharide type 5 (CP5) conjugated to a carrier protein, and an isolated *S. aureus* capsular polysaccharide type 8 (CP8) conjugated to a carrier protein.

In one embodiment, the invention provides an immunogenic composition comprising: an isolated *S. aureus* clumping factor A (ClfA) polypeptide, an isolated *S. aureus* clumping factor B (ClfB), an isolated *S. aureus* capsular polysaccharide type 5 (CP5) conjugated to a carrier protein, and an isolated *S. aureus* capsular polysaccharide type 8 (CP8) conjugated to a carrier protein.

In one embodiment, the invention provides an immunogenic composition comprising: an isolated *S. aureus* clumping factor A (ClfA) polypeptide, an isolated *S. aureus* clumping factor B (ClfB) polypeptide, an isolated *S. aureus* MntC protein, an isolated *S. aureus* capsular polysaccharide type 5 (CP5) conjugated to a carrier protein, and an isolated *S. aureus* capsular polysaccharide type 8 (CP8) conjugated to a carrier protein.

In one embodiment, the invention provides an immunogenic composition comprising: an isolated *S. aureus* clumping factor A (ClfA) polypeptide, an isolated *S. aureus* MntC protein, an isolated *S. aureus* capsular polysaccharide type 5 (CP5) conjugated to a carrier protein, and an isolated *S. aureus* capsular polysaccharide type 8 (CP8) conjugated to a carrier protein.

In one embodiment, the invention provides an immunogenic composition comprising: an isolated *S. aureus* clumping factor B (ClfB) polypeptide, an isolated *S. aureus* capsular polysaccharide type 5 (CP5) conjugated to a carrier protein, and an isolated *S. aureus* capsular polysaccharide type 8 (CP8) conjugated to a carrier protein.

In one embodiment, the invention provides an immunogenic composition comprising: an isolated *S. aureus* clumping factor B (ClfB) polypeptide, an isolated *S. aureus* MntC protein, an isolated *S. aureus* capsular polysaccharide type 5 (CP5) conjugated to a carrier protein, and an isolated *S. aureus* capsular polysaccharide type 8 (CP8) conjugated to a carrier protein.

In one embodiment, the invention provides an immunogenic composition comprising: an isolated *S. aureus* clumping factor A (ClfA) polypeptide, an isolated *S. aureus* clumping factor B (ClfB) polypeptide, and an isolated *S. aureus* MntC protein.

In one embodiment, the invention provides an immunogenic composition comprising: an isolated *S. aureus* MntC protein, an isolated *S. aureus* capsular polysaccharide type 5 (CP5) conjugated to a carrier protein, and an isolated *S. aureus* capsular polysaccharide type 8 (CP8) conjugated to a carrier protein.

In one embodiment, the immunogenic composition comprises an isolated ClfA polypeptide fragment, wherein the ClfA polypeptide fragment comprises the fibrinogen binding domain of ClfA. In one embodiment, the ClfA polypeptide fragment comprises a fibrinogen binding domain comprising the N1, N2 and N3 domains of ClfA. In one embodiment, the ClfA polypeptide fragment comprises a fibrinogen binding domain comprising the N2 and N3 domains of ClfA. In one embodiment, the compositions containing the ClfA fibrinogen binding domain display reduced binding to fibrinogen. In one embodiment, the fibrinogen binding domain of ClfA binds to fibrinogen at a reduced level compared to the binding observed to fibrinogen with the native fibrinogen binding domain of ClfA. In one embodiment, the compositions containing the ClfA fibrinogen binding domain display reduced binding to fibrinogen and have an amino acid substitution at one or more of Tyr 338, Tyr 256, Pro 336. Lys 389, Ala 254 and Ile 387 of the full length protein containing the signal sequence. In one embodiment, the compositions containing the ClfA fibrinogen binding domain display an amino acid substitution at one or more of Tyr 338, Tyr 256, Pro 336, Lys 389. Ala 254 and Ile 387, wherein the amino acid at any one or more of these positions is changed to an Ala or Ser. In one embodiment, the composition comprises a ClfA fibrinogen binding domain wherein the Tyr at position 338 is changed to an Ala.

In one embodiment, the immunogenic composition comprises an isolated ClfB polypeptide fragment, wherein the ClfB polypeptide fragment comprises the fibrinogen binding domain of ClfB. In one embodiment, the ClfB polypeptide fragment comprises a fibrinogen binding domain comprising the N1, N2 and N3 domains of ClfB. In one embodiment, the ClfB polypeptide fragment comprises a fibrinogen binding domain comprising the N2 and N3 domains of ClfB. In one embodiment, the compositions containing the ClfB fibrinogen binding domain display reduced binding to fibrinogen. In one embodiment, the fibrinogen binding domain of ClfB binds to fibrinogen at a reduced level compared to the binding observed to fibrinogen with the native fibrinogen binding domain of ClfB.

In one embodiment, the immunogenic composition comprises *S. aureus* capsular polysaccharide type 5 (CP5) which is a high molecular weight polysaccharide of between 20 and 1000 kDa. In one embodiment, the type 5 high molecular weight polysaccharide has a molecular weight of between 50 and 300 kDa. In one embodiment, the type 5 high molecular weight polysaccharide has a molecular weight of between 70 and 150 kDa.

In one embodiment, the immunogenic composition comprises an *S. aureus* capsular polysaccharide type 5, which is between 10% and 100% O-acetylated. In one embodiment, the immunogenic composition comprises an *S. aureus* capsular polysaccharide type 5, which is between 50% and 100% O-acetylated. In one embodiment, the immunogenic composition comprises an *S. aureus* capsular polysaccharide type 5, which is between 75% and 100% O-acetylated.

In one embodiment, the immunogenic composition comprises *S. aureus* capsular polysaccharide type 8 which is a high molecular weight polysaccharide of between 20 and 1000 kDa. In one embodiment, the type 8 high molecular weight polysaccharide has a molecular weight of between 50 and 300 kDa. In one embodiment, the type 8 high molecular weight polysaccharide has a molecular weight of between 70 and 150 kDa.

In one embodiment, the immunogenic composition comprises an *S. aureus* capsular polysaccharide type 8, which is between 10% and 100% O-acetylated. In one embodiment, the immunogenic composition comprises an *S. aureus* capsular polysaccharide type 8, which is between 50% and 100% O-acetylated. In one embodiment, the immunogenic composition comprises an *S. aureus* capsular polysaccharide type 8, which is between 75% and 100% O-acetylated.

In one embodiment, the capsular polysaccharide 5 and/or 8 present in an immunogenic composition is conjugated to a carrier protein. In one embodiment, the carrier protein is the *Corynebacterium diphtheriae* (*C. diphtheriae*) toxoid $CRM_{197}$.

In one embodiment, the immunogenic composition comprises the *S. aureus* MntC, which is a lipidated protein. In one embodiment, the immunogenic composition comprises the *S. aureus* MntC, which is not a lipidated protein.

In one embodiment, the invention provides an immunogenic composition as described herein, further comprising at least one protein from the serine-aspartate repeat (Sdr) protein family selected from the group consisting of SdrC, SdrD and SdrE.

In one embodiment, the invention provides an immunogenic composition as described herein, further comprising the iron surface determinant B (IsdB) protein.

In each of the embodiments described herein in which an immunogenic composition comprises three or more recited antigens, that composition may further comprise other immunogenic and/or non-immunogenic substances. In certain embodiments, each immunogenic composition may, alternatively, "consist essentially of" or "consist of" the three or more recited antigens and further comprise one or more non-immunogenic substances, as described in more detail herein.

In one embodiment, the invention provides an immunogenic composition as described herein, further comprising any one of the following antigens: Opp3a, DltD, HtsA. LtaS, IsdA, IsdC, SdrF, SdrG, SdrH, SrtA, SpA, Sbi FmtB, alpha-hemolysin (hla), beta-hemolysin, fibronectin-binding protein A (fnbA), fibronectin-binding protein B (fnbB), coagulase, Fig, map, Panton-Valentine leukocidin (pvl), alpha-toxin and its variants, gamma-toxin (hig) and variants, ica, immunodominant ABC transporter, Mg2+ transporter, Ni ABC transporter, RAP, autolysin, laminin receptors, IsaA/P isA, IsaB/PisB, SPOHIE, SsaA, EbpS, Sas A, SasF, SasH, EFB (FIB), SBI, Npase, EBP, bone sialo binding protein II, aureolysin precursor (AUR)/Sepp1, Cna, and fragments thereof such as M55, TSST-1, mecA, poly-N-acetylglucosamine (PNAG/dPNAG) exopolysaccharide. GehD, EbhA, EbhB, SSP-1, SSP-2, HBP, vitronectin binding protein, HarA, EsxA, EsxB, Enterotoxin A. Enterotoxin B, Enterotoxin C1, and novel autolysin. In certain embodiments of the invention, when the immunogenic composition comprises certain forms of CP5 and/or CP8, it may not further comprise PNAG.

In one embodiment, the immunogenic composition further comprises an adjuvant. In one embodiment, the immunogenic composition further comprises a pharmaceutically acceptable carrier.

In one embodiment, the immunogenic composition is used to formulate a vaccine. In one embodiment, the vaccine is used to induce an immune response in a subject against *S.* aureus. In one embodiment, the immunogenic composition is used to generate an antibody formulation to confer passive immunity on a subject.

In one embodiment, the invention provides a method of inducing an immune response against S. aureus comprising administering to a subject an immunogenic amount of any of the immunogenic compositions described herein and a pharmaceutically acceptable carrier.

In one embodiment, the invention provides a method of preventing or reducing infection with S. aureus, or a method of preventing or reducing the severity of at least one symptom associated with an infection caused by S. aureus, the methods comprising administering to a subject an immunogenic amount of any of the immunogenic compositions described herein and a pharmaceutically acceptable carrier.

In one embodiment, the methods for inducing an immune response against S. aureus comprise delivery of the immunogenic compositions with an adjuvant. In one embodiment, the methods for inducing an immune response against S. aureus provide for delivery of the immunogenic compositions with a pharmaceutically acceptable carrier.

In one embodiment, the immune response induced by the immunogenic compositions described herein, prevents or reduces a disease or condition associated with a staphylococcal organism in a subject, or prevents or reduces one or more symptoms associated with a staphylococcal organism in a subject. In one embodiment, the disease is selected from the group consisting of invasive S. aureus disease, sepsis and carriage.

In one embodiment, the immune response induced comprises the generation of antibodies having opsonophagocytic activity (OPA) against S. aureus. In one embodiment, the immune response induced comprises the generation of higher titers of opsonophagocytic antibodies specific for S. aureus compared to that observed in non-immunized subjects. In one embodiment, the opsonophagocytic titer is at least 1:20.

In one embodiment, the S. aureus against which the immune response is induced is MRSA. In one embodiment, the S. aureus against which the immune response is induced is MSSA. In one embodiment, the S. aureus against which the immune response is induced is VRSA. In one embodiment, the S. aureus against which the immune response is induced is VISA.

In one embodiment, the invention provides a method of preventing a staphylococcal infection in a subject undergoing a surgical procedure, the method comprising administering an immunologically effective amount of any of the immunogenic compositions as described herein to the subject prior to the surgical procedure. The surgical procedure can be an elective surgical procedure or a non-elective surgical procedure. In one embodiment, the surgical procedure is a cardiothoracic surgical procedure. In one embodiment, the subject is a human, veterinary animal, or a livestock animal.

In one embodiment, the invention provides a method of conferring passive immunity to a subject comprising the steps of (1) generating an antibody preparation using an immunogenic compositions of the invention; and (2) administering the antibody preparation to the subject to confer passive immunity.

BRIEF DESCRIPTION OF THE DRAWINGS

FIG. 4 depicts the repeating structure of the CP5 and CP8 polysaccharides.

FIGS. 5A and 5B depict molecular weight profiles of CP5 (A) and CP8 (B) produced at different broth pHs.

FIGS. 6A and 6B depict molecular weight profiles of CP5 (A) and CP8 (B) produced at different temperatures.

FIG. 8A-8E depict the alignment of ClfA between various strains of S. aureus (SEQ ID NOs: 62, 64, 68, 84, 70, 104, 66, 78, 86, 88, 90, 72, 74, 76, 80, 94, 82, 92, 96, 98, 100, 102, 106, and 108, respectively, in order of appearance).

FIG. 10A-10E depict the alignment of ClfB between various strains of S. aureus (SEQ ID NOs: 26, 28, 32, 18, 54, 34, 36, 30, 16, 20, 22, 24, 38, 40, 42, 44, 46, 48, 50, 52, 56, 58, and 60, respectively, in order of appearance).

FIG. 12 depicts the alignment of MntC between various strains of S. aureus (SEQ ID NOs: 2, 8, 10, 4, 6, 14 and 12, respectively, in order of appearance).

DETAILED DESCRIPTION OF THE INVENTION

Figure 1:
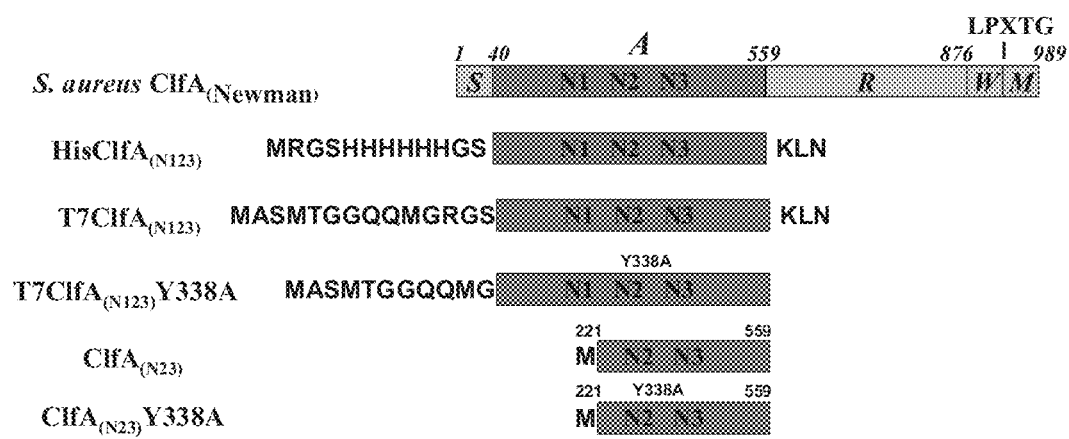
FIG. 1 depicts the various forms of recombinant ClfA and discloses SEQ ID NOs: 125 and 127-129, respectively, in order of appearance.

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting.

Although any methods and materials similar or equivalent to those described herein can be used in the practice or testing of the invention, the preferred methods and materials are now described. All publications mentioned herein are incorporated by reference in their entirety.

The terms used herein have the meanings recognized and known to those of skill in the art, however, for convenience and completeness, particular terms and their meanings are set forth below.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

The term "about" or "approximately" means within a statistically meaningful range of a value. Such a range can be within an order of magnitude, typically within 20%, more typically still within 10%, and even more typically within 5% of a given value or range. The allowable variation encompassed by the term "about" or "approximately" depends on the particular system under study, and can be readily appreciated by one of ordinary skill in the art. Whenever a range is recited within this application, every whole number integer within the range is also contemplated as an embodiment of the invention.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, unless otherwise indicated by context, the term is intended to encompass not only intact polyclonal or monoclonal antibodies, but also engineered antibodies (e.g., chimeric, humanized and/or derivatized to alter effector functions, stability and other biological activities) and fragments thereof (such as Fab, Fab', F(ab')2, Fv), single chain (ScFv) and domain antibodies, including shark and camelid antibodies), and fusion proteins comprising an antibody portion, multivalent antibodies, multispecific antibodies (e.g., bispecific antibodies so long as they exhibit the desired biological activity) and antibody fragments as described herein, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE. IgG, and IgM, and several of these may be further divided into subclasses (isotypes), e.g., IgG1, IgG2, IgG3, IgG4, IgA1 and IgA2 in humans. The heavy-chain constant domains that correspond to the different classes of immunoglobulins are called alpha, delta, epsilon, ganuna, and mu, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody.

The term "antigen" generally refers to a biological molecule, usually a protein, peptide, polysaccharide, lipid or conjugate which contains at least one epitope to which a cognate antibody can selectively bind; or in some instances to an immunogenic substance that can stimulate the production of antibodies or T-cell responses, or both, in an animal, including compositions that are injected or absorbed into an animal. The immune response may be generated to the whole molecule, or to one or more various portions of the molecule (e.g., an epitope or hapten). The term may be used to refer to an individual molecule or to a homogeneous or heterogeneous population of antigenic molecules. An antigen is recognized by antibodies, T-cell receptors or other elements of specific humoral and/or cellular immunity. The term "antigen" includes all related antigenic epitopes. Epitopes of a given antigen can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708, 871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes may be identified by determining spatial conformation of amino acids such as by, e.g., x-ray crystallography and 2-dimensional nuclear magnetic resonance. See, e.g., Epitope Mapping Protocols, supra. Furthermore, for purposes of the present invention, an "antigen" may also be used to refer to a protein that includes modifications, such as deletions, additions and substitutions (generally conservative in nature, but they may be non-conservative), to the native sequence, so long as the protein maintains the ability to elicit an immunological response. These modifications may be deliberate, as through site-directed mutagenesis, or through particular synthetic procedures, or through a genetic engineering approach, or may be accidental such as through mutations of hosts, which produce the antigens. Furthermore, the antigen can be derived, obtained, or isolated from a microbe, e.g. a bacterium, or can be a whole organism. Similarly, an oligonucleotide or polynucleotide, which expresses an antigen, such as in nucleic acid immunization applications, is also included in the definition. Synthetic antigens are also included, for example, polyepitopes, flanking epitopes, and other recombinant or synthetically derived antigens (Bergmann et al. (1993) *Eur. J. Immunol.* 23:2777 2781; Bergmann et al. (1996) *J. Immunol.* 157:3242 3249; Suhrbier, A. (1997) *Immunol. and Cell Biol.* 75:402 408; Gardner et al. (1998) 12th World AIDS Conference, Geneva, Switzerland, Jun. 28-Jul. 3, 1998).

The term "adjuvant" refers to a compound or mixture that enhances the immune response to an antigen as further described and exemplified herein.

"Bacteremia" is a transient presence of bacteria in the blood. A bacteremia can progress to septicemia, or sepsis, which would be considered an infection and is the persistent presence of bacteria in the blood with associated clinical signs/symptoms. Not all bacteria are capable of surviving in the blood. Those that do have special genetic traits that provide for that ability. Also, the host factors play an important role as well.

"Capsular polysaccharide" or "capsule polysaccharide" refers to the polysaccharide capsule that is external to the cell wall of most isolates of Staphylococci. For example, *S. aureus* includes a cell wall component composed of a peptidoglycan complex, which enables the organism to survive under unfavorable osmotic conditions and also includes a unique teichoic acid linked to the peptidoglycan. External to the cell wall a thin polysaccharide capsule coats most isolates of *S. aureus*. This serologically distinct capsule can be used to serotype various isolates of *S. aureus*. Many of the clinically significant isolates have been shown to include two capsular types: serotype 5 (CP5) and serotype 8 (CP8). The structures of CP5 and CP8 are shown schematically in FIG. 4.

As used herein, "conjugates" comprise a capsule polysaccharide usually of a desired range of molecular weight and a carrier protein, wherein the capsule polysaccharide is conjugated to the carrier protein. Conjugates may or may not contain some amount of free capsule polysaccharide. As used herein, "free capsule polysaccharide" refers to capsule polysaccharide that is non-covalently associated with (i.e., non-covalently bound to, adsorbed to or entrapped in or with) the conjugated capsular polysaccharide-carrier protein. The terms "free capsule polysaccharide," "free polysaccharide" and "free saccharide" may be used interchangeably and are intended to convey the same meaning. Regardless of the nature of the carrier molecule, it can be conjugated to the capsular polysaccharide either directly or through a linker. As used herein, "to conjugate", "conjugated" and "conjugating" refers to a process whereby a bacterial capsular polysaccharide is covalently attached to the carrier molecule. Conjugation enhances the immunogenicity of the bacterial capsular polysaccharide. The conjugation can be performed according to the methods described below or by processes known in the art.

As described above, the present invention relates to conjugates comprising *S. aureus* serotype 5 capsular polysaccharides (CP5) conjugated to carrier proteins and conjugates comprising *S. aureus* serotype 8 capsular polysaccharides (CP8) conjugated to carrier proteins. One embodiment of the invention provides conjugates comprising a *S. aureus* serotype 5 capsular polysaccharide conjugated to a carrier protein and a *S. aureus* serotype 8 capsular polysaccharide conjugated to a carrier protein wherein: the type 5 capsular polysaccharide has a molecular weight of between 50 kDa and 800 kDa; the type 8 capsular polysaccharide has a molecular weight of between 50 and 700 kDa; the immunogenic conjugates have molecular weights of between about 1000 kDa and about 5000 kDa; and the conjugates comprise less than about 30% free polysaccharide relative to total polysaccharide. In one embodiment, the conjugates comprise less than about 25%, about 20%, about 15%, about 10%, or about 5% free polysaccharide relative to total polysaccharide. In one embodiment, the type 5 or 8 polysaccharide has a molecular weight between 20 kDa and 1000 kDa.

In one embodiment, the conjugate has a molecular weight of between about 50 kDa and about 5000 kDa. In one embodiment, the conjugate has a molecular weight of between about 200 kDa and about 5000 kDa. In one embodiment, the immunogenic conjugate has a molecular weight of between about 400 kDa and about 2500 kDa. In one embodiment, the immunogenic conjugate has a molecular weight of between about 500 kDa and about 2500 kDa. In one embodiment, the immunogenic conjugate has a molecular weight of between about 600 kDa and about 2800 kDa. In one embodiment, the immunogenic conjugate has a molecular weight of between about 700 kDa and about 2700 kDa. In one embodiment, the immunogenic conjugate has a molecular weight of between about 1000 kDa and about 2000 kDa; between about 1800 kDa and about 2500 kDa; between about 1100 kDa and about 2200 kDa; between about 1900 kDa and about 2700 kDa; between about 1200 kDa and about 2400 kDa; between about 1700 kDa and about 2600 kDa; between about 1300 kDa and about 2600 kDa; between about 1600 kDa and about 3000 kDa.

Accordingly, in one embodiment, the carrier protein within the immunogenic conjugate of the invention is $CRM_{197}$, and the $CRM_{197}$ is covalently linked to the capsular polysaccharide via a carbamate linkage, an amide linkage, or both. The number of lysine residues in the carrier protein that become conjugated to a capsular polysaccharide can be characterized as a range of conjugated lysines. For example, in a given immunogenic composition, the $CRM_{197}$ may comprise 5 to 15 lysines out of 39 covalently linked to the capsular polysaccharide. Another way to express this parameter is that 12% to 40% of $CRM_{197}$ lysines are covalently linked to the capsular polysaccharide. In some embodiments, the $CRM_{197}$ portion of the polysaccharide covalently bound to the $CRM_{197}$ comprises 5 to 22 lysines covalently linked to the polysaccharide. In some embodiments, the $CRM_{197}$ portion of the polysaccharide covalently bound to the $CRM_{197}$ comprises 5 to 23 lysines covalently linked to the polysaccharide. In some embodiments, the $CRM_{197}$ portion of the polysaccharide covalently bound to carrier protein of comprises 8 to 15 lysines covalently linked to the polysaccharide. In some embodiments, the $CRM_{197}$ portion of the polysaccharide covalently bound to carrier protein of comprises 8 to 12 lysines covalently linked to the polysaccharide. For example, in a given immunogenic composition, the $CRM_{197}$ may comprise 18 to 22 lysines out of 39 covalently linked to the capsular polysaccharide. Another way to express this parameter is that 40% to 60% of $CRM_{197}$ lysines are covalently linked to the capsular polysaccharide. In some embodiments, the $CRM_{197}$ comprises 5 to 15 lysines out of 39 covalently linked to CP8. Another way to express this parameter is that 12% to 40% of $CRM_{197}$ lysines are covalently linked to CP8. In some embodiments, the $CRM_{197}$ comprises 18 to 22 lysines out of 39 covalently linked to CP5. Another way to express this parameter is that 40% to 60% of $CRM_{197}$ lysines are covalently linked to CP5.

As discussed above, the number of lysine residues in the carrier protein conjugated to the capsular polysaccharide can be characterized as a range of conjugated lysines, which may be expressed as a molar ratio. For example, the molar ratio of conjugated lysines to $CRM_{197}$ in the CP8 immunogenic conjugate can be between about 18:1 to about 22:1. In one embodiment, the range of molar ratio of conjugated lysines to $CRM_{197}$ in the CP8 immunogenic conjugate can be between about 15:1 to about 25:1. In some embodiments, the range of molar ratio of conjugated lysines to $CRM_{197}$ in the CP8 immunogenic conjugate can be between about 14:1 to about 20:1; about 12:1 to about 18:1; about 10:1 to about 16:1; about 8:1 to about 14:1; about 6:1 to about 12:1; about 4:1 to about 10:1; about 20:1 to about 26:1; about 22:1 to about 28:1; about 24:1 to about 30:1; about 26:1 to about 32:1; about 28:1 to about 34:1; about 30:1 to about 36:1; about 5:1 to about 10:1; about 5:1 to about 20:1; about 10:1 to about 20:1; or about 10:1 to about 30:1. Also, the molar ratio of conjugated lysines to CRM197 in the CP5 immunogenic conjugate can be between about 3:1 and 25:1. In one embodiment, the range of molar ratio of conjugated lysines to CRM197 in the CP5 immunogenic conjugate can be between about 5:1 to about 20:1. In one embodiment, the range of molar ratio of conjugated lysines to CRM197 in the CP5 immunogenic conjugate can be between about 4:1 to about 20:1; about 6:1 to about 20:1; about 7:1 to about 20:1; about 8:1 to about 20:1; about 10:1 to about 20:1; about 11:1 to about 20:1; about 12:1 to about 20:1; about 13:1 to about 20:1; about 14:1 to about 20:1; about 15:1 to about 20:1; about 16:1 to about 20:1; about 17:1 to about 20:1; about 18:1 to about 20:1; about 5:1 to about 18:1; about 7:1 to about 16:1; or about 9:1 to about 14:1.

Another way to express the number of lysine residues in the carrier protein conjugated to the capsular polysaccharide can be as a range of conjugated lysines. For example, in a given CP8 immunogenic conjugate, the $CRM_{197}$ may comprise 5 to 15 lysines out of 39 covalently linked to the capsular polysaccharide. Alternatively, this parameter can be expressed as a percentage. For example, in a given CP8 immunogenic conjugate, the percentage of conjugated lysines can be between 10% to 50%. In some embodiments, 20% to 50% of lysines can be covalently linked to CP8. Alternatively still, 30% to 50% of $CRM_{197}$ lysines can be covalently linked to the CP8; 10% to 40% of $CRM_{197}$ lysines; 10% to 30% of $CRM_9$, lysines; 20% to 40% of $CRM_{197}$ lysines; 25% to 40% of $CRM_{197}$ lysines; 30% to 40% of $CRM_{197}$ lysines; 10% to 30% of $CRM_{197}$ lysines; 15% to 30% of $CRM_{197}$ lysines; 20% to 30% of $CRM_{197}$ lysines; 25% to 30% of $CRM_{197}$ lysines; 10% to 15% of $CRM_{197}$ lysines; or 10% to 12% of $CRM_{197}$ lysines are covalently linked to CP8. Also, in a given CP5 immunogenic conjugate, the $CRM_{197}$ may comprise 18 to 22 lysines out of 39 covalently linked to the capsular polysaccharide. Alternatively, this parameter can be expressed as a percentage. For example, in a given CP5 immunogenic conjugate, the percentage of conjugated lysines can be between 40% to 60%. In some embodiments, 40% to 60% of lysines can be covalently linked to CP5. Alternatively still, 30% to 50% of $CRM_{197}$ lysines can be covalently linked to CP5; 20% to 40 of $CRM_{197}$ lysines; 10% to 30% of $CRM_{197}$ lysines; 50% to 70% of $CRM_{197}$ lysines; 35% to 65% of $CRM_{197}$ lysines; 30% to 60% of $CRM_{197}$ lysines; 25% to 55% of $CRM_{197}$ lysines; 20% to 50% of $CRM_{197}$ lysines; 15% to 45% of $CRM_{197}$ lysines; 10% to 40% of $CRM_{197}$ lysines; 40% to 70% of $CRM_{197}$ lysines; or 45% to 75% of $CRM_{197}$ lysines are covalently linked to CP5.

The frequency of attachment of the capsular polysaccharide chain to a lysine on the carrier molecule is another parameter for characterizing conjugates of capsule polysaccharides. For example, in one embodiment, at least one covalent linkage between $CRM_{197}$ and polysaccharide occurs for at least every 5 to 10 saccharide repeat units of the capsular polysaccharide. In another embodiment, there is at least one covalent linkage between $CRM_{197}$ and capsular polysaccharide for every 5 to 10 saccharide repeat units; every 2 to 7 saccharide repeat units, every 3 to 8 saccharide repeat units; every 4 to 9 saccharide repeat units; every 6 to 11 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; every 5 to 10 saccharide repeat units of the capsular polysaccharide. In another embodiment, at least one linkage between $CRM_{197}$ and capsular polysaccharide occurs for every 2, 3, 4, 5, 6, 7, 8, 9, 10, 11, 12, 13, 14, 15, 16, 17, 18, 19, or 20 saccharide repeat units of the capsular polysaccharide.

The chemical activation of the polysaccharides and subsequent conjugation to the carrier protein may be achieved by conventional means. See, for example, U.S. Pat. Nos. 4,673,574 and 4,902,506. Other activation and conjugation methods may alternatively be used.

"Carrier protein" or "protein carrier" as used herein, refers to any protein molecule that may be conjugated to an antigen (such as the capsular polysaccharides) against which an immune response is desired. Conjugation of an antigen such as a polysaccharide to a carrier protein can render the antigen immunogenic. Carrier proteins are preferably proteins that are non-toxic and non-reactogenic and obtainable in sufficient amount and purity. Examples of carrier proteins are toxins, toxoids or any mutant cross-reactive material ($CRM_{197}$) of the toxin from tetanus, diphtheria, pertussis, *Pseudomonas* species, *E. coli*, *Staphylococcus* species, and *Streptococcus* species. Carrier proteins should be amenable to standard conjugation procedures. In a particular embodiment of the present invention, $CRM_{197}$ is used as the carrier protein.

$CRM_{197}$ (Wyeth/Pfizer, Sanford. NC) is a non-toxic variant (i.e., toxoid) of diphtheria toxin isolated from cultures of *Corynebacterium diphtheria* strain C7 ($\beta_{197}$) grown in casamino acids and yeast extract-based medium. $CRM_{197}$ is purified through ultra-filtration, ammonium sulfate precipitation, and ion-exchange chromatography. A culture of *Corynebacterium diphtheriae* strain C7 ($_{197}$), which produces $CRM_{197}$ protein, has been deposited with the American Type Culture Collection, Rockville, Md. and has been assigned accession number ATCC 53281. Other diphtheria toxoids are also suitable for use as carrier proteins.

Other suitable carrier proteins include inactivated bacterial toxins such as tetanus toxoid, pertussis toxoid, cholera toxoid (e.g., as described in International Patent Application WO2004/083251), *E. coli* LT, *E. coli* ST, and exotoxin A from *Pseudomonas aeruginosa*. Bacterial outer membrane proteins such as outer membrane protein complex c (OMPC), porins, transferrin binding proteins, pneumolysin, pneumococcal surface protein A (PspA), pneumococcal adhesin protein (PsaA), *C. difficile* enterotoxin (toxin A) and cytotoxin (toxin B) or *Haemophilus influenzae* protein D, can also be used. Other proteins, such as ovalbumin, keyhole limpet hemocyanin (KLH), bovine serum albumin (BSA) or purified protein derivative of tuberculin (PPD) can also be used as carrier proteins.

After conjugation of the capsular polysaccharide to the carrier protein, the polysaccharide-protein conjugates are purified (enriched with respect to the amount of polysaccharide-protein conjugate) by a variety of techniques. These techniques include, e.g., concentration/diafiltration operations, precipitation/elution, column chromatography, and depth filtration. See examples below.

After the individual conjugates are purified, they may be combined to formulate an immunogenic composition of the present invention, which may be used, for example, in a vaccine. Formulation of the immunogenic composition of the present invention can be accomplished using art-recognized methods.

It is noted that in this disclosure, terms such as "comprises", "comprised", "comprising", "contains", "containing" and the like can have the meaning attributed to them in U.S. patent law; e.g., they can mean "includes", "included", "including" and the like. Such terms refer to the inclusion of a particular ingredients or set of ingredients without excluding any other ingredients. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. patent law; namely, that these terms are close-ended. Accordingly, these terms refer to the inclusion of a particular ingredient or set of ingredients and the exclusion of all other ingredients.

A "conservative amino acid substitution" refers to the substitution of one or more of the amino acid residues of a protein with other amino acid residues having similar physical and/or chemical properties. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point. Particularly preferred substitutions are: Lys for Arg and vice versa such that a positive charge may be maintained; Glu for Asp and vice versa such that a negative charge may be maintained; Ser for Thr such that a free —OH can be maintained; and Gln for Asn such that a free $NH_2$ can be maintained.

"Fragment" refers to proteins where only specific domains of a larger protein are included. For example, ClfA and ClfB proteins contain as many as 8 domains each if the signal sequences are included. A polypeptide corresponding to the N1N2N3, N2N3, N1N2, N1N2, or N3 domains are each considered to be fragments of ClfA or ClfB. "Fragment" also refers to either a protein or polypeptide comprising an amino acid sequence of at least 4 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues) of the amino acid sequence of a parent protein or polypeptide or a nucleic acid comprising a nucleotide sequence of at least 10 base pairs (preferably at least 20 base pairs, at least 30 base pairs, at least 40 base pairs, at least 50 base pairs, at least 50 base pairs, at least 100 base pairs, at least 200 base pairs) of the nucleotide sequence of the parent nucleic acid.

"Functional activity" of an antibody or "functional antibody" as used herein refers to an antibody that, at a minimum, can bind specifically to an antigen. Additional functions are known in the art and may include additional components of the immune system that effect clearance or killing of the pathogen such as through opsonization, ADCC or complement-mediated cytotoxicity. After antigen binding, any subsequent antibody functions can be mediated through the Fc region of the antibody. The antibody opsonophagocytic assay (OPA) is an in vitro assay designed to measure in vitro Ig complement-assisted killing of bacteria with effector cells (white blood cells), thus mimicking a biological process. Antibody binding may also directly inhibit the biological function of the antigen it binds, e.g., antibodies that bind ClfA can neutralize its enzymatic function. In some embodiments, a "functional antibody" refers to an antibody that is functional as measured by the killing of bacteria in an animal efficacy model or an opsonophagocytic killing assay that demonstrates that the antibodies kill the bacteria.

The molecular weight of the S. aureus capsule polysaccharides is a consideration for use in immunogenic compositions. For example, high molecular weight capsule polysaccharides may be able to induce certain antibody immune responses due to a higher valency of the epitopes present on the antigenic surface. The isolation of "high molecular weight capsular polysaccharides" is contemplated for use in the compositions and methods of the present invention. For example, in one embodiment of the invention, the isolation of type 5 high molecular weight polysaccharides ranging in size from about 50 to about 800 kDa in molecular weight is contemplated. In one embodiment of the invention, the isolation of type 5 high molecular weight polysaccharides ranging in size from about 20 to about 1000 kDa in molecular weight is contemplated. In one embodiment of the invention, the isolation and purification of type 5 high molecular weight capsular polysaccharides ranging in size from about 50 to about 300 kDa in molecular weight is contemplated. In one embodiment, the isolation and purification of type 5 high molecular weight capsular polysaccharide ranging from 70 kDa to 300 kDa in molecular weight is contemplated. In one embodiment, the isolation and purification of type 5 high molecular weight capsular polysaccharide ranging from 90 kDa to 250 kDa in molecular weight is contemplated. In one embodiment, the isolation and purification of type 5 high molecular weight capsular polysaccharide ranging from 90 kDa to 150 kDa in molecular weight is contemplated. In one embodiment, the isolation and purification of type 5 high molecular weight capsular polysaccharide ranging from 90 kDa to 140 kDa in molecular weight is contemplated. In one embodiment, the isolation and purification of type 5 high molecular weight capsular polysaccharide ranging from 80 kDa to 120 kDa in molecular weight is contemplated. Other ranges of high molecular weight serotype 5 capsular polysaccharide that can be isolated and purified by the methods of this invention include size ranges of about 70 kDa to about 100 kDa in molecular weight; 70 kDa to 110 kDa in molecular weight; 70 kDa to 120 kDa in molecular weight; 70 kDa to 130 kDa in molecular weight; 70 kDa to 140 kDa in molecular weight; 70 kDa to 150 kDa in molecular weight; 70 kDa to 160 kDa in molecular weight; 80 kDa to 110 kDa in molecular weight; 80 kDa to 120 kDa in molecular weight; 80 kDa to 130 kDa in molecular weight; 80 kDa to 140 kDa in molecular weight; 80 kDa to 150 kDa in molecular weight; 80 kDa to 160 kDa in molecular weight; 90 kDa to 110 kDa in molecular weight; 90 kDa to 120 kDa in molecular weight; 90 kDa to 130 kDa in molecular weight; 90 kDa to 140 kDa in molecular weight; 90 kDa to 150 kDa in molecular weight; 90 kDa to 160 kDa in molecular weight; 100 kDa to 120 kDa in molecular weight; 100 kDa to 130 kDa in molecular weight; 100 kDa to 140 kDa in molecular weight; 100 kDa to 150 kDa in molecular weight; 100 kDa to 160 kDa in molecular weight; and similar desired molecular weight ranges.

As discussed above, the molecular weight of the S. aureus capsule polysaccharides is a consideration for use in immunogenic compositions. For example, high molecular weight capsule polysaccharides may be able to induce certain antibody immune responses due to a higher valency of the epitopes present on the antigenic surface. In one embodiment of the invention, the isolation and purification of type 8 high molecular weight capsular polysaccharides ranging from about 20 kDa to about 1000 kDa in molecular weight is contemplated. In one embodiment of the invention, the isolation and purification of type 8 high molecular weight capsular polysaccharides ranging from about 50 kDa to about 700 kDa in molecular weight is contemplated. In one embodiment of the invention, the isolation and purification of type 8 high molecular weight capsular polysaccharides ranging from 50 kDa to 300 kDa in molecular weight is contemplated. In one embodiment, the isolation and purification of type 8 high molecular weight capsular polysaccharide ranging from 70 kDa to 300 kDa in molecular weight is contemplated. In one embodiment, the isolation and purification of type 8 high molecular weight capsular polysaccharides ranging from 90 kDa to 250 kDa in molecular weight is contemplated. In one embodiment, the isolation and purification of type 8 high molecular weight capsular polysaccharides ranging from 90 kDa to 150 kDa in molecular weight is contemplated. In one embodiment, the isolation and purification of type 8 high molecular weight capsular polysaccharides ranging from 90 kDa to 120 kDa in molecular weight is contemplated. In one embodiment, the isolation and purification of type 8 high molecular weight capsular polysaccharides ranging from 80 kDa to 120 kDa in molecular weight is contemplated. Other ranges of high molecular weight serotype 8 capsular polysaccharides that can be isolated and purified by the methods of this invention include size ranges of about 70 kDa to about 100 kDa in molecular weight; 70 kDa to 110 kDa in molecular weight; 70 kDa to 120 kDa in molecular weight; 70 kDa to 130 kDa in molecular weight; 70 kDa to 140 kDa in molecular weight; 70 kDa to 150 kDa in molecular weight; 70 kDa to 160 kDa in molecular weight; 80 kDa to 110 kDa in molecular weight; 80 kDa to 120 kDa in molecular weight; 80 kDa to 130 kDa in molecular weight; 80 kDa to 140 kDa in molecular weight; 80 kDa to 150 kDa in molecular weight; 80 kDa to 160 kDa in molecular weight; 90 kDa to 110 kDa in molecular weight; 90 kDa to 120 kDa in molecular weight; 90 kDa to 130 kDa in molecular weight; 90 kDa to 140 kDa in molecular weight; 90 kDa to 150 kDa in molecular weight; 90 kDa to 160 kDa in molecular weight; 100 kDa to 120 kDa in molecular weight; 100 kDa to 130 kDa in molecular weight; 100 kDa to 140 kDa in molecular weight; 100 kDa to 150 kDa in molecular weight; 100 kDa to 160 kDa in molecular weight; and similar desired molecular weight ranges.

An "immune response" to an immunogenic composition is the development in a subject of a humoral and/or a cell-mediated immune response to molecules present in the composition of interest (for example, an antigen, such as a protein or polysaccharide). For purposes of the present invention, a "humoral immune response" is an antibody-mediated immune response and involves the generation of antibodies with affinity for the antigens present in the immunogenic compositions of the invention, while a "cell-mediated immune response" is one mediated by T-lymphocytes and/or other white blood cells. A "cell-mediated immune response" is elicited by the presentation of antigenic epitopes in association with Class I or Class II molecules of the major histocompatibility complex (MHC). This activates antigen-specific CD4+ T helper cells or CD8+ cytotoxic T lymphocyte cells ("CTLs"). CTLs have specificity for peptide or lipid antigens that are presented in association with proteins encoded by the major histocompatibility complex (MHC) or CD1 and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with classical or nonclassical MHC molecules on their surface. A "cell-mediated immune response" also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al., *J. Immunol.* (1993) 151:4189-4199; Doe et al., *Eur. J. Immunol.* (1994) 24:2369-2376.

The term "immunogenic" refers to the ability of an antigen or a vaccine to elicit an immune response, either humoral or cell-mediated, or both.

An "immunogenic amount", or an "immunologically effective amount" or "dose", each of which is used interchangeably herein, generally refers to the amount of antigen or immunogenic composition sufficient to elicit an immune response, either a cellular (T cell) or humoral (B cell or antibody) response, or both, as measured by standard assays known to one skilled in the art.

The amount of a particular conjugate in a composition is generally calculated based on total polysaccharide, conjugated and non-conjugated for that conjugate. For example, a CP5 conjugate with 20% free polysaccharide will have about 80 mcg of conjugated CP5 polysaccharide and about 20 mcg of non-conjugated CP5 polysaccharide in a 100 mcg CP5 polysaccharide dose. The protein contribution to the conjugate is usually not considered when calculating the dose of a conjugate. The amount of conjugate can vary depending upon the staphylococcal serotype. Generally, each dose will comprise 0.01 to 100 mcg of polysaccharide, particularly 0.1 to 10 mcg, and more particularly 1 to 10 mcg. The "immunogenic amount" of the different polysaccharide components in the immunogenic composition, may diverge and each may comprise 0.01 mcg, 0.1 mcg, 0.25 mcg, 0.5 mcg, 1 mcg, 2 mcg, 3 mcg, 4 mcg, 5 mcg, 6 mcg, 7 mcg, 8 mcg, 9 mcg, 10 mcg, 15 mcg, 20 mcg, 30 mcg, 40 mcg, 50 mcg, 60 mcg, 70 mcg, 80 mcg, 90 mcg, or about 100 mcg of any particular polysaccharide antigen.

In another embodiment, the "immunogenic amount" of the protein components in the immunogenic composition, may range from about 10 mcg to about 300 mcg of each protein antigen. In a particular embodiment, the "immunogenic amount" of the protein components in the immunogenic composition, may range from about 20 mcg to about 200 mcg of each protein antigen. The "immunogenic amount" of the different protein components in the immunogenic composition may diverge, and each comprise 10 mcg, 20 mcg, 30 mcg, 40 mcg, 50 mcg, 60 mcg, 70 mcg, 80 mcg, 90 mcg, 100 mcg, 125 mcg, 150 mcg, 175 mcg or about 200 mcg of any particular protein antigen.

The effectiveness of an antigen as an immunogen can be measured by measuring the levels of B cell activity by measuring the levels of circulating antibodies specific for the antigen in serum using immunoassays, immunoprecipitation assays, functional antibody assays, such as in vitro opsonic assay and many other assays known in the art. Another measure of effectiveness of an antigen as an T-cell immunogen can be measured by either by proliferation assays, by cytolytic assays, such as chromium release assays to measure the ability of a T cell to lyse its specific target cell. Furthermore, in the present invention, an "immunogenic amount" may also be defined by measuring the serum levels of antigen specific antibody induced following administration of the antigen, or, by measuring the ability of the antibodies so induced to enhance the opsonophagocytic ability of particular white blood cells, as described herein. The level of protection of the immune response may be measured by challenging the immunized host with the antigen that has been injected. For example, if the antigen to which an immune response is desired is a bacterium, the level of protection induced by the "immunogenic amount" of the antigen can be measured by detecting the percent survival or the percent mortality after challenge of the animals with the bacterial cells. In one embodiment, the amount of protection may be measured by measuring at least one symptom associated with the bacterial infection, for example, a fever associated with the infection. The amount of each of the antigens in the multi-antigen or multi-component vaccine or immunogenic compositions will vary with respect to each of the other components and can be determined by methods known to the skilled artisan. Such methods would include, for example, procedures for measuring immunogenicity and/or in vivo efficacy.

The term "immunogenic composition" relates to any pharmaceutical composition containing an antigen, e.g. a microorganism, or a component thereof, which composition can be used to elicit an immune response in a subject. The immunogenic compositions of the present invention can be used to treat a human susceptible to $S.$ $aureus$ infection, by means of administering the immunogenic compositions via a systemic transdermal or mucosal route. These administrations can include injection via the intramuscular (i.m.), intraperitoneal (i.p.), intradermal (i.d.) or subcutaneous routes; application by a patch or other transdermal delivery device; or via mucosal administration to the oral/alimentary, respiratory or genitourinary tracts. In one embodiment, intranasal administration is used for the treatment or prevention of nasopharyngeal carriage of $S.$ $aureus$, thus attenuating infection at its earliest stage. In one embodiment, the immunogenic composition may be used in the manufacture of a vaccine or in the elicitation of a polyclonal or monoclonal antibodies that could be used to passively protect or treat an animal.

Optimal amounts of components for a particular immunogenic composition can be ascertained by standard studies involving observation of appropriate immune responses in subjects. Following an initial vaccination, subjects can receive one or several booster immunizations adequately spaced.

In one embodiment of the present invention, the $S.$ $aureus$ immunogenic composition comprises a recombinant $S.$ $aureus$ clumping factor A (ClfA) fragment (N1N2N3, or combinations thereof), an isolated capsular polysaccharides type 5 conjugated to $CRM_{197}$ and an isolated capsular polysaccharides type 8 conjugated to $CRM_{197}$. In another embodiment, the $S.$ $aureus$ immunogenic composition is a sterile formulation (liquid, lyophilized, DNA vaccine, intradermal preparation) of recombinant $S.$ $aureus$ clumping factor (ClfA) fragment (N1N2N3, or combinations thereof), recombinant $S.$ $aureus$ clumping factor B (ClfB) fragment (N1N2N3, or combinations thereof), an isolated capsular polysaccharides type 5 conjugated to $CRM_{197}$ and an isolated capsular polysaccharides type 8 conjugated to $CRM_{197}$. In one embodiment of the present invention, the $S.$ $aureus$ immunogenic composition comprises a recombinant $S.$ $aureus$ clumping factor A (ClfA) fragment (N1N2N3, or combinations thereof), $S.$ $aureus$ iron binding protein MntC, an isolated capsular polysaccharides type 5 conjugated to $CRM_{197}$ and an isolated capsular polysaccharides type 8 conjugated to $CRM_{197}$. In one embodiment of the present invention, the $S.$ $aureus$ immunogenic composition is a sterile formulation (liquid, lyophilized, DNA vaccine, intradermal preparation) of recombinant $S.$ $aureus$ clumping factor (ClfA) fragment (N1N2N3, or combinations thereof), recombinant $S.$ $aureus$ clumping factor B (ClfB) fragment (N1N2N3, or combinations thereof), $S.$ $aureus$ iron binding protein MntC, an isolated capsular polysaccharides type 5 conjugated to $CRM_{197}$ and an isolated capsular polysaccharides type 8 conjugated to $CRM_{197}$. In one embodiment of the present invention, the $S.$ $aureus$ immunogenic composition comprises a recombinant $S.$ $aureus$ clumping factor B (ClfB) fragment (N1N2N3, or combinations thereof), an isolated capsular polysaccharides type 5 conjugated to $CRM_{197}$ and an isolated capsular polysaccharides type 8 conjugated to $CRM_{197}$. In one embodiment of the present invention, the $S.$ $aureus$ immunogenic composition comprises a recombinant $S.$ $aureus$ clumping factor B (ClfB) fragment (N1N2N3, or combinations thereof), $S.$ $aureus$ iron binding protein MntC, an isolated capsular polysaccharides type 5 conjugated to $CRM_{197}$ and an isolated capsular polysaccharides type 8 conjugated to $CRM_{197}$. In one embodiment of the present invention, the $S.$ $aureus$ immunogenic composition comprises a $S.$ $aureus$ iron binding protein MntC, an isolated capsular polysaccharides type 5 conjugated to $CRM_{197}$ and an isolated capsular polysaccharides type 8 conjugated to $CRM_{197}$.

The immunogenic compositions of the present invention can further comprise one or more additional "immunomodulators", which are agents that perturb or alter the immune system, such that either up-regulation or down-regulation of humoral and/or cell-mediated immunity is observed. In one particular embodiment, up-regulation of the humoral and/or cell-mediated arms of the immune system is preferred. Examples of certain immunomodulators include, for example, an adjuvant or cytokine, or ISCOMATRIX (CSL Limited, Parkville, Australia), described in U.S. Pat. No. 5,254,339 among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.). SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) Polysorbate® 80 detergent (ICI Surfactants), 2.5% (v/v) ethanol 200 µg/ml Quil A, 100 µg/ml cholesterol and 0.5% (v/v) lecithin. Modified SEAM 1/2 is an oil-in-water emulsion comprising 5% (v/v) squalene, 11% (v/v) SPAN® 85 detergent, 0.7% (v/v) polysorbate 80 detergent, 2.5% (v/v) ethanol, 100 µg/ml Quil A, and 50 µg/ml cholesterol. Other "immunomodulators" that can be included in the vaccine include, e.g., one or more interleukins, interferons, or other known cytokines or chemokines. In one embodiment, the adjuvant may be a cyclodextrin derivative or a polyanionic polymer, such as those described in U.S. Pat. Nos. 6,165,995 and 6,610,310, respectively. It is to be understood that the immunomodulator and/or adjuvant to be used will depend on the subject to which the vaccine or immunogenic composition will be administered, the route of injection and the number of injections to be given.

$S.$ $aureus$ "invasive disease" is the isolation of bacteria from a normally sterile site, where there is associated clinical signs/symptoms of disease. Normally sterile body sites include blood, CSF, pleural fluid, pericardial fluid, peritoneal fluid, joint/synovial fluid, bone, internal body site (lymph node, brain, heart, liver, spleen, vitreous fluid, kidney, pancreas, ovary), or other normally sterile sites. Clinical conditions characterizing invasive diseases include bacteremia, pneumonia, cellulitis, osteomyelitis, endocarditis, septic shock and more.

The term "isolated" means that the material is removed from its original environment (e.g., the natural environment if it is naturally occurring or from it's host organism if it is a recombinant entity, or taken from one environment to a different environment). For example, an "isolated" capsule polysaccharide, protein or peptide is substantially free of cellular material or other contaminating proteins from the cell or tissue source from which the protein is derived, or substantially free of chemical precursors or other chemicals when chemically synthesized, or otherwise present in a mixture as part of a chemical reaction. In the present invention, the proteins or polysaccharides may be isolated from the bacterial cell or from cellular debris, so that they are provided in a form useful in the manufacture of an immunogenic composition. The term "isolated" or "isolating" may include purifying, or purification, including for example, the methods of purification of the proteins or capsular polysaccharides, as described herein. The language "substantially free of cellular material" includes preparations of a polypeptide/protein in which the polypeptide/protein is separated from cellular components of the cells from which it is isolated or recombinantly produced. Thus, a capsule polysaccharide, protein or peptide that is substantially free of cellular material includes preparations of the capsule polysaccharide, protein or peptide having less than about 30%, 20%, 10%, 5%, 2.5%, or 1%, (by dry weight) of contaminating protein or polysaccharide or other cellular material. When the polypeptide/protein is recombinantly produced, it is also preferably substantially free of culture medium, i.e., culture medium represents less than about 20%, 10%, or 5% of the volume of the protein preparation. When polypeptide/protein or polysaccharide is produced by chemical synthesis, it is preferably substantially free of chemical precursors or other chemicals, i.e., it is separated from chemical precursors or other chemicals which are involved in the synthesis of the protein or polysaccharide. Accordingly, such preparations of the polypeptide/protein or polysaccharide have less than about 30%, 20%, 10%, 5% (by dry weight) of chemical precursors or compounds other than polypeptide/protein or polysaccharide fragment of interest.

A "non-conservative amino acid substitution" refers to the substitution of one or more of the amino acid residues of a protein with other amino acid residues having dissimilar physical and/or chemical properties, using the characteristics defined above.

The term "pharmaceutically acceptable carrier" means a carrier approved by a regulatory agency of a Federal, a state government, or other regulatory agency, or listed in the U.S. Pharmacopeia or other generally recognized pharmacopeia for use in animals, including humans as well as non-human mammals. The term "carrier" refers to a diluent, adjuvant, excipient, or vehicle with which the pharmaceutical composition is administered. Such pharmaceutical carriers can be sterile liquids, such as water and oils, including those of petroleum, animal, vegetable or synthetic origin. Water, saline solutions and aqueous dextrose and glycerol solutions can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting, bulking, emulsifying agents, or pH buffering agents. These compositions can take the form of solutions, suspensions, emulsion, sustained release formulations and the like. Examples of suitable pharmaceutical carriers are described in "Remington's Pharmaceutical Sciences" by E. W. Martin. The formulation should suit the mode of administration.

The terms "protein", "polypeptide" and "peptide" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature, but which may be non-conservative), to a native sequence, preferably such that the protein maintains the ability to elicit an immunological response within an animal to which the protein is administered. Also included are post-expression modifications, e.g. glycosylation, acetylation, lipidation, phosphorylation and the like.

A "protective" immune response refers to the ability of an immunogenic composition to elicit an immune response, either humoral or cell mediated, which serves to protect the subject from an infection. The protection provided need not be absolute. i.e., the infection need not be totally prevented or eradicated, if there is a statistically significant improvement compared with a control population of subjects, e.g. infected animals not administered the vaccine or immunogenic composition. Protection may be limited to mitigating the severity or rapidity of onset of symptoms of the infection. In general, a "protective immune response" would include the induction of an increase in antibody levels specific for a particular antigen in at least 50% of subjects, including some level of measurable functional antibody responses to each antigen. In particular situations, a "protective immune response" could include the induction of a two fold increase in antibody levels or a four fold increase in antibody levels specific for a particular antigen in at least 50% of subjects, including some level of measurable functional antibody responses to each antigen. In certain embodiments, opsonising antibodies correlate with a protective immune response. Thus, protective immune response may be assayed by measuring the percent decrease in the bacterial count in an opsonophagocytosis assay, for instance those described below. Preferably, there is a decrease in bacterial count of at least 10%, 25%, 50%, 65%, 75%, 80%, 85%, 90%, 95% or more.

The term "recombinant" as used herein simply refers to any protein, polypeptide, or cell expressing a gene of interest that is produced by genetic engineering methods. The term "recombinant" as used with respect to a protein or polypeptide, means a polypeptide produced by expression of a recombinant polynucleotide. The proteins used in the immunogenic compositions of the invention may be isolated from a natural source or produced by genetic engineering methods, such as, for example recombinant ClfA, recombinant ClfB or recombinant MntC. "Recombinant," as used herein, further describes a nucleic acid molecule, which, by virtue of its origin or manipulation, is not associated with all or a portion of the polynucleotide with which it is associated in nature. The term "recombinant" as used with respect to a host cell means a host cell into which a recombinant polynucleotide has been introduced.

Recombinant ClfA (rClfA) and recombinant ClfB (rClfB) as used herein refers to forms of ClfA or ClfB for use in the immunogenic compositions of the invention. In one embodiment, rClfA is a fragment of ClfA comprising one or more of the N domains, for example, N1N2N3. N2N3, N2 or N3 and is referred to herein as "recombinant ClfA" or "rClfA". In one embodiment, rClfB is a fragment of ClfB comprising one or more of the N domains of ClfB, for example, N1N2N3, N2N3, N2 or N3 and is referred to herein as "recombinant ClfB" or "rClfB".

The term "subject" refers to a mammal bird, fish, reptile, or any other animal. The term "subject" also includes humans. The term "subject" also includes household pets. Non-limiting examples of household pets include: dogs, cats, pigs, rabbits, rats, mice, gerbils, hamsters, guinea pigs, ferrets, birds, snakes, lizards, fish, turtles, and frogs. The term "subject" also includes livestock animals. Non-limiting examples of livestock animals include: alpaca, bison, camel, cattle, deer, pigs, horses, llamas, mules, donkeys, sheep, goats, rabbits, reindeer, yak, chickens, geese, and turkeys.

As used herein, "treatment" (including variations thereof, for example, "treat" or "treated") refers to any one or more of the following: (i) the prevention of infection or reinfection, as in a traditional vaccine, (ii) the reduction in the severity of, or, in the elimination of symptoms, and (iii) the substantial or complete elimination of the pathogen or disorder in question. Hence, treatment may be effected prophylactically (prior to infection) or therapeutically (following infection). In the present invention, prophylactic or therapeutic treatments can be used. According to a particular embodiment of the present invention, compositions and methods are provided which treat, including prophylactically and/or therapeutically immunize, a host animal against a microbial infection (e.g. a bacterium such as Staphylococcus species). The methods of the present invention are useful for conferring prophylactic and/or therapeutic immunity to a subject. The methods of the present invention can also be practiced on subjects for biomedical research applications.

The terms "vaccine" or "vaccine composition", which are used interchangeably, refer to pharmaceutical compositions comprising at least one immunogenic composition that induces an immune response in an animal.

General Description

The present invention relates to immunogenic compositions comprising at least three antigens from a staphylococcal organism, for example S. aureus. The antigens may be isolated from the organism using biochemical isolation procedures, or they may be produced synthetically or by recombinant means. The antigens may be polypeptides, or polysaccharides, or a combination thereof. These immunogenic compositions may be used in the manufacture of a vaccine to immunize subjects against infections caused by a staphylococcal organism. The components suitable for use in these compositions are described in greater detail below.

Staphylococcal Immunogenic Compositions

S. aureus is the causative agent of a wide variety of human diseases ranging from superficial skin infections to life threatening conditions such as pneumonia, sepsis and endocarditis. See Lowy N. Eng. J. Med. 339:580-532 (1998). In cases of invasive disease, S. aureus can be isolated from normally sterile body sites including blood, cerebral spinal fluid CSF, pleural fluid, pericardial fluid, peritoneal fluid, joint/synovial fluid, bone, internal body site (lymph node, brain, heart, liver, spleen, vitreous fluid, kidney, pancreas, ovary), or other normally sterile sites. This can lead to life threatening clinical conditions such as bacteremia, pneumonia, cellulitis, osteomyelitis, endocarditis, and septic shock. Adults, elderly and pediatric patients are most at risk for S. aureus infections.

Embodiments of the present invention describe selected antigens in immunogenic compositions including an isolated S. aureus clumping factor A (ClfA) polypeptide, an isolated S. aureus capsular polysaccharide type 5 conjugated to a carrier protein, an isolated S. aureus capsular polysaccharide type 8 conjugated to a carrier protein, an isolated S. aureus clumping factor B (ClfB), and recombinant S. aureus MntC protein. Next, the antigens were characterized in immunogenic compositions as a series of combinations, to demonstrate that specific combinations provide immune responses that may be superior to that produced using individual components for immunogenic compositions. Accordingly, one combination provides an immunogenic composition comprising: an isolated S. aureus clumping factor A (ClfA) polypeptide, an isolated S. aureus capsular polysaccharide type 5 conjugated to a carrier protein, and an isolated S. aureus capsular polysaccharide type 8 conjugated to a carrier protein. A second combination provides an immunogenic composition comprising: an isolated S. aureus clumping factor A (ClfA) polypeptide, an isolated S. aureus clumping factor B (ClfB), isolated S. aureus capsular polysaccharide type 5 conjugated to a carrier protein, and an isolated S. aureus capsular polysaccharide type 8 conjugated to a carrier protein. A third combination provides an immunogenic composition comprising: an isolated S. aureus clumping factor A (ClfA) polypeptide, an isolated S. aureus clumping factor B (ClfB) polypeptide, an isolated S. aureus MntC protein, an isolated S. aureus capsular polysaccharide type 5 conjugated to a carrier protein, and an isolated S. aureus capsular polysaccharide type 8 conjugated to a carrier protein. A fourth combination provides an immunogenic composition comprising: an isolated S. aureus clumping factor A (ClfA) polypeptide, an isolated S. aureus MntC protein, an isolated S. aureus capsular polysaccharide type 5 conjugated to a carrier protein, and an isolated S. aureus capsular polysaccharide type 8 conjugated to a carrier protein. A fifth combination provides an immunogenic composition comprising: an isolated S. aureus clumping factor B (ClfB) polypeptide, an isolated S. aureus capsular polysaccharide type 5 conjugated to a carrier protein, and an isolated S. aureus capsular polysaccharide type 8 conjugated to a carrier protein. A sixth combination provides an immunogenic composition comprising: an isolated S. aureus clumping factor B (ClfB) polypeptide, an isolated S. aureus MntC protein, an isolated S. aureus capsular polysaccharide type 5 conjugated to a carrier protein, and an isolated S. aureus capsular polysaccharide type 8 conjugated to a carrier protein. A seventh combination provides an immunogenic composition comprising: an isolated S. aureus MntC protein, an isolated S. aureus capsular polysaccharide type 5 conjugated to a carrier protein, and an isolated S. aureus capsular polysaccharide type 8 conjugated to a carrier protein. An eighth combination provides an immunogenic composition comprising: an isolated S. aureus clumping factor A (ClfA) polypeptide, an isolated S. aureus clumping factor B (ClfB) polypeptide, and an isolated S. aureus MntC protein. In some embodiments, the above combinations further comprise at least one of the following antigens: EkeS, DsqA, KesK, KrkN, KrkN2, RkaS, RrkN, KnkA, SdrC, SdrD, SdrE, Opp3a, DltD, HtsA, LtaS, IsdA, IsdB, IsdC, SdrF, SdrG, SdrH, SrtA, SpA, Sbi alpha-hemolysin (hla), beta-hemolysin, fibronectin-binding protein A (fnbA), fibronectin-binding protein B (fnbB), coagulase, Fig, map, Panton-Valentine leukocidin (pvl), alpha-toxin and its variants, gamma-toxin (hlg) and variants, ica, immunodominant ABC transporter, $Mg^{2+}$ transporter, Ni ABC transporter, RAP, autolysin, laminin receptors, IsaA/P isA, IsaB/PisB. SPOIIIE, SsaA, EbpS. Sas A, SasF, SasH, EFB (FIB), SBI, Npase, EBP, bone sialo binding protein II, aureolysin precursor (AUR)/Sepp1, Cna, and fragments thereof such as M55, TSST-1, mecA, poly-N-acetylglucosamine (PNAG/dPNAG) exopolysaccharide, GehD, EbhA, EbhB, SSP-1, SSP-2, HBP, vitronectin binding protein. HarA, EsxA, EsxB, Enterotoxin A. Enterotoxin B, Enterotoxin C1, and novel autolysin.

Epidemiological studies of *S. aureus* outbreaks indicate that evolution of *S. aureus* is clonal in nature, where a single clone that acquired a successful genotype has spread rapidly and caused many of the infections. Therefore, evolution is considered to be clonal. The bacterial genome is comprised of a larger more stable species core genome and a more diversified set of accessory genes. See Feil et al., Nature Reviews: Microbiology 2:483-495 (2004). The core genes are ubiquitously present in all clones of the species, and the accessory genes are not necessarily present in any given clone. Considering *S. aureus*, one study using a DNA microarray representing more than 90% of the *S. aureus* genome found that 78% of the genes in the genome was common to all *S. aureus* thus representing the "species core", and the remaining 22% are the "accessory genes". The accessory genes comprise dispensable genetic material much of which codes for virulence factors, proteins mediating antibiotic resistance and genes coding for proteins specific for interacting with a particular host environment. See Fitzgerald et al., PNAS 98:8821-8826 (2001); Feil et al., Nature Reviews: Microbiology 2:483-495 (2004). In general, the core genes are more slowly evolving and the accessory genes are polymorphic. See Kuhn et al., J. Bact. 188:169-178 (2006). Therefore, appropriately selected core genes provide better target antigens for use in immunogenic compositions to prevent infection.

Surface expressed antigens from disease-causing isolates or clonal types of *S. aureus* offer a source for antigens able to induce immunity and functional antibodies. At the macromolecular level (either amino acid or polysaccharide sequence), conserved forms of the antigen expressed by the different disease isolates may be chosen to permit broad cross reactivity of antibodies to those strains that may possess antigenic variations of the vaccine target.

One important consideration for including an antigen in the multi-antigen immunogenic compositions described herein is whether the antigen has demonstrated efficacy when administered as an immunogenic composition by providing protection in one or more animal models of bacterial infection. There are numerous animal models for various *S. aureus* diseases. Each of these models has strengths and weaknesses.

Human clearance of bacterial infections can proceed via opsonic killing that is mediated after phagocyte uptake. There are many convincing examples for this from studies using Gram-positive polysaccharide antigens, such as *Streptococcus pneumoniae* capsular polysaccharide and *S. aureus* capsular polysaccharide. See Lee et al., Crit. Rev. Micro. 29:333-349 (2003). There is less evidence for opsonic activity induced by Gram-positive protein antigens. Uptake by phagocytes has been observed, but direct killing has been harder to demonstrate. Monoclonal antibodies to proteins have been shown to confer protection against *S. aureus* challenge in animal models of infection; and mechanisms other than opsonophagocytic killing may account for the protection observed.

The induction of antibodies having a measurable functional activity, such as opsonophagocytic activity (OPA) is one indicator of whether a particular antigen is useful for inclusion in the immunogenic compositions of the present invention. Other indicators include but are not limited to antigen expression on the cell surface during in vivo expression as measured using antigen specific antibodies or the ability of antibodies to inhibit/neutralize antigen function.

Species/Strains

The type of any particular hospital or disease strain is useful for determining the origin, clonal relatedness and monitoring the epidemiology of outbreaks. Numerous methods are available for typing *S. aureus* strains. The classical practical definition for a bacterial species is a group of strains that are characterized by over 70% genomic hybridization (DNA-DNA genomic hybridization of DDI 1H) and over 97% of 16S ribosomal RNA gene sequence identity. See Vandamme et al., Microbiol Rev. 60:407-438 (1996). Bacteriophage typing (BT) is a method of typing *S. aureus* strains based on their susceptibility to lysis by certain phage types. See Blair et al., Bull W.H.O. 24:771-784 (1961). This older method suffers from a lack of reproducibility between laboratories and a failure to type 15-20% of isolates.

Single-Antigen Vs Multi-Antigen Immunogenic Compositions

The question arises as to whether the optimal immunogenic composition to protect against infection of the predominant *S. aureus* strains should be comprised of a single component or multiple components. Numerous studies have shown that immunogenic compositions based on a single protein or carbohydrate component can offer some protection from challenge with a strain of *S. aureus* expressing that component in certain animal models. Importantly, it has also been demonstrated that protection from a single antigen can be dependent on the strain selected.

Surface proteins such as adhesins have been investigated as single component vaccines. For example, mice immunized with *S. aureus* ClfA developed less severe arthritis than did mice with a control protein. See Josefsson et al., J. Infect. Dis. 184:1572-1580 (2001). Fragments of the collagen binding adhesin (cna) offered protection in a mouse sepsis model. See Nilsson, et al., J. Clin. Invest., 101:2640-2649 (1998). Immunization of mice with the A domain of ClfB could reduce nasal colonization in a mouse model. See Schaffer et al., Infect. Immun. 74:2145-2153 (2006).

One of the fourteen *S. aureus* iron sequestering proteins known as IsdB is being investigated in a monovalent immunogenic formulation for protection from *S. aureus* infection. This protein has shown a good protective effect in mice and good immunogenicity in non-human primates. See Kuklin et al., Infect. Immun. 74:2215-2223 (2006).

Due to the vast potential of *S. aureus* to evolve or substitute different proteins to perform the same or similar functions, the optimal immunogenic formulation for protecting the most people from the most *S. aureus* diseases is a multi-antigen formulation comprising 2 or more (e.g., 3, 4, 5, etc.) antigens properly selected and presented in an immunogenic formulation. In certain embodiments, an immunogenic composition of the invention comprises three or more antigens selected from an isolated *S. aureus* clumping factor A (ClfA) polypeptide, an isolated *S. aureus* clumping factor B (ClfB) polypeptide, an isolated *S. aureus* capsular polysaccharide type 5 (CP5) conjugated to a carrier protein, an isolated *S. aureus* capsular polysaccharide type 8 (CP8) conjugated to a carrier protein and an isolated *S. aureus* MntC protein. In certain embodiments, an immunogenic composition of the invention comprises four or more antigens selected from an isolated *S. aureus* clumping factor A (ClfA) polypeptide, an isolated *S. aureus* clumping factor B (ClfB) polypeptide, an isolated *S. aureus* capsular polysaccharide type 5 (CP5) conjugated to a carrier protein, an isolated *S. aureus* capsular polysaccharide type 8 (CP8) conjugated to a carrier protein and an isolated *S. aureus* MntC protein. In certain embodiments, an immunogenic composition of the invention comprises an isolated *S. aureus* clumping factor A (CfA) polypeptide, an isolated *S. aureus* clumping factor B (ClfB) polypeptide, an isolated *S. aureus* capsular polysaccharide type 5 (CP5) conjugated to a carrier protein, an isolated *S. aureus* capsular polysaccharide type 8 (CP8) conjugated to a carrier protein and an isolated *S. aureus* MntC protein as antigens.

Adjuvants

Immunogenic compositions as described herein also comprise, in certain embodiments, one or more adjuvants. An adjuvant is a substance that enhances the immune response when administered together with an immunogen or antigen. A number of cytokines or lymphokines have been shown to have immune modulating activity, and thus are useful as adjuvants, including, but not limited to, the interleukins 1-α, 1-β, 2, 4, 5, 6, 7, 8, 10, 12 (see, e.g., U.S. Pat. No. 5,723,127), 13, 14, 15, 16, 17 and 18 (and its mutant forms); the interferons-α, β and γ; granulocyte-macrophage colony stimulating factor (GM-CSF) (see, e.g., U.S. Pat. No. 5,078,996 and ATCC Accession Number 39900); macrophage colony stimulating factor (M-CSF); granulocyte colony stimulating factor (G-CSF); and the tumor necrosis factors α and β. Still other adjuvants that are useful with the immunogenic compositions described herein include chemokines, including without limitation, MCP-1, MIP-1α, MIP-1β, and RANTES; adhesion molecules, such as a selectin, e.g., L-selectin, P-selectin and E-selectin; mucin-like molecules, e.g., CD34, Gly-CAM-1 and MadCAM-1; a member of the integrin family such as LFA-1, VLA-1, Mac-1 and p150.95; a member of the immunoglobulin superfamily such as PECAM, ICAMs, e.g., ICAM-1, ICAM-2 and ICAM-3, CD2 and LFA-3; co-stimulatory molecules such as B7-1, B7-2, CD40 and CD40L; growth factors including vascular growth factor, nerve growth factor, fibroblast growth factor, epidermal growth factor, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspase (ICE).

Suitable adjuvants used to enhance an immune response further include, without limitation, MPL™ (3-O-deacylated monophosphoryl lipid A, Corixa, Hamilton, Mont.), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918. One such AGP is 2-[(R)-3-Tetradecanoyloxytetradecanoylamino]ethyl 2-Deoxy-4-O-phosphono-3-O—[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form (AF) or as a stable emulsion (SE).

Still other adjuvants include muramyl peptides, such as N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE); oil-in-water emulsions, such as MF59 (U.S. Pat. No. 6,299,884) (containing 5% Squalene, 0.5% polysorbate 80, and 0.5% Span 85 (optionally containing various amounts of MTP-PE) formulated into submicron particles using a microfluidizer such as Model 110Y microfluidizer (Microfluidics. Newton, Mass.)), and SAF (containing 10% Squalene, 0.4% polysorbate 80, 5% pluronic-blocked polymer L121, and thr-MDP, either microfluidized into a submicron emulsion or vortexed to generate a larger particle size emulsion); incomplete Freund's adjuvant (IFA); aluminum salts (alum), such as aluminum hydroxide, aluminum phosphate, aluminum sulfate; Amphigen; Avridine; L121/squalene; D-lactide-polylactide/glycoside; pluronic polyols; killed *Bordetella*; saponins, such as Stimulon™ QS-21 (Antigenics, Framingham, Mass.), described in U.S. Pat. No. 5,057,540, ISCOMATRIX (CSL Limited, Parkville, Australia), described in U.S. Pat. No. 5,254,339, and immunostimulating complexes (ISCOMATRIX); *Mycobacterium tuberculosis*; bacterial lipopolysaccharides; synthetic polynucleotides such as oligonucleotides containing a CpG motif (e.g., U.S. Pat. No. 6,207,646); IC-31 (Intercell AG, Vienna, Austria), described in European Patent Nos. 1,296,713 and 1,326,634; a pertussis toxin (PT) or mutant thereof, a cholera toxin or mutant thereof (e.g., U.S. Pat. Nos. 7,285,281, 7,332,174, 7,361,355 and 7,384,640); or an *E. coli* heat-labile toxin (LT) or mutant thereof, particularly LT-K63, LT-R72 (e.g., U.S. Pat. Nos. 6,149,919, 7,115,730 and 7,291,588).

Candidate Antigens:

ClfA: Domain Organization

Clumping factor A (ClfA) is a *S. aureus* surface protein associated with binding to host matrix proteins via a fibrinogen binding site. ClfA is a member of a family of proteins containing the carboxyl terminal LPXTG (SEQ ID NO: 125) motif that enables the protein to become covalently linked to the cell surface. ClfA also belongs to another family of proteins (Microbial Surface Components Recognizing Adhesive Matrix Molecule, or MSCRAMMs) that are associated with binding host proteins such as fibrinogen (bound by ClfA), the fibronectin binding proteins (FnbA and FnbB), the collagen binding protein (Cna) and others. These proteins all share the amino terminal signal sequence that mediates transport to the cell surface. The MSCRAMMs also include an A-domain that is the functional region containing the active site for ligand binding (e.g., fibrinogen, fibronectin, elastin, keratin). The A-domain is followed by a region composed of serine aspartate repeats (SD repeat), which is thought to span the peptidoglycan layer. The SD repeat is followed by a membrane-spanning region that includes the LPXTG (SEQ ID NO: 125) motif for covalent linkage of the protein to peptidoglycan. ClfA is described in U.S. Pat. No. 6,008,341.

The ligand binding region of ClfA comprising N1N2N3 of the A domain (FIG. 1) spans amino acids 40-559. The N domains of ClfA have been assigned as follows: N1 encompasses residues 45-220; N2 encompasses residues 229-369; and N3 encompasses residues 370-559. See Deivanayagam et al. EMBO J. 21:6660-6672 (2002). For case of reference the N1N2N3 domains may be referred to as N123, likewise N2N3 may be referred to as N23. In preparations of recombinant N1N2N3, the N1 domain has been found to be protease sensitive and is easily cleaved or hydrolyzed to leave the N2N3 as a stable ligand binding recombinant fragment. See Deivanayagam et al. EMBO J. 21:6660-6672 (2002). The crystal structure of the fibrinogen binding N2N3 fragment of ClfA A domain, revealed that both N2 and N3 are dominated by anti-parallel beta strands. In addition to the anti-parallel beta strands, the N2 domain contains a single turn alpha helix and two $3_{10}$ helices and the N3 domain contains three $3_{10}$ helices. See Deivanayagam et al. EMBO J. 21:6660-6672 (2002). Sequence alignment of N2 and N3 reveals only 13% sequence identity and 36% sequence similarity over their lengths. See Deivanayagam et al. EMBO J. 21:6660-6672 (2002). The topology of the N2 and N3 domains are similar to the classic IgG fold and have been proposed to be novel variants of the IgG fold. See Deivanayagam et al. EMBO J. 21:6660-6672 (2002).

ClfA Sequence

The gene for clumping factor protein A, designated ClfA, has been cloned, sequenced and analyzed in detail at the molecular level (McDevitt et al., Mol. Microbiol. 11: 237-248 (1994); McDevitt et al., Mol. Microbiol. 16:895-907 (1995)). The sequence identifiers for the amino acid sequences of ClfA from Ill *S. aureus* disease-causing isolates are shown in Table 10. The amino acid sequence of the full length (including the signal sequence) wild type ClfA from *S. aureus* strain PFESA0237, is shown in SEQ ID NO: 130. This sequence shows a tyrosine at position 338, which is changed to an alanine in the mutated form of ClfA. The full length gene encoding the wild type ClfA from *S. aureus* strain PFESA0237, comprising the N123 region, the repeat region and the anchor region is shown in SEQ ID NO: 131. The amino acid sequence of the Y338A mutated forms of ClfA is shown in SEQ ID NO: 123. However, it should be noted that the change from a tyrosine to an alanine, which occurs in the wild type ClfA at position 338 of SEQ ID NO: 130, and which is designated as Y338A, is shown in the mutated form of ClfA, in SEQ ID NO: 123 at position 310. Furthermore, the mutated form of ClfA shown in the amino acid sequence of SEQ ID NO: 123 is the mature form of ClfA without the signal sequence, thus accounting for the difference in position of this mutation between SEQ ID NO: 130 and SEQ ID NO: 123.

ClfB: Domain Organization

ClfB is a *S. aureus* protein having fibrinogen binding activity and triggers *S. aureus* to form clumps in the presence of plasma. ClfB is an MSCRAMM protein and displays the characteristic MSCRAMM domain organization including an A-domain that is the functional region containing the active site for ligand binding (e.g., fibrinogen, fibronectin, elastin, keratin). The A-domain is followed by a region composed of serine aspartate repeats (SD repeat), which is thought to span the peptidoglycan layer. The SD repeat is followed by a membrane-spanning region that includes the LPXTG (SEQ ID NO: 125) motif for covalent linkage of the protein to peptidoglycan. ClfB is described in WO 99/27109 and in U.S. Pat. No. 6,680,195.

The internal organization of ClfB N-terminal A domain is very similar organization as found in ClfA. The A domain is composed of three subdomains N1, N2, and N3. The ligand binding region of ClfB comprising N1N2N3 of the A domain (FIG. 1) spans amino acids 44-585. For ease of reference the N1N2N3 domains may be referred to as N123, likewise N2N3 may be referred to as N23. The N domains of ClfB have been assigned as follows: N1 encompasses residues 44-197; N2 encompasses residues 198-375; and N3 encompasses residues 375-585. In ClfA, the crystal structure of the A domain was found to have a unique version of the immunoglobulin fold and by analogy the same may be speculated to be the case for ClfB. See Deivanayagam et al., EMBO J. 21:6660-6672 (2002). Even though organization of the A domains of ClfB and ClfA are similar, sequence identity is only 26%. See Ni Eidhin et al., Mol. Microbiol. 30:245-257 (2002).

ClfB Sequence

The gene encoding ClfB is classified as a core adhesion gene. ClfB sequences from 92 strains of *S. aureus* associated with multiple disease states are summarized in Table 11. Additional sequences were obtained from GenBank.

Other MSCRAMMS

Other MSCRAMMS may be considered for use in an immunogenic composition of the present invention. For example, the serine-aspartate repeat (Sdr) proteins, SdrC, SdrD, and SdrE are related in primary sequence and structural organization to the ClfA and ClfB proteins and are localized on the cell surface. The SdrC, SdrD and SdrE proteins are cell wall-associated proteins, having a signal sequence at the N-terminus and an LPXTG (SEQ ID NO:125) motif, hydrophobic domain and positively charged residues at the C-terminus. Each also has an SD repeat containing region R of sufficient length to allow, along with the B motifs, efficient expression of the ligand binding domain region A on the cell surface. With the A region of the SdrC, SdrD and SdrE proteins located on the cell surface, the proteins can interact with proteins in plasma, the extracellular matrix or with molecules on the surface of host cells. The Sdr proteins share some limited amino acid sequence similarity with ClfA and ClfB. Like ClfA and ClfB, SdrC, SdrD and SdrE also exhibit cation-dependent ligand binding of extracellular matrix proteins.

The sdr genes are closely linked and tandemly arrayed. The Sdr proteins (of SdrC, SdrD, SdrE, ClfA, and ClfB) characteristically comprise an A region where there is highly conserved amino acid sequence that can be used to derive a consensus TYTFTDYVD (SEQ ID NO: 126) motif. The motif exhibits slight variation between the different proteins. This variation, along with the consensus sequence of the motif is described in U.S. Pat. No. 6,680,195. In the Clf-Sdr proteins, this motif is highly conserved. The motif can be used in immunogenic compositions to impart broad spectrum immunity to bacterial infections, and also can be used as an antigen in the production of monoclonal or polyclonal antibodies. Such an antibody can be used to impart broad spectrum passive immunity.

The Sdr proteins differ from ClfA and ClfB by having two to five additional 110-113 residue repeated sequences (B-motifs) located between region A and the R-region. Each B-motif contains a consensus $Ca^{2+}$-binding EF-hand loop normally found in eukaryotic proteins. The structural integrity of a recombinant protein comprising the five B-repeats of SdrD was shown by bisANS fluorescence analysis to be $Ca^{2+}$-dependent, suggesting that the EF-hands are functional. When $Ca^{2+}$ was removed the structure collapsed to an unfolded conformation. The original structure was restored by addition of $Ca^{2+}$. The C-terminal R-domains of the Sdr proteins contain 132-170 SD residues. These are followed by conserved wall-anchoring regions characteristic of many surface proteins of Gram positive bacteria.

In the Sdr and Clf proteins this B motif is highly conserved while a degenerate version occurs in fibronectin binding MSCRAMMS, as well as the collagen binding protein Cna. The B motifs, in conjunction with the R regions, are necessary for displaying the ligand-binding domain at some distance from the cell surface. The repeated B motifs are one common denominator of the sub-group of SD repeat proteins described herein. These motifs are found in different numbers in the three Sdr proteins from strain PFESA0237. There are clear distinctions between the individual B motifs. The most conserved units are those located adjacent to the R regions (SdrC B2, SdrD B5 and SdrE B3). They differ from the rest at several sites, especially in the C-terminal half. A noteworthy structural detail is that adjacent B repeats are always separated by a proline residue present in the C-terminal region, but a proline never occurs between the last B repeats and the R region. Instead this linker is characterized by a short acidic stretch. These differences are evidence that the end units have a different structural or functional role compared to the other B motifs. The N-terminal B motifs of SdrD and SdrE have drifted apart from the others, and there are numerous amino acid alterations, including small insertions and deletions whereas the remaining internal B motifs are more highly conserved. Note that each of the three Sdr proteins has at least one B motif of each kind.

The C-terminal R-domains of the Sdr proteins contain 132-170 SD residues. These are followed by conserved wall-anchoring regions characteristic of many surface proteins of Gram positive bacteria.

Other candidate SdrD molecules may be derived from various species of organisms for use in an immunogenic composition of the invention, some of which include the following SdrD from *S. aureus*: strain USA300 FPR3757 (protein accession number SAUSA300 0547); strain NCTC8325 (protein accession number SAOUHSC 00545); strain MW2 (protein accession number MW0517); strain MSSA476 (protein accession number SAS0520; and strain Mu50 (protein accession number SAV0562).

Further MSCRAMMS which may be considered for use in an immunogenic composition of the present invention include EkeS, DsqA, KesK, KrkN, KrkN2, RkaS, RrkN, and KnkA. These MSCRAMMS are described in WO 02/102829, which is hereby incorporated by reference. Additional MSCRAMMS, identified by GenBank Accession No., include NP_373261.1, NP_373371.1, NP_374246.1, NP_374248.1, NP_374841.1, NP_374866.1, NP_375140.1, NP_375614.1, NP_375615.1, NP_375707.1, NP_375765.1, and NP_375773.1.

Capsule Polysaccharides Type 5 and Type 8

Staphylococcal microorganisms capable of causing invasive disease generally also are capable of producing a capsule polysaccharide (CP) that encapsulates the bacterium and enhances its resistance to clearance by host innate immune system. The CP serves to cloak the bacterial cell in a protective capsule that renders the bacteria resistant to phagocytosis and intracellular killing. Bacteria lacking a capsule are more susceptible to phagocytosis. Capsular polysaccharides are frequently an important virulence factor for many bacterial pathogens, including *Haemophilus influenzae, Streptooccccus pneumoniae* and Group B streptococci.

The capsule polysaccharide can be used to serotype a particular species of bacteria. Typing is usually accomplished by reaction with a specific antiserum or monoclonal antibody generated to a specific structure or unique epitope characteristic of the capsule polysaccharide. Encapsulated bacteria tend to grow in smooth colonies whereas colonies of bacteria that have lost their capsules appear rough. Colonies producing a mucoid appearance are known as Heavily Encapsulated. Types 1 and 2 of *S. aureus* are heavily encapsulated and are rarely associated with disease.

Most clinical isolates of *S. aureus* are encapsulated with either serotypes 5 or 8. The type 5 (CP5) and type 8 (CP8) capsular polysaccharides have similar trisaccharide repeating units comprised of N-acetyl mannosaminuronic acid, N-acetyl L-fucosamine, and N-acetyl D-fucosamine. See Fournier, J. M. et al., Infect. Immun. 45:97-93 (1984) and Moreau, M., et al., Carbohydrate Res. 201:285-297 (1990). The two CPs, which have the same sugars, but differ in the sugar linkages and in sites of O acetylation to produce serologically distinct patterns of immunoreactivity.

In some embodiments, the serotype 5 and/or 8 capsular polysaccharides of the invention are O-acetylated. In some embodiments, the degree of O-acetylation of type 5 capsular polysaccharide or oligosaccharide is 10-100%, 20-100%, 30-100%, 40-100%, 50-100%. 60-100%, 70-1006, 80-100%, 90-100%, 50-90%, 60-90%, 70-90% or 80-90%. In some embodiments, the degree of O-acetylation of type 8 capsular polysaccharide or oligosaccharide is 10-100%, 20-100%, 30-100%, 40-100%, 50-100%. 60-100%, 70-100%, 80-100%, 90-100%, 50-90%, 60-90%, 70-90% or 80-90%. In some embodiments, the degree of O-acetylation of type 5 and type 8 capsular polysaccharides or oligosaccharides is 10-100%, 20-100%, 30-100%, 40-100%, 50-100%. 60-100%, 70-100%, 80-100%, 90-100%, 50-90%, 60-90%, 70-90% or 80-90%.

The degree of O-acetylation of the polysaccharide or oligosaccharide can be determined by any method known in the art, for example, by proton NMR (Lemercinier and Jones 1996, Carbohydrate Research 296; 83-96, Jones and Lemercinier 2002, J Pharmaceutical and Biomedical Analysis 30; 1233-1247, WO 05/033148 or WO 00/56357). Another commonly used method is described by Hestrin (1949) J. Biol. Chem. 180; 249-261.

In some embodiments, the serotype 5 and/or 8 capsular polysaccharides of the invention are used to generate antibodies that are functional as measured by the killing of bacteria in an animal efficacy model or an opsonophagocytic killing assay that demonstrates that the antibodies kill the bacteria. Such functionality may not be observed using an assay that monitors the generation of antibodies alone, which is not indicative of the importance of O-acetylation in efficacy.

Capsule Epidemiology

The association of particular capsule serotypes with disease is possible through monitoring of clinical isolates. Of the eight different serotypes of *S. aureus* identified (Karakawa and Vann (1982) only serotypes 1 and 2 are heavily encapsulated, and these are rarely isolated. See Capsular Polysaccharides of *Staphylococcus aureus*, p. 285-293, In J. B. Robbins. J. C. Hill and J. C. Sadoff (ed.), Seminars in infectious disease, vol. 4, Bacterial Vaccines. Thieme Stratton. Inc. New York). Surveys have shown that approximately 85-90% of *S. aureus* clinical isolates express CP5 or CP8 (Arbeit R D, et al., Diagn. Microbiol. Infect. Dis. (1984) April; 2(2):85-91; Karakawa W W, et at, J. Clin. Microbiol. (1985) September; 22(3):445-7; Essawi T, et al., Trop. Med. Int. Health. (1998) July; 3(7):576-83; Na'was T, et al., J. Clin. Microbiol. (1998) 36(2):414-20. Most of CP5 and CP8 non-typeable strains are genetically type 5 or type 8 containing mutations in cap5/8 locus (Cocchiaro, Gomez et al., (2006), Mol. Microbiol. February 59(3):948-960). Capsulation for some strains is lost rapidly within few passages in vitro which is due to a repressive effect of high phosphate concentration in media used in clinical diagnosis on capsule production. It was also reported that non-capsulated isolates recover capsule expression after passing through cows. See Opdebeck, J. P. et al., J. Med. Microbiol. 19:275-278 (1985). Some non-typeable strains become capsule positive under appropriate growth conditions.

CP5 and CP8 Structure

The repeat unit of both CP5 and CP8 is comprised of 2-acetamido-2-deoxy-D-mannuronic acid, 2-acetamido-2-deoxy-L-fucose and 2-acetamido-2-deoxy-D-fucose. See C. Jones et al., Carbohydr. Res. 340:1097-1106 (2005). Although CP5 and CP8 have the same sugar composition, they have been demonstrated to be immunologically distinct. They differ in glycosidic linkages and site of O-acetylation of uronic acid. Strain dependent incomplete N-acetylation of one of the FucNAc residues was observed. See Tzianabos et al., PNAS V98: 9365 (2001).

*S. aureus* Capsule Polysaccharide in an Immunogenic Composition

The molecular weight of the *S. aureus* capsule polysaccharides is an important consideration for use in immunogenic compositions. High molecular weight capsule polysaccharides are able to induce certain antibody immune responses due to a higher valency of the epitopes present on the antigenic surface. The methods described herein provide for isolation and purification of much higher molecular weight capsule polysaccharide type 5 and type 8 than was previously available.

MntC/SitC/Saliva Binding Protein

MntC/SitC/Saliva Binding Protein is an ABC transporter protein and has homologues in *S. epidermidis* and *S. aureus*. It is referred to in the present invention as MntC. This protein is a 32 kDa lipoprotein and is located in the bacterial cell wall. See Sellman et al., and Cockayne et al., Infect. Immun. 66: 3767 (1998). In *S. epidermidis*, it is a component of an iron-regulated operon. It shows considerable homology to both adhesins including FimA of *S. parasanguis*, and with lipoproteins of a family of ABC transporters with proven or putative metal iron transport functions. (See Table 12 for strains of *S. aureus* and sequences.)

*S. aureus* MntC Protein

The *S. aureus* homologue of MntC is known as saliva binding protein and was disclosed in U.S. Pat. No. 5,801,234 and can be included in an immunogenic composition of the invention. The protein sequence for the *S. aureus* homologue of MntC/SitC/Saliva Binding Protein is found in GenBank accession number NP_371155 for strain Mu50. (Also known as SAV0631.) The sequence identifier is SEQ ID NO: 119. The accession number for the nucleotide sequence for the complete genome of strain Mu50 is NC_002758.2 (coordinates 704988-705917).

*S. epidermidis* SitC Protein

The *S. epidermidis* homologue of MntC/SitC/Saliva Binding Protein is known as SitC and was disclosed in Sellman et al., (Sellman et al., Infect. Immun. 2005 October; 73(10): 6591-6600). The protein sequence for the *S. epidermidis* homologue of MntC/SitC/Saliva Binding Protein is found in GenBank accession number YP_187886.1. (Also known as SERP0290.). The sequence identifier is SEQ ID NO: 121.

The accession number for the nucleotide sequence for the complete genome of strain RP62A, is NC_002976 (coordinates 293030-293959). Other candidate SitC molecules may be derived from various species of organisms for use in an immunogenic composition of the invention, some of which are listed in Table I below.

TABLE 1

| Protein | Species | Example strain | Protein Accession |
|---------|---------|----------------|-------------------|
| SitC | *S. haemolyticus* | JCSC1435 | BAE03450.1 |
| SitC | *S. epidermidis* | ATCC 12228 | AAO04002.1 |
| SitC | *S. saprophyticus* | ATCC 15305 | BAE19233.1 |
| SitC | *S. xylosus* | DSM20267 | ABR57162.1 |
| SitC | *S. carnosus* | TM300 | CAL27186.1 |

*S. aureus* Iron Binding Proteins

Another potential candidate antigen to be considered for use in the immunogenic compositions of the invention include the *S. aureus* surface protein iron surface determinant B (IsdB). This MSCRAMM was described by Mazmanian et al. (Mazmanian, S K et al Proc. Natl. Acad. Sci., USA 99:2293-2298 (2002)) and it has subsequently been tested and shown to be effective as a vaccine candidate in a murine model of infection and a rhesus macaque immunogenicity study by Kuklin, et al. (Kuklin, N A, et al. Infection and Immunity, Vol. 74, No. 4, 2215-2223, (2006)). This IsdB molecule is present in various strains of *S. aureus*, including strain MRSA252 (protein accession number CAG40104.1); strain Newman (protein accession number BAF67312.1); strain MSSA476 (protein accession number CAG42837.1); strain Mu3 (protein accession number BAF78003.1); strain RF122 (protein accession number CA180681.1).

Candidate Antigens:

The immunogenic compositions of the present invention may also include one or more of the following antigens: Opp3a, DltD, HtsA, LtaS, IsdA, IsdC, SdrF, SdrG, SdrH, SrtA, SpA, Sbi alpha-hemolysin (hla), beta-hemolysin, fibronectin-binding protein A (fnbA), fibronectin-binding protein B (fnbB), coagulase, Fig, map, Panton-Valentine leukocidin (pvl), alpha-toxin and its variants, gamma-toxin (hlg) and variants, ica, immunodominant ABC transporter. Mg2+ transporter, Ni ABC transporter, RAP, autolysin, laminin receptors, IsaA/PisA, IsaB/PisB, SPOIIIE. SsaA, EbpS. Sas A, SasF, SasH. EFB (FIB), SBI, Npase. EBP, bone sialo binding protein II, aureolysin precursor (AUR)/Sepp1, Cna, and fragments thereof such as M55, TSST-1, mecA, poly-N-acetylglucosamine (PNAG/dPNAG) exopolysaccharide, GehD. EbhA, EbhB, SSP-1, SSP-2, HBP, vitronectin binding protein. HarA, EsxA, EsxB, Enterotoxin A. Enterotoxin B, Enterotoxin C1, and novel autolysin. In certain embodiments of the invention, when the immunogenic composition comprises certain forms of CP5 and/or CP8, it may not further comprise PNAG.

Immunogenic Composition Formulations

In one embodiment, the immunogenic compositions of the invention further comprise at least one of an adjuvant, a buffer, a cryoprotectant, a salt, a divalent cation, a non-ionic detergent, an inhibitor of free radical oxidation, a diluent or a carrier.

The immunogenic compositions of the invention may further comprise one or more preservatives in addition to a plurality of staphylococcal protein antigens and capsular polysaccharide-protein conjugates. The FDA requires that biological products in multiple-dose (multi-dose) vials contain a preservative, with only a few exceptions. Vaccine products containing preservatives include vaccines containing benzethonium chloride (anthrax), 2-phenoxyethanol (DTaP, HepA, Lyme, Polio (parenteral)), phenol (Pneumo, Typhoid (parenteral), Vaccinia) and thimerosal (DTaP, DT, Td, HepB, Hib, Influenza, JE, Mening, Pneumo, Rabies). Preservatives approved for use in injectable drugs include, e.g., chlorobutanol m-cresol, methylparaben, propylparaben, 2-phenoxyethanol, benzethonium chloride, benzalkonium chloride, benzoic acid, benzyl alcohol, phenol, thimerosal and phenylmercuric nitrate.

Formulations of the invention may further comprise one or more of a buffer, a salt, a divalent cation, a non-ionic detergent, a cryoprotectant such as a sugar, and an anti-oxidant such as a free radical scavenger or chelating agent, or any multiple combination thereof. The choice of any one component, e.g., a chelator, may determine whether or not another component (e.g., a scavenger) is desirable. The final composition formulated for administration should be sterile and/or pyrogen free. The skilled artisan may empirically determine which combinations of these and other components will be optimal for inclusion in the preservative containing immunogenic compositions of the invention depending on a variety of factors such as the particular storage and administration conditions required.

In certain embodiments, a formulation of the invention which is compatible with parenteral administration comprises one or more physiologically acceptable buffers selected from, but not limited to, Tris (trimethamine), phosphate, acetate, borate, citrate, glycine, histidine and succinate. In certain embodiments, the formulation is buffered to within a pH range of about 6.0 to about 9.0, preferably from about 6.4 to about 7.4.

In certain embodiments, it may be desirable to adjust the pH of the immunogenic composition or formulation of the invention. The pH of a formulation of the invention may be adjusted using standard techniques in the art. The pH of the formulation may be adjusted to be between 3.0 and 8.0. In certain embodiments, the pH of the formulation may be, or may adjusted to be, between 3.0 and 6.0, 4.0 and 6.0, or 5.0 and 8.0. In other embodiments, the pH of the formulation may be, or may adjusted to be, about 3.0, about 3.5, about 4.0, about 4.5, about 5.0, about 5.5, about 5.8, about 6.0, about 6.5, about 7.0, about 7.5, or about 8.0. In certain embodiments, the pH may be, or may adjusted to be, in a range from 4.5 to 7.5, or from 4.5 to 6.5, from 5.0 to 5.4, from 5.4 to 5.5, from 5.5 to 5.6, from 5.6 to 5.7, from 5.7 to 5.8, from 5.8 to 5.9, from 5.9 to 6.0, from 6.0 to 6.1, from 6.1 to 6.2, from 6.2 to 6.3, from 6.3 to 6.5, from 6.5 to 7.0, from 7.0 to 7.5 or from 7.5 to 8.0. In a specific embodiment, the pH of the formulation is about 5.8.

In certain embodiments, a formulation of the invention which is compatible with parenteral administration comprises one or more divalent cations, including but not limited to $MgCl_2$, $CaCl_2$ and $MnCl_2$, at a concentration ranging from about 0.1 mM to about 10 mM, with up to about 5 mM being preferred.

In certain embodiments, a formulation of the invention which is compatible with parenteral administration comprises one or more salts, including but not limited to sodium chloride, potassium chloride, sodium sulfate, and potassium sulfate, present at an ionic strength which is physiologically acceptable to the subject upon parenteral administration and included at a final concentration to produce a selected ionic strength or osmolarity in the final formulation. The final ionic strength or osmolality of the formulation will be determined by multiple components (e.g., ions from buffering compound(s) and other non-buffering salts. A preferred salt, NaCl, is present from a range of up to about 250 mM, with salt concentrations being selected to complement other components (e.g., sugars) so that the final total osmolarity of the formulation is compatible with parenteral administration (e.g., intramuscular or subcutaneous injection) and will promote long term stability of the immunogenic components of the immunogenic composition formulation over various temperature ranges. Salt-free formulations will tolerate increased ranges of the one or more selected cryoprotectants to maintain desired final osmolarity levels.

In certain embodiments, a formulation of the invention which is compatible with parenteral administration comprises one or more cryoprotectants selected from but not limited to disaccharides (e.g., lactose, maltose, sucrose or trehalose) and polyhydroxy hydrocarbons (e.g., dulcitol, glycerol, mannitol and sorbitol).

In certain embodiments, the osmolarity of the formulation is in a range of from about 200 mOs/L to about 800 mOs/L, with a preferred range of from about 250 mOs/L to about 500 mOs/L, or about 300 mOs/L-about 400 mOs/L. A salt-free formulation may contain, for example, from about 5% to about 25% sucrose, and preferably from about 7% to about 15%, or about 10% to about 12% sucrose. Alternatively, a salt-free formulation may contain, for example, from about 3% to about 12% sorbitol, and preferably from about 4% to 7%, or about 5% to about 6% sorbitol. If salt such as sodium chloride is added, then the effective range of sucrose or sorbitol is relatively decreased. These and other such osmolality and osmolarity considerations are well within the skill of the art.

In certain embodiments, a formulation of the invention which is compatible with parenteral administration comprises one or more free radical oxidation inhibitors and/or chelating agents. A variety of free radical scavengers and chelators are known in the art and apply to the formulations and methods of use described herein. Examples include but are not limited to ethanol, EDTA, a EDTA/ethanol combination, triethanolamine, mannitol, histidine, glycerol, sodium citrate, inositol hexaphosphate, tripolyphosphate, ascorbic acid/ascorbate, succinic acid/succinate, malic acid/maleate, desferal EDDHA and DTPA, and various combinations of two or more of the above. In certain embodiments, at least one non-reducing free radical scavenger may be added at a concentration that effectively enhances long term stability of the formulation. One or more free radical oxidation inhibitors/chelators may also be added in various combinations, such as a scavenger and a divalent cation. The choice of chelator will determine whether or not the addition of a scavenger is needed.

In certain embodiments, a formulation of the invention which is compatible with parenteral administration comprises one or more non-ionic surfactants, including but not limited to polyoxyethylene sorbitan Fatty acid esters, Polysorbate-80 (Tween 80), Polysorbate-60 (Tween 60), Polysorbate-40 (Tween 40) and Polysorbate-20 (Tween 20), polyoxyethylene alkyl ethers, including but not limited to Brij 58, Brij 35, as well as others such as Triton X-100; Triton X-114, NP40, Span 85 and the Pluronic series of non-ionic surfactants (e.g., Pluronic 121), with preferred components Polysorbate-80 at a concentration from about 0.001% to about 2% (with up to about 0.25% being preferred) or Polysorbate-40 at a concentration from about 0.001% to 1% (with up to about 0.5% being preferred).

In certain embodiments, a formulation of the invention comprises one or more additional stabilizing agents suitable for parenteral administration, e.g., a reducing agent comprising at least one thiol (—SH) group (e.g., cysteine, N-acetyl cysteine, reduced glutathione, sodium thioglycolate, thiosulfate, monothioglycerol, or mixtures thereof). Alternatively or optionally, preservative-containing immunogenic composition formulations of the invention may be further stabilized by removing oxygen from storage containers, protecting the formulation from light (e.g., by using amber glass containers).

Preservative-containing immunogenic composition formulations of the invention may comprise one or more pharmaceutically acceptable carriers or excipients, which includes any excipient that does not itself induce an immune response. Suitable excipients include but are not limited to macromolecules such as proteins, saccharides, polylactic acids, polyglycolic acids, polymeric amino acids, amino acid copolymers, sucrose (Paoletti et al, 2001, Vaccine, 19:2118), trehalose, lactose and lipid aggregates (such as oil droplets or liposomes). Such carriers are well known to the skilled artisan. Pharmaceutically acceptable excipients are discussed, e.g., in Gennaro, 2000, Remington: The Science and Practice of Pharmacy, $20^{th}$ edition, ISBN:0683306472.

Compositions of the invention may be lyophilized or in aqueous form, i.e. solutions or suspensions. Liquid formulations may advantageously be administered directly from their packaged form and are thus ideal for injection without the need for reconstitution in aqueous medium as otherwise required for lyophilized compositions of the invention.

Direct delivery of immunogenic compositions of the present invention to a subject may be accomplished by parenteral administration (intramuscularly, intraperitoneally, intradermally, subcutaneously, intravenously, or to the interstitial space of a tissue); or by rectal, oral, vaginal, topical, transdermal, intranasal, ocular, aural, pulmonary or other mucosal administration. In a preferred embodiment, parenteral administration is by intramuscular injection, e.g., to the thigh or upper arm of the subject. Injection may be via a needle (e.g., a hypodermic needle), but needle free injection may alternatively be used. A typical intramuscular dose is 0.5 mL. Compositions of the invention may be prepared in various forms, e.g., for injection either as liquid solutions or suspensions. In certain embodiments, the composition may be prepared as a powder or spray for pulmonary administration, e.g., in an inhaler. In other embodiments, the composition may be prepared as a suppository or pessary, or for nasal, aural or ocular administration, e.g., as a spray, drops, gel or powder.

Optimal amounts of components for a particular immunogenic composition may be ascertained by standard studies involving observation of appropriate immune responses in subjects. Following an initial vaccination, subjects can receive one or several booster immunizations adequately spaced.

Packaging and Dosage Forms

Immunogenic compositions of the invention may be packaged in unit dose or multi-dose form (e.g. 2 doses, 4 doses, or more). For multi-dose forms, vials are typically but not necessarily preferred over pre-filled syringes. Suitable multi-dose formats include but are not limited to: 2 to 10 doses per container at 0.1 to 2 mL per dose. In certain embodiments, the dose is a 0.5 mL dose. See, e.g., International Patent Application WO2007/127668, which is incorporated by reference herein.

Compositions may be presented in vials or other suitable storage containers, or may be presented in pre-filled delivery devices, e.g., single or multiple component syringes, which may be supplied with or without needles. A syringe typically but need not necessarily contains a single dose of the preservative-containing immunogenic composition of the invention, although multi-dose, pre-filled syringes are also envisioned. Likewise, a vial may include a single dose but may alternatively include multiple doses.

Effective dosage volumes can be routinely established, but a typical dose of the composition for injection has a volume of 0.5 mL. In certain embodiments, the dose is formulated for administration to a human subject. In certain embodiments, the dose is formulated for administration to an adult, teen, adolescent, toddler or infant (i.e., no more than one year old) human subject and may in preferred embodiments be administered by injection.

Liquid immunogenic compositions of the invention are also suitable for reconstituting other immunogenic compositions which are presented in lyophilized form. Where an immunogenic composition is to be used for such extemporaneous reconstitution, the invention provides a kit with two or more vials, two or more ready-filled syringes, or one or more of each, with the contents of the syringe being used to reconstitute the contents of the vial prior to injection, or vice versa.

Alternatively, immunogenic compositions of the present invention may be lyophilized and reconstituted, e.g., using one of a multitude of methods for freeze drying well known in the art to form dry, regular shaped (e.g., spherical) particles, such as micropellets or microspheres, having particle characteristics such as mean diameter sizes that may be selected and controlled by varying the exact methods used to prepare them. The immunogenic compositions may further comprise an adjuvant which may optionally be prepared with or contained in separate dry, regular shaped (e.g., spherical) particles such as micropellets or microspheres. In such embodiments, the present invention further provides an immunogenic composition kit comprising a first component that includes a stabilized, dry immunogenic composition, optionally further comprising one or more preservatives of the invention, and a second component comprising a sterile, aqueous solution for reconstitution of the first component. In certain embodiments, the aqueous solution comprises one or more preservatives, and may optionally comprise at least one adjuvant (see, e.g., WO2009/109550 (incorporated herein by reference).

In yet another embodiment, a container of the multi-dose format is selected from one or more of the group consisting of, but not limited to, general laboratory glassware, flasks, beakers, graduated cylinders, fermentors, bioreactors, tubings, pipes, bags, jars, vials, vial closures (e.g., a rubber stopper, a screw on cap), ampoules, syringes, dual or multi-chamber syringes, syringe stoppers, syringe plungers, rubber closures, plastic closures, glass closures, cartridges and disposable pens and the like. The container of the present invention is not limited by material of manufacture, and includes materials such as glass, metals (e.g., steel, stainless steel, aluminum, etc.) and polymers (e.g., thermoplastics, elastomers, thermoplastic-elastomers). In a particular embodiment, the container of the format is a 5 mL Schott Type 1 glass vial with a butyl stopper. The skilled artisan will appreciate that the format set forth above is by no means an exhaustive list, but merely serve as guidance to the artisan with respect to the variety of formats available for the present invention. Additional formats contemplated for use in the present invention may be found in published catalogues from laboratory equipment vendors and manufacturers such as United States Plastic Corp. (Lima, Ohio), VWR.

Evaluation of Immunogenic Compositions

In one embodiment, the present invention provides immunogenic compositions comprising at least three antigens from a *S. aureus* organism.

Various in vitro tests are used to assess the immunogenicity of the immunogenic compositions of the invention. For example, an in vitro opsonic assay is conducted by incubating together a mixture of staphylococcal cells, heat inactivated serum containing specific antibodies to the antigens in question, and an exogenous complement source. Opsonophagocytosis proceeds during incubation of freshly isolated polymorphonuclear cells (PMN's) or differentiated effector cells such as HL60s and the antibody/complement/staphylococcal cell mixture. Bacterial cells that are coated with antibody and complement are killed upon opsonophagocytosis. Colony forming units (cfu) of surviving bacteria that are recovered from opsonophagocytosis are determined by plating the assay mixture. Titers are reported as the reciprocal of the highest dilution that gives 50% bacterial killing, as determined by comparison to assay controls.

A whole cell ELISA assay is also used to assess in vitro immunogenicity and surface exposure of the antigen, wherein the bacterial strain of interest (*S. aureus*) is coated onto a plate, such as a 96 well plate, and test sera from an immunized animal is reacted with the bacterial cells. If any antibody, specific for the test antigen, is reactive with a surface exposed epitope of the antigen, it can be detected by standard methods known to one skilled in the art.

Any antigen demonstrating the desired in vitro activity is then tested in an in vivo animal challenge model. In certain embodiments, immunogenic compositions are used in the immunization of an animal (e.g., a mouse) by methods and routes of immunization known to those of skill in the art (e.g., intranasal, parenteral, oral, rectal, vaginal, transdermal, intraperitoneal, intravenous, subcutaneous, etc.). Following immunization of the animal with a particular *Staphylococcus* sp. immunogenic composition, the animal is challenged with a *Staphylococcus* sp. and assayed for resistance to the staphylococcal infection.

In one embodiment, pathogen-free mice are immunized and challenged with *S. aureus*. For example, mice are immunized with one or more doses of the desired antigen in an immunogenic composition. Subsequently, the mice are challenged with *S. aureus* and survival is monitored over time post challenge.

Methods of Immunizing

Provided also are methods for immunizing a host to prevent staphylococcal infection. In a preferred embodiment, the host is human. Thus, a host or subject is administered an immunogenic amount of an immunogenic composition as described herein. An immunogenic amount of an immunogenic composition can be determined by doing a dose response study in which subjects are immunized with gradually increasing amounts of the immunogenic composition and the immune response analyzed to determine the optimal dosage. Starting points for the study can be inferred from immunization data in animal models. The dosage amount can vary depending upon specific conditions of the individual. The amount can be determined in routine trials by means known to those skilled in the art. In some embodiments, the method of immunizing a host to prevent staphylococcal infection, disease or condition comprises human, veterinary, animal, or agricultural treatment. Another embodiment provides a method of immunizing a host to prevent staphylococcal infection, disease or condition associated with a *Staphylococcus* sp. in a subject, the method comprising generating a polyclonal or monoclonal antibody preparation from the immunogenic composition described herein, and using said antibody preparation to confer passive immunity to the subject.

An immunologically effective amount of the immunogenic composition in an appropriate number of doses is administered to the subject to elicit an immune response. The treated individual should not exhibit the more serious clinical manifestations of the staphylococcal infection. The dosage amount can vary depending upon specific conditions of the individual, such as age and weight. This amount can be determined in routine trials by means known to those skilled in the art.

In one embodiment, patients being administered immunogenic compositions of the invention show a reduction in *S. aureus* carriage rates. Such reduction in carriage or a prolonged interval of time spent as a non-carrier following administration of an immunogenic composition is significant from a medical need perspective. For example, reduction in overall *S. aureus* carriage in carriers may be assessed following one dose of *S. aureus* multi-antigen vaccine. For example, 1 day prior to administration of an immunogenic composition, a group of adults aged 18-50 years may be screened for carriage by nasal and throat swabs followed by cultivation to determine their carriage state. Next, the group can be administered an immunogenic composition of the invention with a group receiving a control. Nasal and throat swabs performed weekly over a 12 week period, and monthly up to 6 months post administration of the immunogenic composition are performed and compared to placebo. One primary endpoint is to compare carriage rates in patients after administration of an immunogenic composition versus placebo at 3 month intervals post immunization.

Animal Models of Staphylococcal Infection

Several animal models are described below for use in assessing the efficacy of any one of the immunogenic compositions described herein.

Murine Sepsis Model (Passive or Active)

Passive Immunization Model

Mice are passively immunized intraperitoneally (i.p.) with immune IgG or monoclonal antibody. The mice are subsequently challenged 24 hours later with a lethal dose of *S. aureus*. The bacterial challenge is administered intravenously (i.v.) or i.p. ensuring that any survival could be attributed to the specific in vivo interaction of the antibody with the bacteria. The bacterial challenge dose is determined to be the dose required to achieve lethal sepsis of approximately 20% of the unimmunized control mice. Statistical evaluation of survival studies can be carried out by Kaplan-Meier analysis.

Active Immunization Model

In this model, mice (e.g. Swiss Webster mice) are actively immunized intraperitoneally (i.p.) or subcutaneously (s.c.) with a target antigen at 0, 3 and 6 weeks (or other similar appropriately spaced vaccination schedule) and subsequently challenged with *S. aureus* at week 8 by the intravenous route. The bacterial challenge dose is calibrated to achieve approximately 20% survival in the control group over a 10-14 day period. Statistical evaluation of survival studies can be carried out by Kaplan-Meier analysis.

Infectious Endocarditis Model (Passive or Active)

A passive immunization model for infectious endocarditis (IE) caused by *S. aureus* has previously been used to show that ClfA can induce protective immunity. See Vernachio et al., Antmicro. Agents & Chemo. 50:511-518 (2006). In this model of IE, rabbits or rats are used to simulate clinical infections that include a central venous catheter, bacteremia, and hematogenous seeding to distal organs. Catheterized rabbits or rats with sterile aortic valve vegetations are administered a single or multiple intravenous injection of a monoclonal or polyclonal antibody specific for the target antigen. Subsequently, the animals are challenged i.v. with a *S. aureus* or *S. epidermidis* strain. Then after challenge, heart, cardiac vegetations, and additional tissues, including kidneys, and blood are harvested and cultured. The frequency of staphylococcal infection in cardiac tissue, kidneys, and blood is then measured. In one study, when animals were challenged with either MRSE ATCC 35984 or MRSA 67-0, significant reductions in infection rate were shown using either the polyclonal antibody preparation or the monoclonal antibody to ClfA. See Vernachio et al., Antmicro. Agents & Chemo. 50:511-518 (2006).

The infectious endocarditis model has also been adapted for active immunization studies in both rabbits and rats. Rabbits or rats are immunized intramuscularly or subcutaneously with target antigen and challenged with *S. aureus* two weeks later via the intravenous route.

Pyelonephritis Model

In the pyelonephritis model, mice are immunized on wks 0, 3 and 6 (or other appropriately spaced immunization schedule) with the target antigens. Subsequently, the animals are challenged i.p. or i.v. with *S. aureus* PFESA0266. After 48 hrs, the kidneys are harvested and bacterial CFU are enumerated.

Antibodies and Antibody Compositions

The invention further provides antibodies and antibody compositions which bind specifically and selectively to one or more antigens of an immunogenic composition of the present invention. In some embodiments, antibodies are generated upon administration to a subject of an immunogenic composition of the present invention. In some embodiments, the invention provides purified or isolated antibodies directed against one or more of the antigens of an immunogenic composition of the present invention. In some embodiments, the antibodies of the present invention are functional as measured by killing bacteria in either an animal efficacy model or via an opsonophagocytic killing assay. In some embodiments, the antibodies of the invention confer passive immunity to a subject. The present invention further provides polynucleotide molecules encoding an antibody or antibody fragment of the invention, and a cell or cell line (such as hybridoma cells or other engineered cell lines for recombinant production of antibodies) and a transgenic animal that produces an antibody or antibody composition of the invention, using techniques well-known to those of skill in the art.

Antibodies or antibody compositions of the invention may be used in a method of treating or preventing a Staphylococcal infection, disease or condition associated with a *Staphylococcus* sp. in a subject, the method comprising generating a polyclonal or monoclonal antibody preparation, and using said antibody or antibody composition to confer passive immunity to the subject. Antibodies of the invention may also be useful for diagnostic methods, e.g., detecting the presence of or quantifying the levels of one or more antigens of the immunogenic compositions of the present invention.

EXAMPLES

The following examples demonstrate some embodiments of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. All parts and percents referred to herein are on a weight basis and all temperatures are expressed in degrees centigrade unless otherwise specified.

Furthermore, the following examples were carried out using standard techniques, which are well known and routine to those of skill in the art, except where otherwise described in detail. As noted above, the following examples are presented for illustrative purpose, and should not be construed in any way limiting the scope of this invention.

Example 1

Production of Antigens ClfA and ClfB

Clumping factor A (ClfA) and B (ClfB) are *S. aureus* surface proteins responsible for binding to host proteins including fibrinogen (ClfA, ClfB) and cytokeratin 10 (ClfB). ClfA and ClfB are members of a family of proteins containing the carboxyl terminal LPXTG (SEQ ID NO: 125) motif that enables the protein to become covalently linked to the cell surface. Both ClfA and ClfB belong to family of proteins (Microbial Surface Components Recognizing Adhesive Matrix Molecule, or MSCRAMMs) that recognize and bind host extracellular matrix proteins such as fibrinogen (ClfA and ClfB), fibronectin (FnbA and FnbB), collagen (Cna), and others. These proteins all share the amino terminal signal sequence that mediates transport to the cell surface. The MSCRAMMs also include an A-domain that is the functional region containing ligand-binding site for fibrinogen, fibronectin, elastin, and keratin. The A-domain can be followed by a region composed of serine-aspartate repeats (SD repeat), which is thought to span the peptidoglycan layer. The SD repeat is followed by a membrane-spanning region that includes the LPXTG (SEQ ID NO: 125) motif for covalent linkage of the protein to peptidoglycan.

The ligand binding regions of ClfA and ClfB comprising N1N2N3 of the A domain spans amino acids 40-559. The N domains of ClfA/ClfB have been assigned as follows: N1 encompasses residues 45-220; N2 encompasses residues 229-369; and N3 encompasses residues 370-559. See Deivanayagam et al. EMBO J. 21:6660-6672 (2002). In preparations of recombinant ClfA N 11N2N3, the N1 domain has been found to be protease sensitive and is easily cleaved or hydrolyzed to leave the N23 as a stable ligand binding recombinant fragment. See Deivanayagam et al. EMBO J. 21:6660-6672 (2002). Similarly, it was demonstrated that N1 domain of ClfB is also protease-sensitive and could be easily cleaved by *S. aureus* metalloprotease (McAleese, F. M. et al. J. Biol. Chem. 2001, 276, pp. 29969-29978). The crystal structure of the fibrinogen binding N23 fragment of ClfA A domain, revealed that both N2 and N3 are dominated by anti-parallel beta strands. In addition to the anti-parallel beta strands, the N2 domain contains a single turn alpha helix and two $3_{10}$ helices and the N3 domain contains three $3_{10}$ helices. See Deivanayagam et al. EMBO J. 21:6660-6672 (2002).

Sequence alignment of N2 and N3 reveals only 13% sequence identity and 36% sequence similarity over their lengths. See Deivanayagam et al. EMBO J. 21:6660-6672 (2002). The topology of the N2 and N3 domains are similar to the classic IgG fold and have been proposed to be novel variants of the IgG fold. See Deivanayagam et al. EMBO J. 21:6660-6672 (2002).

Recombinant forms of ClfA used in the immunogenic compositions described herein are fragments of ClfA comprising one or more of the N domains, for example, N1N2N3, N2N3 and are referred to herein as "recombinant ClfA" or "rClfA". In addition, any rClfA should be one that maintains the native structure of the individual N domains and critical epitopes but does not interfere with normal processes of the immunized individual after administration (i.e., does not bind fibrinogen). Mutational studies have shown that mutating Y338A (N2) completely eliminated binding of the N23 fragment to fibrinogen. (This Y338A position refers to a change from a tyrosine to an alanine at position 338 in the immature form of the polypeptide sequence with the leader sequence still attached. This change can be seen at position 310 in the mature form of the mutated ClfA polypeptide of SEQ ID NO: 123 that demonstrates a lack of binding to fibrinogen). See Deivanayagam et al. EMBO J. 21:6660-6672 (2002). Therefore, the Y338A mutation has been adopted for all fragments of ClfA in the following studies.

Similarly, recombinant forms of ClfB used in the immunogenic compositions described herein are fragments of ClfB comprising one or more of the N domains, for example, N1N2N3. N2N3 and are referred to herein as "recombinant ClfB" or "rClfB". In addition, any rClfB should be one that maintains the native structure of the individual N domains and critical epitopes but does not interfere with normal processes of the immunized individual after administration (i.e., does not bind fibrinogen). (See, for example, Walsh, E. J. et al. Microbiology (2008), 154, 550-558).

ClfA and ClfB: Overview of Cloning Strategy

The different forms of rClfA protein used to generate preclinical efficacy data include $HisClfA_{(N123)}$; $T7Clf_{(N123)}$; $T7ClfA_{(N123)}$; Y338A; $ClfA_{(N23)}$, and $ClfA_{(N23)}Y338A$. See FIG. 1. The ClfA gene contains the A region coding sequence from *S. aureus* PFESA0237 corresponding to residues 40-559. The reading frame cloned from *S. aureus* was fused to the N-terminal HisTag and linker sequences of the vector (MRGSHHHHHHGS SEQ ID NO: 127) along with three additional coding sequences (KLN) introduced at the C-terminus. (See below for detailed procedure.) Protein expressed from this vector was used for all experiments where it is referred to as $HisClfA_{(N123)}$.

The different forms of rClfA were derived from the A region (residues 40-559 of ClfA expressed by *S. aureus* PFESA0237 (top row). The $HisClfA_{(N123)}$ is expressed using the T5 promoter contained in pQE30 and all other forms are expressed using the T7 based pET expression system.

Two forms of ClfB (T7ClfB N1N2N3 and ClfB N23) were utilized for preclinical animal studies.

ClfA Cloning Procedure

The ClfA coding sequence corresponding to amino acid residues 40-559 from *S. aureus* strain PFESA0237 was cloned and the mutation, Y338A, was introduced to eliminate fibrinogen binding. The mutated ClfA gene was introduced into a T7 RNA polymerase expression vector, pET9a (Novagen) to provide plasmid, pLP1179. The DNA sequence of the region comprising the T7 promoter and coding region in pLP1179 is SEQ ID: 124. The expression vector was transformed into *E. coli* BLR(DE3) (Novagen) for production of recombinant ClfA.

Figure 2:
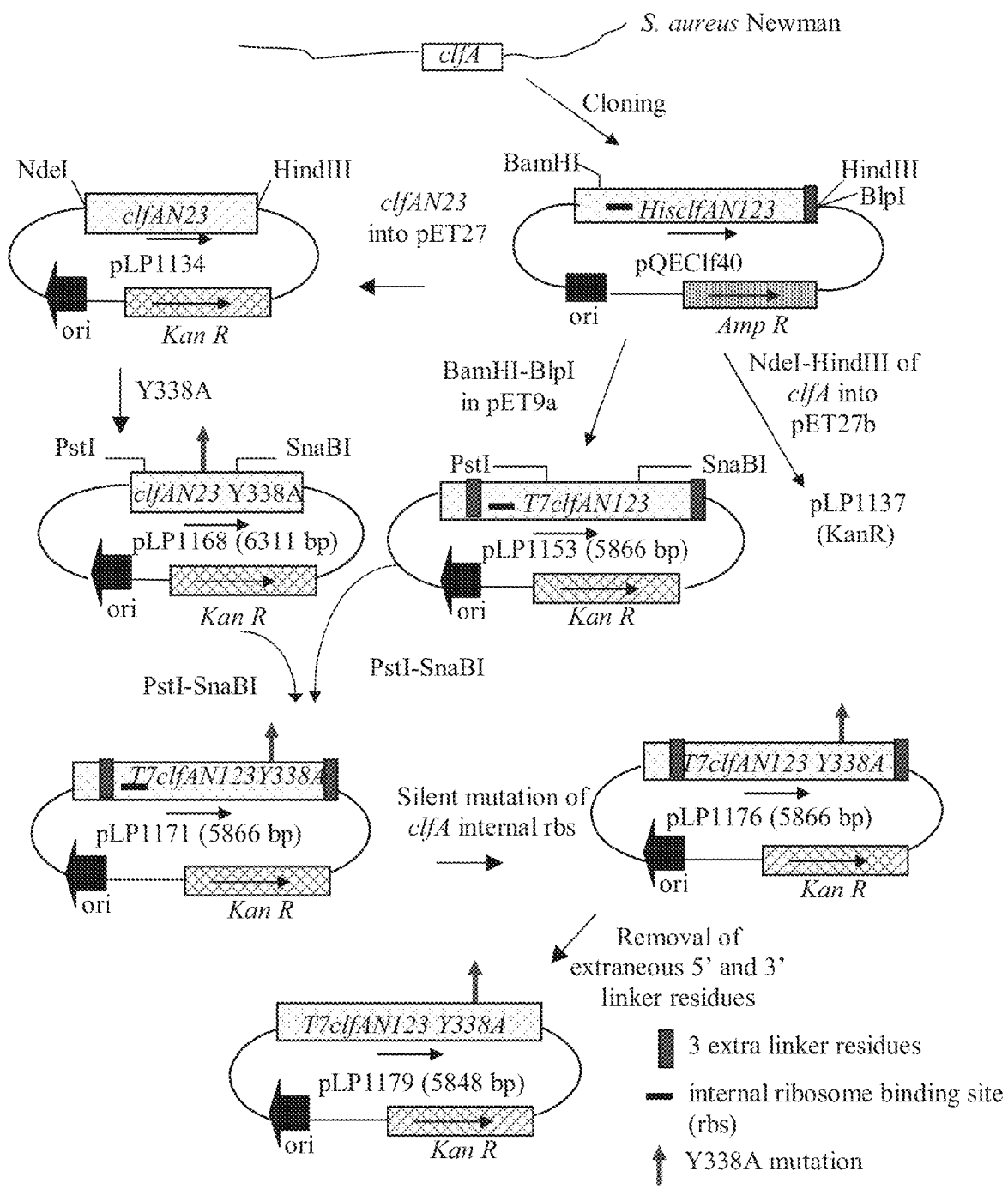
FIG. 2 depicts the cloning steps used for construction of pLP1179 for expressing ClfA.

The construction of T7ClfA$_{(N123)}$Y338A involved several steps. A summary of the cloning steps used to construct the final expression plasmid, pLP1179 is shown in FIG. 2.

The clfA DNA sequence present in pQEClf40 correspond to amino acid residues 40-559 of ClfA that was originally cloned into the BamHI/HindIII cloning site of pQE30. This creates a HisTag fusion at the N-terminal end of ClfA and the addition of three residues at the C-terminus. The ClfA coding region present in (AmpR) pQEClf40 was sub-cloned into the KanR pET 27b vector (Novagen) to create pLP1137. In addition the clfA DNA sequence corresponding to amino acid residues 221-559 was cloned into the NdeI-HindIII cloning site of pET27b to create pLP134. The N-terminal HisTag of ClfA was replaced with the N-terminal T7 by subcloning the BamHI-BlpI DNA fragment from pQEClf40 into pET9a (Novagen) to create pLP1153. The coding sequence of T7ClfA$_{(N123)}$ present in pLP1153 contains 11 N-terminal amino acid residues from the T7 tag of pET9a followed by three amino acid residues from linker sequences plus the three C-terminal linker derived residues originally present in pQE30Clf40. The Y338A mutation was first introduced into the ClfA$_{(N23)}$ coding sequence of pLP1134 to create pLP1168. Later a PstI-SnaBI DNA fragment containing the Y338A mutation from ClfA$_{(N23)}$ of pLP1168 was replaced into PstI-SnaBI of T7ClfA$_{(N123)}$ coding sequence of pLP1153 to create pLP1171. An internal ribosome binding site present in the coding sequence of T7ClfA$_{(123)}$Y338A of pLP1171 was altered by silent mutations at DNA positions 339 and 342 of the T7 rClfA Y338A ORF, changing from G to T and G to A, respectively. The resulting plasmid, pLP1176, was then used to remove the three extraneous residues, originally derived from pQE30Clf40, between the T7 tag and the start of the ClfA coding region. The three linker derived C-terminal residues were also removed at this time.

Figure 3:
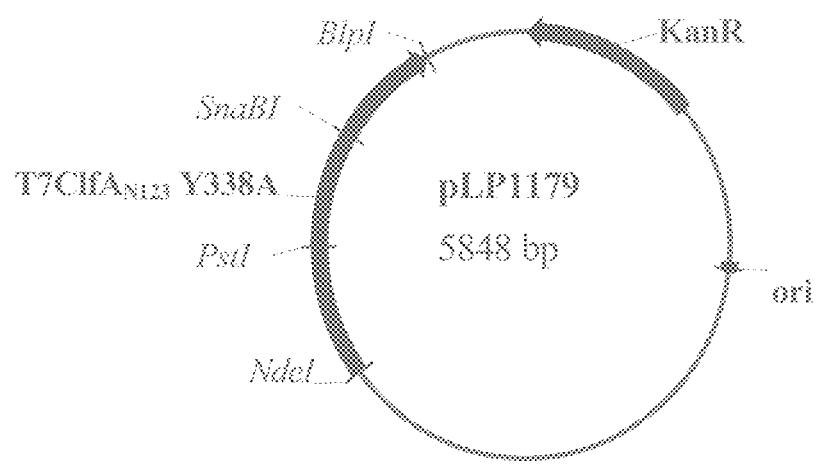
FIG. 3 depicts the T7ClfA$_{(N123)}$Y338A expression Vector, pLP1179.

The rClfA expressed by the resulting plasmid, pLP1179 (FIGS. 2 and 3), contains only the 11 N-terminal amino acids fused to residue 40-559 of ClfA$_{(N123)}$Y338A. The DNA sequence of the region comprising the T7 promoter and the coding sequence of T7 rClfA$_{(N123)}$Y338A of pLP1179 is SEQ ID NO 124.

Bacterial Strains and Plasmids

The plasmid backbone pET9a (obtained from Novagen) was used for construction of pLP1179, which expresses T7ClfA$_{(N123)}$Y338A from a T7 promoter. The plasmid contains the kanamycin resistance gene (KanR) for positive selection. The BL21(DE3) *E. coli* host strain [F-ompThsdS$_B$ ($r_B^- m_B^-$) $^{gal\ dcm\ (DE}$3)](Novagen) was originally used to obtain expression of T7ClfA$_{(N123)}$Y338A. The DE3 designation denotes the lambda lysogen containing the T7 RNA polymerase gene under control of the lacUV5 (IPTG inducible) promoter that is used for induced expression of T7 RNA polymerase and subsequent transcription from the T7 promoter proximal to the ClfA$_{(N123)}$Y338A coding sequence present in pLP1179. Upon receiving information that the BL21(DE3) lysogenic host strain is capable of inducing lytic phage upon large scale fermentations, the host strain was changed to the recA BLR(DE3) host strain [F-ompT hsdS$_B$ ($r_B^- m_B^-$) gal dcm Δ(sri-recA)306::Tn10(TcR) (DE3)] (Novagen).

Production and Purification of ClfA

For the production of ClfA, *E. coli* BLR(DE3)/pLP1179 was grown in defined medium in glucose fed-batch mode in bioreactors. When the culture reached an optical density (OD$_{600}$) between 30-50, the expression of ClfA was induced by the addition of IPTG. The culture was harvested between 3-16 hours post induction.

The cells were disrupted and the clarified soluble fraction was collected. After the addition of ammonium sulfate, the material was applied to a column containing Phenyl-Sepharose resin and eluted. Fractions containing ClfA were identified, dialyzed and loaded onto an anion exchange column (Q-Sepharose). After elution with a salt gradient, fractions containing ClfA were identified, concentrated by ultrafiltration and loaded on to a size-exclusion column (Superdex-75). Fractions containing ClfA were identified and pooled. The purity of the ClfA at this point was about 98% as measured by SDS-PAGE.

Cloning and Purification of ClfB N1N2N3

The ClfB coding sequence corresponding to amino acid residues 44-542 was cloned into a T7 RNA polymerase expression vector, pET28a (Novagen) to provide plasmid pPX1189. The expression vector was transformed into *E. coli* BLR(DE3) (Novagen) for the production of recombinant ClfB. (See Walsh, et al., Microbiology 154: 550-558 (2008).)

For the production of ClfB, *E. coli* BLR(DE3)/pLP1179 was grown in defined medium in glucose fed-batch mode in bioreactors. When the culture reached an optical density (OD$_{600}$) between 30-50, the expression of ClfB was induced by the addition of IPTG. The culture was harvested between 3-16 hours post induction.

The cells were disrupted and the clarified soluble fraction was collected. The pH of the soluble fraction was adjusted to about pH 3.2 and the precipitated impurities were removed. The pH of the soluble fraction containing ClfB was readjusted to about pH 8.0 and dialyzed to remove salts. After the addition of ammonium sulfate, the material was applied to a column containing Phenyl-Sepharose resin and eluted. Fractions containing ClfB were identified, dialyzed and loaded onto an anion exchange column (Q-Sepharose). After elution with a salt gradient, fractions containing ClfB were identified, concentrated by ultrafiltration and loaded on to a size-exclusion column (Superdex-75). Fractions containing ClfB were identified and pooled. The purity of the ClfB at this point was about 94% as measured by SDS-PAGE.

Example 2

Productions of Antigens: *Staph Aureus* MntC

Cloning *S. aureus* Lipidated MntC

Recombinant MntC was originally cloned from *S. aureus* strain Mu50. The rMntC coding sequence was amplified by PCR from *S. aureus* Mu50 genomic DNA. Two pairs of nested primers were used for the amplification (Table 2). The first pair of primers, 5'SA926-MntC ups and 3'SA926-MntC down, align to the sequence upstream and downstream of the open reading frame of rMntC. The second set of primers align to the coding sequence of rMntC allowing to amplify the sequence corresponding to amino acid residues 19-309. Restriction enzymes sites were incorporated at the 5' ends of these primers to facilitate directional cloning. PCR was carried out in a Peltier Thermal Cycler (MJ Research Inc, Walthan, Mass.) with TaKaRa PrimeSTAR HS DNA Polymerase Premix (Takara Bio USA, Madison, Wis.). PCR product was purified by QIAEX II (Qiagen, Valencia, Calif.), cleaved with the appropriate restriction endonucleases (New England BioLabs, Ipswich. MA) and sub-cloned into the araBAD promoter-driven expression vector pBAD18 Cm. This vector also contains the signal peptide of the lipoprotein P4 from *H. influenza*. The MntC PCR product was sub-cloned in frame downstream from the P4 signal peptide to create pLP1194. The DNA sequence of the MntC coding region of pLP1194 is shown in SEQ ID NO: 120. The MntC expressed from pLP1194 is a lipoprotein. The recombinant plasmid DNA was sequenced by ABI PRISM BigDye™ Terminator V.3.1 (Applied Biosystems, Foster City, Calif.) and the recombinant protein was expressed in *E. coli* BLR (NOVAGEN) for the production of lipidated rMntC.

Production and Purification of Lipidated MntC

For the production of lipidated MntC, *E. coli* BLR/pLP1194 was grown in defined medium in glucose fed-batch mode in bioreactors. When the culture reached an optical density ($OD_{600}$) of about 60, the expression of rMntC was induced by switching the feed to a mixture of glucose and arabinose. The culture was harvested about 24 hours post induction.

The cells were disrupted and the insoluble fraction was collected. Lipidated MntC was found associated with the cell membranes due to the lipid modification. MntC was extracted from the membrane fraction with a detergent (Zwittergent ZW-312). After removal of the insoluble debris, the lipidated MntC was found in the soluble fraction. The soluble fraction was applied to a column containing a mixed-mode resin and eluted with a linear salt and pH gradient. Fractions containing MntC were identified and pooled. Ammonium sulfate was added to the pool and the material was applied to a column containing Butyl-Sepharose and eluted. Fractions containing MntC were identified, desalted and loaded onto a cation exchange column (SP-Sepharose). After elution with a salt gradient, fractions containing rMntC were identified and pooled.

Cloning *S. aureus* Non-Lipidated MntC

The DNA sequence employed to express non-lipidated rMntC was isolated by PCR amplification from plasmid pLP1194. The resulting sequence corresponds to amino acid residues 19-309 and does not contain the signal sequence that directs secretion and lipidation. The DNA sequence of the rMntC coding region of pLP1215 is found in DNA SEQ ID NO: 120.

To create pLP1215, MntC was amplified by PCR from pLP1194. The MntC DNA sequence present in pLP1215 corresponds to amino acid residues 19-309 and the first codon for this construct was introduced in the forward primer used in the amplification of the gene. The primers used for PCR also contain restriction enzymes sites at the 5' ends to facilitate directional cloning (Table 2). PCR and purification of the amplified gene was carried out as described above. Purified PCR product was cleaved with the appropriate restriction endonucleases (New England BioLabs, Ipswich, Mass.) and sub-cloned into the T7 promoter-driven expression vector pET28a (Novagen, Madison, Wis.). The recombinant plasmid DNA pLP1215 was sequenced by ABI PRISM BigDye™ Terminator V.3.1 (Applied Biosystems, Foster City, Calif.) and the recombinant protein was expressed in *E. coli* BLR(DE3). Plasmid DNA for pLP1215 was purified and used to transform *E. coli* HMS174(DE3) to evaluate protein expression.

TABLE 2

MntC primers.

| Expression constructs | Primer name | Sequence (5'-3') |
|---|---|---|
| Lipidated MntC (pLP1194) | 5'SA926-MntCups | CAC AAA ATT TAC GAA TAG AAA GAA ACG AG (SEQ ID NO: 109) |
| | 3'SA926-MntCdown | AAA ATA TTG GAG ATA CCA ATA TTT TAG GTT G (SEQ ID NO: 110) |
| | 5'BamHISA926_MntC | TTT CTT <u>GGA TCC</u> GGT ACT GGT GGT AAA CAA AGC AGT G (SEQ ID NO: 111) |
| | 3'SphISA926_MntC | TTT CTT <u>GCA TGC</u> TTA TTT CAT GCT TCC GTG TAC AGT TTC (SEQ ID NO: 112) |
| Non lipidated MntC (pLP1215) | 5'NcoIMntC | TTT CTT <u>CCA TGG</u> GTA CTG GTG GTA AAC AAA GCA G (SEQ ID NO: 113) |
| | 3'BlpIMntC | TTT CTT <u>GCT CAG CAT</u> TAT TTC ATG CTT CCG TGT ACA G (SEQ ID NO: 114) |

Synthetic oligonucleotides used to generate rMntC constructs. Restriction endonuclease sites are underlined. The nucleotides in boldface indicate the first codon for the non-lipidated rMntC construct.

Production and Purification of Non-Lipidated rMntC

For the production of non-lipidated rMntC, *E. coli* HMS174(DE3)/pLP1215 was grown in defined medium in glucose fed-batch mode in bioreactors. When the culture reached an optical density ($OD_{600}$) of about 60 to 80, the expression of rMntC was induced by addition of IPTG. The culture was harvested about 24 hours post induction. The cells were disrupted and the clarified soluble fraction was collected. The lysate was applied to a column containing a cation exchange resin (SP-Sepharose) and eluted with a linear salt gradient. Fractions containing MntC were identified. After the addition of ammonium sulfate, the material was applied to a column containing Phenyl-Sepharose resin and eluted. After elution, fractions containing rMntC were identified, pooled, and desalted. The purity of the rMntC at this point was >95% as measured by SDS-PAGE.

Example 3

Production of Capsule Polysaccharides CP5 and CP8

In this example, production of various sizes of *S. aureus* capsule polysaccharides type 5 and 8 is described. The structures of the CP5 and CP8 polysaccharides are shown in FIG. 4. The methods described herein are effective in producing CP5 and CP8 with molecular weights ranging from about 50 kDa to 800 kDa. Based on growth characteristics and the quantity of capsule produced, strain PFESA0266 was chosen for CP5 production while strains PFESA0005 or PFESA0286 were used for the production of CP8. The capsules isolated from strains PFESA0005 and PFESA0286 were shown to be identical.

For production of capsular polysaccharides, the strains were grown in a complex medium consisting primarily of a carbon source (either lactose or sucrose), hydrolyzed soyflour as the nitrogen source, and trace metals. The strains were grown in bioreactors for 2 to 5 days.

Purification of CP5 and CP8 used for the preparation of conjugates was performed by two different methods that rely on elevated temperature and low pH to effect the release of capsule from the cell and reduce the molecular weight of the polysaccharide. The resulting molecular weight is dependent on the time, temperature and pH of the hydrolysis step.

Characterization of CP5 and CP8 was performed using the techniques specified in Table 3. Capsule polysaccharides produced by this procedure result in pure polysaccharides with low levels of protein, NA, peptidoglycan and TA contaminants. See Tables 4 and 5.

TABLE 3

| Characterization Assays for Purified *S. aureus* CP5 and CP8 | |
| --- | --- |
| Specificity | Assay |
| Residual Protein | Lowry colorimetric assay |
| Residual Nucleic acids | 260 nm scan |
| Residual Teichoic Acid | Phosphate colorimetric assay |
| Residual Peptidoglycan | HPAEC-PAD |
| Size | SEC-MALLS |
| Composition | HPAEC-PAD |
| Identity | 1H-NMR or reaction with specific mAb |
| O-acetylation | 1H-NMR |
| Concentration | MALLS-RI or HPAEC-PAD |

In the first method, following release of the capsule from the cell and reduction of molecular weight, the capsule preparation is treated with a cocktail of enzymes (ribonuclease, deoxyribonuclease, lysozyme, and protease) to digest impurities. After incubation, residual impurities are precipitated by the addition of ethanol (final concentration about 25%). After removal of the residual ethanol, solution containing capsule was loaded onto an anion exchange column (Q-Sepharose) and eluted with a linear salt gradient. Fractions containing capsule were pooled and treated with sodium meta-periodate. This treatment resulted in the oxidative hydrolysis of residual teichoic acid contaminant, but did not affect the CP5 or CP8. The reaction was quenched by the addition of ethylene glycol. The material was concentrated and diafiltered against dH20 to remove any residual reagents and by-products.

The second method used to produce capsules did not involve the use of enzymes to digest the various cell-derived impurities. In this method, following release of the capsule from the cell and reduction of molecular weight the hydrolyzed fermentation broth was clarified by microfiltration followed by ultrafiltration and diafiltration. The solution was treated with activated carbon to remove impurities. After carbon treatment, the material was treated with sodium meta-periodate to oxidize residual teichoic acid followed by quenching with propylene glycol. The material was concentrated and diafiltered against $dH_2O$ to remove any residual reagents and by-products.

Capsules produced using either method result in pure polysaccharides with low levels of protein, nucleic acid and teichoic acid contaminants. The methods described can be used to produce specific ranges of the desired high molecular weight polysaccharides simply by varying the conditions of hydrolysis. A particularly advantageous range of high molecular weight polysaccharides, ranging from 70 to 150 kDa, is useful in making immunogenic compositions by conjugating polysaccharide to a carrier protein.

Examples of High Molecular Weight Capsule Polysaccharide obtainable by the methods described herein are shown in Table 4 below. Batches of purified higher MW CP5 also had high purity as indicated by no TA, peptidoglycan and low residual protein. See Table 4. The range of molecular weights in these examples spanned 132.7 kDa to 800 kDa and the purified polysaccharides were highly O-acetylated, ranging from 90-100%, and 100% for N-Acetylation. See Table 4.

Examples of lower Molecular Weight Capsule Polysaccharide obtainable by the methods described herein are shown in Table 5 below. Batches of purified lower MW CP8 had high purity as indicated by no teichoic acid (TA), peptidoglycan and low residual protein. See Table 5. The range of lower molecular weights spanned 20.4 kDa to 65.1 kDa and the purified polysaccharides were highly O-acetylated, ranging from 75-96%. The levels of nucleic acid contamination was low, ranging from 0.5-%-2.45%. See Table 5.

TABLE 4

| Characterization of CP5 Preparations | | | | | |
| --- | --- | --- | --- | --- | --- |
| SA CP-5 | MW (kDa) | CP (mg/ml) | O-acetyl (%) NMR | Identity NMR | N-acetyl (%) NMR |
| 1 | 800.1 | 3.164 | 100 | Pass | 100 |
| 2 | 132.7 | 1.172 | 90 | Pass | 100 |
| 3 | 335.4 | 0.975 | 90 | Pass | 100 |
| 4 | 366.8 | 0.865 | 90 | Pass | ND |

TABLE 5

| Characterization of CP8 Preparations | | | | | |
| --- | --- | --- | --- | --- | --- |
| SA CP-8 | Total CP Purified mg | MW (kDa) (g/mol) | Protein (Lowry) % (w/w) | NA (260 nm scan) % (w/w) | O-Acetyl NMR % |
| 5 | 310 | 27.0 | 1.2 | 0.94 | 100 |
| 6 | 438 | 29.0 | 2.4 | 2 | 100 |
| 7 | 179 | 20.4 | 0.37 | 0.12 | 108 |
| 8 | 101 | 46.9 | Below Detection | 0.5 | 94 |
| 9 | 91 | 65.1 | 1.15 | 2.45 | 96 |
| 10 | 578 | 35.5 | 2.47 | 0.65 | 75 |

Molecular Weight Selection of Capsular Polysaccharides

This kinetic analysis demonstrates that a broad range of molecular weights of capsule polysaccharides can be generated by the methods described herein. Initially, larger polysaccharides were produced by the bacterial cells, and subsequently, a desired molecular weight range may be selected and then purified by manipulation of the pH1 and heat conditions of the heat and hydrolysis steps.

Heat treatment of *S. aureus* fermentation broth was a process step between fermentation and CP recovery. This process step uses heat to treat pH-adjusted broth for a specified period. The goals of the heat treatment at low pH were to kill cells, inactivate enterotoxins, release cell bound polysaccharide, and reduce molecular weight to the desired size. Among these goals, the reduction of molecular weight was the slowest in terms of processing time required in this step. Therefore, the other goals were inevitably achieved within the treatment time considered.

Heat Treatment

Temperature and pH conditions for selecting various molecular weight ranges of capsule polysaccharides were determined. The broth pH was adjusted with concentrated sulfuric acid. Then, the broth temperature was raised to the set value. The heat treatment time started as soon as the temperature reached the set point. When the desired treatment time was reached, the broth was cooled to room temperature. In-process samples were taken to determine polysaccharide concentration and molecular weight by HPLC and SEC-MALLS systems, respectively. The MW data was used in the kinetic analysis. The MW profiles were determined over time of CP5 at pH 4.0, 4.5 and 5.0 and CP8 at pH 3.5, 4.0, and 5.0. See FIGS. 5A and 5B.

The kinetics of mild acid hydrolysis of polysaccharides was conducted using purified CP-5 and CP-8 obtained from the process. The purified polysaccharide solution was adjusted to the desired pH for the experiment with sulfuric acid. The samples were placed in an oil bath equipped with a precision temperature control system. Each sample was taken out at a predetermined time interval and was quenched in an ice bucket. At the end of the experiment, an aliquot of 1M Tris buffer (pH 7.5) was added to the sample to adjust the pH back to about 7. The samples were analyzed by a SEC-MALLS system. The MW data was used in the kinetic analysis. The effect of temperature on MW profiles of CP5 at pH 4.5 and CP8 at pH 3.5 was determined over time. See FIGS. 6A and 6B. This acid hydrolysis procedure may be implemented using the fermenter culture or at an intermediate stage of purification or, as shown here, using the purified polysaccharide. Other molecular weight reduction steps, such as sonication or sheer, may be similarly be implemented.

Results

The effect of pH on the reduction of MW in heat treatment is shown in FIGS. 5A and 5B for CP-5 and CP-8, respectively. It can be seen that a lower pH was more effective in reducing the size of polysaccharide. The data also suggest that CP-5 was more difficult to hydrolyze than CP-8 at the same pH. Considering the CP8 profiles, ranges of molecular weights between 300 kDa and 600 kDa can be generated using a pH of 5 at 95° C. for between 15 minutes and 120 minutes. Likewise, choosing a pH of 4 at 95° C. for between 15 minutes and 120 minutes can yield CP8 polysaccharide molecular weight ranges between 250 kDa and 450 kDa. In addition, choosing a pH of 3.5 at 95° C. for between 15 minutes and 120 minutes can yield CP8 polysaccharide molecular weight ranges between 120 kDa and 450 kDa.

The effect of temperature on MW reduction was conducted using the purified polysaccharides recovered from the recovery process. The results are shown in FIGS. 6A and 6B. As shown, the higher the temperature, the faster the rate of hydrolysis and broader the range of the molecular weights of polysaccharide produced with time. Use of a lower temperature, 55° C. versus 95° C. at the same pH, produces a narrower range of polysaccharide molecular weights.

Figure 7:
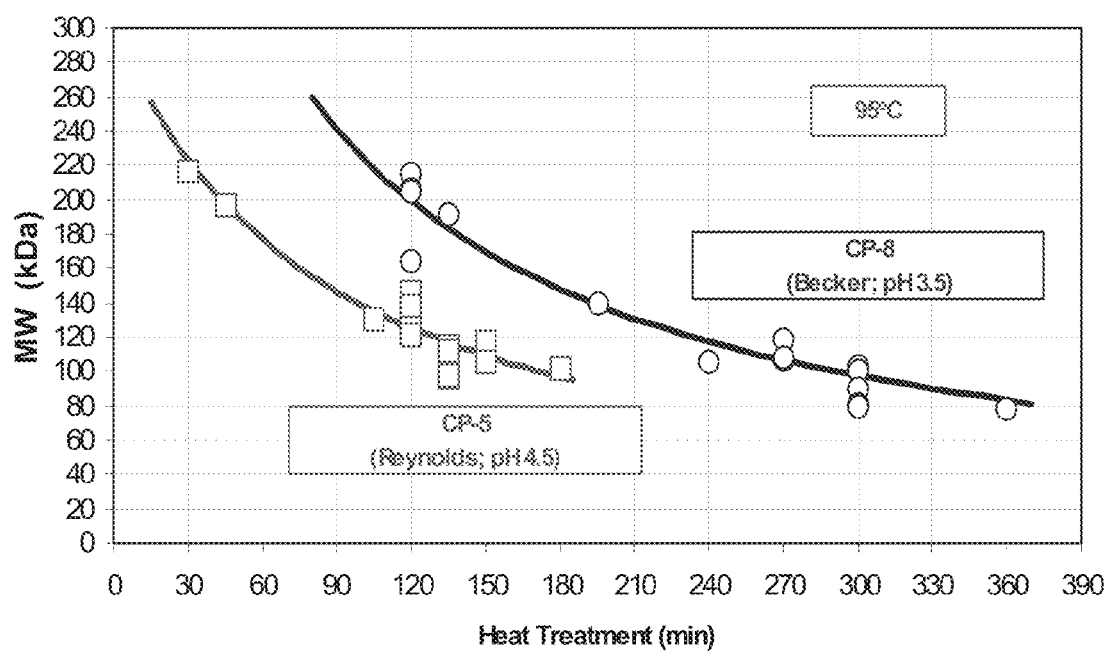
FIG. 7 demonstrates the correlation of the molecular weight of purified CP5 and CP8 with the treatment time for mild acid hydrolysis.

Furthermore, FIG. 7 demonstrates the correlation between the molecular weight of purified CP5 and CP8 with the treatment time for mild acid hydrolysis. The purified polysaccharide is the final product obtained from the recovery process detailed previously. As shown in FIG. 7, the increase in time of heat treatment of the *S. aureus* PFESA0266 strain at pH 4.5 results in the generation of smaller molecular weight CP5 polysaccharides, whereas shorter heat treatment times at pH 4.5 result in the generation of higher molecular weight CP5 polysaccharides. The size of the CP5 polysaccharides ranged from about 90 kDa to about 220 kDa depending on the length of time of heat treatment at low pH (4.5). Likewise, the increase in time of heat treatment of the *S. aureus* PFESA0005 strain at pH 3.5 results in the generation of smaller molecular weight CP8 polysaccharides, whereas shorter heat treatment times at pH 3.5 result in the generation of higher molecular weight CP8 polysaccharides. The size of the CP8 polysaccharides ranged from about 80 kDa to about 220 kDa depending on the length of time of heat treatment at low pH (3.5). The correlation between the time of heat treatment at low pH and the size of the purified CP5 and CP8 polysaccharides, as shown in this study, allows for an estimation of the treatment time required to produce purified polysaccharide with a specified range of molecular weight.

It is important to note that as demonstrated above the full range of molecular weights of capsule polysaccharides for both CP5 and CP8 from 20 kDa to more than 800 kDa can be produced, released and purified. The methods described may be used to produce specific ranges of desired high molecular weight capsule polysaccharides. A particularly advantageous range of high molecular weight capsule polysaccharide type 5 and type 8 can be generated from these methods having molecular weights ranging from 70 to 150 kDa. See Table 6. This range of molecular weights of capsule polysaccharide is useful in making immunogenic compositions by conjugating the polysaccharide to a carrier protein. Alternatively, this advantageous range of high molecular weight capsule polysaccharide ranges from 80 to 140 kDa of CP5 and CP8. See Table 6. Another advantageous range of high molecular weight capsule polysaccharide CP5 and CP8 is from 90 to 130 kDa, or from 90 to 120 kDa of CP5 and CP8. See Table 6. The conditions used to generate the CP5 capsule polysaccharide having a molecular weight range of from about 100 to 140 kDa are as follows: 95° C., pH 4.5 for 135 minutes. The conditions used to generate the CP8 capsule polysaccharide having a molecular weight range of from about 80 to 120 kDa are as follows: 95° C., pH 3.5 for 300 minutes.

TABLE 6

Production of Specific Range of High Molecular Weight CP5 and CP8

| Run | CP8 MW (kDa) | CP5 MW (kDa) |
|-----|--------------|--------------|
| 1 | 98 | 142 |
| 2 | 89 | 108 |
| 3 | 108 | 142 |
| 4 | 108 | 108 |
| 5 | 89 | ND |
| 6 | 100 | ND |
| 7 | 99 | 63 |
| 8 | 113 | 72 |
| 9 | 105 | 74 |

TABLE 6-continued

Production of Specific Range of
High Molecular Weight CP5 and CP8

| Run | CP8 MW (kDa) | CP5 MW (kDa) |
|---|---|---|
| 10 | 100 | 63 |
| 11 | 87 | ND |

ND = not done

Example 4

Conjugation of Capsule Polysaccharides CP5 and CP8 to CRM$_{197}$

This example describes processes and characterization assays used in the production of S. aureus CP5-CRM$_{197}$ and CP8-CRM$_{197}$ conjugates. Several conjugation chemistries were evaluated for conjugating S. aureus capsule polysaccharides CP5 and CP8 to a carrier protein. Conjugation using PDPH (3-2-pyridyldithio)-propionyl hydrazide) results in covalent thioether bond and CDI/CDT (1,1-carboyldiimidazole/1,1-carboyl-di-1,2,4-triazole) results in a one-carbon or zero-carbon linker between CP and carrier protein.

Conjugation of CP to CRM$_{197}$ by PDPH Conjugation Chemistry

The PDPH conjugation chemistry is a multi-step process that involves activation of the polysaccharide, removal of the thiol protecting group, purification of the activated polysaccharide intermediate, activation and purification of the CRM$_{197}$ protein, and conjugation of the activated components followed by purification. After introduction of a thiol group containing linker to the polysaccharide and a haloacetyl group to the CRM$_{197}$ protein carrier, S. aureus CP5 and CP8 polysaccharides were linked to the protein carrier through a thioether bond. Bromoacetyl groups were introduced into the CRM$_{197}$ protein by reaction of amine groups with the N-hydroxysuccimide ester of bromoacetic acid. To generate thiolated CP, the carbodiimide activated carboxylate groups of N-acetylmannosaminouronic acid in CP were coupled to the hydrazide group of the sulfhydryl-reactive hydrazide heterobifunctional linker 3-(2-pyridyldithio)-propionyl hydrazide (PDPH). Thiols of PDPH-thiolated CP, generated by reduction with DTT and purified by SEC on a Sephadex G25 column, reacted with bromoacetyl groups of activated protein resulting in covalent thioether linkage formed by bromine displacement between CP and the protein. Non-reacted bromoacetyl groups were "capped" with cysteamine hydrochloride (2-aminoethanethiol hydrochloride). The reaction mixture was then concentrated and diafiltered. The remaining unconjugated bromoacetyl groups were capped with cysteamine hydrochloride to ensure no reactive bromoacetyl groups were left after conjugation. This formed a covalent bond between the thiol end of cysteamine and the acetyl group on the lysine residue after displacement of bromine.

Thiolation of S. aureus Capsular Polysaccharide with PDPH

The polysaccharide was first activated by thiolation with PDPH. The polysaccharide was mixed with a freshly prepared PDPH stock solution (250 mg/mL in DMSO), an EDAC stock solution (90 mg/mL in diH$_2$O), and MES buffer stock solution (0.5M, pH 4.85) to make the final solution 0.1 M MES, and 2 and 4 mg CP/mL while maintaining a CP:PDPH:EDAC ratio by weight of 1:5:3 for CP 5 and 1:0.6:1.25 for CP 8. This mixture was incubated for 1 hour at room temperature and then dialyzed against a 1000× volume of distilled H$_2$O four times using a 3500 MWCO dialysis device at between 4° and 8° C. to remove unreacted PDPH. The PDPH-linked polysaccharide was made 0.2 M DTT and incubated at room temperature for 3 hours or overnight at between 4 and 8° C. Excess DTT as well as the by-products of the reaction were separated from the activated saccharide by SEC using Sephadex G25 resin and distilled water as the mobile phase. Fractions were assayed by the DTDP assay for thiol groups and thiol-positive fractions that eluted near the void volume of the column were pooled. The pool of fractions was assayed by the PAHBAH and the O-acetyl assays to determine the degree of activation which is expressed as a molar percent of the repeat units containing a thiol group (molar concentration of thiols/molar concentration of repeat units). The activated polysaccharide was lyophilized and stored at −25° C. until needed for conjugation.

Carrier Protein Activation

Separately, the carrier protein was activated by bromoacetylation. CRM$_{197}$ was diluted to 5 mg/mL with 10 mM phosphate buffered 0.9% NaCl pH 7 (PBS) and then made 0.1 M NaHCO$_3$ pH 7.0 using 1 M stock solution. The N-hydroxysuccinimide ester of bromoacetic acid (BAANS) was added at a CRM$_{197}$:BAANS ratio 1:0.25 (w:w) using a BAANS stock solution of 20 mg/mL DMSO. This reaction mixture was incubated at between 4 and 8° C. for 1 hour then purified using SEC on Sephadex G-25. The purified activated CRM$_{19}$; was assayed by the Lowry assay to determine the protein concentration and then diluted with PBS to 5 mg/mL. Sucrose was added to 5% wt/vol as a cryoprotectant and the activated protein was frozen and stored at −25° C. until needed for conjugation.

Coupling Reaction

Once the activated capsule polysaccharide and activated carrier protein were prepared, the two were combined in a conjugation reaction. The lyophilized and thiolated polysaccharide was dissolved in 0.16 M borate pH 8.95, mixed with thawed bromoacetylated CRM$_{197}$ and distilled water to make the final solution 0.1 M borate, 1:1 wt/wt ratio of CRM$_{197}$:CP, and 1 mg/mL polysaccharide for CP8 and 2 mg/mL polysaccharide for CP5. This mixture was incubated at room temperature for between 16 and 24 hours. Unreacted bromoacetyl groups on the protein were capped by adding cysteamine hydrochloride at a ratio of CRM$_{197}$:cysteamine of 1:2 (wt/wt) using a 135 mg/mL stock solution of cysteamine dissolved in 0.1 M borate pH 8.95 and incubated for 4 hours at room temperature. The capsule polysaccharide-CRM$_{197}$ conjugate (conjugate) was purified by diafiltering 50-fold against 0.9% NaCl using a 100K polyethersulfone ultrafilter.

The results from the reproducibility of CP5 and CP8 thiolation studies with PDPH demonstrated that the degree of activation of CP5 was in the range 11 to 19% which corresponds to approximately one linker molecule attached per ten CP repeat units to one linker molecule per five repeat units. The CP8 activation was in the range of 12 to 16%, which was very similar to activation of CP5.

Bromoacetylation of lysine residues of CRM$_{197}$ was very consistent, resulting in the activation of 19 to 25 lysines from 39 lysines available. The reaction produced high yields of activated protein.

Conjugation of CP to CRM$_{197}$ by CDI/CDT Conjugation Chemistry

CDI and CDT afford a one-step conjugation process where the polysaccharide is activated in an anhydrous environment (DMSO) to form imidazole or triazole carbamate moieties with available hydroxyls and acylimidazole or acyltriazole moieties with carboxylic acids. Addition of a protein carrier (in DMSO) leads to the nucleophilic displacement of the imidazole or triazole by lysine and formation of a carbamate linkage (for activated hydroxyls) and the amide linkage (for activated carboxylic acids). The reaction solution is diluted 10-fold into an aqueous solution to remove unreacted activation groups and then purified by diafiltration.

Both conjugation chemistries produced CP covalently linked to the carrier protein, which was indicated by the presence of the saccharide and protein in the fractions from size exclusion chromatography, and by amino acid analysis of glycolaldehyde capped or cysteamine hydrochloride capped conjugate.

Summary of the results from the preparation of several lots of conjugates prepared by both PDPH and CDI/CDT chemistries for both capsular serotypes with polysaccharide size in the range of 20 to 40 kDa are shown in Table 7 below. There were no significant differences in the free capsule polysaccharide, ratio of CP:Protein and yields of conjugates generated by these two conjugation methods. The antigenicity of conjugated CP was not altered by conjugation as portrayed by identity precipitin line between conjugates and native CP.

TABLE 7

Characterization of SA CP5-$CRM_{197}$ and CP8-$CRM_{197}$ Prepared by Two Conjugation Chemistries

| Conjugate | Chemistry | CP Yield (%) | Protein Yield (%) | Output Ratio | Free saccharide (%) | Free Protein (%) | Lysines Modified | Size (Mw or Kd (% less than 0.3), sacc/prot)) |
|---|---|---|---|---|---|---|---|---|
| SA CP5-$CRM_{197}$ | CDT | 19-27 | 35 | 0.5-0.8 | 10-40 | <1 | 18-22 | 38/61 to 76/74 |
|  | PDPH | 26-52 | 40-99 | 0.4-1.0 | 23-50 | ND | ND | $7.5 \times 10^5$ to $2.3 \times 10^6$ |
| SA CP8-$CRM_{97}$ | CDI | 46-62 | 54-55 | 0.8-0.9 | 22-25 | <1 | 7-8 | 34/57 to 60/57 |
|  | PDPH | 34-70 | 61-83 | 0.6-0.9 | 15-41 | ND | 11-16 | 74-92% |

As shown above, the methods described herein may be used to produce specific ranges of desired high molecular weight capsule polysaccharides. The aim of this study was to prepare conjugates from a pre-selected range of high molecular weights that could be filtered and purified CP for use in immunogenic compositions. In this example, eight batches where the CP5 capsule polysaccharide ranged in molecular weight from about 90 kDa to about 120 kDa were selected and conjugation was performed using activation with triazole (CDT). See Table 8. The molecular weights of the resulting conjugates ranged from 1533 kDa to 2656 kDa. The number of conjugated lysines per $CRM_{197}$ ranged from a high of 22 to a low of 15. The free capsule polysaccharide ranged from a high of 18% to a low of 11%. See Table 8.

TABLE 8

Conjugates With Preselected MW Range of CP5

| Run | Poly MW (kDa) | Sacc Yield (%) | Free saccharide (%) | MW by SEC-MALLS (kDa) | Lysines Modified |
|---|---|---|---|---|---|
| 1 | 121 | 63 | 11 | 2130 | 19 |
| 2 | 92 | 72 | 16 | 1533 | 22 |
| 3 | 119 | 74 | 14 | 2656 | 15 |
| 4 | 115 | 63 | 18 | 1911 | 15 |

Table 9 summarizes the analysis of CP8 conjugates where the CP8 capsule polysaccharide ranged in molecular weight from about 87 kDa to 113 kDa and the imidazole conjugation chemistry was utilized. The molecular weights of the resulting conjugates ranged from 595 kDa to 943 kDa. The number of conjugated lysines per $CRM_{197}$ ranged from a high of 9 to a low of 3. The free capsule polysaccharide ranged from a high of 6% to a low of 2%. See Table 9.

TABLE 9

Conjugates With Preselected MW Range of CP8

| Run | Poly MW (kDa) | Sacc Yield (%) | Free saccharide (%) | MW by SEC-MALLS (kDa) | Lysines Modified |
|---|---|---|---|---|---|
| 1 | 99 | 88 | 6 | 943 | 4 |
| 2 | 113 | 73 | 5 | 841 | 3 |
| 3 | 105 | 79 | 3 | 719 | 7 |
| 4 | 100 | 86 | 2 | 630 | 9 |
| 5 | 87 | 90 | 3 | 595 | 6 |

Both conjugation chemistries produce CP covalently linked to carrier protein. There were no significant differences in free capsule polysaccharide, ratio of CP:Protein and yields of conjugates generated by these two methods.

Example 5

Sequence Diversity of Polypeptide Fragments N1, N2 and N3 of ClfA

In this example the protein sequence heterogeneity of ClfA polypeptide fragments N1, N2 and N3 from disease causing isolates obtained from various sources was evaluated. ClfA genes were sequenced from strains of S. aureus associated with multiple disease states. Sequence information from additional strains was obtained from GenBank to generate sequences from relevant strains. Table 10 lists different ClfA sequences.

The sequence alignment of ClfA proteins from different disease-causing strains of S. aureus is shown in FIG. 8A-8E. The protein sequences were aligned using MUSCLE. See Edgar, R. C. Nucleic Acids Research 32 (5):1792-1797 (2004). The alignments were displayed using SHOWALIGN. See Rice, P. et al., "EMBOSS: The European Molecular Biology Open Software Suite" Trends in Genetics, 16 (6): 276-277 (2000). Many of the sequences recurred multiple times without variation. For clarity each unique sequence was placed in the alignment only once. See FIG. 8A-8E. Only unique sequences were included in the sequence listing. For example, the protein sequence of ClfA_001 was obtained from multiple different strains without any variation. See FIG. 8A-8E. The sequence listing number for any sequence can also be obtained from Table 10: ClfA strains and Sequence Listings. Table 10 lists one example strain that contained this same ClfA_001 protein sequence. This sequence is shown in the first row of the alignment in FIG. 8A-8E. This alignment of unique sequences of the ClfA antigen indicates that polymorphisms were distributed throughout the entire A region (N1-N2-N3) of ClfA. In some cases, for any given unique protein sequence of ClfA, more than one nucleotide sequence, encoding the same protein, was discovered. Only the most frequently occurring DNA sequence was included in the sequence listing and in Table 10. For ClfA, the following sequences are disclosed herein and are not found in GenBank: ClfA_003, ClfA_005, ClfA_008, ClfA_009, ClfA_013, ClfA_014, ClfA_015, ClfA_016, ClfA_017, ClfA_018, ClfA_019, ClfA_020, ClfA_021, ClfA_022, ClfA_023, and ClfA_024.

TABLE 10

ClfA strains and Sequence Listings

| Example Strain | DNA-ClfA | NT SEQ ID NO: | Protein-ClfA | AA SEQ ID NO: | % Identity to Antigen |
|---|---|---|---|---|---|
| PFESA0131 | clfA_001-1 | 61 | clfA_001 | 62 | 99 |
| PFESA0074 | clfA_002-1 | 63 | clfA_002 | 64 | 92 |
| PFESA0072 | clfA_003-1 | 65 | clfA_003 | 66 | 99 |
| PFESA0159 | clfA_004-1 | 67 | clfA_004 | 68 | 94 |
| PFESA0154 | clfA_005-1 | 69 | clfA_005 | 70 | 91 |
| PFESA0096 | clfA_006-1 | 71 | clfA_006 | 72 | 91 |
| PFESA0269 | clfA_007-1 | 73 | clfA_007 | 74 | 91 |
| PFESA0081 | clfA_008-1 | 75 | clfA_008 | 76 | 97 |
| PFESA0005 | clfA_009-1 | 77 | clfA_009 | 78 | 95 |
| PFESA0139 | clfA_010-1 | 79 | clfA_010 | 80 | 99 |
| PFESA0237 | clfA_011-1 | 81 | clfA_011 | 82 | 100 |
| PFESA0157 | clfA_012-1 | 83 | clfA_012 | 84 | 96 |
| PFESA0069 | clfA_013-1 | 85 | clfA_013 | 86 | 92 |
| PFESA0002 | clfA_014-1 | 87 | clfA_014 | 88 | 98 |
| PFESA0147 | clfA_015-1 | 89 | clfA_015 | 90 | 91 |
| PFESA0094 | clfA_016-1 | 91 | clfA_016 | 92 | 98 |
| PFESA0143 | clfA_017-1 | 93 | clfA_017 | 94 | 97 |
| PFESA0129 | clfA_018-1 | 95 | clfA_018 | 96 | 99 |
| PFESA0128 | clfA_019-1 | 97 | clfA_019 | 98 | 92 |
| PFESA0148 | clfA_020-1 | 99 | clfA_020 | 100 | 91 |
| PFESA0140 | clfA_021-1 | 101 | clfA_021 | 102 | 98 |
| PFESA0152 | clfA_022-1 | 103 | clfA_022 | 104 | 91 |
| PFESA0141 | clfA_023-1 | 105 | clfA_023 | 106 | 96 |
| PFESA0160 | clfA_024-1 | 107 | clfA_024 | 108 | 94 |

The phylogeny of the ClfA protein sequences was examined and a phylogenetic tree was constructed. Sequences were aligned using ClustalW. See Chenna R, Sugawara H. Koike T. et al. Nucleic Acids Research. 31(13):3497-3500 (2003). Neighbor-joining trees were bootstrapped 1000 times and were displayed with MEGA 4.0. See Tamura K, et al., Molecular Biology & Evolution. 24(8):1596-1599 (2007). Bootstrap values, indicated on the branches, are the number of times that branch was reproduced in 1,000 trials. Values less than 500 (50% reproducibility) are considered to be poorly supported.

Figure 9:
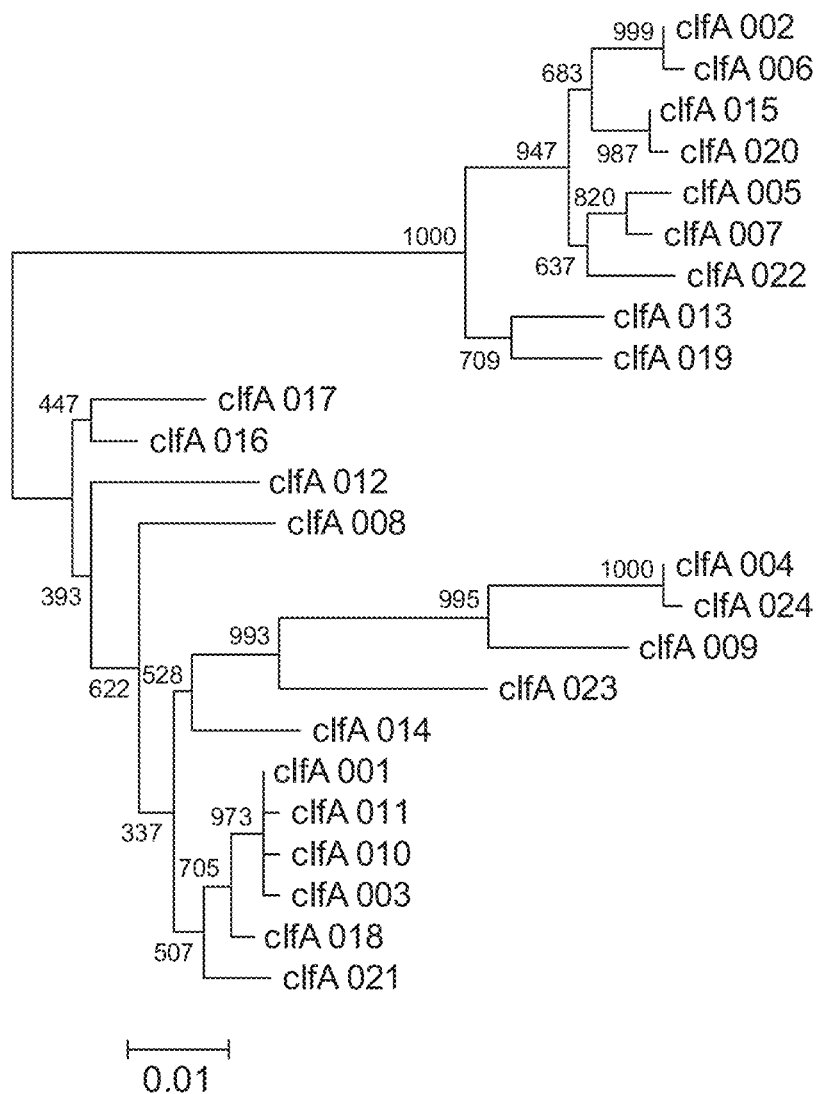
FIG. 9 depicts the ClfA phylogenetic tree.

The ClfA sequences form a tree with 2 major branches. See FIG. 9. The separation of these two groups is very well supported in the phylogeny. One branch (top) includes 9 sequences that are fairly closely related to one another (96-99% identity) but more distantly related to the candidate sequence clfA_011, to which they are 91-92% identical. The second group, which includes clfA_011, is more diverse and the phylogeny in this group is not as well supported. These protein sequences range from 93-99% identical to one another.

Example 6

Sequence Diversity of Polypeptide Fragments N1, N2 and N3 of ClfB

In this example, the protein sequence heterogeneity of ClfB N1, N2 and N3 polypeptide fragments from 92 disease-causing isolates obtained from various sources was evaluated. ClfB genes were sequenced from strains of *S. aureus* associated with multiple disease states. See Table II. Information from additional strains was obtained from GenBank to generate additional sequences.

Figure 11:
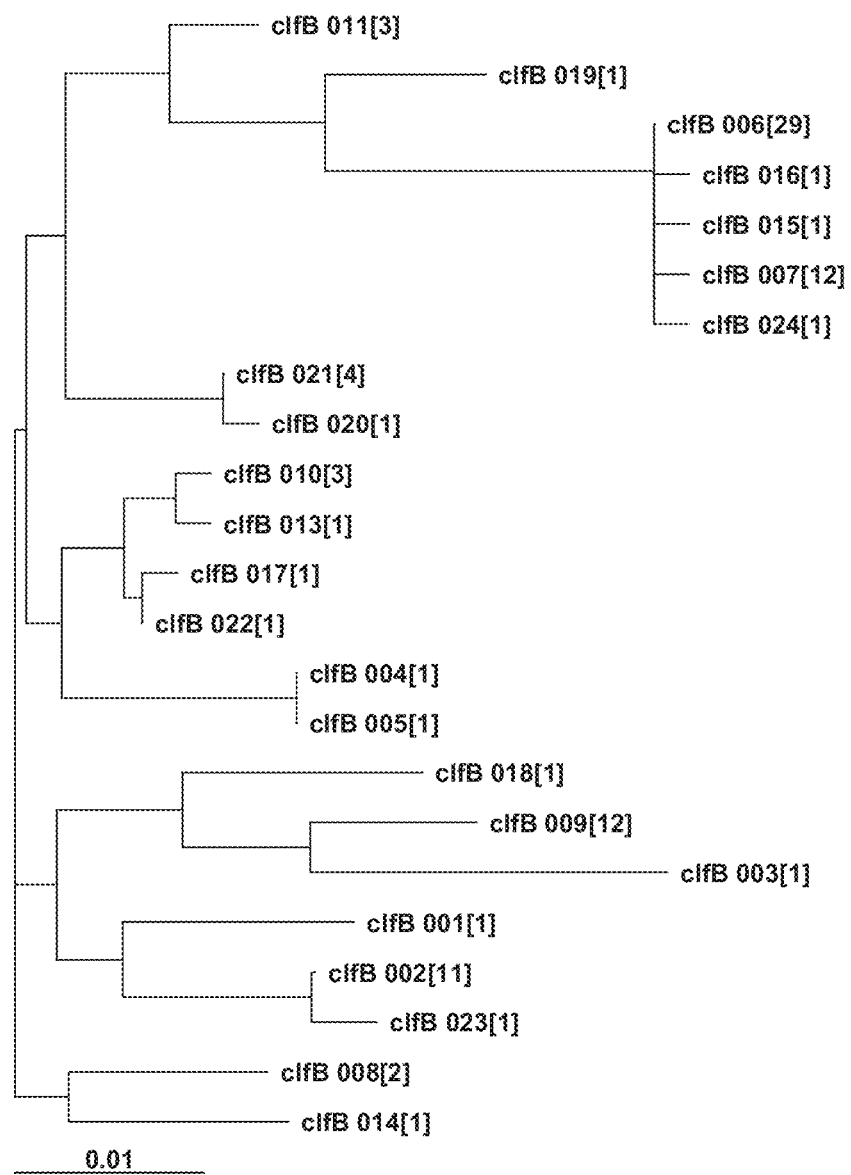
FIG. 11 depicts the ClfB phylogenetic tree.

The sequence alignment of ClfB proteins from different disease-causing strains of *S. aureus* is shown in FIG. 10A-10E. The protein sequences were aligned using MUSCLE. See Edgar, R. C. Nucleic Acids Research 32 (5): 1792-1797 (2004). The alignments were displayed using SHOWALIGN. See Rice, P. et al., "EMBOSS: The European Molecular Biology Open Software Suite" Trends in Genetics, 16 (6): 276-277 (2000). See FIG. 10A-10E ClfB align. As with ClfA, many of the sequences recurred multiple times without variation. For clarity, each unique sequence was placed in the alignment only once. See FIG. 10A-10E. Only unique ClfB sequences were included in the sequence listing. For example, the sequence of ClfB_006 was obtained from multiple different strains without any variation. This sequence is shown in the first row of the alignment in FIG. 10A-10E. The sequence listing number for any sequence can also be obtained from Table 11. This alignment of representative unique sequences of the ClfB antigen indicates that polymorphisms were distributed throughout the entire A region (N-1-N2-N3) of ClfB. Similar to ClfA, for any given unique protein sequence of ClfB, more than one nucleotide sequence encoding the same protein was discovered. Only the most frequently occurring DNA sequence was included in the sequence listing and in Table 11. For ClfB, the following sequences are disclosed herein and are not found in GenBank: ClfB_001, ClfB_004, ClfB_005, ClfB_010, ClfB_011, ClfB_013, ClfB_014, ClfB_015, ClfB_016, ClfB_017, ClfB_018, ClfB_019, ClfB_020, ClfB_021, ClfB_022, ClfB_023, and ClfB_024. The phylogenetic tree is shown in FIG. 11.

TABLE 11

ClfB Strains and Sequence Listings

| Example Strain | DNA-ClfB | SEQ ID NO: | Protein-ClfB | SEQ ID NO: | % Identity to Antigen |
|---|---|---|---|---|---|
| PFESA0286 | ClfB_001-1 | 15 | ClfB_001 | 16 | 95 |
| PFESA0159 | ClfB_002-1 | 17 | ClfB_002 | 18 | 95 |
| RF122 | ClfB_003-1 | 19 | ClfB_003 | 20 | 94 |
| PFESA0271 | ClfB_004-1 | 21 | ClfB_004 | 22 | 95 |
| PFESA0081 | ClfB_005-1 | 23 | ClfB_005 | 24 | 95 |
| PFESA0080 | ClfB_006-1 | 25 | ClfB_006 | 26 | 100 |
| PFESA0270 | ClfB_007-1 | 27 | ClfB_007 | 28 | 99 |
| PFESA0269 | ClfB_008-1 | 29 | ClfB_008 | 30 | 95 |
| PFESA0145 | ClfB_009-1 | 31 | ClfB_009 | 32 | 94 |
| PFESA0069 | ClfB_010-1 | 33 | ClfB_010 | 34 | 95 |
| PFESA0002 | ClfB_011-1 | 35 | ClfB_011 | 36 | 96 |
| PFESA0128 | ClfB_013-1 | 37 | ClfB_013 | 38 | 96 |
| PFESA0129 | ClfB_014-1 | 39 | ClfB_014 | 40 | 95 |
| PFESA0136 | ClfB_015-1 | 41 | ClfB_015 | 42 | 99 |
| PFESA0139 | ClfB_016-1 | 43 | ClfB_016 | 44 | 99 |
| PFESA0140 | ClfB_017-1 | 45 | ClfB_017 | 46 | 96 |
| PFESA0141 | ClfB_018-1 | 47 | ClfB_018 | 48 | 94 |
| PFESA0144 | ClfB_019-1 | 49 | ClfB_019 | 50 | 97 |
| PFESA0150 | ClfB_020-1 | 51 | ClfB_020 | 52 | 96 |
| PFESA0152 | ClfB_021-1 | 53 | ClfB_021 | 54 | 96 |
| PFESA0156 | ClfB_022-1 | 55 | ClfB_022 | 56 | 96 |

TABLE 11-continued

CIfB Strains and Sequence Listings

| Example Strain | DNA-ClfB | SEQ ID NO: | Protein-ClfB | SEQ ID NO: | % Identity to Antigen |
|---|---|---|---|---|---|
| PFESA0163 | ClfB_023-1 | 57 | ClfB_023 | 58 | 94 |
| PFESA0211 | ClfB_024-1 | 59 | ClfB_024 | 60 | 99 |

Example 7

Sequence Diversity of MntC in Disease-Causing Clones of *S. aureus*

In this example, the protein sequence heterogeneity of MntC genes from 104 disease-causing isolates obtained from various sources was evaluated. MntC genes were sequenced from strains of *S. aureus* associated with multiple disease states. See Table 12. Information from additional strains was obtained from GenBank to generate strain sequences.

The sequence alignment of MntC proteins from different disease-causing strains of *S. aureus* is shown in FIG. 12A-12B. The protein sequences were aligned using MUSCLE. See Edgar, R. C. Nucleic Acids Research 32 (5):1792-1797 (2004). The alignments were displayed using SHOWALIGN. See Rice, P. et al., "EMBOSS: The European Molecular Biology Open Software Suite" Trends in Genetics, 16 (6): 276-277 (2000). See FIG. 12. As with ClfA, many of the sequences recurred multiple times without variation. For clarity, each unique sequence was placed in the alignment only once. See FIG. 12. Only unique MntC sequences were included in the sequence listing. For example, the sequence of MntC_001 was obtained from different strains without any variation. See FIG. 12. This sequence is shown in the first row of the alignment in FIG. 12. The sequence listing number for any sequence can also be obtained from Table 12. Only the most frequent corresponding DNA sequence was included in the sequence listing. For MntC, the following sequences are disclosed herein and are not found in GenBank: MntC_002, MntC_006, MntC_007. MntC_008, and MntC_009.

TABLE 12

MntC strains and Sequence Listings

| Strain | DNA-MntC | SEQ ID NO: | Protein-MntC | SEQ ID NO: | % Identity to Antigen |
|---|---|---|---|---|---|
| PFESA0129 | MntC_001-1 | 1 | MntC_001 | 2 | 99 |
| PFESA0142 | MntC_002-1 | 3 | MntC_002 | 4 | 99 |
| PFESA0139 | MntC_003-1 | 5 | MntC_003 | 6 | 99 |
| PFESA0286 | MntC_006-1 | 7 | MntC_006 | 8 | 99 |
| PFESA0136 | MntC_007-1 | 9 | MntC_007 | 10 | 99 |
| PFESA0150 | MntC_008-1 | 11 | MntC_008 | 12 | 99 |
| PFESA0153 | MntC_009-1 | 13 | MntC_009 | 14 | 99 |

Example 8

Surface Expression of ClfA, CP5, CP8 and MntC In Vivo During Infection

*S. aureus* is responsible for causing a diverse array of human infections. Consequently the bacteria must adapt to different environmental niches by differential expression of virulence factors required for infection. The expression of target antigens was studied in three in vivo rodent assays to assess their expression during infection: a wound model to measure expression of the antigen at the primary site of infection, a bacteremia model that monitors antigen expression in the blood, and an indwelling chamber model that monitors antigen expression during nutrient/oxygen limited conditions. For all these models the rodents were challenged with bacteria at the site of study. Following infection, bacteria were harvested at various time-points and antigen expression (ClfA, CP5, CP8, MntC) was assessed using immunofluorescent microscopy (wound and bacteremia) or flow cytometry (chamber).

Materials and Methods

Expression in the Wound Model

Wound infection experiments consist of 5 animals/group and up to 5 groups for a maximum of 25 animals/experiment. Six to eight week (wk) old C57BL/6 male mice underwent surgery to embed a loop of suture into a thigh muscle incision. This provides a foreign-body substrate for bacterial attachment and significantly reduces the minimum infectious dose needed to produce a staphylococcal wound infection. Five μL of either *S. aureus* or sterile saline were introduced into the incision under the deep tissue suture of 4-0 silk. The skin was closed with 4-0 Prolene sutures or surgical adhesive (e.g., cyanoacrylate). The animals were euthanized at time points between 30 min and 10 days following infection and the thigh muscle excised, homogenized and the bacteria enumerated. Bacteria at the sight of infection were analyzed for antigen expression by immunofluorescent (IF) confocal microscopy.

Expression in the Bacteremia Model

Groups of 10 four-wk old CD-1 or Balb/C mice were immunized with 1 μg of protein or CP conjugate by subcutaneous injection on wks 0, 3 and 6. The animals were bled on wks 0 and 8 followed by an intraperitoneal challenge with *S. aureus* grown to late log phase in TSB. Three hours following challenge the animals were euthanized and blood collected for IF confocal microscopy.

Expression in the Indwelling Dialysis Tubing Model

*S. aureus* isolates were grown overnight on TSA plates at 37° C. Bacteria were scraped from the plates and resuspended in sterile PBS and the $OD_{600}$ adjusted to 1, approximately $10^9$ colony forming units (cfu)/mL. Bacteria were diluted to a concentration of $10^3$ cfu/mL and inoculated into dialysis tubing. An aliquot of the suspension was plated to determine the actual number of cfu. Dialysis tubing with 3.5 kDa MWCO was prepared for implant by sterilizing in 70% ethanol for 30 minutes followed by extensive rinsing in sterile water and then sterile saline. A 2 mL aliquot of the bacterial suspension was transferred to the dialysis tubing, the bag closed with a knot, and then rinsed extensively with sterile saline. Male Sprague Dawley rats (6 weeks old) were anaesthetized and a 2-3 cm incision made along the dorsal midline. Pockets were created at the site of incision by gently separating the skin from the underlying tissue. Tubing was implanted in the pockets and skin was closed using surgical staples. After 24 h, rats were euthanized, the tubing removed, and the bacteria recovered for flow cytometric analysis.

Immunofluorescent Microscopy (IF)

The blood from 5 mice was pooled into ice-cold sodium citrate, pH 7.0 (final concentration, 0.4%). The eukaryotic cells were lysed with 1% NP-40 (Pierce Biotechnology). The bacteria were washed with PBS and incubated overnight at 4° C. with rabbit immune or preimmune serum (1:100) and detected with ALEXA488 conjugated goat-a-rabbit antibody (1:250, Invitrogen). The labeled bacteria were dried on a microscope slide and a coverslip was mounted with Vectashield HardSet medium (Vector Laboratories. Inc.). Images were obtained with a Leica TCS SL spectral confocal microscope (Leica Microsystems).

Flow Cytometric Analysis

*S. aureus* isolates were grown as described in the rat dialysis tubing model procedure. Approximately $10^7$ bacterial cells were blocked in staining buffer (Hank's balanced salt solution with 10% goat sera) for 1 hour on ice. Bacterial cells were centrifuged for 5 minutes at 10,000 rpm, supernatant removed, and cells incubated with mouse antibody or isotype control antibody for 30 minutes on ice. Cells were then washed and stained with FITC conjugated goat anti-mouse IgG (Jackson ImmunoResearch) on ice for 30 minutes. Bacteria were washed with staining buffer, fixed with 2% paraformaldehyde and data acquired and analyzed using FACS Caliber flow cytometer and Cell quest software (Becton, Dickinson and Co.). A total of 30,000 events were collected for each sample.

TABLE 13a

Antigen Expression Profiles in *S. aureus* CP Type 5 Isolates.

| | | CP | | | | | | ClfA | | | | | | MntC | | | | | |
|---|---|---|---|---|---|---|---|---|---|---|---|---|---|---|---|---|---|---|---|
| | | | | | | | | Time [h] | | | | | | | | | | | |
| | | $T_0$ | 1 | 4 | 6 | 24 | 72 | $T_0$ | 1 | 4 | 6 | 24 | 72 | $T_0$ | 1 | 4 | 6 | 24 | 72 |
| PFESA0266 | bacteremia | + | − | ± | + | / | / | + | − | ± | + | / | / | NT | NT | NT | NT | NT | NT |
| | wound | + | − | − | − | ± | + | + | − | ± | + | + | − | ± | ± | ± | ± | ± |
| PFESA0272 | bacteremia | + | + | + | + | / | / | + | − | + | + | / | / | − | − | − | − | / | / |
| | wound | + | − | − | − | + | ! | + | − | ± | ± | ± | ! | − | − | − | ± | ! | ! |
| PFESA0094 | bacteremia | + | − | ± | + | / | / | + | − | ± | ! | / | / | − | − | − | − | / | / |
| | wound | + | − | + | + | + | + | − | − | + | + | + | − | − | − | − | ± | ± | ± |
| PFESA0093 | bacteremia | + | − | ± | + | / | / | + | − | ± | + | / | / | NT | NT | NT | NT | NT | NT |
| | wound | + | − | − | ± | + | + | + | − | − | − | ± | ± | − | − | − | ± | ± | ± |
| PFESA0028 | bacteremia | + | − | − | + | / | / | + | − | ± | ± | / | / | − | − | − | ± | ± | / | / |
| | wound | + | − | − | − | − | − | + | − | − | ± | ± | ± | − | − | − | ± | ± | − |
| PFESA0029 | bacteremia | − | − | ± | + | / | / | + | − | − | + | / | / | − | − | − | + | / | / |
| | wound | − | − | − | − | ± | ± | + | − | − | − | − | ± | − | − | − | ± | ± | − |

/ = bacteremia experiments were conducted for 6 hours ! = animal died during experiment NT = not tested TABLE 13b Antigen Expression Profiles in *S. aureus* CP Type 8 Isolates.

| | | CP | | | | | | ClfA | | | | | | MntC | | | | | |
|---|---|---|---|---|---|---|---|---|---|---|---|---|---|---|---|---|---|---|---|
| | | | | | | | | Time (h) | | | | | | | | | | | |
| | | T0 | 1 | 4 | 6 | 24 | 72 | T0 | 1 | 4 | 6 | 24 | 72 | T0 | 1 | 4 | 6 | 24 | 72 |
| PFESA0003 | Bacteremia | + | ± | + | + | / | / | + | − | ± | + | / | / | NT | NT | NT | NT | NT | NT |
| | Wound | + | − | ± | + | + | + | + | − | ± | + | + | ! | NT | NT | NT | NT | NT | NT |
| PFESA0286 | Bacteremia | + | − | − | + | / | / | + | − | − | + | / | / | NT | NT | NT | NT | NT | NT |
| | Wound | + | − | − | + | ! | ! | + | − | + | + | ! | ! | NT | NT | NT | NT | NT | NT |
| PFESA0005 | Bacteremia | + | − | ± | ± | / | / | + | + | + | + | / | / | NT | NT | NT | NT | NT | NT |
| | Wound | NT | NT | | | ! | ! | NT | NT | NT | NT | NT | NT | NT | NT | NT | NT | NT | NT |
| PFESA0002 | Bacteremia | + | − | − | − | / | / | + | ± | − | − | / | / | − | ± | ± | + | / | / |
| | Wound | + | − | − | + | + | ! | + | − | − | − | ± | NT | − | − | ± | ± | ± | + |
| PFESA0269 | Bacteremia | + | − | − | − | / | / | + | − | − | − | / | / | − | − | ± | ± | / | / |
| | Wound | + | − | − | ± | + | + | + | − | − | ± | ± | NT | − | ± | − | − | ± | ± |
| PFESA0268 | Bacteremia | + | + | + | + | / | / | + | + | − | − | / | / | − | ± | − | + | / | / |
| | Wound | + | − | − | − | + | + | + | − | − | − | ± | NT | − | − | − | ± | ± | − |
| PFESA0025 | Bacteremia | + | − | − | − | / | / | + | + | − | − | / | / | NT | NT | NT | NT | NT | NT |
| | Wound | + | − | − | − | + | ± | + | − | − | − | − | NT | − | − | − | − | ± | + |
| PFESA0283 | Bacteremia | + | − | − | − | / | / | + | + | + | − | / | / | ± | ± | ± | ± | / | / |
| | Wound | + | − | − | + | ! | ! | + | − | − | + | ! | NT | − | − | − | ± | ± | ± |
| PFESA0027 | Bacteremia | + | − | − | ± | / | / | + | − | ± | ± | / | / | NT | NT | NT | NT | NT | NT |
| | Wound | + | − | ± | ± | + | + | + | − | − | ± | + | NT | − | − | − | − | ± | + |
| PFESA0001 | Bacteremia | + | − | − | − | / | / | + | − | − | − | / | / | NT | NT | NT | NT | NT | NT |
| | Wound | + | − | − | ± | ± | + | + | − | − | − | ± | NT | − | − | − | − | − | ± |
| PFESA0095 | Bacteremia | + | − | − | ± | / | / | + | − | − | + | / | / | NT | NT | NT | NT | NT | NT |
| | | + | − | − | + | + | + | − | − | − | − | ± | NT | − | − | − | − | ± | |
| PFESA0271 | Bacteremia | + | − | − | − | / | / | + | + | − | − | / | / | NT | NT | NT | NT | NT | NT |
| | Wound | + | − | − | − | + | + | + | − | − | + | + | NT | − | − | ± | ± | ± | ± |
| PFESA0271 | Bacteremia | + | − | ± | + | / | / | + | − | ± | ± | / | / | NT | NT | NT | NT | NT | NT |
| | Wound | + | − | − | + | + | + | + | − | − | − | + | NT | − | − | − | − | ± | ± |

/ = bacteremia experiments were conducted for 6 hours. ! = animal died during experiment NT = not tested TABLE 13c Expression of S. aureus antigens in the Indwelling Dialysis Tubing. Frequency of positive cells (% of total)

| | | \multicolumn{7}{c}{Time (hrs)} | | | | | | |
|---|---|---|---|---|---|---|---|---|
| | | 0 | 3 | 6.0 | 9.0 | 13.0 | 18.0 | 30.0 |
| S. aureus PFESA0266 | ClfA | 69.8 | 13.7 | 8.5 | 8.0 | 12.5 | 8.8 | 16.4 |
| | CP5 | 28.0 | 1.9 | 1.8 | 6.1 | 7.1 | 5.2 | 9.6 |
| | MntC | 91.4 | 4.3 | 5.6 | 2.9 | 20.8 | 37.0 | 33.2 |

| | | \multicolumn{7}{c}{Time (hrs)} | | | | | | |
|---|---|---|---|---|---|---|---|---|
| | | 0 | 3 | 6.0 | 9.0 | 13.0 | 18.0 | 24.0 |
| S. aureus PFESA0005 | ClfA | 98.6 | 63.9 | 69.7 | 24.3 | 36.1 | 98.6 | 99.0 |
| | CP8 | 77.3 | 43.0 | 18.0 | 7.5 | 11.8 | 96.4 | 94.0 |
| | MntC | 5.9 | 7.7 | 12.5 | 2.6 | 2.9 | 9.3 | 9.9 |

A combination of nineteen S. aureus isolates were tested for expression of ClfA, CP5, CP8, or MntC on the S. aureus cell surface during infection (Table 13a, 13b, and 13c). These isolates included recent clinically relevant strains and were diverse as monitored by MLST. Antigen expression was dependent on the strain, time point, and the infection model. The variation in antigen expression between isolates in different in vivo environments (bloodstream vs. wound) supports the use of a multi-antigen immunogenic composition to induce broad coverage of staphylococcal isolates in a variety of different infections. The antigens were surface expressed within the first 24 hours of infection and are thus valid components for an anti-staphylococcal immunogenic composition. Protein antigens ClfA and MntC were accessible to staining in the presence of capsule expression indicating that the presence of capsule does not mask the proteins from antibodies directed against them.

Most of the tested type 8 isolates did not express CP in the blood until later time points post-challenge (>4 hour) (See Table 13a-c). These results demonstrate that in S. aureus CP is differentially regulated depending on the in vivo microenvironment. i.e., site of infection. These results may explain the inconsistent efficacy results reported for CP8 conjugates in animal models.

In vivo expression results suggest that no single antigen immunogenic formulation will provide broad coverage against the majority of S. aureus infections. There is too much diversity of expression phenotypes by individual strains within in vivo microenvironments. Therefore, an immunogenic composition consisting of more than one antigen is required to prevent S. aureus disease.

Example 9

Immunogenicity of Multi-Antigen Formulations Containing ClfA, CP5- and CP8-CRM$_{197}$ Conjugates In this example, we evaluated the immunogenicity of combinations of ClfA, CP5-CRM$_{197}$ and CP8-CRM$_{197}$.

A. Bi-Antigen (CP5-CRM$_{197}$/CP8-CRM$_{197}$) Immunogenic Composition Formulation—Dose Effect on the Anti-Capsular Antibody Responses in Rabbit In this example, the dose effect on the immunogenicity of the combined CP5-CRM$_{197}$ and CP8-CRM$_{197}$ immunogenic formulation in rabbits was evaluated. Rabbits were immunized on week 0, 3 and 6 with bivalent conjugate plus 125 µg AlPO$_4$ administered by subcutaneous injection. The doses evaluated in this study were 0.1 µg, 1 µg, or 10 µg each of CP5-CRM$_{197}$ and CP8-CRM$_{197}$ (final combined CP-CRM$_{197}$ doses of 0.2 µg, 2 µg, and 20 µg). The dose of the conjugate reflects the total polysaccharide component of the protein polysaccharide conjugate. Rabbits were bled on week 0, 3, 6 and 8. ELISA was performed on pooled and individual sera. Endpoint antibody titers were determined as the reciprocal dilution at 0.1 OD$_{405}$. Statistical analysis was performed on individual week 8 titers. The results demonstrated that the highest CP5 and CP8 specific antibody titers of $5\times10^5$ for CP5 and $1\times10^6$ for CP8 were induced by vaccination of rabbits with bivalent immunogenic formulation at 1 µg CP dose of each component (Data not shown.).

B. Tri-Antigen Formulation (CP5-CRM$_{197}$+CP8-CRM$_{197}$+rClfA)—rClfA Dose Range Study with Fixed Dose (1 µg) of Each Conjugate in Rabbits The effect of a combination of rClfA and CP5 and CP8 conjugates on immune response to each component was tested. Three groups were immunized with bivalent S. aureus CP5-CRM$_{197}$+CP8-CRM$_{197}$ (1 µg dose of each conjugate) combined with T7-ClfA (N1N2N3) at three different doses 1, 10 and 100 µg. The control group was immunized with unconjugated CP5 and CP8 (50 µg each) combined with 100 µg of T7-ClfA (N1 N2N3). Each immunogenic composition was formulated with 500 µg of adjuvant AlPO$_4$. Immunogenic compositions were administered by subcutaneous injection in the neck. Rabbits were bled on week 0, 6 and 8. ELISA was performed on pooled and individual sera and endpoint antibody titers were determined as the reciprocal dilution at 0.1 OD$_{405}$.

Results showed that increased amount of rClfA when combined with bivalent conjugate did not affect capsular antibody responses. The antibody levels to both capsular serotypes were in the same range as in rabbits immunized with bivalent conjugate only (Data not shown). The antibody levels to CP5 and CP8 were 2.5 fold lower at 10 (103 K) and 100 µg (106 K) dose compared to 1 µg dose of rClfA (273 K). There was a booster effect after the second and third injection. Unconjugated bivalent polysaccharide immunogenic formulation (CP5+CP8, 50 µg each) combined with 100 µg of rClfA did not induce CP specific antibodies. The rClfA specific antibody response was also not greatly affected by the dose, where titers were between $1\times10^5$ and $1\times10^6$ after three doses for 1, 10 and 100 µg doses (Data not shown.). Also the levels of anti-ClfA response achieved when administered with conjugated or unconjugated CP5 and CP8 polysaccharides were similar.

Example 10

Tri-Antigen Formulation—Immunogenicity in Rabbits with High Pre-Immunization CP5, CP8 and ClfA Ab Titers The staphylococcal immunogenic composition is targeted for adult populations that have pre-existing antibodies to S. aureus surface components. To study the effect of pre-existing antibodies to immunogenic formulation components on the response to the immunogenic formulation, we selected rabbits with high titers of naturally acquired anti-CP5, anti-CP8, and anti-ClfA antibody titers. Two groups of rabbits (n=6/7) were immunized on week 0, 3 and 6 with tri-antigen immunogenic formulation (CP5-CRM$_{197}$ (1 µg) and CP8-CRM$_{197}$ (1 µg) and T7-ClfA (N1N2N3)Y338A (10 µg)). One group was immunized with the immunogenic composition formulated with 500 µg AlPO$_4$ as adjuvant and the second group was immunized with immunogenic composition formulation containing no adjuvant. Immunogenic compositions were administered by subcutaneous injection. Rabbits were bled on wk. 0, 3, 6 and 8. Antibody titers to CP5, CP8 and rClfA were determined by ELISA as endpoint antibody titers on pooled and individual sera (determined as the reciprocal dilution at 0.1 $OD_{405}$).

Results showed that rabbits with pre-existing antibody titers induced by natural infection responded to trivalent immunogenic formulation with an increase in levels of antibodies to all immunogenic formulation components CP5, CP8 and rClfA. An increase of Ab levels to each antigen of between 5 fold to 10 fold was shown even in animals with antibody titers of $1 \times 10^6$. Presence of the adjuvant in the immunogenic formulation resulted in higher antibody titers compared to the group immunized without adjuvant (Data not shown).

Example 11

Effect of the Adjuvant on Responses to Capsule Polysaccharide Components

A. Effect of Two Different Doses of $AlPO_4$ on Response to Bivalent CP5-$CRM_{197}$/CP8-$CRM_{197}$ Conjugate Immunogenic Composition in Rabbits The dose effect of the adjuvant $AlPO_4$ on the anti CP5 and CP8 responses in rabbits was studied. Rabbits were immunized on week 0, 3 and 6 with bivalent S. aureus CP5-$CRM_{197}$+CP8-$CRM_{197}$ (1 μg dose of each conjugate). One group (n=5/group) was immunized with immunogenic composition formulated with 125 μg and a 2nd group with 500 μg of $AlPO_4$ as adjuvant. Immunogenic compositions were administered by subcutaneous injection in neck. Rabbits were bled on week 0, 6 and 8 and anti-capsular antibodies were determined by ELISA as endpoint antibody titers determined as the reciprocal dilution at 0.1 $OD_{405}$. Results indicated that there was no difference in CP8 specific antibody responses in rabbits immunized with either 125 μg or 500 μg of $AlPO_4$. The formulation with 125 μg of adjuvant gave higher CP5 antibody responses. Also, all rabbits in the 125 μg group responded with higher CP5 antibody responses, while in the 500 μg adjuvant group, there were two rabbits with low response to the formulation.

B. Effect of $AlPO_4$ on the Immunogenicity of Tri-Antigen Formulation

Rabbits (NZW, n=6/7 rabbits per group) were immunized on week 0, 3 and 6 with Tri-antigen formulation comprised of CP5-$CRM_{197}$ (1 μg) and CP8-$CRM_{197}$ (g) and T7-ClfA (N1N2N3)Y338A (10 μg). One group of rabbits was immunized with immunogenic formulation with 500 μg $AlPO_4$, a second group was formulated with no adjuvant, the third group was immunized at week 0 with immunogenic formulation with 500 μg $AlPO_4$ and weeks 3 and 6 with immunogenic formulation with no adjuvant. Immunogenic formulations were administered by subcutaneous injection, rabbits were bled on week 0, 3, 6 and 8 and sera evaluated by antigen specific ELISA. Results showed that the presence of adjuvant in the immunogenic formulation did not have an effect on anti-CP5 or anti-CP8 responses in rabbits (Data not shown.). The GMT titers of Abs to both capsules were comparable. However, there was an adjuvant effect on ClfA specific antibody response shown in groups immunized with adjuvant present in all three vaccinations. The second and third boost with immunogenic formulation not containing $AlPO_4$ in the rabbits primed with the immunogenic formulation containing adjuvant gave higher ClfA responses compared to group with no adjuvant.

Examples 12-29

Preclinical Evaluation of S. Aureus ClfA, MntC, CP5-$CRM_{197}$ and CP8-$CRM_{17}$ Described below in Examples 12 through 29 are the results of the preclinical evaluation of the CP5 and CP8 conjugates, ClfA and MntC. The examples demonstrate the efficacy of these antigens in preclinical animal models. The examples also demonstrate that antibodies generated by the CP conjugates, ClfA and MntC have functional activity in in vitro assays.

Two different chemistries were used to conjugate CP to $CRM_{197}$, but no difference was observed in efficacy for the conjugates prepared by the different methods. O-acetylation of the capsular polysaccharides was shown to impact eliciting functional antibodies. Evaluation of a combined immunogenic composition comprising CP5-$CRM_{197}$, CP8-$CRM_{197}$ and ClfA showed no interference on specific antibody (Ab) levels to each immunogenic formulation component.

Materials and Methods

ELISA

Maxisorp microtiter ELISA plates (Nalge Nunc International, Rochester, N.Y.) were coated 18 hours at 4° C. or for 90 min at 37° C. with 1 μg/mL of ClfA antigen in PBS pH 7.5. The plates were washed five times in PBST (1×PBS, 0.1% polysorbate 20) and blocked with 1% (w/v) non-fat milk in PBS, with 0.05% polysorbate 20 for 1 h at room temperature. Plates were washed with PBST, and serially diluted (3-fold) and individual week 0, 3, 6 and 8 rabbit antisera were added to the plates and incubated either overnight at 4° C. or 2 h at 37° C. The plates were washed, and bound primary antibodies were detected with horseradish peroxidase-conjugated goat anti-rabbit IgG (1:1000 dilution) in PBST. The plates were incubated for 1 h at 37° C. then washed and developed with ABTS-peroxidase substrate solution. (KPL, Inc., Gaithersburg, Md.), at room temperature for approximately 20 minutes. The reaction was stopped by the addition of a 1% (v/v) SDS solution. Absorbance was measured at 405 nm in an automated plate reader (Molecular Devices Corporation, Sunnyvale, Calif.). Antibody titers were expressed as the reciprocal of the highest serum dilution with an absorbance value of 0.1. Student's t-test using JMP Software (SAS Institute, Cary, N.C.) was used to determine differences in antibody titers between the different groups. A probability of less than 0.05 was considered to indicate a statistically significant difference.

Murine Sepsis Models

The murine sepsis model mimics blood borne disease. For passive immunization, groups of 15 Swiss-Webster mice were treated intraperitoneally (i.p.) with IgG. Twenty four hours later mice were challenged with S. aureus 659-018 via by a single intravenous (i.v.) injection (0.1 ml) via the tail vein. All animals were followed for 14 to 15 days, at which point all remaining mice were sacrificed.

For active immunization, mice were immunized with antigen at 0, 2 and 4 weeks and challenged at week 6 by the intravenous route with S. aureus.

Active Immunization Rabbit Endocarditis Model

Adult New Zealand White rabbits were immunized intramuscularly 4 times with 25 μg antigen. One day post-surgery, animals are challenged i.v. with a bolus of S. aureus and the number of colony forming units (cfu) in the heart tissue are determined 24 hours post-challenge.

Murine Bacteremia

A 3 hr bacteremia model was used to determine the effect of vaccination on bacterial numbers early during an infection.

Mice were immunized at weeks 0, 3, and 6 with antigen followed by i.p. challenge with *S. aureus* on week 8. Animals were exsanguinated 3 hours later and serial dilutions of blood plated to enumerate the bacteria.

Murine Pyelonephritis Model

The murine pyelonephritis model mimics the dissemination of *S. aureus* from bacteremia. Groups of 10 four week-old female CD-1 mice were immunized at 0, 3 and 6 weeks with antigen. The mice were challenged by i.p. injection of *S. aureus*. Forty-eight hours following challenge the mice were sacrificed and the bacteria were enumerated in the kidney and blood.

Rat Endocarditis Model

The rat endocarditis model mimics human endocarditis in which colonization occurs after a blood borne infection leads to colonization of damaged heart tissue. Five 5 week-old male Sprague-Dawley rats (Charles River, Kingston, N.Y.) were immunized on wks 0, 2 and 4 with 1 µg of CP5-CRM$_{197}$ conjugate formulated with 100 µg of AlPO$_4$. The animals were bled prior to vaccination on wk 0 and at the end of wk 5. Seventy-two hours later, a catheter (PE-10 tubing) was surgically placed through the carotid artery into the left ventricle of the heart. Placement of the catheter results in the formation of a sterile vegetation to which the staphylococci can attach upon infection. To prevent infection resulting from the surgical procedure, the animals were treated with the antibiotic Baytril (5 mg/kg) at the time of surgery and 8 hr following surgery. Forty-eight hours after surgery, the rats were challenged with PFESA0266 (approximately 4×10$^8$ cfu) or SA315 (approximately 1×10$^9$ cfu) by intraperitoneal injection. Forty-eight hours following challenge the rats were euthanized and the hearts and kidneys removed and placed into 3 mL of phosphate buffered saline (PBS). The organs were then homogenized with a tissue homogenizer (Kinematica AG. Luzernerstrasse, Germany) and brought to 10 mL with PBS. The homogenates were then serially diluted and plated for bacterial enumeration.

Monitoring functional antibodies using onsonophagocytic killing assays

Differentiated effector cells from a cell line (e.g. HL60s) or polymorphonuclear cells (PMNs) isolated from donor human blood using LYMPHOLYTE®-poly solution (Cedarlane laboratories limited, Ontario, Canada) as per manufacturer's protocol can be used for this assay. Effector cells were resuspended in assay buffer (Modified Eagle's media containing 1% bovine serum albumin) at approximately 2×10$^7$ cells/ml concentration and placed in 37° C. incubator until ready to use. *S. aureus* strain PFESA0266 was grown overnight on tryptic soy agar plates. Bacterial cells were scraped, washed twice and resuspended in assay buffer containing 5% glycerol to an OD$_{600}$=1, which equals to approximately 5×10$^8$ cfu/ml concentration. One ml aliquots of the bacterial suspension were frozen and stored at −40° C. until ready to use. Frozen bacterial suspension were thawed and adjusted to a concentration of 10$^6$ cfu/ml in assay buffer and placed on ice. The assay was performed using a sterile 96 deep well 1 ml polypropylene plates. Two fold serial dilutions of antibody samples (50 µl) were prepared and followed by addition of 300 µl of assay buffer to the antibody mix. Bacteria were added (50 µl) to the plates and placed on a rotary shaker at 4° C. for 30 minutes. The opsonization step was followed by addition of 50l of human complement (1% final concentration). Finally, 50 µl of effector cells (10$^7$ cells/ml concentration) were added to the plate and the suspension mixed well by repeated pipetting. A 50 µl aliquot of the suspension was 10 fold serially diluted in sterile 1% saponin solution, vortexed to minimize bacterial clumping and plated on tryptic soy agar in duplicate. The assay plate was incubated at 37° C. for 1 hour with continuous mixing using rotisserie style shaker. At the end of the incubation a 50 µl aliquot of suspension was 10 fold serially diluted in sterile 1% saponin solution, mixed by vortexing to minimize bacterial clumping and plated on tryptic soy agar in duplicate. The percentage killing was calculated by determining the ratio of the number of cfu surviving at 60 minutes in wells with bacteria, antibodies, complement and effector cells to the number of cfu surviving in tubes lacking antibodies but containing bacteria, complement and effector cells. Controls containing bacteria, complement, and sera were included to adjust for any reduction in cfu due to clumping.

Complement Adsorption

Serum from human donors adsorbed against *S. aureus* strains PFESA0266, PFESA0286 and PFESA0270 can be used as a source of complement in the assay. *S. aureus* strains were grown overnight on TSA plates at 37° C. Cells were scraped from the plate and resuspended in sterile PBS. Bacterial cells were centrifuged at 10,000 rpm for 10 minutes at 4° C. and cell pellet was resuspended in human serum for adsorption. Serum was incubated with bacteria on a nutator at 4° C. for 30 minutes. Cells were centrifuged, serum transferred to another tube containing bacteria and the adsorption step repeated again for 30 minutes. Finally, the cells were centrifuged and the serum passed through a 0.2 micron filter before 0.5 ml aliquots were frozen down in liquid nitrogen.

Method II—OPA Using HL-60 Cells

HL-60 cells were differentiated according to S. Romero-Steiner, et al., Clin Diagn Lab Immunol 4 (4) (1997), pp. 415-422. Harvested HL-60 cells were resuspended in assay buffer (Modified Eagle's media containing 1% bovine serum albumin) at approximately 10$^8$ cells/ml and placed in 37° C. incubator until ready to use. *S. aureus* was grown overnight on tryptic soy agar plates. Bacterial cells were scraped, washed twice and resuspended in assay buffer containing 5% glycerol to an OD$_{600}$=1, which equals to approximately 5×10$^8$ cfu/ml. One ml aliquots of the bacterial suspension were frozen and stored at −40° C. until ready to use. Frozen bacterial suspension were thawed and adjusted to a concentration of 10$^6$ cfu/ml in assay buffer and placed on ice. The assay was performed using a sterile 96 deep well 1 ml polypropylene plates. Two fold serial dilutions of monoclonal antibody samples (251) were prepared and followed by addition of 150 µl of assay buffer to the antibody suspension. Bacteria were added (25 µl) to the plates and placed on a rotary shaker at 4° C. for 30 minutes followed by addition of 25 µl of human complement (1% final concentration). Finally, 25 µl of HL-60 cells (10$^7$ cells/ml) were added to the plate and the suspension mixed well by repeated pipetting. A 25 µl aliquot of the suspension was 10 fold serially diluted in sterile 1% saponin solution, mixed by vortexing to minimize bacterial clumping and plated on tryptic soy agar in duplicates. The assay plate was incubated at 37° C. for 1 hour with continuous mixing using rotisserie style shaker. At the end of incubation a 25 µl aliquot of suspension was 10 fold serially diluted in sterile 1% saponin solution, mixed by vortexing to and plated on tryptic soy agar in duplicate. The percentage killing was calculated by determining the ratio of the number of cfu surviving at 60 minutes in wells with bacteria, antibodies, complement and HL-60 cells to the number of cfu surviving in tubes lacking antibodies but containing bacteria, complement and HL-60 cells. Controls containing bacteria, complement and mAb was included to adjust for any reduction in cfu due to clumping.

Example 12

Demonstration of a Protective Effect by ClfA in In Vivo Animal Models

Figure 13:
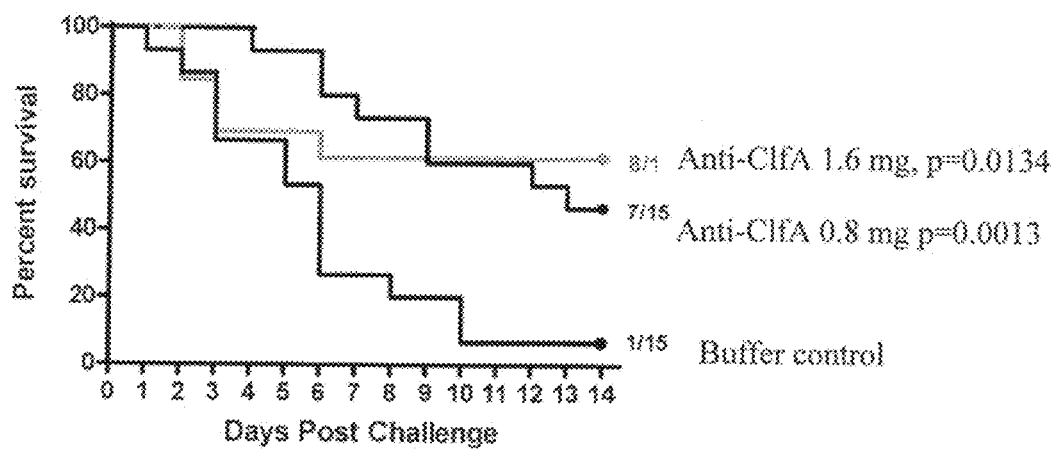
FIG. 13 demonstrates that polyclonal rabbit anti-ClfA antibodies reduce S. aureus 659-018 colony counts in a murine sepsis model.

To evaluate whether polyclonal rabbit antibodies elicited against ClfA were capable of reducing S. aureus colony counts in a murine sepsis model, purified rabbit polyclonal anti-ClfA IgG was used at two dosages (0.8 mg and 1.6 mg) in a passive immunization study (FIG. 13). The S. aureus challenge strain was a recent clinical isolate, 659-018. Both antibody dosages resulted in a significant reduction of bacterial colony counts in the murine sepsis model (p=0.0134 for 1.8 mg dose and p=0.0013 for 0.8 mg dose). This experiment has been repeated with additional S. aureus isolates with similar results (data not shown).

Example 13

Figure 14:
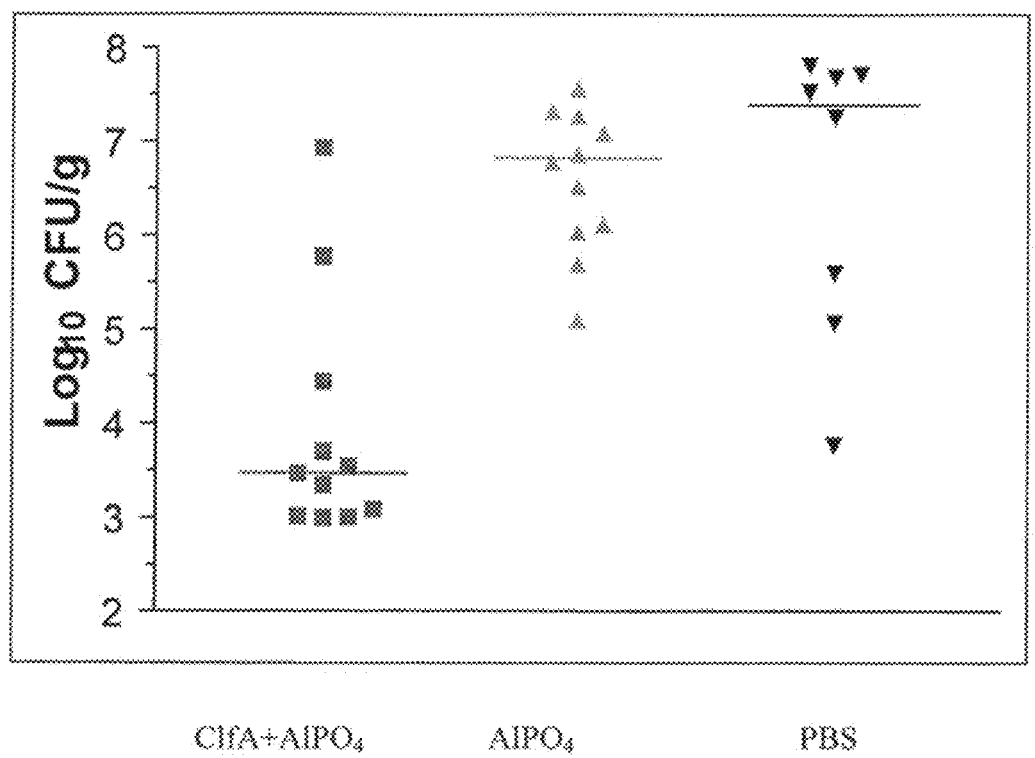
FIG. 14 demonstrates that active immunization with ClfA reduces colonization of the heart by S. aureus PFESA0003 in the rabbit infective endocarditis model.

Active Immunization With ClfA Reduced Colonization of the Heart by S. Aureus Active immunization of rabbits with ClfA resulted in protection in the rabbit endocarditis model We found a 3-4 log reduction in S. aureus cfu recovered from cardiac vegetations for animals immunized with ClfA compared to negative control (PBS or AlPO$_4$) immunized animals (FIG. 14).

Example 14

Protective Effect of MntC in In Vivo Animal Models

Figure 15A:
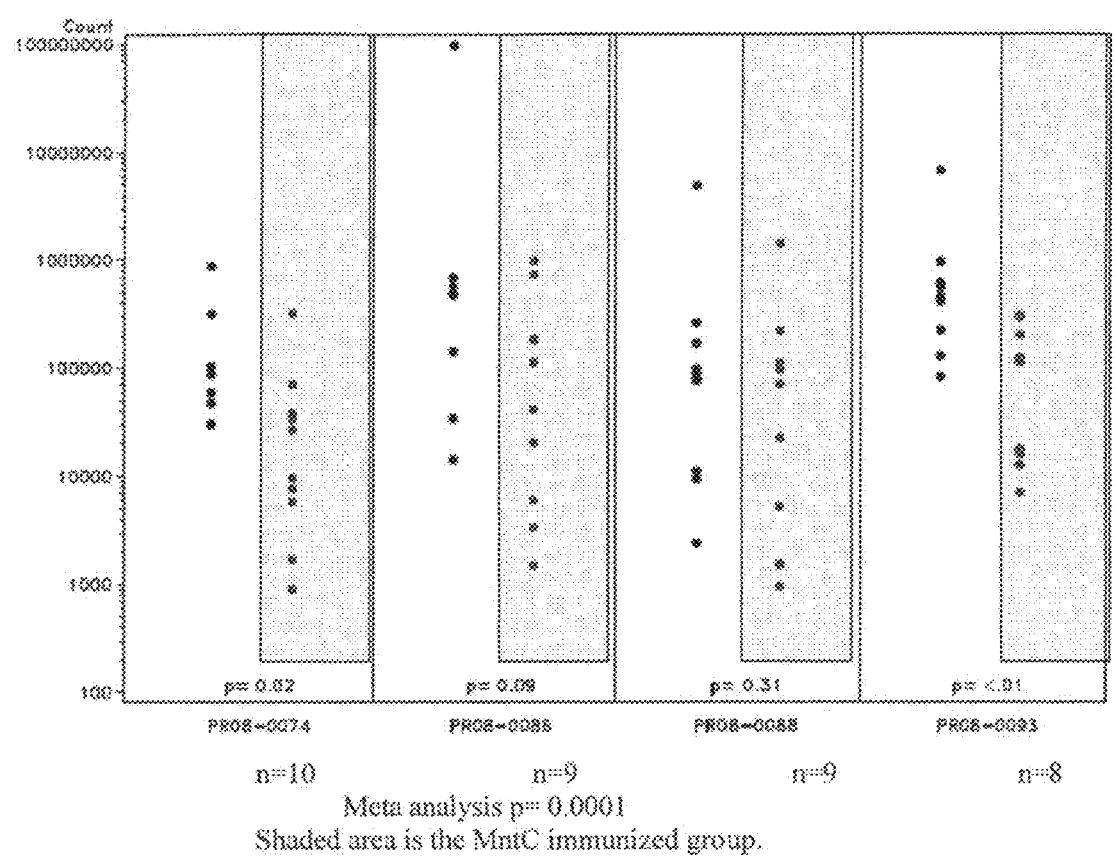
FIGS. 15A and 15B demonstrate that immunization with MntC reduces S. aureus in the blood. A: S. aureus PFESA0237 strain; B: S. aureus PFESA0266 strain.
Figure 15B:
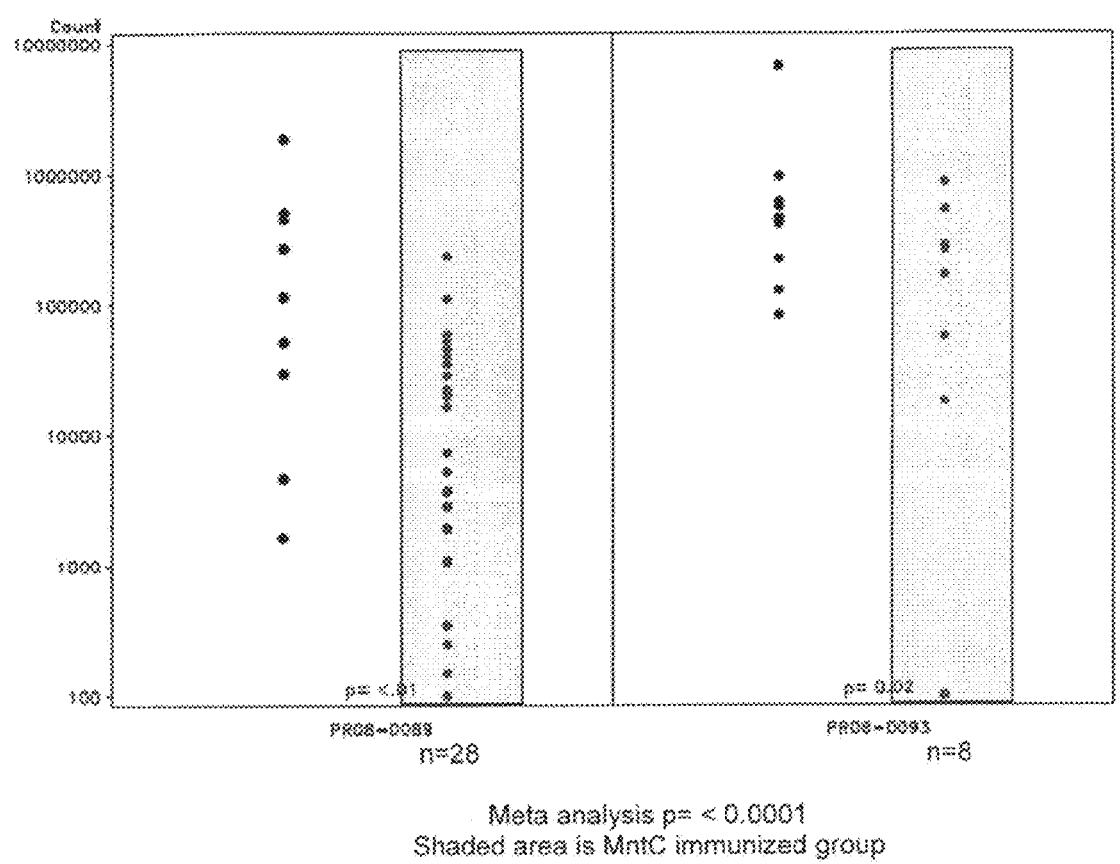

Active immunization with MntC has shown consistent protection of mice from at early time points following S. aureus challenge. Bacterial counts in the blood of mice receiving i.p. S. aureus challenge were significantly reduced as compared to controls immunized with PBS (FIGS. 15A and 15B). Four out of six individual studies showed a significant reduction in cfu/ml blood in immunized animals. Protection mediated by MntC immunization was demonstrated using 2 different S. aureus challenge strains, PFESA0237 (FIG. 15A) and PFESA0266 (FIG. 15B).

Example 15

CP5 Conjugates Protect in Murine Pyelonephritis Model

Figure 16:
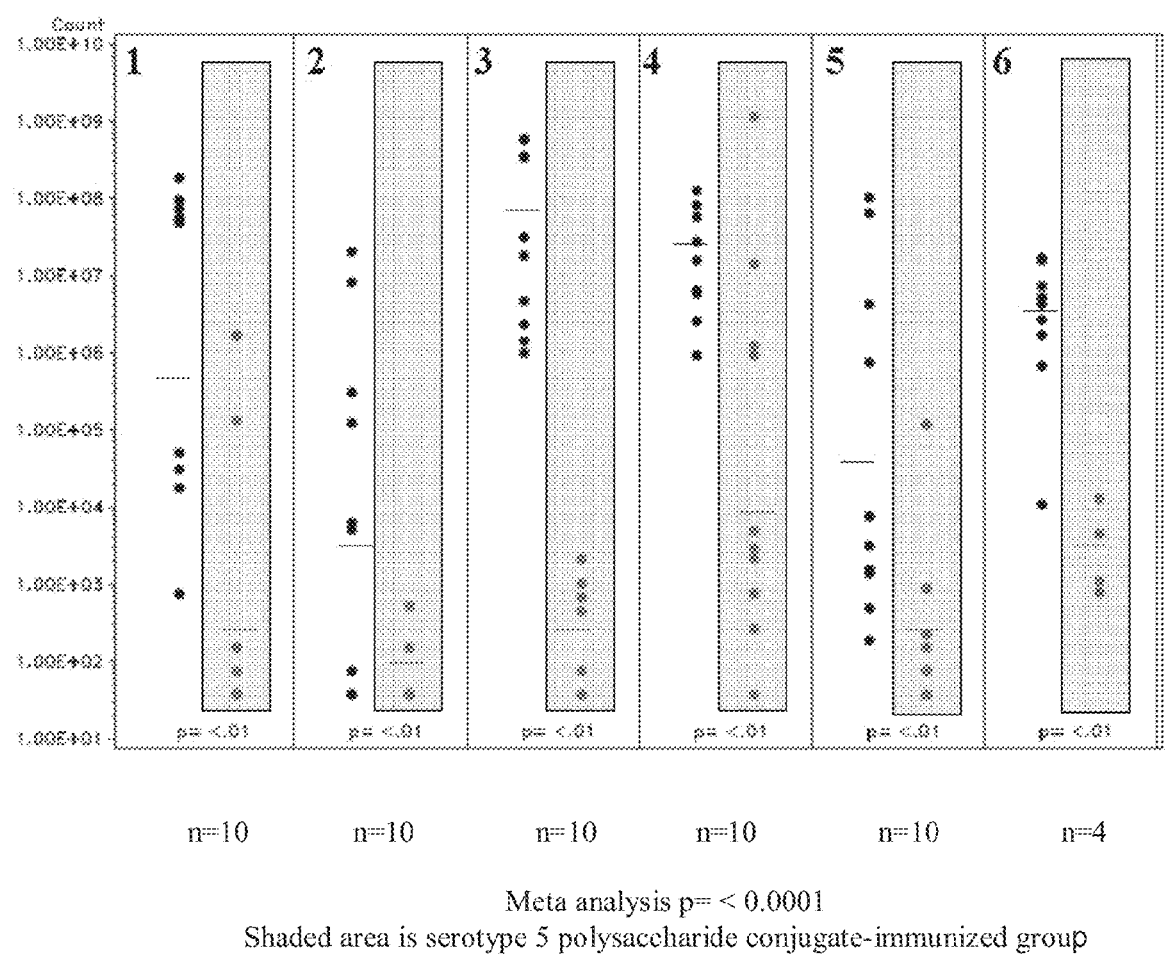
FIG. 16 demonstrates that S. aureus CP5-CRM$_{197}$ conjugate immunogenic formulation consistently exhibits protection in a murine pyelonephritis model.

CP5 conjugates were evaluated for their ability to protect mice in an active immunization pyelonephritis model. FIG. 16 shows the results from several studies. Bacterial counts in the blood of mice receiving i.p. S. aureus challenge were significantly reduced as compared to controls immunized with pbs (FIG. 16). Six out of six individual studies showed a significant reduction in cfu/ml kidneys in immunized animals. The data showed consistent reduction of kidney colonization after active immunization with CP5 conjugate.

Example 16

CP5 Conjugates Prepared by Different Conjugation Chemistries Protect Mice Against Experimental Infections Active immunization studies in the murine pyelonephritis model were conducted using CP5 conjugate prepared either by PDPH or CDT chemistry. The methods for conjugating CP5 or CP8 to CRM$_{197}$ were described above. Results showed that both conjugates significantly reduce colonization in mice compared to the sham immunized animals (Table 14).

TABLE 14

Effect of PDPH vs. CDT Conjugation in Pyelonephritis Model

| Study # | Antigens | Strain/Dose | logCFU/Kidney | Significance |
| --- | --- | --- | --- | --- |
| Study 1 | Saline + AlPO$_4$ | PFESA0266 $2 \times 10^8$ | 5.53 ± 1.90 | — |
|  | 1 µg CP5-CRM$_{197}$ (PDPH) + AlPO$_4$ |  | 3.01 ± 1.83 | p < 0.001 |
|  | 1 µg CP5-CRM$_{197}$ (CDT) + AlPO$_4$ |  | 1.67 ± 0.23 | p < 0.0001 |
| Study 2 | Saline + AlPO$_4$ | PFESA0266 $2.7 \times 10^8$ | 6.17 ± 1.76 | — |
|  | 1 µg CP5-CRM$_{197}$ (PDPH) + AlPO$_4$ |  | 3.06 ± 1.69 | p < 0.0001 |
|  | 1 µg CP5-CRM$_{197}$ (CDT) + AlPO$_4$ |  | 1.87 ± 0.69 | p < 0.0001 |

Example 17

CP5 Conjugate Protects in a Rat Endocarditis Model

Four studies were conducted with CP5-CRM$_{197}$ PDPH conjugate and an unrelated conjugate (PP5-CRM$_{197}$) at 1 µg dose. The CP5 conjugates significantly reduced colonization in both the heart and kidneys in 2 of 3 experiments in which the challenge Type 5 challenge strain was PFESA0266 (Table 15). In the third study, the Geometric Mean Titer (GMT) anti-CP5 titer was the lowest of the three experiments, but it was only slightly lower than the titer in the previous experiment (51,000 vs. 67,000).

TABLE 15

CP5-CRM$_{197}$ Immunization Reduces cfu in Rat Endocarditis Model

| Immunogenic Composition | Challenge Strain/Dose | logCFU Recovered | | Significance | | GMT CP Titer |
| --- | --- | --- | --- | --- | --- | --- |
|  |  | Heart | Kidney | Heart | Kidney |  |
| 1 µg CP5-CRM$_{197}$ | PFESA0266 | 4.34 ± 1.78 | 3.92 ± 1.73 |  |  | 103,000 |
| 1 µg PP5-CRM$_{197}$ | $2.21 \times 10^8$ cfu | 7.94 ± 0.78 | 6.77 ± 0.79 | p < 0.001 | p < 0.05 |  |
| 1 µg CP5-CRM$_{197}$ | PFESA0266 | 4.43 ± 2.30 | 3.109 ± 2.33 |  |  | 51,000 |
| Saline | $6.5 \times 10^7$ cfu | 5.63 ± 2.48 | 4.19 ± 2.05 | No | No |  |
| 1 µg CP5-CRM$_{197}$ | PFESA0266 | 4.01 ± 2.49 | 3.90 ± 1.92 |  |  | 67,000 |

TABLE 15-continued

CP5-CRM$_{197}$ Immunization Reduces cfu in Rat Endocarditis Model

| Immunogenic Composition | Challenge Strain/Dose | logCFU Recovered Heart | logCFU Recovered Kidney | Significance Heart | Significance Kidney | GMT CP Titer |
|---|---|---|---|---|---|---|
| Saline | 4.0 × 10$^8$ cfu SA315 | 7.52 ± 1.38 | 6.52 ± 1.17 | p < 0.0002 | p < 0.0002 | |
| 1 µg CP5-CRM$_{197}$ | | 8.17 ± 1.02 | 6.92 ± 1.20 | | | 186,000 |
| Saline | 1 × 10$^9$ cfu | 8.25 ± 0.60 | 6.74 ± 0.95 | No | No | |

Example 18

CP5-CRM$_{197}$ Conjugates in a Pyelonephritis Model

Initial studies investigating efficacy of conjugates were performed with 25 kDa MW CP5. Improvements in fermentation process resulted in production of the high MW polysaccharide, which was conjugated to protein carrier and tested side by side with 25 kDa CP5 conjugate. Conjugates comprising CP with MW of 25 kDa (Low MW) and 300 kDa (High MW) were prepared using CDT conjugation chemistry and evaluated in the murine pyelonephritis model. Three doses (0.01, 0.1 and 1 µg) of the HMW conjugates were tested and compared to the control LMW CP5-CRM$_{197}$ and an unrelated conjugate (PP5-CRM$_{197}$) at 1 µg dose. The results showed a significant reduction in CFU of *S. aureus* PFESA0266 recovered from the kidneys at a 1 µg dose. There was no statistical difference between protection from conjugates prepared with different size CP5 at the 1 µg dose (Table 16). The lower doses (0.01 µg and 0.1 µg) of the conjugate failed to elicit an immune response sufficient to significantly reduce the infection. The experiment was repeated using an identical immunization and challenge procedure. In the repeated experiment, only the 1 µg dose of LMW CP5-CRM$_{197}$ resulted in a significant reduction in colonization (p=0.01). The 1 µg dose of HMW CP5-CRM$_{197}$ lowered cfu in kidneys, however the reduction was not statistically significant (p=−0.056).

TABLE 16

CP5 Conjugates Protect in a Mouse Pyelonephritis Model.

| Study | Antigen | Strain/Dose | logCFU/ Kidney | Significance (p value) |
|---|---|---|---|---|
| 1 | 1 µg PP5-CRM$_{197}$ | PFESA0266 1.7 × 10$^8$ | 5.34 | 0.0048 |
| | 1 µg 25 kDa CP5-CRM$_{197}$ | | 2.94 | |
| | 1 µg 300 kDa CP5-CRM$_{197}$ | | 2.74 | 0.0056 |
| | 0.1 µg 300 kDa CP5-CRM$_{197}$ | | 5.59 | |
| | 0.01 µg 300 kDa CP5-CRM$_{197}$ | | 4.70 | |
| 2 | 1 µg PP5-CRM$_{197}$ | PFESA0266 1.7 × 10$^8$ | 5.35 | |
| | 1 µg 25 kDa CP5-CRM$_{197}$ | | 3.25 | 1.01 |
| | 1 µg 300 kDa CP5-CRM$_{197}$ | | 3.78 | 0.06 |
| | 0.1 µg 300 kDa CP5-CRM$_{197}$ | | 4.45 | |
| | 0.01 µg 300 kDa CP5-CRM$_{197}$ | | 6.08 | |

Example 19

Polysaccharide O-Acetylation is Important for Induction of Protective Antibody Response to CP5 Conjugate Immunogenic Formulation To evaluate the importance of O-Acetylation of CP5, the native CP5 was de-O-acetylated (dOAc) and conjugated to CRM$_{197}$ (dOAc-CRM$_{197}$) using PDPH conjugation chemistry. The efficacy of dOAcCP-CRM$_{197}$ conjugate was compared side by side with CP5-CRM$_{197}$ in a murine pyelonephritis model. The results showed that conjugate lacking O-acetyl groups (dOAc CP5-CRM$_{197}$) is not efficacious in this model as demonstrated by no significant change in the bacterial colonization in kidneys. These data (Table 17) indicate that O-acetylation was important for elicitation of functional antibodies against CP5.

TABLE 17

Immunization With de-O-acetylated CP5-CRM$_{197}$ Does Not Protect Mice From Kidney Colonization

| Study # | Antigens | Strain/Dose | logCFU/ Kidney | Significance |
|---|---|---|---|---|
| Study 1 | 1 µg PP5-CRM$_{197}$ | PFESA0266 7 × 10$^8$ | 3.89 ± 2.24 | |
| | 1 µg dOAc CP5-CRM$_{197}$ | | 4.20 ± 1.75 | |
| | 1 µg CP5-CRM$_{197}$ | | 1.75 ± 0.39 | p-value < 0.008 |
| Study 2 | Saline | PFESA0266 2.4 × 10$^8$ | 5.08 ± 1.96 | |
| | 1 µg dOAc CP5-CRM$_{197}$ | | 5.89 ± 1.29 | |
| | 1 µg CP5-CRM$_{197}$ | | 2.93 ± 2.11 | p-value < 0.02 |

Example 20

Immunization with CP8-Conjugate Reduces Death in a Sepsis Model

Figure 17:
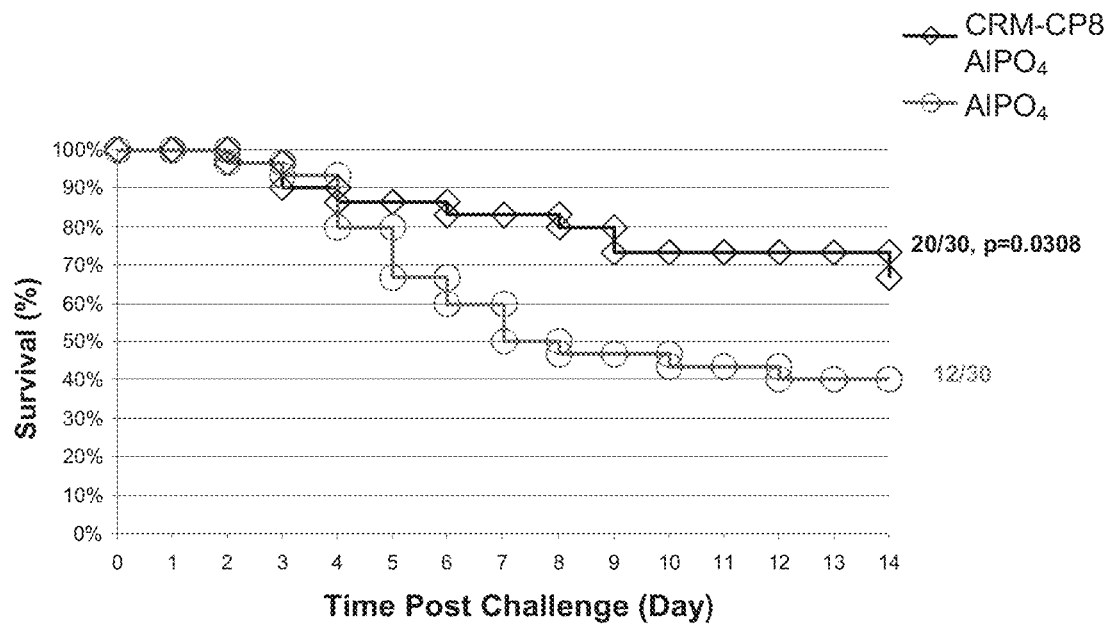
FIG. 17 demonstrates that vaccination with CP8-CRM$_{197}$ conjugate immunogenic formulation reduces death in a sepsis model.

The efficacy of CP8-CRM$_{197}$ conjugate was evaluated in the murine sepsis model after challenge with *S. aureus* PFESA0268 (Type 8). Swiss Webster mice (n=30) were actively immunized by subcutaneous injection with 1 µg CP8-CRM$_{197}$ and saline both formulated with 100 µg AlPO$_4$. The study showed a significant reduction of sepsis (p=0.0308) as compared to mice immunized with AlPO$_4$ alone. See FIG. 17.

Example 21

Evaluation of the Conjugated Native and Base Treated CP8 in the Murine Bacteremia Model The importance of O-Acetyl groups present on native CP8 before conjugation for induction of functional antibody responses was evaluated for CP8 conjugate. CP8 polysaccharide was de-O-Acetylated under mild basic conditions and both NMR and Ion Chromatography (IC) confirmed absence of O-Acetylation in CP8 de-O-Ac-CRM$_{197}$.

The murine bacteremia model was used to evaluate efficacy of the native versus base treated CP8 conjugated to CRM$_{197}$. Groups of female BALB/c mice (15/group) were immunized at weeks 0, 3 and 6, with 1 μg CP8 de-O-Ac-CRM$_{197}$ or 1 μg CP8 O-Ac-CRM$_{197}$. Immunogenic formulations were formulated with 22 μg AlPO$_4$. Animals were challenged with *S. aureus* PFESA0003. Three hours post challenge the mice were sacrificed and the bacteria were enumerated in blood. The data showed that there was a statistically significant (p=0.0362) reduction in bacterial cfu recovered from the blood of animals immunized with untreated native CP8 conjugate as determined by the student t test (Table 18). In animals that were immunized with base treated CP8 conjugate the bacterial cfu recovered from blood were similar to the saline control group.

TABLE 18

CP8-CRM$_{197}$ Conjugate Reduces
Bacteremia *S. aureus* PFESA0003 in Mice.

| Antigen | Strain/Dose | logCFU/Blood | Significance (p value) |
|---|---|---|---|
| Saline | PFESA0003 | 4.35 | |
| CP8 de-O—Ac-CRM$_{197}$ | 1.14 × 10$^8$ | 4.45 | |
| CP8 O—Ac-CRM$_{197}$ | | 3.93 | 0.03 |

Example 22

Confirmation of the Importance of O-Acetylation as Functional Epitope of CP5 by OPA Using MAbs With Known Specificities CP5 monoclonal antibodies with specificities to CP5 OAc+ (CP5-7-1), CP5 OAc+/− (CP5-5-1) and CP5 OAc− (CP5-6-1) were evaluated for OP killing activity against type 5 strain PFESA0266 (Table 19). MAb CP8-3-1 specific to CP8 OAc+ was used as negative control. Results showed that CP5-7-1 mAb (CP5 OAc+ specific) mediates killing of both type 5 strains tested. Also mAb CP5-5-1 recognizing epitopes shared by both CP5 OAc+ and CP5 OAc− mediated killing of PFESA0266 strain. The MAb specific for epitopes present on CP5 OAc-polysaccharide did not mediate killing of PFESA0266 strain. These results indicate that O-Acetyl epitopes on CP5 are involved in functional activity of CP5 specific antibodies.

TABLE 19 mAbs Specific to O-Acetylated (+) CP5 and O- and de-O-Acetylated (+/−)
CP5 are Opsonic against *S. aureus* PFESA0266 (Type 5).

| | CP5-5-1 (O-Ac +/−) (μg) | | | | CP5-6 -1 (O-Ac −) (μg) | | | | CP5-7-1 (O-Ac +) (μg) | | | | CP8-3-1 (neg. control) (μg) | | | |
|---|---|---|---|---|---|---|---|---|---|---|---|---|---|---|---|---|
| μg | 20 | 10 | 5 | 2.5 | 20 | 10 | 5 | 2.5 | 20 | 10 | 5 | 2.5 | 20 | 10 | 5 | 2.5 |
| % kill | 28 | 33 | 30 | 21 | −12 | −5 | −12 | −5 | 31 | 46 | 49 | 55 | −18 | −3 | −13 | −5 |

Data reported as percent killing and was calculated by determining the ratio of the number of cfu surviving at 60 minutes in wells with bacteria, antibodies, complement and HL-60 cells to the number of cfu surviving in wells lacking antibodies but containing bacteria, complement and HL-60 cells.

Example 23

Opsonic Activity of Mouse Antibodies Induced to High and Low MW CP5 Conjugates

Sera from mice (n=5) with high CP5 ELISA titers from 1 μg high molecular weight and low molecular weight groups from Example 18 were compared for opsonic activity using *S. aureus* PFESA0266. OPA results showed that both conjugates elicited opsonic antibodies in mice (Table 20). There was a trend observed for high MW conjugates to elicit higher titer opsonic antibodies. Data shown as a mean % killing±SEM for 5 individual mouse sera. Antibodies need to be functional as measured by killing of bacteria in either an animal efficacy model or via an opsonophagocytic killing assay that demonstrates the antibodies kill the bacteria. Functional killing may not be demonstrated using an assay that just monitors the generation of antibodies alone, which is not indicative of the importance of high molecular weight conjugates in efficacy.

TABLE 20

Both LMW and HMW CP5 conjugates elicit opsonic antibodies

| Antigen: 1 μg CP5-CRM$_{197}$ (25 kDa) | | Antigen: 1 μg CP5-CRM$_{197}$ (300 kDa) | |
|---|---|---|---|
| OPA titer wk 0 | OPA titer wk 8 | OPA titer wk 0 | OPA titer wk 8 |
| <100 | 400 | <100 | 6400 |
| <100 | <100 | <100 | 800 |
| <100 | 400 | <100 | 3200 |
| <100 | 3200 | <100 | 3200 |
| <100 | <100 | <100 | 3200 |

Example 24

Opsonic Activity of Sera from Mice Immunized with Native and Chemically Modified CP8 Conjugates Select mouse sera (n=5) with high CP8 titers from the study in Example 21 were compared for opsonic activity using PFESA0005 strain. The OPA results (Table 21) show that only conjugates prepared by the conjugation of native CP8 elicited opsonic antibodies in mice. It is noteworthy that the de-OAc CP8 conjugate was immunogenic in mice but the antibodies elicited were not opsonic in this assay. OPA titers are reported as reciprocal of dilution at which 40% killing was observed. Antibodies need to be functional as measured by killing of bacteria in either an animal efficacy model or via opsonophagocytic killing assay that demonstrates the antibodies kill the bacteria. Functional killing may not be demonstrated using an assay that just monitors the generation of antibodies alone, which is not indicative of the importance of O-acetylation in efficacy.

TABLE 21

Opsonic Activity of Native CP8 vs. de-O—Ac CP8-CRM$_{197}$

| De-O—Ac CP8-CRM$_{197}$ | | CP8-CRM$_{197}$ | |
|---|---|---|---|
| OP titer Wk 0 sera | OP titer Wk 8 sera | OP titer Wk 0 sera | OP titer Wk 8 sera |
| <50 | <50 | 50 | 150 |
| <50 | <50 | <50 | 1350 |

TABLE 21-continued

Opsonic Activity of Native CP8 vs. de-O—Ac CP8-CRM$_{197}$

| De-O—Ac CP8-CRM$_{197}$ | | CP8-CRM$_{197}$ | |
|---|---|---|---|
| OP titer Wk 0 sera | OP titer Wk 8 sera | OP titer Wk 0 sera | OP titer Wk 8 sera |
| <50 | <50 | <50 | 450 |
| <50 | <50 | <50 | 1350 |
| <50 | <50 | <50 | 4050 |

Example 25

Killing of Type 8 Strains by CP8 Conjugate Non-Human Primate Antisera is Inhibited by Addition of Native CP8

To confirm the specificity of the killing activity in the sera of non-human primates immunized with CP8-conjugate, an assay was performed in the presence of native CP8. The OP method II was used with the following modifications. Two fold serial dilutions of antibody samples (25 µl) were prepared and followed by addition of either 150 µl (Pn14 competitor) or 125 µl (CP8 competitor) of assay buffer to the antibody suspension. The competitor was purified CP8 polysaccharide (CP8 poly) and unrelated pneumococcal polysaccharide (Pn 14 poly) was used as a control. The polysaccharides were added (50 µg) to the antibody suspension and the plate incubated at 4° C. for 30 minutes with end over end mixing. Following incubation with polysaccharides, bacteria were added (25 µl) to the plates and placed on a rotary shaker at 4° C. for 30 minutes followed by addition of 25 µl of human complement (1% final concentration). The results (Table 22) showed that the presence of native CP8 in reaction mixture inhibited opsonophagocytic killing of S. aureus Type 8 These results confirm that opsonophagocytic killing by immune sera was mediated by capsule specific Abs.

TABLE 22

Addition of CP8 Polysaccharide Inhibits Opsonophagocytic Killing Of S. aureus by Immune Sera.

| Monkey | Sera Sample | OPA titer |
|---|---|---|
| 02D133 | Wk 0 | <50 |
| | Wk 8 | 4050 |
| | Wk 0 + 20 µg CP8 poly | <50 |
| | Wk 8 + 20 µg CP8 poly | <50 |
| | Wk 0 + 20 µg Pn14 poly | <50 |
| | Wk 8 + 20 µg Pn14 poly | 4050 |
| A4N122 | Wk 0 | <50 |
| | Wk 8 | 4050 |
| | Wk 0 + 20 µg CP8 poly | <50 |
| | Wk 8 + 20 µg CP8 poly | <50 |
| | Wk 0 + 20 µg Pn14 poly | <50 |
| | Wk 8 + 20 µg Pn14 poly | 1350 |

Example 26

Naturally Acquired Antibodies to ClfA Mediate Opsonophagocytic Killing of S. Aureus Humans in the population are naturally exposed to S. aureus and thus have preexisting antibodies to that bacterium in their circulation. We affinity purified anti-ClfA antibodies from human serum and evaluated whether the antibodies could mediate opsonic killing. It has been shown that antibodies to ClfA are opsonic for S. aureus capsular polysaccharide (data not shown). Strain PFESA0266 was grown overnight in Columbia broth with 2% NaCl. Bacteria were opsonized with ClfA affinity purified human IgG or irrelevant antigen affinity purified human IgG (negative control, streptococcal SCP protein) and the opsonic activity tested. Differentiated HL-60 cells were used in the opsonophagocytic assay at an effector/target ratio of 100:1. As an additional control a CP5 mAb was included in the experiment to demonstrate the presence of CP5 on the surface. The results are average of two independent experiments. ClfA and CP5 specific antibodies did mediate opsonic killing and SCP specific (negative control) antibodies had no activity in this assay.

Example 27

CP5-CRM$_{197}$ Conjugate Elicits Opsonic Antibodies in Non-Human Primates (NHP)

To compare the functionality of high vs. low molecular weight CP5-CRM$_{197}$ conjugates in NHP, groups of five monkeys were immunized with 2 and 20 µg doses of the conjugates with or without AlPO$_4$ adjuvant. The monkeys received the first and second vaccination on day 0 and 28, respectively. Bleeds from day 0, 14, 28 and 42 were tested for OP activity. Results are summarized in Table 23. The 20 µg HMW conjugate had the highest OP titers compared to other groups. Also, the frequency of OP positive monkeys was higher at both doses of the high MW groups than for the corresponding low MW groups. These results demonstrate that there is a trend for HMW CP5-CRM$_{197}$ conjugate to elicit better OP responses than LMW CP5 conjugate in NHP.

TABLE 23

OPA of NHP serum following immunization with CP5 conjugates.

| | | | OPA Titer (40% Kill) | | |
|---|---|---|---|---|---|
| Group | Monkey ID | Day 0 | Day 14 | Day 28 | Day 42 |
| 20 µg CP5 | A2N053 | 450 | 1350 | 4050 | 4050 |
| (HMW) + | 149N | <100 | 4050 | 4050 | 4050 |
| 0.5 mg/mL | A4L069 | <100 | 450 | 150 | <100 |
| AlPO$_4$ | A1N097 | <100 | 4050 | 1350 | 1350 |
| | A4L014 | <100 | <100 | <100 | <100 |
| 2 µg CP5 | 02D125 | <100 | 150 | 150 | 150 |
| (HMW)) + | A4L081 | <100 | 150 | 150 | 150 |
| 0.5 mg/mL | A2N055 | 150 | 450 | 150 | 150 |
| AlPO$_4$ | A4N084 | <100 | <100 | <100 | <100 |
| | A1N085 | <100 | 150 | 450 | 4050 |
| 2 µg CP5 | A4L084 | 150 | 150 | <100 | <100 |
| (HMW) | 97N004 | 150 | 450 | 450 | 450 |
| no AlPO$_4$ | A4L055 | <100 | <100 | <100 | <100 |
| | 97N123 | <100 | <100 | 150 | 150 |
| | 225N | <100 | <100 | <100 | <100 |
| 20 µg CP5 | 02D017 | <100 | <100 | <100 | <100 |
| (LMW)) + | A4N100 | <100 | 150 | 150 | 4050 |
| 0.5 mg/mL | 257N | <100 | <100 | <100 | <100 |
| AlPO$_4$ | A4L046 | <100 | <100 | <100 | <100 |
| | A1N098 | <100 | 150 | <100 | <100 |
| 2 µg CP5 | 96N022 | 1150 | 150 | 450 | 150 |
| (LMW)) + | 02D005 | <100 | 1350 | 450 | 1350 |
| 0.5 mg/mL | 02D113 | <100 | 150 | 150 | <100 |
| AlPO$_4$ | A2N040 | 150 | 150 | <100 | <100 |
| | A4L056 | 150 | 150 | <100 | <100 |

Example 28

Capsule Polysaccharide Conjugates Comprising High Molecular Weight Polysaccharides Show Enhanced Immunogenicity Compared to Conjugates Comprising Low Molecular Weight Polysaccharides Non human primate (NHP) studies were conducted to evaluate the immunogenicity of different capsule conjugate formulations. Two formulations were tested at two different dosage levels (2 and 20 µg). The first formulation was composed of a high molecular weight (HMW) polysaccharide (approximately 130 kDa) conjugated to $CRM_{197}$. The second formulation contained a low molecular weight (LMW) polysaccharide (approximately 25 kDa) conjugated to $CRM_{197}$. Groups of five primates were vaccinated with a single dose of either vaccine and immune titers were monitored prior to vaccination and two weeks post vaccination. OPA titers were defined as the dilution of serum required to kill 40% of S. aureus Strain PFESA0266 in an OPA assay. Antibody titers were also monitored by ELISA. Enhanced activity was seen for the HMW vaccine compared to the LMW formulation (Table 24), evidenced by a ten fold rise in antibody titers for the HMW vaccine compared to the LMW vaccine. The OPA responder rate for the NHPs that received the HMW vaccine were also higher (80% compared to 40%).

TABLE 24

Enhanced Immunogenicity is observed for HMW polysaccharide conjugate vaccines compared to LMW polysaccharide conjugate vaccine.

| | CP5-CRM197 dose level (mcg) per animal | Geometric Mean of PD1* | OPA Responder Rate (%)± |
|---|---|---|---|
| HMW (125 kDa) | 20 | 32 | 80 |
| | 2 | 21 | 80 |
| LMW (25 kDa) | 20 | 3 | 40 |
| | 2 | 8 | 40 |

*Fold rise calculated from CP5 ELISA titer 2 weeks post vaccination compared to pre vaccine titers.
±Responder rate calculated from monkeys generating a rise in OPA titer following a single dose of vaccine 2 weeks post vaccination. Each group contained 5 Rhesus maccaques and vaccines were formulated with AlPO4 (250 mcg/dose)

Example 29

Bi-Antigen (CP5-$CRM_{197}$ and ClfA) Formulation-Antibody Responses in Non-Human Primates To evaluate the immune response to a single dose of two antigen immunogenic compositions (CP5-$CRM_{197}$ and ClfA) in NHP, groups of five monkeys were immunized with different doses of the two antigens without the addition of $AlPO_4$. Bleeds from day 0, 14, and 28 were tested for opsnophagocytic (OP) activity and ELISA titers and the results are summarized in Table 24. Results showed that OP activity was consistently observed with CP5 immunized animals as compared to a CP5 sham group. Overall, the 100 µg group had the highest ELISA and OP titers compared to other groups. There was no OP killing activity observed with sera from the ClfA alone group. No interference was observed in the groups given ascending doses of ClfA or CP5. See Table 25.

TABLE 25

OPA Results From Bi-Valent Immunization Study In NHP

| | | OPA Titer (40% Killing) | | |
|---|---|---|---|---|
| Group # | ID Number | Week: 0 | Week: 2 | Week: 4 |
| 180 µg ClfA + 20 µg 130 kDa CP5 | A4R054 | <100 | 150 | <100 |
| | A4R056 | <100 | 150 | 150 |
| | A4N087 | <100 | 450 | 450 |
| | 97N152 | <100 | 450 | 1350 |
| | A4R027 | <100 | 1350 | 1350 |
| 180 µg ClfA + 2 µg 130 kDa CP5 | A4R062 | <100 | 150 | <100 |
| | 97N149 | <100 | 150 | <100 |
| | A4R131 | <100 | 450 | 150 |
| | 97N025 | <100 | 450 | 450 |
| | A4N064 | <100 | 450 | 450 |
| 60 µg ClfA + 20 µg 130 kDa CP5 | A4L005 | <100 | <100 | <100 |
| | A4R029 | <100 | 1350 | 1350 |
| | A3N015 | <100 | <100 | <100 |
| | 98N021 | 150 | 4050 | 4050 |
| | A4R137 | <100 | <100 | <100 |
| 60 µg ClfA + 2 µg 130 kDa CP5 | A1N040 | <100 | 150 | 150 |
| | A2N104 | <100 | 1350 | <100 |
| | A4L033 | <100 | 150 | <100 |
| | 96N048 | <100 | <100 | <100 |
| | A4R032 | <100 | <100 | <100 |
| 2 µg 130 kDa CP5 | A4R135 | <100 | 450 | 150 |
| | A1N118 | <100 | 150 | 150 |
| | A4R061 | <100 | <100 | 1350 |
| | A4R101 | <100 | 4050 | 1350 |
| | 97N137 | <100 | 1350 | 1350 |
| 20 µg 130 kDa CP5 | A4R135 | <100 | <100 | <100 |
| | A4N115 | <100 | 150 | 150 |
| | 95N038 | <100 | <100 | <100 |
| | A4N120 | <100 | 450 | 450 |
| | 96N004 | <100 | 150 | 150 |
| 100 µg 130 kDa CP5 | A4N116 | <100 | 450 | 450 |
| | A3N097 | <100 | 450 | 450 |
| | A4N108 | <100 | 1350 | 1350 |
| | 98N034 | <100 | 450 | 150 |
| | 99N034 | <100 | 1350 | 4050 |
| 60 µg ClfA | 97N057 | <100 | <100 | <100 |
| | A4R112 | 150 | <100 | 150 |
| | A4L022 | <100 | <100 | <100 |
| | 97N100 | <100 | <100 | <100 |
| | 99N041 | 150 | 150 | 150 |

Animal Models Demonstrate Potential of S. Aureus CP5 and CP8 Capsule Polysaccharide Antigens Both CP5-$CRM_{197}$ and CP8-$CRM_{197}$ conjugates induced capsular serotype specific antibody responses in mice, rats, rabbits and non-human primates (NHP). Conjugate induced antibodies were functional in the in vitro functional opsonophagocytosis killing assay. Data were generated to demonstrate that O-Acetylation is important for elicitation of protective antibodies for both CP5 and CP8, and that O-acetyl groups are part of an epitope recognized by $OPA^+$ mAbs against CP5. MAbs that recognize native CP5 which is O-acetylated are functional in OPA and mediate killing of the bacteria. CP8 conjugate induced functional antibodies in both mice and rabbits that mediated killing of Type 8 strain in OPA. The specificity of killing by polyclonal or monoclonal antibodies was confirmed by abolition of the killing after addition of the homologous native polysaccharide to the assay. The various active immunization models were used to show preclinical efficacy of both CP5- and CP8-$CRM_{197}$ conjugates. The CP5 conjugate showed consistent efficacy in the murine pyelonephritis model and the rat endocarditis model. The importance of O-acetylation of CP5 was confirmed in the murine pyelonephritis model, where de-O-acetylated CP5 conjugated to $CRM_{197}$ failed to protect animals against experimental infection.

The combination of the conjugates in a bi-antigen formulation induced antibodies to both capsules CP5 and CP8 and there was no interference to the specific antibody levels induced compared to single antigen immunizations. The combination of conjugates and ClfA in a tri-antigen formulation induced high CP5, CP8 and ClfA levels, and there was no interference to the antibody responses induced against any antigen present in the combination. The tri-antigen immunogenic compositions induced antibody (Ab) responses capable of being boosted to all three components in rabbits with high pre-immune titers.

These results suggest that CP5 and CP8 conjugated to $CRM_{197}$ should be included as immunogenic formulation components of a protective S. aureus immunogenic composition.

Example 30

Requirement of Different Antigens to Protect from Multiple Possible S. aureus Diseases S. aureus cause a wide array of infections ranging from relatively mild skin infections to more serious and invasive infections such as endocarditis, necrotizing fasciitis, osteomyelitis, septic arthritis and pneumonia. Each of these in vivo sites is unique and the bacteria likely respond to the differences in environmental stimuli by altering their antigen expression profiles to ones most suitable for the individual strain to colonize, grow and ultimately cause disease. As exemplified in Example 12, S. aureus strains show diversity of antigen expression in vivo. A multi-component immunogenic composition composed of different antigens is more likely to protect against the diverse disease manifestation caused by S. aureus.

ClfA was shown to protect in rodent endocarditis and sepsis models. ClfB has been reported to be important in nasal colonization of S. aureus. MntC protected mice in a murine bacteremia model. The CP5 conjugate protected in pyelonephritis and endocarditis, and the CP8 conjugate protected in rodent pyelonephritis and sepsis models. These results demonstrate that a multi-component vaccine containing these antigens will protect against multiple types of S. aureus disease.

In vivo animal models approximate the course of an actual infection and help to elucidate which antigens may be useful in protecting from a particular disease. Table 26 summarizes results from numerous experiments performed in various in vivo models. The results are reported in each block as four numbers separated by a slash, for example ClfA in a sepsis model has the numbers 27/1/3/31. The first number represents the number of experiments where ClfA immunization produced a statistically significant positive result of protection. The second number represents the number of experiments where ClfA immunization produced a positive result of protection that trended toward significance but was not statistically significant. The third number represents the number of experiments where ClfA immunization produced a negative result, but was not statistically significant. The fourth number is the total number of experiments performed. The first three numbers should add up to equal the fourth number.

TABLE 26

Summary Of Protection In Animal Models For S. aureus Antigens

| | ClfA | CP5 | CP8 | $MntC^{20}$ |
|---|---|---|---|---|
| Bacteremia | 1/4/0/5 | 3/0/3/6 | 1/1/1/3 | 6/2/5/13 |
| Sepsis | 27/1/3/31 | 1/0/0/1 | NT | NT |

TABLE 26-continued

Summary Of Protection In Animal Models For S. aureus Antigens

| | ClfA | CP5 | CP8 | $MntC^{20}$ |
|---|---|---|---|---|
| Pyelonephritis | 0/4/2/6 | 13/1/0/14 | NT | $1/0/4/5^{25}$ |
| Endocarditis | 3/6/1/10 | 3/2/2/7 | NT | NT |

NT: Not Tested

Example 31

Testing of Various Multi-Antigen Immunogenic Compositions In Vitro and In Vivo

Various multi-antigen staphylococcal immunogenic formulations containing either three, four or five antigens selected from the following polypeptides and/or polysaccharides are tested for immunogenicity and efficacy in various in vivo models: ClfA. ClfB, MntC, CP5- and CP8. The immunogenic compositions are as follows:

(1) an immunogenic composition comprising: an isolated S. aureus clumping factor A (ClfA) polypeptide, an isolated S. aureus capsular polysaccharide type 5 conjugated to $CRM_{197}$, and an isolated S. aureus capsular polysaccharide type 8 conjugated to $CRM_{197}$;

(2) A second combination provides clumping factor A (ClfA), clumping factor B (ClfB), an isolated MntC, isolated staphylococcal capsular polysaccharide CP5 conjugated to $CRM_{197}$, and isolated staphylococcal capsular polysaccharide CP8 conjugated to $CRM_{197}$;

(3) A third combination provides an immunogenic composition comprising: an isolated S. aureus clumping factor A (ClfA) polypeptide, an isolated S. aureus clumping factor B (ClfB) polypeptide, or an isolated S. aureus MntC protein, an isolated S. aureus capsular polysaccharide type 5 conjugated to $CRM_{197}$, and an isolated S. aureus capsular polysaccharide type 8 conjugated to $CRM_{197}$; isolated (4) A fourth combination provides an immunogenic composition comprising: an isolated S. aureus clumping factor B (ClfB) polypeptide, an isolated S. aureus capsular polysaccharide type 5 conjugated to $CRM_{197}$, and an isolated S. aureus capsular polysaccharide type 8 conjugated to $CRM_{197}$;

(5) A fifth combination provides an immunogenic composition comprising: an isolated S. aureus clumping factor B (ClfB) polypeptide, an isolated S. aureus MntC protein, an isolated S. aureus capsular polysaccharide type 5 conjugated to $CRM_{197}$, and an isolated S. aureus capsular polysaccharide type 8 conjugated to $CRM_{197}$; and (6) A sixth combination provides an immunogenic composition comprising: an isolated S. aureus clumping factor A (ClfA) polypeptide, an isolated S. aureus clumping factor B (ClfB) polypeptide, and an isolated S. aureus MntC protein.

rClfA and rClfB are prepared and purified as described in Example 1. MntC is prepared and purified as described in Example 2. Isolated CP5 and CP8 are prepared and purified as described in Example 3 and are conjugated to $CRM_{197}$ as described in Example 4.

More particularly, the procedures described in the previous Examples above are used to measure immunogenicity and efficacy. Studies are done to determine whether each of the three, four or five components, when delivered alone, or together, induce an immune response. These same studies are used to determine whether or not the presence of any one of the four or five components interferes with the ability of any of the other three or four components to induce an immune response. Moreover, studies are done to determine whether the four or five components when tested alone, or when tested together, will confer protection in any one or more of the animal models described above. The four or five components are administered as a single dose or as multiple doses to an animal e.g. mice, rats, rabbits or non-human primates, as noted in the previous examples above. The animals are bled and the serum collected and tested for the presence of antibodies to each of the four or five components. The presence of antigen specific antibodies is measured by any immunoassay known to those skilled in the art, for example, an ELISA (See Examples 11-29) or a Western blot (See Example 1) is used to assess the presence or absence of antigen-specific antibodies. In addition, an opsonophagocytic assay is used to determine whether the antigen specific antibodies are effective at mediating killing of the staphylococcal organisms by phagocytic cells (See Examples 11-29).

In vivo efficacy is also assessed using any one or more of the animal studies described above, such as, but not limited to, the in-dwelling tubing model; the murine bacteremia model; the wound infection model; the murine pyelonephritis model; the rat endocarditis model and the murine sepsis model (See Examples 11-30).

Example 32

Combinations of *S. Aureus* Antigens Generate Antibodies in Non-Human Primates that Enhance Killing of *S. Aureus* Strain Pfe5-1

Figure 18:
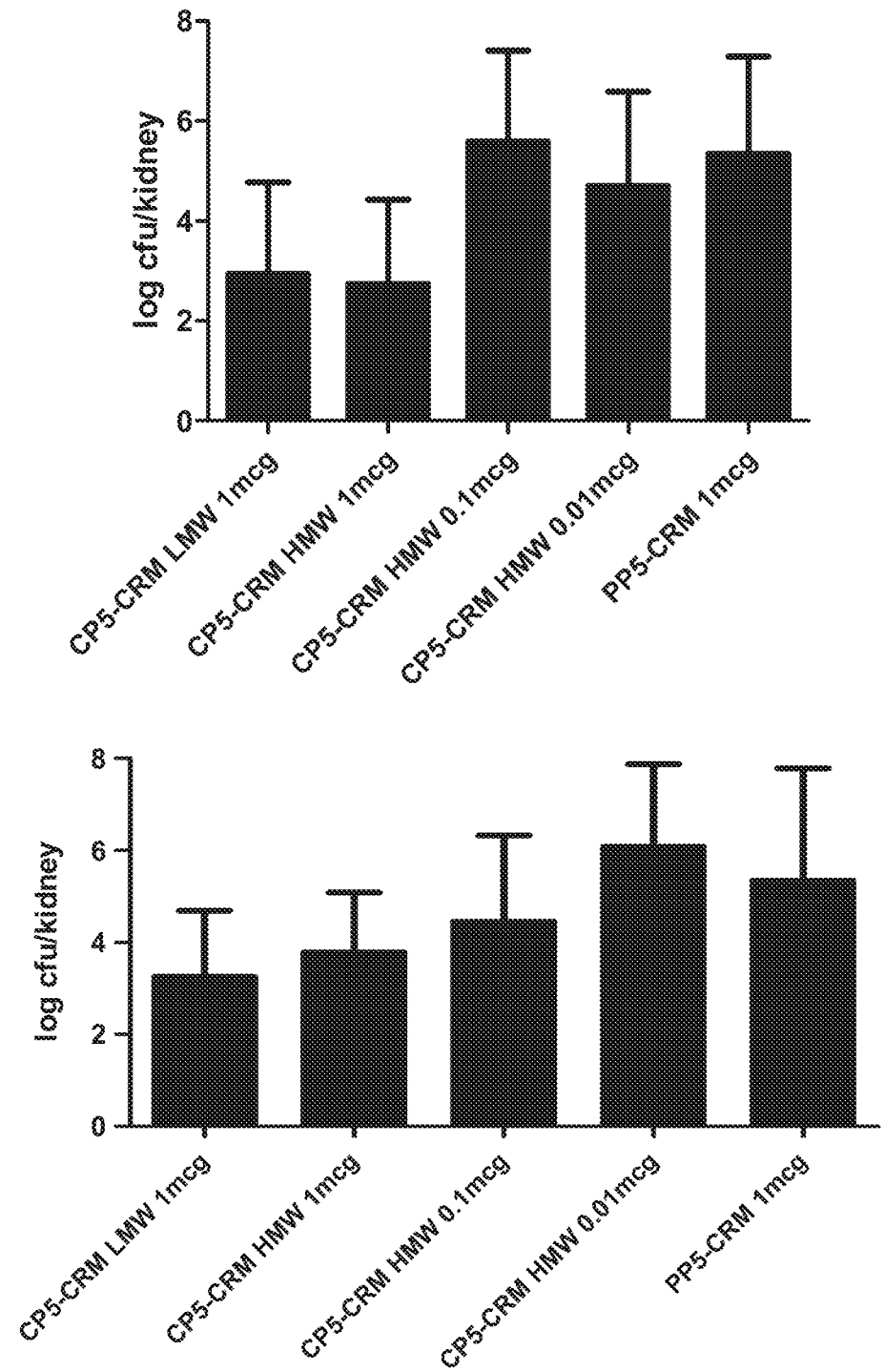
FIG. 18 shows colony forming units (CFU) recovered in kidneys after challenge with S. aureus PFESA0266 in mice vaccinated with high molecular weight (HMW) CP5-CRM, low molecular weight (LMW) CP5-CRM or PP5-CRM control.
Figure 19:
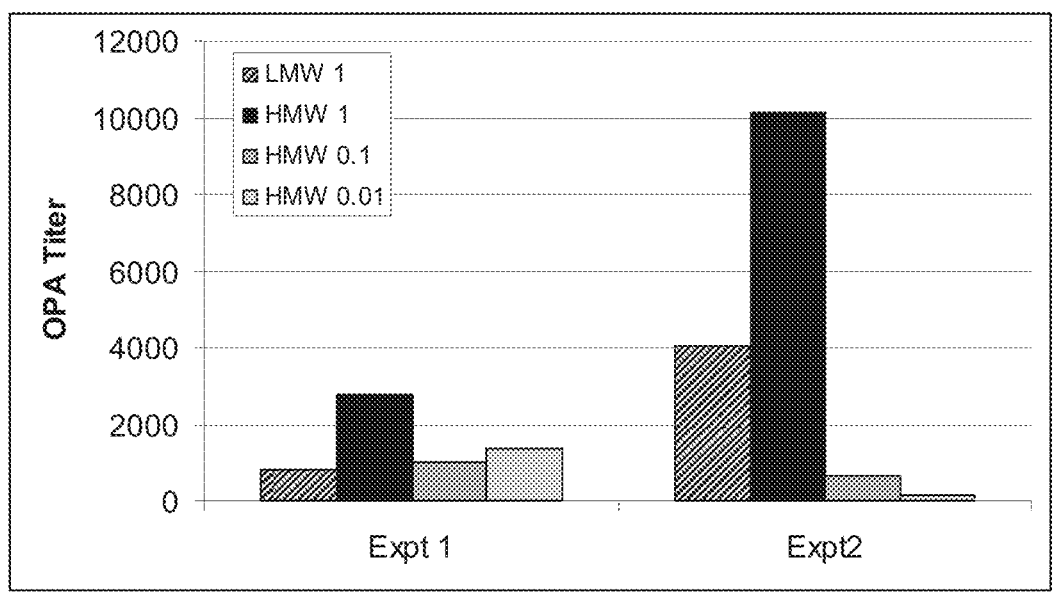
FIG. 19 shows a comparison of OPA titers (geomean) from serum obtained from mice vaccinated with different formulations of polysaccharide conjugate (high molecular weight (HMW) CP5-CRM, low molecular weight (LMW) CP5-CRM). Groups consisted of 5 to 9 mice.
Figure 20:
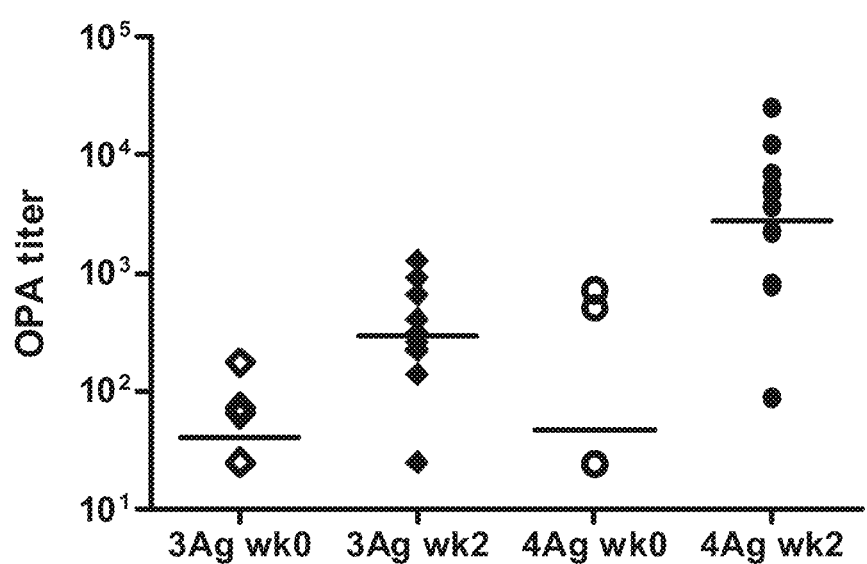
FIG. 20 demonstrates OPA titer for non-human primate serum before (wk0, open symbols) and 2 weeks after (wk2, closed symbols) vaccination with different combinations of S. aureus antigens. The 3-antigen (3Ag) vaccine was composed of three antigens and the 4-antigen (4Ag) vaccine was composed of four antigens. Each formulation has two CP conjugates and either 1 or 2 peptides.

Enhanced efficacy, as measured using the OPA assay, was observed using combinations of antigens. A non-human primate study was conducted where groups of 3-10 monkeys were immunized with multi-component vaccines. Animals received a single dose of vaccine and OPA titers were monitored at day 0 and two weeks post vaccination. OPA titers were defined as the dilution of serum required to kill 50% of *S. aureus* Strain Pfe5-1 in an OPA assay. Enhanced activity was seen for a combination of 4 antigens compared to a 3-antigen vaccine formulation (p=0.0272; FIG. 18).

What is claimed is:

1. An immunogenic composition comprising an isolated *Staphylococcus aureus* clumping factor A (ClfA) polypeptide, an isolated *S. aureus* manganese transporter protein C (MntC protein), an isolated *S. aureus* capsular polysaccharide type 5 conjugated to $CRM_{197}$, and an isolated *S. aureus* capsular polysaccharide type 8 conjugated to $CRM_{197}$, wherein the capsular polysaccharide type 5 has a molecular weight of between 70 and 300 kDa and the capsular polysaccharide type 8 has a molecular weight of between 70 and 150 kDa.

2. The immunogenic composition of claim 1, wherein the ClfA polypeptide is a polypeptide fragment comprising (a) a fibrinogen binding domain; (b) N1, N2, and N3 domains; or (c) N2 and N3 domains of ClfA.

3. The immunogenic composition according to claim 1, wherein the ClfA polypeptide is a mutated ClfA polypeptide.

4. The immunogenic composition of claim 3, wherein the mutated ClfA polypeptide has an amino acid substitution at one or more of Tyr 338, Tyr 256, Pro 336, Lys 389, Ala 254 and Ile 387 in SEQ ID NO:130.

5. The immunogenic composition of claim 4, wherein the amino acid substitution at one or more of Tyr 338, Tyr 256, Pro 336, Lys 389, Ala 254 and Ile 387 is to Ala or Ser.

6. The immunogenic composition of claim 5, wherein the Tyr 338 is substituted to Ala.

7. The immunogenic composition of claim 1, wherein the capsular polysaccharide type 5 has a molecular weight of between 70 and 150 kDa.

8. The immunogenic composition of claim 1, wherein the capsular polysaccharide type 5 is between 10% and 100% O acetylated, between 50 and 100% O acetylated, or between 75% and 100% O acetylated.

9. The immunogenic composition of claim 1, wherein the capsular polysaccharide type 8 is between 10% and 100% O acetylated, between 50 and 100% O acetylated, or between 75% and 100% O acetylated.

10. The immunogenic composition of claim 1, wherein the *S. aureus* MntC protein is a lipidated or a non-lipidated protein.

11. An immunogenic composition comprising an isolated *Staphylococcus aureus* manganese transporter protein C (MntC protein), an isolated *S. aureus* capsular polysaccharide type 5 conjugated to $CRM_{197}$, and an isolated *S. aureus* capsular polysaccharide type 8 conjugated to $CRM_{197}$, wherein the capsular polysaccharide type 5 has a molecular weight of between 70 and 300 kDa and the capsular polysaccharide type 8 has a molecular weight of between 70 and 150 kDa.

12. The immunogenic composition of claim 1, further comprising an adjuvant.

13. The immunogenic composition of claim 1, further comprising a pharmaceutically acceptable carrier.

14. The immunogenic composition of claim 1, further comprising an antigen selected from the group consisting of Opp3a, DItD, HtsA, LtaS, IsdA, IsdB IsdC, SdrC, SdrD, SdrE, SdrF, SdrG, SdrH, SrtA, SpA, Sbi, FmtB, alpha-hemolysin (hla), beta-hemolysin, fibronectin-binding protein A (fnbA), fibronectin-binding protein B (fnbB), coagulase, Fig, map, Panton-Valentine leukocidin (pvl), alpha-toxin and its variants, gamma toxin (hlg) and variants, ica, immunodominant ABC transporter, Mg2+ transporter, Ni ABC transporter, RAP, autolysin, laminin receptors, IsaA/PisA, IsaB/PisB, SPOIIIE, SsaA, EbpS, Sas A, SasF, SasH, EFB (FIB), SBI, Npase, EBP, bone sialo binding protein II, aureolysin precursor (AUR)/Sepp1, CNA, and fragments thereof such as M55, TSST-1, mecA, poly-N-acetylglucosamine (PNAG/dPNAG) exopolysaccharide, GehD, EbhA, EbhB, SSP-1, SSP-2, HBP, vitronectin binding protein, HarA, EsxA, EsxB, Enterotoxin A, Enterotoxin B, Enterotoxin C1, and novel autolysin.

15. A method of inducing an immune response against *Staphylococcus aureus* comprising administering to a subject an immunologically effective amount of the immunogenic composition of claim 1.

16. The method of claim 15, wherein the immune response reduces a disease associated with a staphylococcal organism in a subject.

17. The method of claim 16, wherein the disease is selected from the group consisting of invasive *S. aureus* disease, sepsis, and carriage.

18. The method of claim 15, wherein the immune response induced comprises the generation of antibodies having opsonophagocytic activity (OPA) against *S. aureus*.

* * * * *